(12) United States Patent
Chikkanna et al.

(10) Patent No.: US 11,365,205 B2
(45) Date of Patent: Jun. 21, 2022

(54) IMIDAZOLIDIN-2-ONE COMPOUNDS AS PRMT5 MODULATORS

(71) Applicant: Aurigene Discovery Technologies Limited, Bangalore (IN)

(72) Inventors: Dinesh Chikkanna, Bangalore (IN); Sunil Kumar Panigrahi, Boudh (IN); Srinivasa Raju Sammeta, Bangalore (IN); Wohlfahrt Gerd, Helsinki (FI); Myllymaki Mikko, Espoo (FI)

(73) Assignee: AURIGENE DISCOVERY TECHNOLOGIES LIMITED, Karnataka (IN)

(*) Notice: Subject to any disclaimer, the term of this patent is extended or adjusted under 35 U.S.C. 154(b) by 86 days.

(21) Appl. No.: 16/982,996

(22) PCT Filed: Mar. 20, 2019

(86) PCT No.: PCT/IB2019/052249
§ 371 (c)(1),
(2) Date: Sep. 21, 2020

(87) PCT Pub. No.: WO2019/180628
PCT Pub. Date: Sep. 26, 2019

(65) Prior Publication Data
US 2021/0002299 A1 Jan. 7, 2021

(30) Foreign Application Priority Data
Mar. 22, 2018 (IN) .............................. 201841010616

(51) Int. Cl.
| | | |
|---|---|---|
| C07D 401/14 | (2006.01) | |
| A61K 31/4725 | (2006.01) | |
| C07D 498/08 | (2006.01) | |
| A61P 35/00 | (2006.01) | |
| C07D 401/06 | (2006.01) | |
| C07D 405/14 | (2006.01) | |
| C07D 413/14 | (2006.01) | |
| C07D 471/04 | (2006.01) | |

(52) U.S. Cl.
CPC ............ *C07D 498/08* (2013.01); *A61P 35/00* (2018.01); *C07D 401/06* (2013.01); *C07D 401/14* (2013.01); *C07D 405/14* (2013.01); *C07D 413/14* (2013.01); *C07D 471/04* (2013.01)

(58) Field of Classification Search
CPC .......................... C07D 401/14; C07D 401/06; A61K 31/4725; A61P 35/00
USPC .......................... 546/139, 148, 150; 514/307
See application file for complete search history.

(56) References Cited

FOREIGN PATENT DOCUMENTS

| | | |
|---|---|---|
| WO | 2014100716 A1 | 6/2014 |
| WO | 2014100719 A2 | 6/2014 |
| WO | 2014100730 A1 | 6/2014 |
| WO | 2014100734 A1 | 6/2014 |
| WO | 2014100764 A2 | 6/2014 |
| WO | 2014128465 A1 | 8/2014 |
| WO | 2014145214 A2 | 9/2014 |
| WO | 2015200677 A2 | 12/2015 |
| WO | 2015200680 A2 | 12/2015 |
| WO | 2016022605 A1 | 2/2016 |
| WO | 2016034675 A1 | 3/2016 |
| WO | 2017153513 A1 | 9/2017 |
| WO | 2017153518 A1 | 9/2017 |
| WO | 2017211958 A1 | 12/2017 |

OTHER PUBLICATIONS

International Search Report issued in connection with PCT Application No. PCT/IB2019/052249 dated Jul. 9, 2019.

*Primary Examiner* — Charanjit Aulakh
(74) *Attorney, Agent, or Firm* — Steven M. Shape; Dennemeyer & Associates, LLC

(57) ABSTRACT

The present invention relates to the derivatives of compound of formula (I) and pharmaceutically acceptable salts thereof. The present invention further provides the methods of preparation of compound of formula (I) and use thereof as PRMT5 inhibitors. The compounds are useful as medicaments in the treatment of conditions where PRMT5 inhibition is desired, such as cancer, metabolic disorders, inflammation, autoimmune disease and hemoglobinopathies.

16 Claims, No Drawings

IMIDAZOLIDIN-2-ONE COMPOUNDS AS PRMT5 MODULATORS

CROSS-REFERENCE TO RELATED APPLICATIONS

This is a 35 U.S.C. 371 National Stage Patent Application of International Application No. PCT/IB2019/052249, filed Mar. 20, 2019, which claims priority to Indian application 201841010616, filed Mar. 22, 2018, each of which is hereby incorporated by reference in its entirety.

FIELD OF THE INVENTION

The present invention relates to therapeutically active novel compounds or pharmaceutically acceptable salts thereof or stereoisomers thereof which are useful in the treatment of PRMT5 dependent conditions and disorders. The present invention also relates to pharmaceutical compositions containing such compounds.

BACKGROUND OF THE INVENTION

Methyltransferase is enzyme which catalyses the transfer of methyl group from one molecule to other. Protein methyltransferase (PMTs) are regulatory system that regulates gene expression by transferring methyl groups to substrates including protein, DNA, RNA and small molecules. The transfer of methyl group to arginine residue of protein is catalysed by PRMT enzymes family which facilitate the transfer of methyl (—$CH_3$) group to specific nucleophilic sites on proteins, nucleic acids or other biomolecules. Methylation is an essential transformation in small-molecule metabolism and it is a common modification of DNA and RNA carried out by PMTs. Broadly, PMTs fall into two major families—protein lysine methyltransferases (PKMTs) and protein arginine methyltransferases (PRMTs). PRMTs utilize S-adenosyl-1-methionine as a ubiquitous cofactor to catalyze the transfer of highly specific methyl group from methyl donor S-adenosyl-1-methionine (SAM) to the arginine residues on different biological targets. Further, based on the products of the enzymatic reactions, PRMTs can be classified as type I-IV enzymes. Type I enzymes catalyze the formation of ω-NG-monomethylarginine (ωMMA) and asymmetric ω-NG, NG-dimethylarginine (ω-aDMA). Type II enzymes catalyze the formation of ωMMA and symmetric ω-NG, NG-dimethylarginine (ω-sDMA). Type III enzymes catalyze the formation of ωMMA only and Type IV enzymes catalyze the formation of 6-NG-MMA. Type I-III exist in mammalian cells and type IV is only described in yeast and possibly in plants. To date, ten PRMTs have been found in mammalian cells. PRMT1, 2, 3, 4, 6 and 8 display type-I activity. PRMT5, 7 and 9 display type-II activity. In addition to type-II activity, PRMT7 also displays type-III activity.

Protein arginine methyltransferase 5 (PRMT5) is a typical type II methyltransferase, transferring methyl groups from SAM to the two ω-guanidino nitrogen atoms of arginine, leading to ω-NG, NG-di-symmetric methylation of a protein substrate. It is localized in both the nucleus and the cytoplasm and performs distinct functions by modifying either histones or non-histone proteins. PRMT5 was initially identified as Janus kinase (JAK)-binding protein 1 (JBP1). It can symmetrically methylate histones H2AR3, H3R2, H3R8 and H4R3. PRMT5 can also methylate many non-histone proteins and many of these events are involved in tumorigenesis. PRMT5 also plays an important role in cell cycle progression and the DNA repair process. PRMT5 has been implicated in the regulation of cell growth, apoptosis and inflammation. PRMT5 interacts with a number of binding partners that influence its substrate specificity. MEP50, a member of the WD40 family of proteins, is a critical PRMT5 cofactor which directly binds PRMT5 and increases histone methyltransferase activity of PRMT5. Nuclear PRMT5 forms complexes with the chromatin-remodeling complexes (hSWI/SNF, NuRD) and epigenetically controls genes involved in development, cell proliferation and differentiation, including tumor suppressor, through methylation of histones (Kharkhanis et al. Trends Biochem Sci. 36, 633-41, 2011). Fabbrizio, E. et al. showed that PRMT5 is a transcriptional repressor (Fabbrizio et al., EMBO Rep. 3, 641-645, 2002). H3R8me2s and H4R3me2s are keys in repressive histone methylation. Hence as a transcriptional repressor PRMT5 has oncogene-like properties because of its ability to repress the expression of tumour suppressor genes. It is shown that PRMT5 overexpression correlates with human glioblastoma cell proliferation and inversely correlates with patient survival (Yan et al., Cancer Res. 74, 1752-1765, 2014). It is reported that PRMT5 is upregulated in human malignant melanoma tumors compared to normal epidermis (Nicholas et al., PLoS One, 30, 8(9): e74710, 2013). It is shown that depletion of PRMT5 via siRNA modulates cellular proliferation in ovarian cancer cell line (Bao et al., J. Histochem. Cytochem., 61, 206-217, 2013). Gu et al. showed that PRMT5 expression is essential for the growth of lung cancer cells (Gu et al. Biochem. J., 446, 235-41, 2012). Pal et al. and Wang et al. reported that PRMT5 levels are elevated in various transformed cells and knockdown of PRMT5 is associated with a slowing of cell growth, whereas PRMT5 overexpression causes cellular hyperproliferation (Pal et al., EMBO J. 8, 26, 3558-69, 2007 and Wang et al., Mol. Cell. Biol., 28, 6262-6277, 2008). Jansson et al. reported that PRMT5 overexpression in an orthotopic mouse model of breast cancer accelerates tumour growth (Jansson et al., Nature Cell Biol, 10, 1431-1439, 2008). PRMT5 suppresses the transcription of the Rb family of tumor suppressors in leukemia and lymphoma cells (Wang et al., Mol. Cell. Biol., 28, 6262-6277, 2008). Several cell lines and patient samples in B-cell lymphoma and leukemia shows PRMT5 overexpression (Pal et al., EMBO J. 8, 26, 3558-69, 2007). Targeting methyltransferase PRMT5 eliminates leukemia stem cells in chronic myelogenous leukemia (Jin et al., J. Clin. Invest., 126, 3961-3980, 2016; Yan et al., Cancer Res., 74, 1752-1765, 2014 and Chan-Penebre et al., Nature Chemical Biology, 11, 432-437, 2015). Selective inhibition of PRMT5 blocks initiation and maintenance of B-cell transformation (Alinari et al., Blood, 125, 2530-43, 2015). In addition to glioblastoma, melanoma, ovarian and lung cancer, PRMT5 is also implicated in other solid tumors such as prostate cancer, breast cancer, colon cancer, gastric cancer, esophageal cancer and hepatocellular carcinoma. Additionally aberrant methylation of PRMT5 substrates has been implicated in other indications such as metabolic disorders, inflammation, autoimmune disease and hemoglobinopathies.

Few PRMT5 inhibitors have been described in e.g. WO 2017/211958, WO 2017/153518, WO 2017/153513, WO 2016/034675, WO 2016/022605, WO 2015/200677, WO 2015/200680, WO 2014/145214, WO 2014/128465, WO 2014/100764, WO 2014/100734, WO 2014/100730, WO 2014/100719 and WO 2014/100716.

Nevertheless, there is a need for potent and selective PRMT5 inhibitors which are suitable for use as a medicament in the treatment of conditions and disorders, where PRMT5 inhibition is desired, such as cancer, metabolic disorders, inflammation, autoimmune disease and hemoglobinopathies.

SUMMARY OF THE INVENTION

It has been found that compounds of formula (I) are potent and selective PRMT5 inhibitors. The compounds of the invention are therefore useful as therapeutic agents in the treatment of cancer, such as medulloblastoma, glioblastoma, melanoma, ovarian cancer, lung cancer, prostate cancer, breast cancer, colon cancer, gastric cancer, esophageal cancer and hepatocellular carcinoma and other conditions and disorders mediated by PRMT5, such as metabolic disorders, inflammation, autoimmune disease and hemoglobinopathies.

In one aspect, the present invention provides with compounds of formula (I):

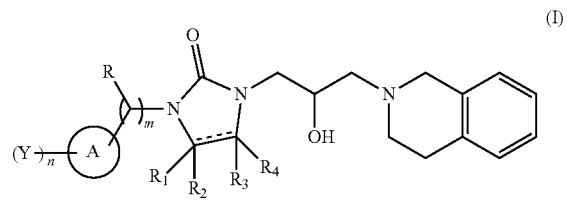

or a pharmaceutically acceptable salt or a stereoisomer thereof; wherein,
- ----- represents a single bond or double bond;
- A is aryl, heteroaryl, cycloalkyl or heterocycloalkyl;
- Y is hydrogen, —SO$_2$R$_a$, —NR$_a$R$_b$, —C(O)R$_a$, —C(O)NR$_a$R$_b$, —NHC(O)R$_a$, —COOH, cyano, halogen, haloalkyl, alkyl, alkenyl, alkynyl, alkoxy, hydroxyl or oxo; wherein the said alkyl, alkenyl and alkynyl are optionally substituted with 1 to 3 groups selected from hydroxyl, halogen, acyl and heterocycloalkyl;
- R is hydrogen, alkyl or halogen;
- R$_a$ is hydrogen, alkyl, halogen, alkoxy, heterocycloalkyl or cycloalkyl; wherein the heterocycloalkyl and cycloalkyl are optionally substituted with 1 to 3 groups selected from alkyl, hydroxyl, halogen and acyl;
- R$_b$ is hydrogen or alkyl;
- R$_1$ is hydrogen or alkyl; R$_2$ is hydrogen, alkyl or absent; or R$_1$ and R$_2$ together represents an oxo group;
- R$_3$ is hydrogen or alkyl; R$_4$ is hydrogen, alkyl, aryl or absent; or R$_3$ and R$_4$ together with the atoms to which they are attached form 3- to 8-membered cycloalkyl ring;
- alternatively, R$_1$ and R$_3$ together with the atoms to which they are attached form an optionally substituted aryl, heteroaryl or cycloalkyl, wherein the optional substituent is selected from 1 to 3 occurrences of R$_5$;
- R$_5$ is alkyl, halogen or cyano;
- 'n' is 1, 2 or 3;
- 'm' is 0 or 1.

DETAILED DESCRIPTION OF THE INVENTION

The present invention provides compounds, referred as compounds of formula (I), which are useful as PRMT5 inhibitors. The present invention further provides pharmaceutical compositions comprising the said compounds and their pharmaceutically acceptable salts or stereoisomers as therapeutic agents.

Each embodiment is provided by way of explanation of the invention and not by way of limitation of the invention. In fact, it will be apparent to those skilled in the art that various modifications and variations can be made to the compounds, compositions and methods described herein without departing from the scope or spirit of the invention. For instance, features illustrated or described as part of one embodiment can be applied to another embodiment to yield a still further embodiment. Thus it is intended that the present invention include such modifications and variations and their equivalents. Other objects, features and aspects of the present invention are disclosed in or are obvious from, the following detailed description. It is to be understood by one of ordinary skill in the art that the present discussion is a description of exemplary embodiments only and is not to be construed as limiting the broader aspects of the present invention.

The present invention provides with compounds of formula (I):

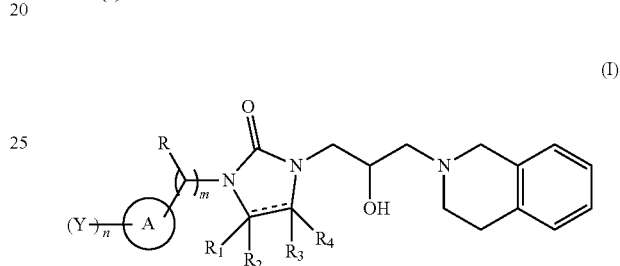

or a pharmaceutically acceptable salt or a stereoisomer thereof; wherein,
- ----- represents a single bond or double bond;
- A is aryl, heteroaryl, cycloalkyl or heterocycloalkyl;
- Y is hydrogen, —SO$_2$R$_a$, —NR$_a$R$_b$, —C(O)R$_a$, —C(O)NR$_a$R$_b$, —NHC(O)R$_a$, —COOH, cyano, halogen, haloalkyl, alkyl, alkenyl, alkynyl, alkoxy, hydroxyl or oxo; wherein the said alkyl, alkenyl and alkynyl are optionally substituted with 1 to 3 groups selected from hydroxyl, halogen, acyl and heterocycloalkyl;
- R is hydrogen, alkyl or halogen;
- R$_a$ is hydrogen, alkyl, halogen, alkoxy, heterocycloalkyl or cycloalkyl; wherein the heterocycloalkyl and cycloalkyl are optionally substituted with 1 to 3 groups selected from alkyl, hydroxyl, halogen and acyl;
- R$_b$ is hydrogen or alkyl;
- R$_1$ is hydrogen or alkyl; R$_2$ is hydrogen, alkyl or absent; or R$_1$ and R$_2$ together represents an oxo group;
- R$_3$ is hydrogen or alkyl; R$_4$ is hydrogen, alkyl, aryl or absent; or R$_3$ and R$_4$ together with the atoms to which they are attached form 3- to 8-membered cycloalkyl ring;
- alternatively, R$_1$ and R$_3$ together with the atoms to which they are attached form an optionally substituted aryl, heteroaryl or cycloalkyl, wherein the optional substituent is selected from 1 to 3 occurrences of R$_5$;
- R$_5$ is alkyl, halogen or cyano;
- 'n' is 1, 2 or 3;
- 'm' is 0 or 1.

According to one embodiment, specifically provided is compound of formula (I) or a pharmaceutically acceptable salt or stereoisomer thereof, wherein A is (C$_6$-C$_{10}$)aryl, 5- to 12-membered heterocycloalkyl or 5- to 12-membered heteroaryl.

In certain embodiments, A represents (C$_6$-C$_{10}$)aryl, 5- to 12-membered heterocycloalkyl or 5- to 12-membered heteroaryl; wherein the said aryl, heteroaryl or heterocycloalkyl is optionally substituted with 1 to 3 groups selected from halogen, hydroxyl, carboxylic acid, alkoxycarbonyl, formyl, acyl, thiocarbonyl, thioester, thioacetate, thioformate, alkoxyl, oxo, phosphoryl, phosphate, phosphonate, phosphinate, amino, amido, amidine, imine, cyano, nitro, azido, sulfhydryl, alkylthio, sulfate, sulfonate, sulfamoyl, sulfonamido and sulfonyl group.

In certain embodiments, A represents phenyl or 5- to 9-membered heteroaryl; wherein the said phenyl or heteroaryl is optionally substituted with 1 to 3 groups selected from halogen, hydroxyl, carboxylic acid, alkoxycarbonyl, formyl, acyl, thiocarbonyl, thioester, thioacetate, thioformate, alkoxyl, oxo, phosphoryl, a phosphate, phosphonate, phosphinate, amino, amido, amidine, imine, cyano, nitro, azido, sulfhydryl, alkylthio, sulfate, sulfonate, sulfamoyl, sulfonamido and sulfonyl group.

In certain embodiments, A represents 5- to 6-membered heteroaryl.

In certain embodiments, A is phenyl, naphthyl, furanyl, thienyl, pyrrolyl, pyrazolyl, imidazolyl, oxazolyl, cinnolinyl, isoxazolyl, thiazolyl, isothiazolyl, 1H-tetrazolyl, oxadiazolyl, triazolyl, pyridyl, pyrimidinyl, pyrazinyl, pyridazinyl, benzoxazolyl, benzisoxazolyl, benzothiazolyl, benzofuranyl, benzothienyl, benzotriazinyl, benzimidazolyl, indolyl, isoindolyl, indazolyl, quinolinyl, isoquinolinyl, quinazolinyl, quinoxalinyl, purinyl, pteridinyl, indolizinyl, benzoisothiazolyl, benzoxazolyl, pyrrolopyridyl, pyrazolopyrimidyl, furopyridinyl, benzothiadiazolyl, benzooxadiazolyl, benzotriazolyl, benzotriadiazolyl, azetidinyl, oxetanyl, imidazolidinyl, pyrrolidinyl, oxazolidinyl, thiazolidinyl, pyrazolidinyl, tetrahydrofuranyl, piperidinyl, piperazinyl, tetrahydropyranyl, morpholinyl, thiomorpholinyl, 1,4-dioxanyl, dioxidothiomorpholinyl, oxapiperazinyl, oxapiperidinyl, tetrahydrofuryl tetrahydropyranyl, tetrahydrothiophenyl, dihydropyranyl, indolinyl, indolinylmethyl, aza-bicyclooctanyl, azocinyl, chromanyl, isochromanyl xanthenyl, 2-oxa-6-azaspiro[3.3]heptanyl or 3-oxa-8-azabicyclo[3.2.1]octanyl.

In certain embodiments, A is phenyl or naphthyl.

In certain embodiments, A is phenyl.

In certain embodiments, A is furanyl, thienyl, pyrrolyl, pyrazolyl, imidazolyl, oxazolyl, cinnolinyl, isoxazolyl, thiazolyl, isothiazolyl, 1H-tetrazolyl, oxadiazolyl, triazolyl, pyridyl, pyrimidinyl, pyrazinyl, pyridazinyl, benzoxazolyl, benzisoxazolyl, benzothiazolyl, benzofuranyl, benzothienyl, benzotriazinyl, benzimidazolyl, indolyl, isoindolyl, indazolyl, quinolinyl, isoquinolinyl, quinazolinyl, quinoxalinyl, pteridinyl, indolizinyl, benzoisothiazolyl, benzoxazolyl, pyrrolopyridyl, pyrazolopyrimidyl, furopyridinyl, purinyl, benzothiadiazolyl, benzooxadiazolyl, benzotriazolyl or benzotriadiazolyl.

In certain embodiments, A is azetidinyl, oxetanyl, imidazolidinyl, pyrrolidinyl, oxazolidinyl, thiazolidinyl, pyrazolidinyl, tetrahydrofuranyl, piperidinyl, piperazinyl, tetrahydropyranyl, morpholinyl, thiomorpholinyl, 1,4-dioxanyl, dioxidothiomorpholinyl, oxapiperazinyl, oxapiperidinyl, tetrahydrofuryl, tetrahydropyranyl, tetrahydrothiophenyl, dihydropyranyl, indolinyl, indolinylmethyl, aza-bicyclooctanyl, azocinyl, chromanyl, isochromanyl xanthenyl, 2-oxa-6-azaspiro[3.3]heptanyl or 3-oxa-8-azabicyclo[3.2.1]octanyl.

In certain embodiments, A is phenyl, 5- to 10-membered heterocycloalkyl or 5- to 9-membered heteroaryl.

In certain embodiments, A is substituted with 'n' occurrences of Y; wherein 'n' and Y are as defined in compound of formula (I).

In certain embodiments, A is

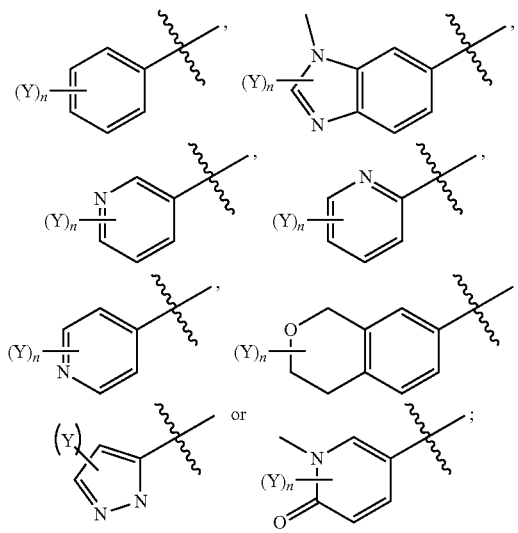

wherein ⌇ represents point of attachment to —(CHR)$_m$ and Y and 'n' are as defined in compound of formula (I).

In certain embodiments, A is phenyl substituted with 'n' occurrences of Y; wherein 'n' and Y are as defined in compound of formula (I).

In certain embodiments, A is pyridyl substituted with 'n' occurrences of Y; wherein 'n' and Y are as defined in compound of formula (I).

In certain embodiments, A is benzimidazolyl substituted with 'n' occurrences of Y; wherein 'n' and Y are as defined in compound of formula (I).

In certain embodiments, A is isochromanyl substituted with 'n' occurrences of Y; wherein 'n' and Y are as defined in compound of formula (I).

In certain embodiments, Y is hydrogen, —SO$_2$R$_a$, —NR$_a$R$_b$, —C(O)R$_a$, —C(O)NR$_a$R$_b$, —NHC(O)R$_a$, —COOH, cyano, halogen, haloalkyl, alkyl, alkenyl, alkynyl, alkoxy, hydroxyl or oxo; wherein the said alkyl, alkenyl and alkynyl are optionally substituted with 1 to 3 groups selected from hydroxyl, halogen, acyl and heterocycloalkyl; wherein R$_a$ and R$_b$ are as defined in compound of formula (I).

In certain embodiments, Y is hydrogen, —SO$_2$-alkyl, —SO$_2$-cycloalkyl, —SO$_2$-heterocycloalkyl, —NH(heterocycloalkyl), —N(alkyl)$_2$, —C(O)-alkyl, —C(O)-heterocycloalkyl, —C(O)NH$_2$, —C(O)NH(alkyl), —C(O)NH(cycloalkyl), —C(O)NH(heterocycloalkyl), —NHC(O)(heterocycloalkyl), —NHC(O)(cycloalkyl), cyano, halogen, haloalkyl, alkyl, alkenyl, alkynyl, alkoxy, hydroxyl or oxo; wherein the said heterocycloalkyl and cycloalkyl, are optionally substituted with 1 to 3 groups selected from alkyl, hydroxyl, halogen and acyl.

In certain embodiments, Y is hydrogen, —SO$_2$-alkyl, —SO$_2$-cycloalkyl, —SO$_2$-heterocycloalkyl, —NH(heterocycloalkyl), —N(alkyl)$_2$, —C(O)-alkyl, —C(O)-heterocycloalkyl, —C(O)NH$_2$, —C(O)NH(alkyl), —C(O)NH(cycloalkyl), —C(O)NH(heterocycloalkyl), —NHC(O)(heterocycloalkyl), —NHC(O)(cycloalkyl), cyano, halogen, haloalkyl, alkyl, alkenyl, alkynyl, alkoxy, hydroxyl or oxo; wherein the said heterocycloalkyl and cycloalkyl, are optionally substituted with 1 to 2 groups selected from halogen and acyl.

In certain embodiments, Y is hydrogen, —SO$_2$R$_a$, —NR$_a$R$_b$, —C(O)R$_a$, —C(O)NR$_a$R$_b$, alkyl, alkoxy or cyano; wherein R$_a$ and R$_b$ are as defined in compound of formula (I).

In certain embodiments, Y is hydrogen, —SO$_2$-alkyl, —SO$_2$-cycloalkyl, —SO$_2$-heterocycloalkyl, —NH(heterocycloalkyl), —N(alkyl)$_2$, —C(O)-alkyl, —C(O)-heterocycloalkyl, —C(O)NH$_2$, —C(O)NH(alkyl), —C(O)NH(cycloalkyl), or —C(O)NH(heterocycloalkyl); wherein the said heterocycloalkyl and cycloalkyl, are optionally substituted with 1 to 2 groups selected from halogen and acyl.

In certain embodiments, Y is —SO$_2$R$_a$, or —C(O)R$_a$; wherein R$_a$ is as defined in compound of formula (I).

In certain embodiments, Y is —SO$_2$-alkyl, —SO$_2$-cycloalkyl, or —SO$_2$-heterocycloalkyl; wherein the said heterocycloalkyl and cycloalkyl, are optionally substituted with 1 to 2 groups selected from halogen and acyl.

In certain embodiments, Y is —SO$_2$-pyrrolidinyl or —SO$_2$-piperidinyl; wherein the said pyrrolidinyl or piperidinyl is optionally substituted with 1 to 2 groups selected from halogen and acyl.

In certain embodiments, Y is —SO$_2$-cyclopropyl wherein the cyclopropyl is optionally substituted with 1 to 2 groups selected from halogen and acyl.

In certain embodiments, Y is —NH(heterocycloalkyl) or —N(alkyl)$_2$; wherein the said heterocycloalkyl is optionally substituted with 1 to 2 groups selected from halogen and acyl.

In certain embodiments, Y is —NH-tetrahydropyranyl or —NH-piperidinyl; wherein the said heterocycloalkyl is optionally substituted with 1 to 2 groups selected from halogen and acyl.

In certain embodiments, Y is —C(O)-alkyl, —C(O)-heterocycloalkyl, wherein the said heterocycloalkyl is optionally substituted with 1 to 2 groups selected from halogen and acyl.

In certain embodiments, Y is —C(O)-piperidinyl, —C(O)-azetidinyl, —C(O)-pyrrolidinyl, —C(O)-piperazinyl, —C(O)-2-oxa-6-azaspiro[3.3]heptanyl, or —C(O)-3-oxa-8-azabicyclo[3.2.1]octanyl; wherein the said piperidinyl, azetidinyl, pyrrolidinyl, or piperazinyl is optionally substituted with 1 to 2 groups selected from halogen and acyl.

In certain embodiments, Y is —C(O)NH$_2$, —C(O)NH(alkyl), —C(O)NH(cycloalkyl), —C(O)NH(heterocycloalkyl); wherein the said heterocycloalkyl and cycloalkyl, are optionally substituted with 1 to 2 groups selected from halogen and acyl.

In certain embodiments, Y is —SO$_2$R$_a$, —NR$_a$R$_b$, —C(O)R$_a$, —C(O)NR$_a$R$_b$, or —NHC(O)R$_a$; wherein R$_a$ is hydrogen, alkyl, heterocycloalkyl, or cycloalkyl, wherein the said heterocycloalkyl, and cycloalkyl are optionally substituted with acyl or haloalkyl; and R$_b$ is hydrogen or alkyl; In certain embodiments, Y is —C(O)R$_a$, or —C(O)NR$_a$R$_b$; wherein R$_a$ is hydrogen, alkyl, 4- to 10-membered heterocycloalkyl, or 3- to 6-membered cycloalkyl, wherein the said heterocycloalkyl, and cycloalkyl are optionally substituted with acyl, halo or haloalkyl; In certain embodiments, R$_a$ is 3- to 6-membered heterocycloalkyl.

In certain embodiments, R$_a$ is fused bicyclcyl or spirocyclyl containing 1-2 heteroatoms selected from N, O or S.

In certain embodiments, Y is —SO$_2$R$_a$, —NR$_a$R$_b$, —C(O)R$_a$, or —C(O)NR$_a$R$_b$; wherein R$_a$ and R$_b$ are as defined in compound of formula (I).

In certain embodiments, Y is hydrogen, —C(O)R$_a$, —C(O)NR$_a$R$_b$, —COOH, alkyl, alkenyl, alkynyl, alkoxy or cyano; wherein the said alkyl, alkenyl and alkynyl are optionally substituted with 1 to 3 groups selected from hydroxyl, halogen, acyl and heterocycloalkyl; and wherein R$_a$ and R$_b$ are as defined in compound of formula (I).

In certain embodiments, Y is alkyl, alkenyl, alkynyl, alkoxy or cyano, wherein the said alkyl, alkenyl and alkynyl, are optionally substituted with 1 to 3 groups selected from hydroxyl, halogen, acyl and heterocycloalkyl.

In certain embodiments, Y is hydrogen,

In certain embodiments, each R$_1$, R$_2$, R$_3$ and R$_4$ independently are hydrogen or alkyl.

In certain embodiments, R$_1$, R$_2$, R$_3$ and R$_4$ are hydrogen.

In certain embodiments, the present invention provides compound of formula (I), wherein, A is (C$_6$-C$_{10}$)aryl, 5- to 12-membered heterocycloalkyl or 5- to 12-membered heteroaryl;

Y is hydrogen, —SO$_2$-alkyl, —SO$_2$-cycloalkyl, —SO$_2$-heterocycloalkyl, —NH(heterocycloalkyl), —N(alkyl)$_2$, —C(O)-alkyl, —C(O)-heterocycloalkyl, —C(O)NH$_2$, —C(O)NH(alkyl), —C(O)NH(cycloalkyl), —C(O)NH(heterocycloalkyl), —NHC(O)(heterocycloalkyl), —NHC(O)(cycloalkyl), cyano, halogen, haloalkyl, alkyl, alkenyl, alkynyl, alkoxy, hydroxyl or oxo; wherein the said heterocycloalkyl and cycloalkyl, are optionally substituted with 1 to 3 groups selected from alkyl, hydroxyl, halogen and acyl.

R$_1$ is hydrogen or alkyl; R$_2$ is hydrogen, alkyl or absent; R$_3$ is hydrogen or alkyl; R$_4$ is hydrogen, alkyl, aryl or absent;

'm' is 0 or 1; and

'n' is 1 or 2.

In certain embodiments, the present invention provides compound of formula (I), wherein A is phenyl, pyridyl, benzimidazolyl or isochromanyl; wherein the said phenyl, pyridyl benzimidazolyl or isochromanyl is optionally substituted with 1 to 3 groups selected from halogen, hydroxyl, carboxylic acid, alkoxycarbonyl, formyl, acyl, thiocarbonyl, alkoxyl, oxo, amino, amido, cyano, nitro, azido, alkylthio, sulfate, sulfonate, sulfamoyl, sulfonamido and sulfonyl group.

Y is hydrogen, —SO$_2$-alkyl, —SO$_2$-cycloalkyl, —SO$_2$-heterocycloalkyl, —NH(heterocycloalkyl), —N(alkyl)$_2$, —C(O)-alkyl, —C(O)-heterocycloalkyl, —C(O)NH$_2$, —C(O)NH(alkyl), —C(O)NH(cycloalkyl), —C(O)NH(heterocycloalkyl), —NHC(O)(heterocycloalkyl), —NHC(O)(cycloalkyl), cyano, halogen, haloalkyl, alkyl, alkenyl, alkynyl, alkoxy, hydroxyl or oxo; wherein the said heterocycloalkyl and cycloalkyl, are optionally substituted with 1 to 3 groups selected from alkyl, hydroxyl, halogen and acyl.

R$_1$ is hydrogen or alkyl; R$_2$ is hydrogen, alkyl or absent; R$_3$ is hydrogen or alkyl; R$_4$ is hydrogen, alkyl, aryl or absent;

'm' is 0 or 1; and

'n' is 1 or 2.

In certain embodiments, the present invention provides compound of formula (I), wherein A is phenyl;

Y is hydrogen, cyano, NR$_a$R$_b$, alkyl, —SO$_2$-alkyl, —SO$_2$-cycloalkyl, —SO$_2$-heterocycloalkyl, halogen or alkoxy;

R$_a$ is hydrogen, alkyl or heterocycloalkyl, wherein the heterocycloalkyl is optionally substituted with acyl;

R$_b$ is hydrogen or alkyl;

R$_1$, R$_2$, R$_3$ and R$_4$ are hydrogen;

'm' is 1;

'n' is 1 or 2.

In certain embodiments, the present invention provides compound of formula (I), wherein A is pyridyl;

Y is hydrogen, alky, alkenyl, alkoxy, cyano, —NH(heterocycloalkyl), —NHC(O)R$_a$, haloalkyl, —SO$_2$-heterocycloalkyl, —C(O)-heterocycloalkyl, C(O)NH(cycloalkyl), —C(O)NH(alkyl), —C(O)NH$_2$, wherein the said heterocycloalkyl and cycloalkyl, are optionally substituted with groups selected from alkyl, hydroxyl, halogen and acyl;

R$_a$ is hydrogen, alkyl, halogen, alkoxy, heterocycloalkyl or cycloalkyl; wherein the heterocycloalkyl and cycloalkyl are optionally substituted with 1 to 3 groups selected from alkyl, hydroxyl, halogen and acyl;

R$_b$ is hydrogen or alkyl;

R$_1$ and R$_2$ is hydrogen or alkyl; or R$_1$ and R$_2$ together represents an oxo group;

R$_3$ and R$_4$ is hydrogen or alkyl; or R$_3$ and R$_4$ together with the atoms to which they are attached form 3- to 8-membered cycloalkyl ring;

'm' is 1;

'n' is 1 or 2.

In yet another embodiment, the present invention provides compound of formula (IA):

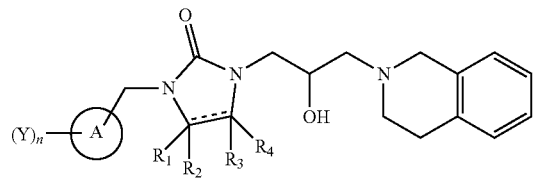

(IA)

or a pharmaceutically acceptable salt or a stereoisomer thereof; wherein,

=====, A, Y, R$_1$, R$_2$, R$_3$, R$_4$ and 'n' are as defined in compound of formula (I).

According to one embodiment, specifically provided is compound of formula (IA) or a pharmaceutically acceptable salt or stereoisomer thereof, wherein A is aryl or heteroaryl.

In certain embodiments, specifically provided is compound of formula (I) or compound of formula (IA) or a pharmaceutically acceptable salt or stereoisomer thereof, wherein A is aryl or heteroaryl; wherein the said aryl or heteroaryl is optionally substituted with 1 to 3 groups selected from halogen, hydroxyl, carboxylic acid, alkoxycarbonyl, formyl, acyl, thiocarbonyl, thioester, thioacetate, thioformate, alkoxyl, oxo, phosphoryl, a phosphate, phosphonate, phosphinate, amino, amido, amidine, imine, cyano, nitro, azido, sulfhydryl, alkylthio, sulfate, sulfonate, sulfamoyl, sulfonamido and sulfonyl group.

In certain embodiments, specifically provided is compound of formula (I) or compound of formula (IA) or a pharmaceutically acceptable salt or stereoisomer thereof, wherein A is phenyl, naphthyl, furanyl, thienyl, pyrrolyl, pyrazolyl, imidazolyl, oxazolyl, cinnolinyl, isoxazolyl, thiazolyl, isothiazolyl, 1H-tetrazolyl, oxadiazolyl, triazolyl, pyridyl, pyrimidinyl, pyrazinyl, pyridazinyl, benzoxazolyl, benzisoxazolyl, benzimidazolyl, benzofuranyl, benzothienyl, benzotriazinyl, benzimidazolyl, indolyl, isoindolyl, indazolyl, quinolinyl, isoquinolinyl, quinazolinyl, quinoxalinyl, purinyl, pteridinyl, indolizinyl, benzoisothiazolyl, benzoxazolyl, pyrrolopyridyl, pyrazolopyrimidyl, furopyridinyl, benzothiadiazolyl, benzooxadiazolyl, benzotriazolyl or benzotriadiazolyl.

In certain embodiments of formula (IA), A is phenyl, thienyl, pyrrolyl, pyrazolyl, imidazolyl, isoxazolyl, thiazolyl, isothiazolyl, 1H-tetrazolyl, oxadiazolyl, triazolyl, pyridyl, pyrimidinyl, benzoxazolyl, benzisoxazolyl, benzimidazolyl, benzothienyl, benzotriazinyl, benzimidazolyl, indazolyl, quinolinyl, isoquinolinyl, quinazolinyl, quinoxalinyl, pteridinyl, indolizinyl, benzoisothiazolyl, benzoxazolyl, pyrrolopyridyl, pyrazolopyrimidyl, furopyridinyl, benzothiadiazolyl, benzooxadiazolyl, benzotriazolyl or benzotriadiazolyl.

In certain embodiments, A is phenyl, pyridyl or benzimidazolyl, wherein the said phenyl, pyridyl, benzimidazolyl is optionally substituted with 1 to 3 groups selected from halogen, hydroxyl, carboxylic acid, alkoxycarbonyl, formyl, acyl, thiocarbonyl, thioester, thioacetate, thioformate, alkoxyl, oxo, phosphoryl, a phosphate, phosphonate, phosphinate, amino, amido, amidine, imine, cyano, nitro, azido, sulfhydryl, alkylthio, sulfate, sulfonate, sulfamoyl, sulfonamido and sulfonyl group.

In certain embodiments, A is aryl or heteroaryl is optionally substituted with 1 to 3 groups selected from halogen, hydroxyl, carboxylic acid, alkoxycarbonyl, formyl, acyl, thiocarbonyl, thioester, thioacetate, thioformate, alkoxyl, oxo, phosphoryl, a phosphate, phosphonate, phosphinate, amino, amido, amidine, imine, cyano, nitro, azido, sulfhydryl, alkylthio, sulfate, sulfonate, sulfamoyl, sulfonamido and sulfonyl group.

In certain embodiments, A is phenyl, naphthyl, furanyl, thienyl, pyrrolyl, pyrazolyl, imidazolyl, oxazolyl, cinnolinyl, isoxazolyl, thiazolyl, isothiazolyl, 1H-tetrazolyl, oxadiazolyl, triazolyl, pyridyl, pyrimidinyl, pyrazinyl, pyridazinyl, benzoxazolyl, benzisoxazolyl, benzimidazolyl, benzofuranyl, benzothienyl, benzotriazinyl, benzimidazolyl, indolyl, isoindolyl, indazolyl, quinolinyl, isoquinolinyl, quinazolinyl, quinoxalinyl, pteridinyl, indolizinyl, benzoisothiazolyl, benzoxazolyl, pyrrolopyridyl, pyrazolopyrimidyl, furopyridinyl, benzothiadiazolyl, benzooxadiazolyl, benzotriazolyl or benzotriadiazolyl.

In certain embodiments, A is cycloalkyl or heterocycloalkyl.

In certain embodiments, A is cyclopropyl, cyclobutyl, cyclopentyl, cyclohexy, cycloheptyl, azetidinyl, oxetanyl, imidazolidinyl, pyrrolidinyl, oxazolidinyl, thiazolidinyl, pyrazolidinyl, tetrahydrofuranyl, piperidinyl, piperazinyl, tetrahydropyranyl, morpholinyl, thiomorpholinyl, 1,4-dioxanyl, dioxidothiomorpholinyl, oxapiperazinyl, oxapiperidinyl, tetrahydrofuryl, tetrahydropyranyl, tetrahydrothiophenyl, dihydropyranyl, indolinyl, indolinylmethyl, azabicyclooctanyl, azocinyl, chromanyl, isochromanyl, xanthenyl, 2-oxa-6-azaspiro[3.3]heptanyl or 3-oxa-8-azabicyclo[3.2.1]octanyl.

According to one embodiment, specifically provided is compound of formula (IA) or a pharmaceutically acceptable salt or stereoisomer thereof, wherein R$_1$, R$_2$, R$_3$ and R$_4$ are, independently, hydrogen or alkyl.

According to one embodiment, specifically provided is compound of formula (IA) or a pharmaceutically acceptable salt or stereoisomer thereof, wherein Y is hydrogen, alkyl, alkynyl, —SO$_2$R$_a$, —NHC(O)R$_a$, —C(O)R$_a$, —C(O)NR$_a$R$_b$, —COOH, alkoxy, cyano, halogen or haloalkyl.

According to one embodiment, specifically provided is compound of formula (IA) or a pharmaceutically acceptable salt or stereoisomer thereof, wherein R$_1$, R$_2$, R$_3$ and R$_4$ are hydrogen.

According to one embodiment, specifically provided is compound of formula (IA) or a pharmaceutically acceptable salt or stereoisomer thereof, wherein Y is hydrogen, alkyl, alkoxy or cyano.

In certain embodiments, Y is hydrogen, alkyl, alkynyl or cyano.

In certain embodiments, $R_1$ and $R_3$ are hydrogen.

In certain embodiments, $R_1$, $R_3$ are hydrogen and $R_2$, $R_4$ are absent.

In certain embodiments, Y is alkyl, alkenyl, alkynyl and alkoxy; wherein the said alkyl, alkenyl and alkynyl is optionally substituted with 1 to 3 groups selected from hydroxyl, halogen, acyl and heterocycloalkyl.

In yet another embodiment, the present invention provides compound of formula (IB):

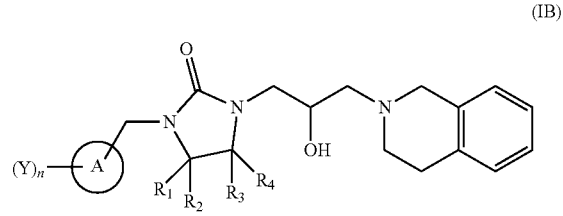

(IB)

or a pharmaceutically acceptable salt or a stereoisomer thereof; wherein, A, Y, $R_1$, $R_2$, $R_3$, $R_4$ and 'n' are as defined in compound of formula (I).

According to one embodiment, specifically provided is compound of formula (IB) or a pharmaceutically acceptable salt or stereoisomer thereof, wherein $R_1$, $R_2$, $R_3$ and $R_4$ are independently, hydrogen or alkyl.

According to one embodiment, specifically provided is compound of formula (IB) or a pharmaceutically acceptable salt or stereoisomer thereof, wherein $R_1$, $R_2$, $R_3$ and $R_4$ are hydrogen.

In certain embodiments, $R_3$ and $R_4$ are alkyl.

In certain embodiments, $R_1$ and $R_2$ together represents an oxo group.

In certain embodiments, $R_1$ and $R_3$ together with the atoms to which they are attached form a cycloalkyl or a heteroaryl ring.

In certain embodiments, $R_3$ and $R_4$ together with the atoms to which they are attached form a 3- to 5-membered cycloalkyl ring.

In certain embodiments, $R_1$ and $R_3$ together with the atoms to which they are attached form a pyridine.

In certain embodiments, $R_3$ and $R_4$ are alkyl.

In certain embodiments, $R_3$ and $R_4$ are methyl.

In certain embodiments, $R_4$ is phenyl.

In certain embodiments, Y is hydrogen, —C(O)$R_a$, —C(O)NR$_a$R$_b$, —COOH, alkyl, alkoxy or cyano, wherein $R_a$ and $R_b$ are as defined in compound of formula (I).

In certain embodiments, Y is hydrogen, alkyl —C(O)$R_a$, —C(O)NR$_a$R$_b$, —COOH, alkoxy or cyano, wherein $R_a$ and $R_b$ are as defined in compound of formula (I).

In certain embodiments, Y is hydrogen, alkyl, —SO$_2$R$_a$, —C(O)R$_a$, —C(O)NR$_a$R$_b$, —COOH, alkoxy and cyano, wherein $R_a$ and $R_b$ are as defined in compound of formula (I).

In certain embodiments, Y is —C(O)R$_a$.

In certain embodiments, Y is —C(O)R$_a$, wherein $R_a$ is heterocycloalkyl.

In certain embodiments, Y is —C(O)NR$_a$R$_b$, wherein $R_a$ and $R_b$ are as defined in compound of formula (I). In certain embodiments, Y is —C(O)R$_a$, wherein $R_a$ is hydrogen, alkyl, 4- to 10-membered heterocycloalkyl, or 3- to 6-membered cycloalkyl, wherein the said heterocycloalkyl, and cycloalkyl are optionally substituted with acyl or haloalkyl; and $R_b$ is hydrogen or alkyl;

In certain embodiments, Y is —SO$_2$R$_a$, wherein $R_a$ is as defined in compound of formula (I).

In certain embodiments, Y is —SO$_2$R$_a$, wherein $R_a$ is a is hydrogen, alkyl, 4- to 10-membered heterocycloalkyl, or 3- to 6-membered cycloalkyl, wherein the said heterocycloalkyl, and cycloalkyl are optionally substituted with acyl or haloalkyl.

In certain embodiments, Y is alkyl, alkoxy or cyano. In certain embodiments, Y is alkyl. In certain embodiments, Y is methyl. In certain embodiments, Y is cyano. In certain embodiments, Y is halogen. In certain embodiments, Y is haloalkyl.

In certain embodiments, A is aryl. In certain embodiments, A is phenyl.

In certain embodiments, A is phenyl substituted with alkyl. In certain embodiments, A is phenyl substituted with cyano.

In certain embodiments, 'n' is 1 or 2. In certain embodiments, 'n' is 1.

In yet another embodiment, the present invention provides compound of formula (IC):

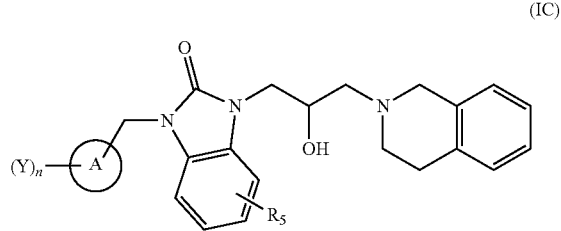

(IC)

or a pharmaceutically acceptable salt or a stereoisomer thereof; wherein, A, Y, $R_5$ and 'n' are as defined in compound of formula (I).

In certain embodiments, in formula (IC), A represents ($C_6$-$C_{10}$)aryl or heteroaryl; Y is hydrogen, SO$_2$R$_a$, alkyl, alkoxy, cyano or halogen; $R_a$ is hydrogen or alkyl; and $R_5$ is alkyl, halogen or cyano.

In certain embodiments, in formula (IC), wherein $R_5$ is halogen.

In certain embodiments, in formula (IC), wherein $R_5$ is fluoro.

In certain embodiments, in formula (IC), A represents phenyl, pyridyl or benzimidazolyl.

In yet another embodiment, the present invention provides compound of formula (ID):

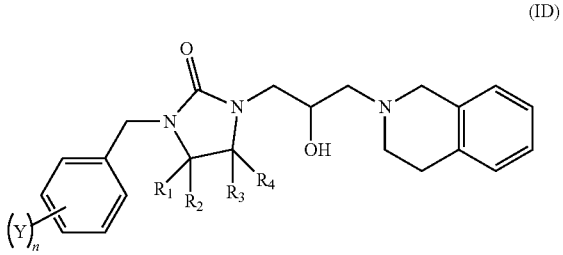

(ID)

or a pharmaceutically acceptable salt or a stereoisomer thereof; wherein, Y, $R_1$, $R_2$, $R_3$, $R_4$ and 'n' are as defined in compound of formula (I).

In certain embodiments of compound of formula (ID), 'n' is 1 or 2.

In certain embodiments, the present invention provides compound of formula (IE):

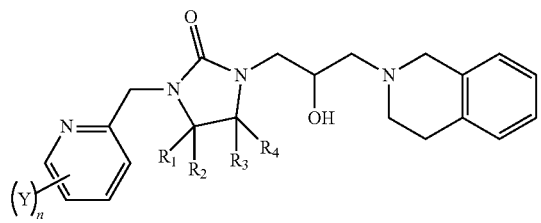

(IE)

or a pharmaceutically acceptable salt or a stereoisomer thereof; wherein, Y, $R_1$, $R_2$, $R_3$, $R_4$ and 'n' are as defined in compound of formula (I).

In certain embodiments, the present invention provides compound of formula (IF):

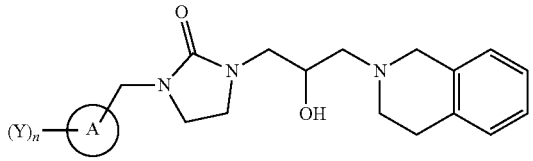

(IF)

or a pharmaceutically acceptable salt or a stereoisomer thereof; wherein, A, Y and 'n' are as defined in compound of formula (I).

In certain embodiments, Y is hydrogen, —$SO_2R_a$, alkyl, alkoxy, cyano or halogen.

In certain embodiments, $R_5$ is alkyl. In certain embodiments, $R_5$ is cyano.

In certain embodiments, 'm' is 0. In certain embodiments of the present invention, if 'm' is 0, then ring A is directly attached to central imidazolidinone ring containing $R_1$ to $R_4$ as described in compound of formula (I).

In certain embodiments, ===== represents a single bond. In certain embodiments, ===== represents a double bond.

In certain embodiments, ===== represents a double bond; and each $R_2$ and $R_4$ are absent.

According to yet another embodiment, the present invention provides a compound or a pharmaceutically acceptable salt or a stereoisomer thereof, selected from:

| Example No. | Structure |
|---|---|
| 1 | ![structure] |
| 1a | ![structure] |
| 1b | ![structure] |
| 2 | ![structure] |

-continued
| Example No. | Structure |
|---|---|
| 2a | 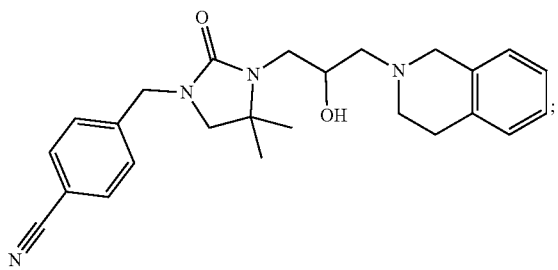 [SMILES: CC1(C)CN(Cc2ccc(C#N)cc2)C(=O)N1CC(O)CN1CCc2ccccc2C1] |
| 2b | 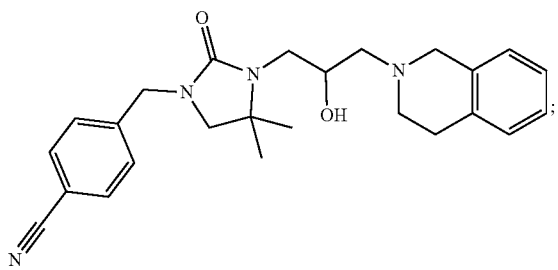 [SMILES: CC1(C)CN(Cc2ccc(C#N)cc2)C(=O)N1CC(O)CN1CCc2ccccc2C1] |
| 3 | 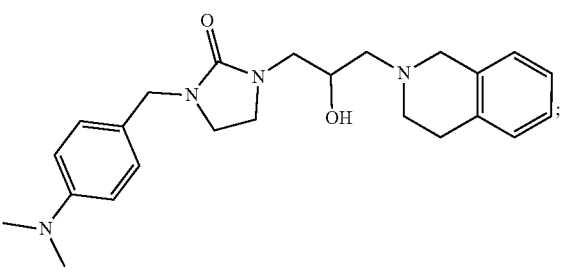 [SMILES: CN(C)c1ccc(CN2CCN(CC(O)CN3CCc4ccccc4C3)C2=O)cc1] |
| 4 | 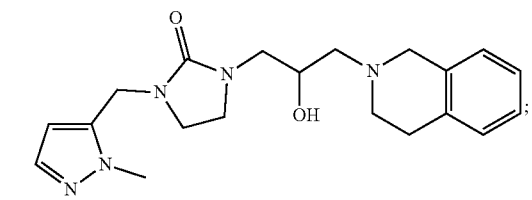 [SMILES: Cn1nccc1CN1CCN(CC(O)CN2CCc3ccccc3C2)C1=O] |
| 5 | 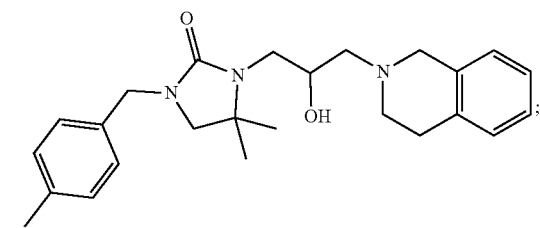 [SMILES: Cc1ccc(CN2CC(C)(C)N(CC(O)CN3CCc4ccccc4C3)C2=O)cc1] |
| 6 | 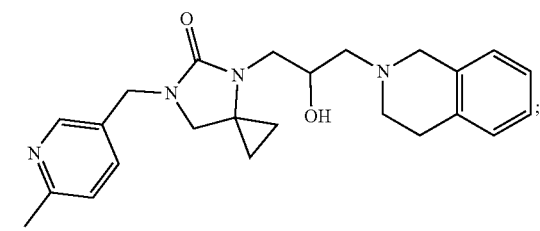 [SMILES: Cc1ccc(CN2CC3(CC3)N(CC(O)CN3CCc4ccccc4C3)C2=O)cn1] |

-continued
| Example No. | Structure |
|---|---|
| 7 | 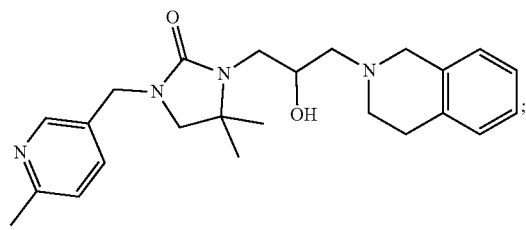 [SMILES: Cc1ccc(CN2CC(C)(C)N(CC(O)CN3CCc4ccccc4C3)C2=O)cn1] |
| 8 | 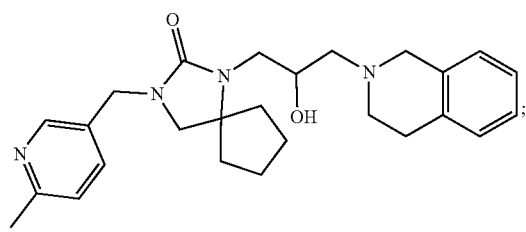 [SMILES: Cc1ccc(CN2CC3(CCCC3)N(CC(O)CN3CCc4ccccc4C3)C2=O)cn1] |
| 9 | 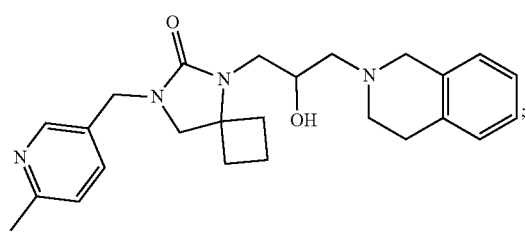 [SMILES: Cc1ccc(CN2CC3(CCC3)N(CC(O)CN3CCc4ccccc4C3)C2=O)cn1] |
| 10 | 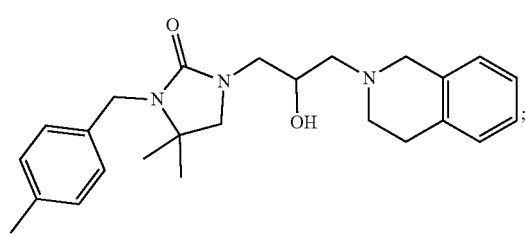 [SMILES: Cc1ccc(CN2C(=O)N(CC(O)CN3CCc4ccccc4C3)CC2(C)C)cc1] |
| 11 | 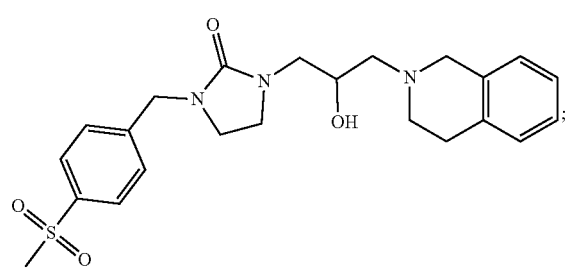 [SMILES: CS(=O)(=O)c1ccc(CN2CCN(CC(O)CN3CCc4ccccc4C3)C2=O)cc1] |
| 12 | 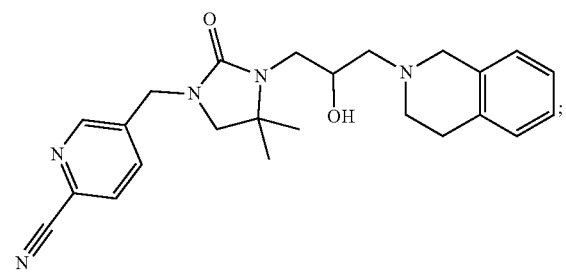 [SMILES: CC1(C)CN(Cc2ccc(C#N)nc2)C(=O)N1CC(O)CN1CCc2ccccc2C1] |

-continued
| Example No. | Structure |
|---|---|
| 13 | 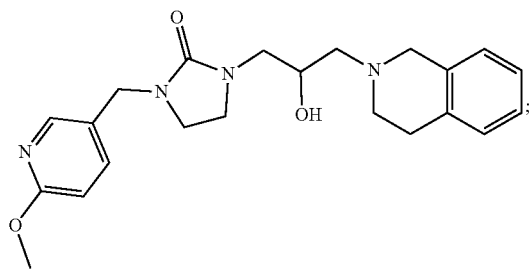 [SMILES: COc1ccc(CN2CCN(CC(O)CN3CCc4ccccc4C3)C2=O)cn1] |
| 14 | 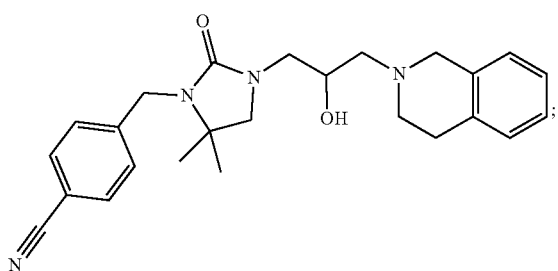 [SMILES: CC1(C)CN(CC(O)CN2CCc3ccccc3C2)C(=O)N1Cc1ccc(C#N)cc1] |
| 15 | 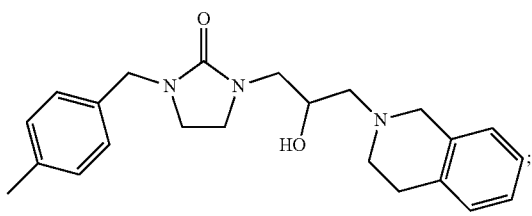 [SMILES: Cc1ccc(CN2CCN(CC(O)CN3CCc4ccccc4C3)C2=O)cc1] |
| 15a | 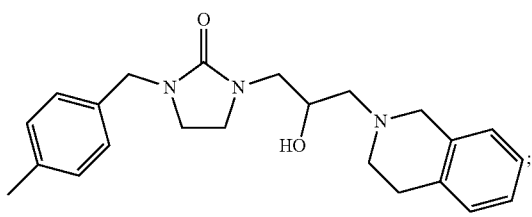 [SMILES: Cc1ccc(CN2CCN(CC(O)CN3CCc4ccccc4C3)C2=O)cc1] |
| 15b | 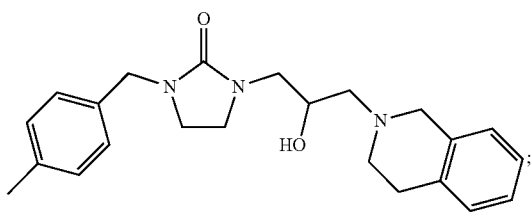 [SMILES: Cc1ccc(CN2CCN(CC(O)CN3CCc4ccccc4C3)C2=O)cc1] |
| 16 | 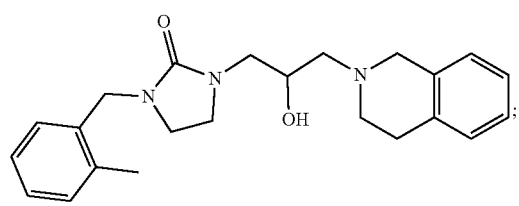 [SMILES: Cc1ccccc1CN1CCN(CC(O)CN2CCc3ccccc3C2)C1=O] |

-continued
| Example No. | Structure |
|---|---|
| 16a | 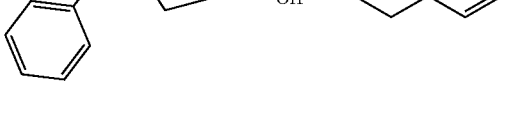 |
| 16b | 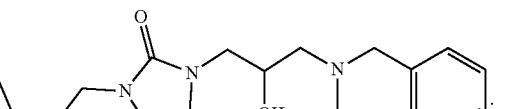 |
| 17 | 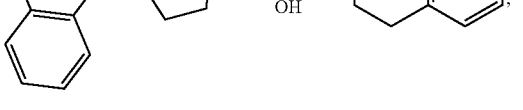 |
| 18 | 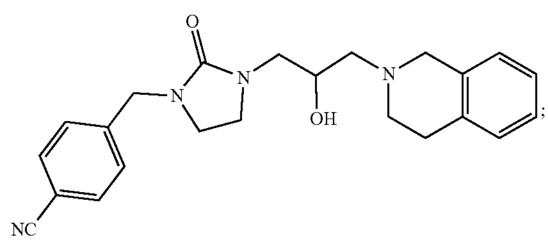 [SMILES: N#Cc1ccc(CN2CCN(CC(O)CN3CCc4ccccc4C3)C2=O)cc1] |
| 18a | 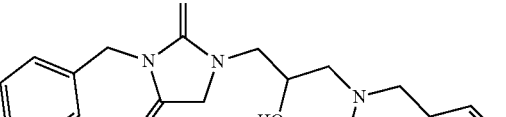 |
| 18b | 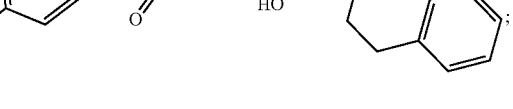 |

| Example No. | Structure |
|---|---|
| 19 | 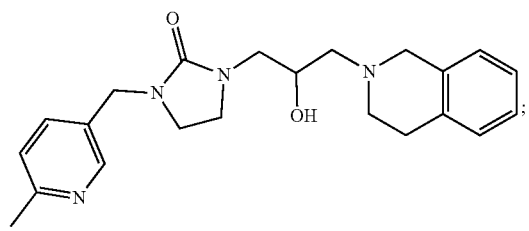 [SMILES: Cc1ccc(CN2CCN(CC(O)CN3CCc4ccccc4C3)C2=O)cn1] |
| 20 | 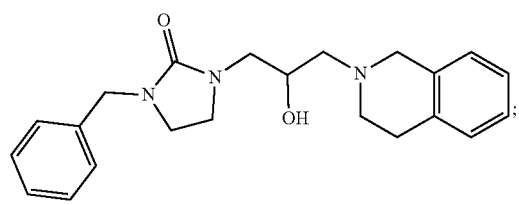 [SMILES: O=C1N(Cc2ccccc2)CCN1CC(O)CN1CCc2ccccc2C1] |
| 21 | 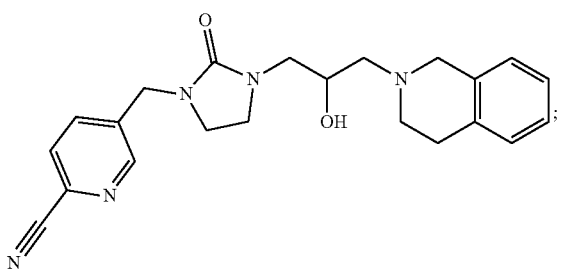 [SMILES: N#Cc1ccc(CN2CCN(CC(O)CN3CCc4ccccc4C3)C2=O)cn1] |
| 22 | 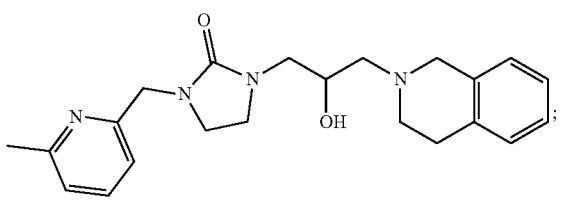 [SMILES: Cc1cccc(CN2CCN(CC(O)CN3CCc4ccccc4C3)C2=O)n1] |
| 23 | 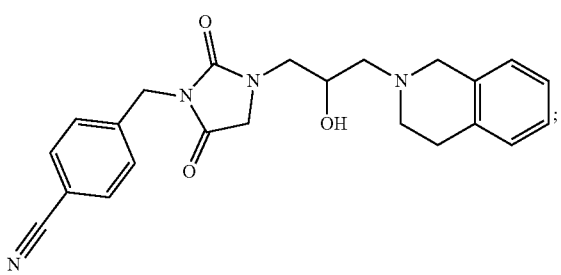 [SMILES: N#Cc1ccc(CN2C(=O)CN(CC(O)CN3CCc4ccccc4C3)C2=O)cc1] |
| 24 | 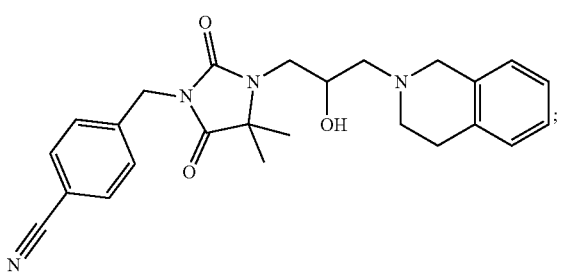 [SMILES: CC1(C)C(=O)N(Cc2ccc(C#N)cc2)C(=O)N1CC(O)CN1CCc2ccccc2C1] |

-continued
| Example No. | Structure |
|---|---|
| 25 | 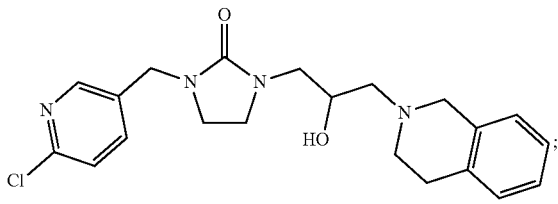 [SMILES: O=C1N(Cc2ccc(Cl)nc2)CCN1CC(O)CN1CCc2ccccc2C1] |
| 26 | 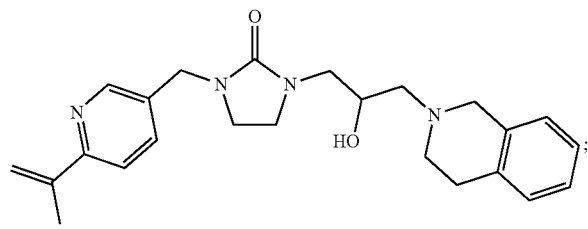 [SMILES: C=C(C)c1ccc(CN2CCN(CC(O)CN3CCc4ccccc4C3)C2=O)cn1] |
| 27 | 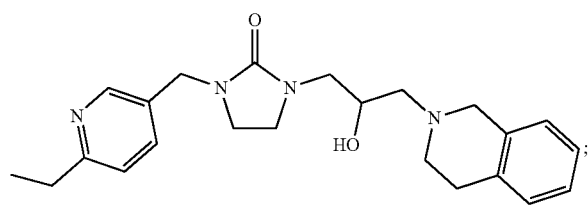 [SMILES: CCc1ccc(CN2CCN(CC(O)CN3CCc4ccccc4C3)C2=O)cn1] |
| 28 | 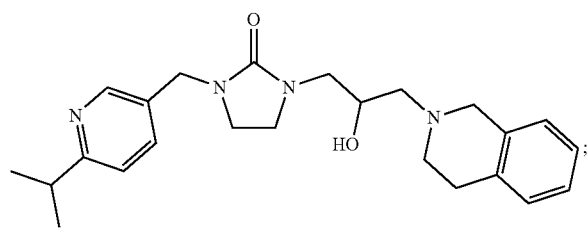 [SMILES: CC(C)c1ccc(CN2CCN(CC(O)CN3CCc4ccccc4C3)C2=O)cn1] |
| 29 | 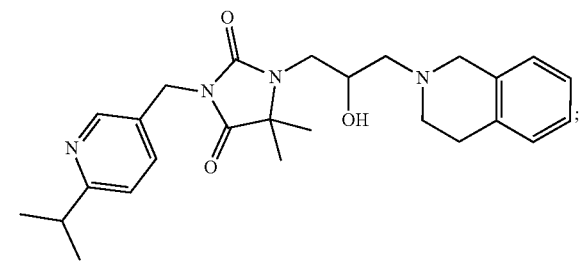 [SMILES: CC(C)c1ccc(CN2C(=O)N(CC(O)CN3CCc4ccccc4C3)C(C)(C)C2=O)cn1] |
| 30 | 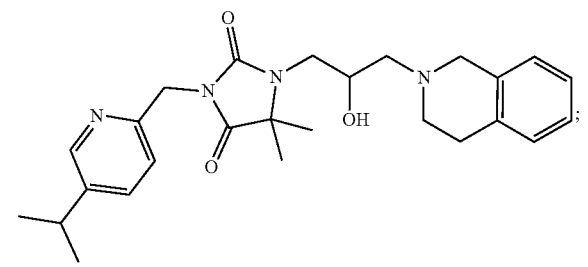 [SMILES: CC(C)c1ccc(CN2C(=O)N(CC(O)CN3CCc4ccccc4C3)C(C)(C)C2=O)nc1] |

-continued
| Example No. | Structure |
|---|---|
| 31 | 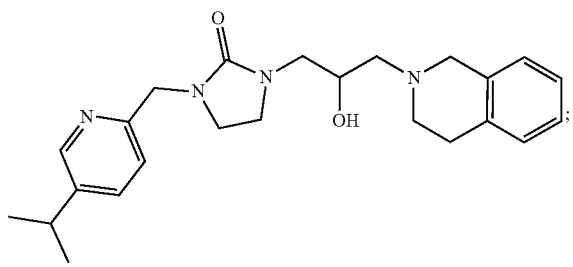 [SMILES: CC(C)c1ccc(CN2CCN(CC(O)CN3CCc4ccccc4C3)C2=O)nc1] ; |
| 32 | 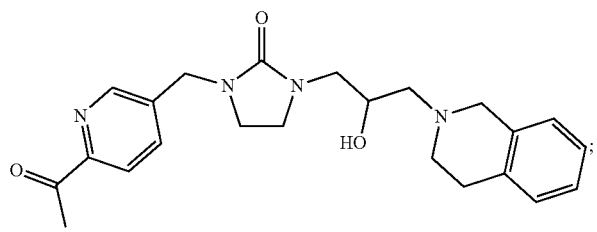 [SMILES: CC(=O)c1ccc(CN2CCN(CC(O)CN3CCc4ccccc4C3)C2=O)cn1] ; |
| 33 | 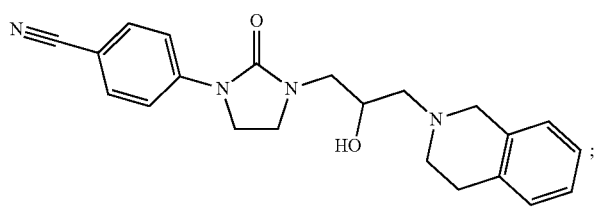 [SMILES: N#Cc1ccc(N2CCN(CC(O)CN3CCc4ccccc4C3)C2=O)cc1] ; |
| 34 | 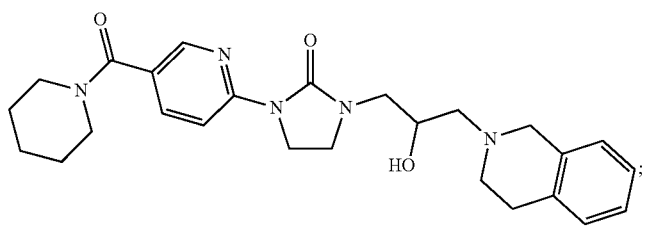 [SMILES: O=C(c1ccc(N2CCN(CC(O)CN3CCc4ccccc4C3)C2=O)nc1)N1CCCCC1] ; |
| 35 | 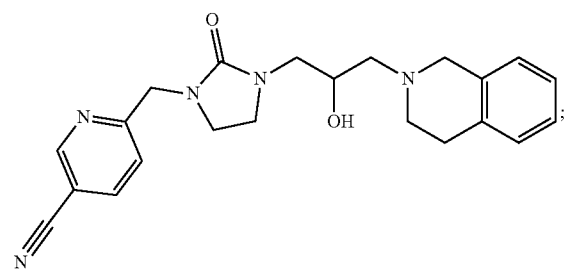 [SMILES: N#Cc1ccc(CN2CCN(CC(O)CN3CCc4ccccc4C3)C2=O)nc1] ; |
| 35a | 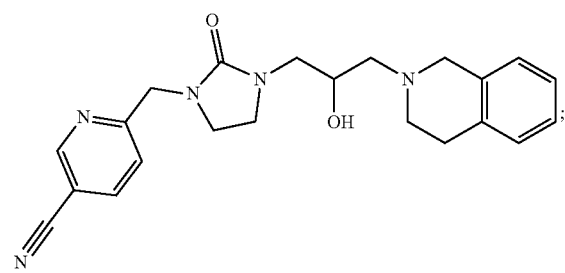 [SMILES: N#Cc1ccc(CN2CCN(CC(O)CN3CCc4ccccc4C3)C2=O)nc1] ; |

-continued
| Example No. | Structure |
|---|---|
| 35b | 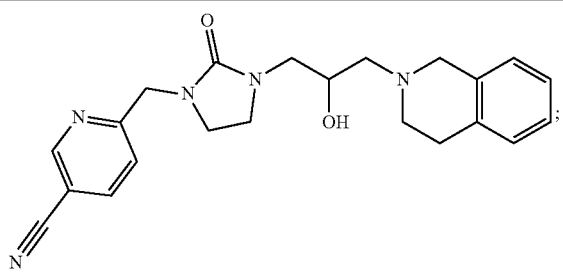 [SMILES: N#Cc1ccc(CN2CCN(CC(O)CN3CCc4ccccc4C3)C2=O)nc1] ; |
| 36 | 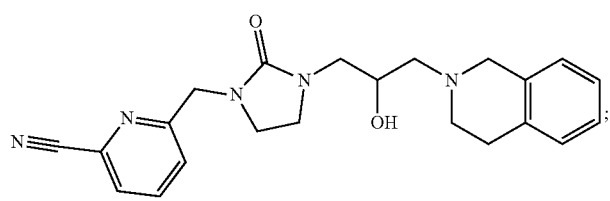 [SMILES: N#Cc1cccc(CN2CCN(CC(O)CN3CCc4ccccc4C3)C2=O)n1] ; |
| 37 | 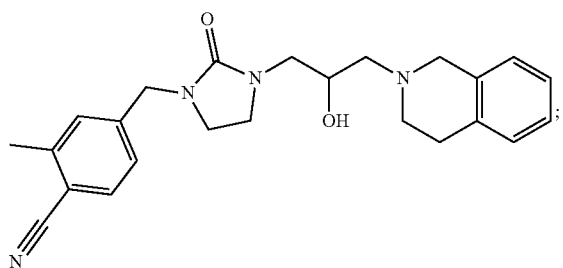 [SMILES: Cc1cc(CN2CCN(CC(O)CN3CCc4ccccc4C3)C2=O)ccc1C#N] ; |
| 38 | 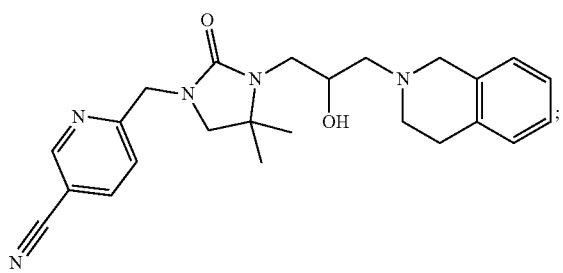 [SMILES: CC1(C)CN(Cc2ccc(C#N)cn2)C(=O)N1CC(O)CN1CCc2ccccc2C1] ; |
| 39 | 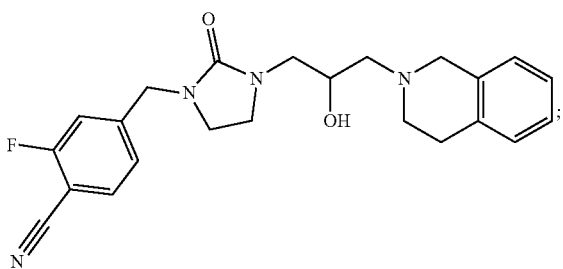 [SMILES: N#Cc1ccc(CN2CCN(CC(O)CN3CCc4ccccc4C3)C2=O)cc1F] ; |
| 40 | 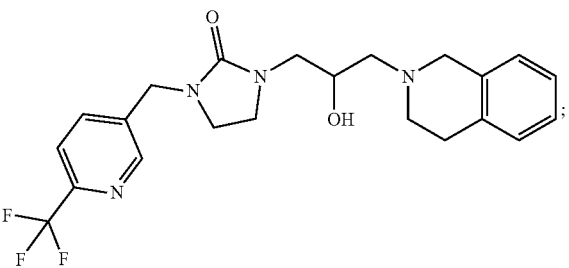 [SMILES: O=C1N(Cc2ccc(C(F)(F)F)nc2)CCN1CC(O)CN1CCc2ccccc2C1] ; |

-continued
| Example No. | Structure |
|---|---|
| 41 | 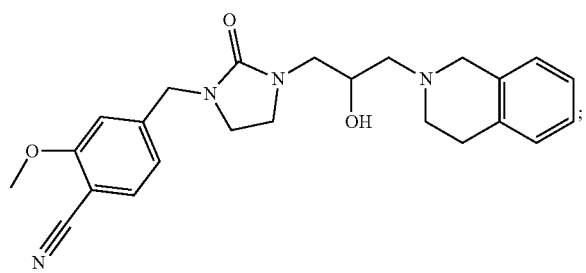 [SMILES: COc1cc(CN2CCN(CC(O)CN3CCc4ccccc4C3)C2=O)ccc1C#N] |
| 42 | 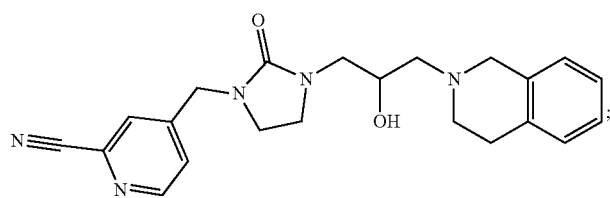 [SMILES: N#Cc1cc(CN2CCN(CC(O)CN3CCc4ccccc4C3)C2=O)ccn1] |
| 43 | 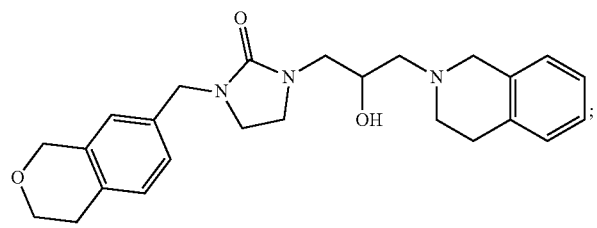 [SMILES: O=C1N(Cc2ccc3c(c2)COCC3)CCN1CC(O)CN1CCc2ccccc2C1] |
| 44 | 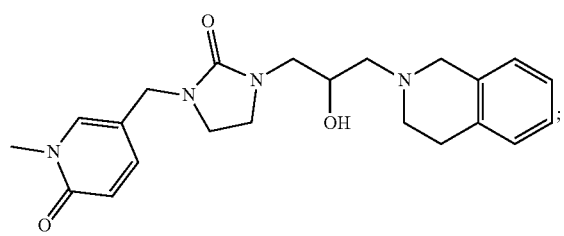 [SMILES: Cn1cc(CN2CCN(CC(O)CN3CCc4ccccc4C3)C2=O)ccc1=O] |
| 45 | 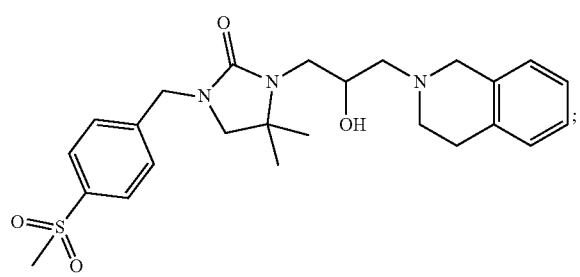 [SMILES: CC1(C)CN(Cc2ccc(S(C)(=O)=O)cc2)C(=O)N1CC(O)CN1CCc2ccccc2C1] |
| 46 | 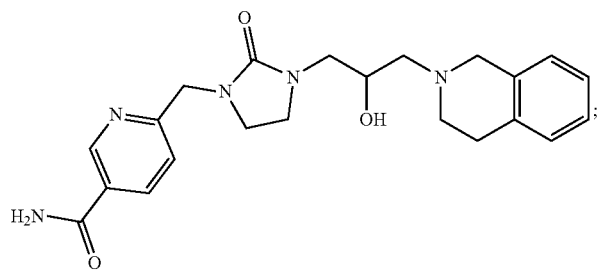 [SMILES: NC(=O)c1ccc(CN2CCN(CC(O)CN3CCc4ccccc4C3)C2=O)nc1] |

-continued
| Example No. | Structure |
|---|---|
| 47 | 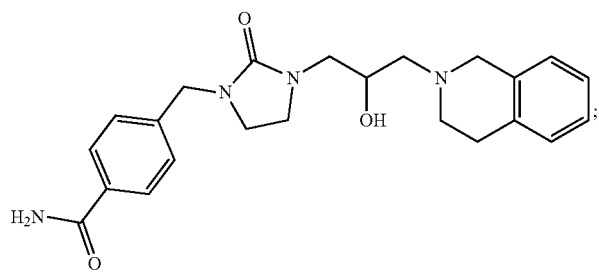 [SMILES: NC(=O)c1ccc(CN2CCN(CC(O)CN3CCc4ccccc4C3)C2=O)cc1] |
| 48 | 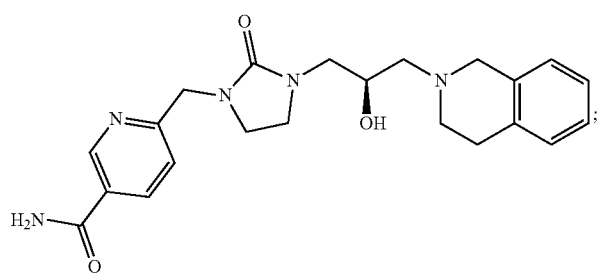 [SMILES: NC(=O)c1ccc(CN2CCN(C[C@H](O)CN3CCc4ccccc4C3)C2=O)nc1] |
| 49 | 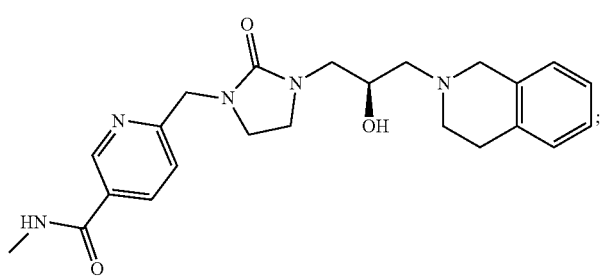 [SMILES: CNC(=O)c1ccc(CN2CCN(C[C@H](O)CN3CCc4ccccc4C3)C2=O)nc1] |
| 50 | 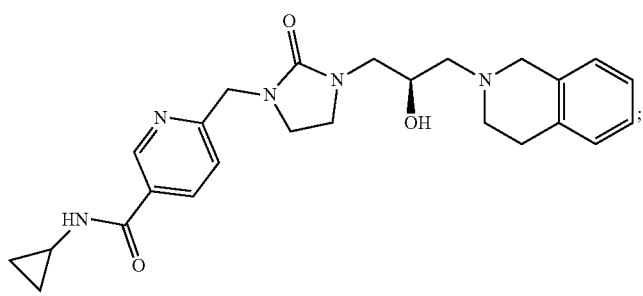 [SMILES: O=C(NC1CC1)c1ccc(CN2CCN(C[C@H](O)CN3CCc4ccccc4C3)C2=O)nc1] |
| 51 | 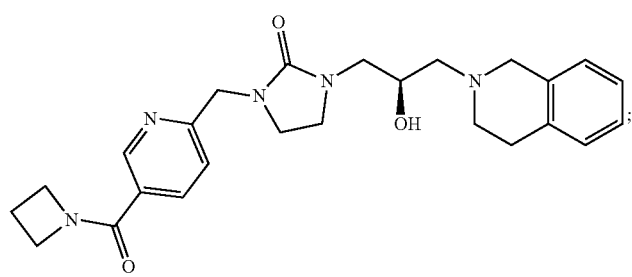 [SMILES: O=C(c1ccc(CN2CCN(C[C@H](O)CN3CCc4ccccc4C3)C2=O)nc1)N1CCC1] |
| 52 | 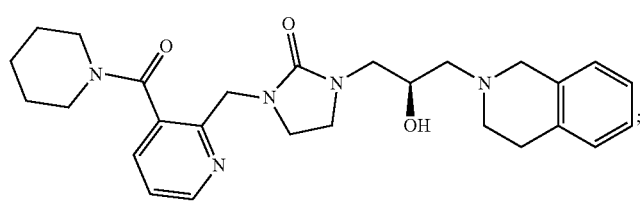 [SMILES: O=C(c1cccnc1CN1CCN(C[C@H](O)CN2CCc3ccccc3C2)C1=O)N1CCCCC1] |

-continued
| Example No. | Structure |
|---|---|
| 53 | 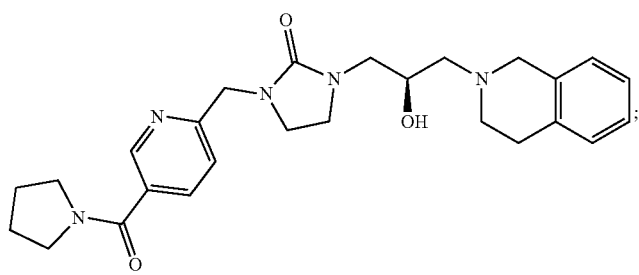 [SMILES: O=C(c1ccc(CN2CCN(C[C@H](O)CN3CCc4ccccc4C3)C2=O)nc1)N1CCCC1] |
| 54 | 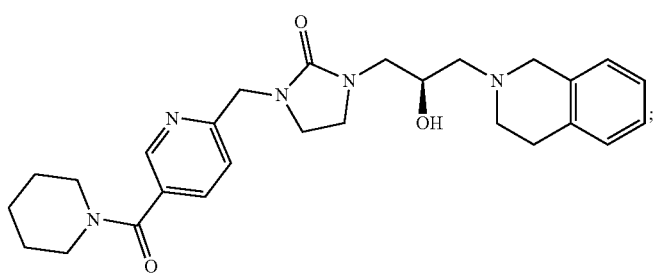 [SMILES: O=C(c1ccc(CN2CCN(C[C@H](O)CN3CCc4ccccc4C3)C2=O)nc1)N1CCCCC1] |
| 55 | 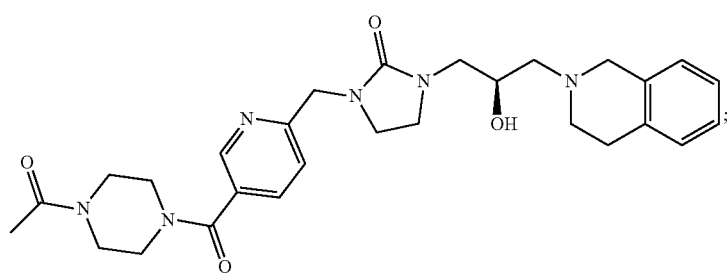 [SMILES: CC(=O)N1CCN(C(=O)c2ccc(CN3CCN(C[C@H](O)CN4CCc5ccccc5C4)C3=O)nc2)CC1] |
| 56 | 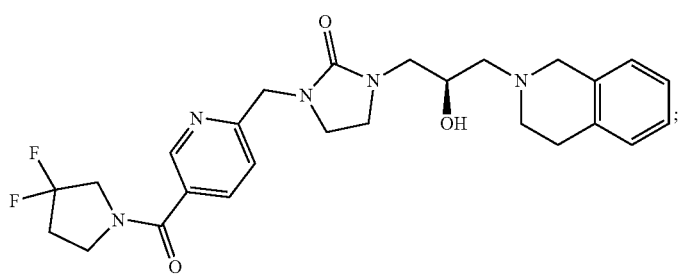 [SMILES: O=C(c1ccc(CN2CCN(C[C@H](O)CN3CCc4ccccc4C3)C2=O)nc1)N1CCC(F)(F)C1] |
| 57 | 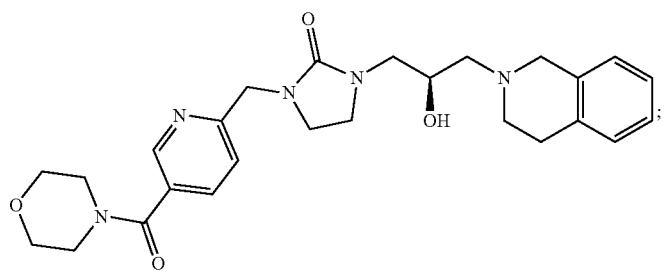 [SMILES: O=C(c1ccc(CN2CCN(C[C@H](O)CN3CCc4ccccc4C3)C2=O)nc1)N1CCOCC1] |

-continued
| Example No. | Structure |
|---|---|
| 58 | 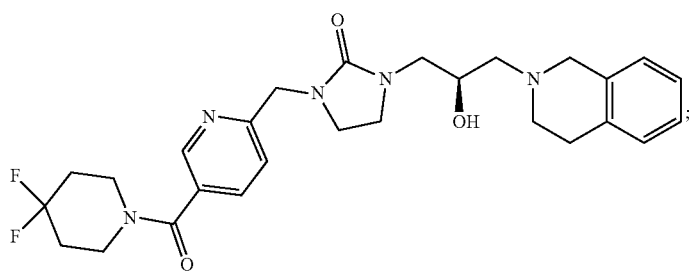 [SMILES: O=C(c1ccc(CN2CCN(C[C@H](O)CN3CCc4ccccc4C3)C2=O)nc1)N1CCC(F)(F)CC1] |
| 59 | 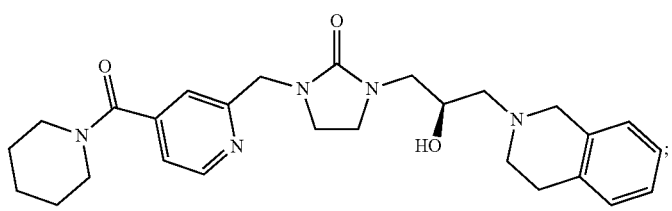 [SMILES: O=C(c1ccnc(CN2CCN(C[C@H](O)CN3CCc4ccccc4C3)C2=O)c1)N1CCCCC1] |
| 60 | 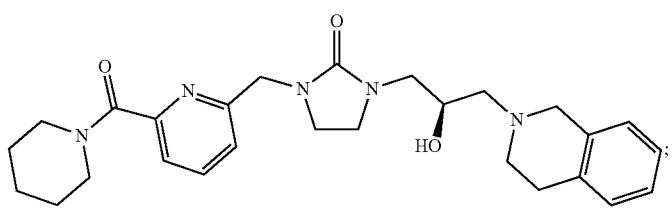 |
| 61 | 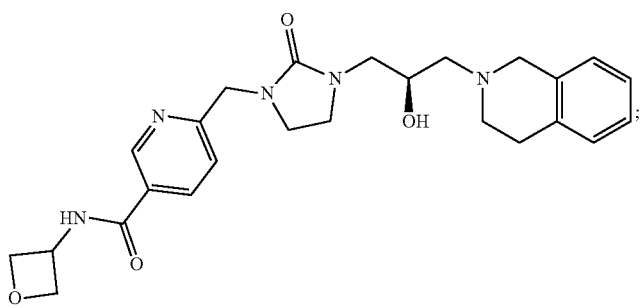 [SMILES: O=C(NC1COC1)c1ccc(CN2CCN(C[C@H](O)CN3CCc4ccccc4C3)C2=O)nc1] |
| 62 | 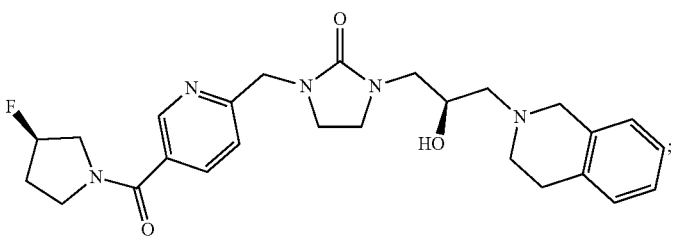 [SMILES: O=C(c1ccc(CN2CCN(C[C@H](O)CN3CCc4ccccc4C3)C2=O)nc1)N1CC[C@@H](F)C1] |
| 63 | 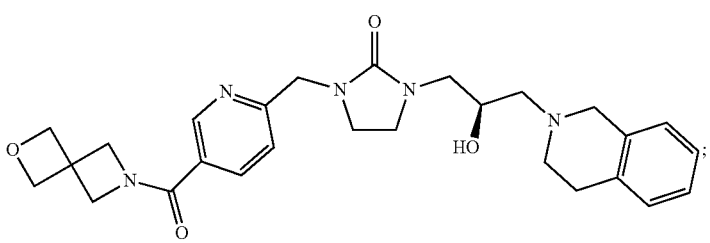 [SMILES: O=C(c1ccc(CN2CCN(C[C@H](O)CN3CCc4ccccc4C3)C2=O)nc1)N1CC2(COC2)C1] |

| Example No. | Structure |
|---|---|
| 64 | 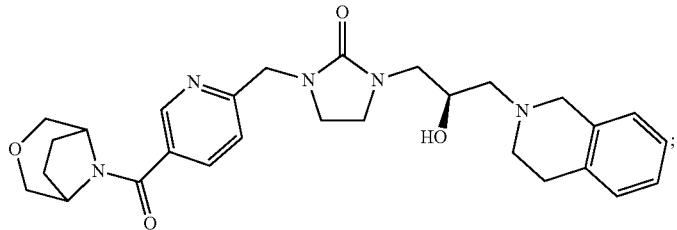 [SMILES: O=C1N(Cc2ccc(C(=O)N3C4CCC3COC4)cn2)CCN1C[C@H](O)CN1CCc2ccccc2C1] |
| 65 | 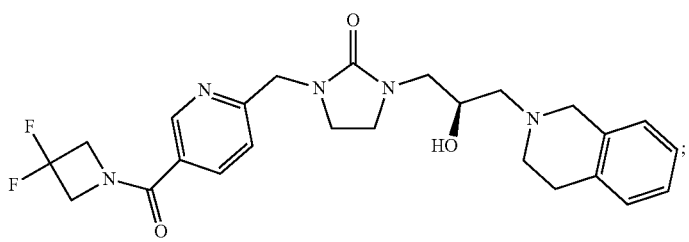 [SMILES: O=C(c1ccc(CN2CCN(C[C@H](O)CN3CCc4ccccc4C3)C2=O)nc1)N1CC(F)(F)C1] |
| 66 | 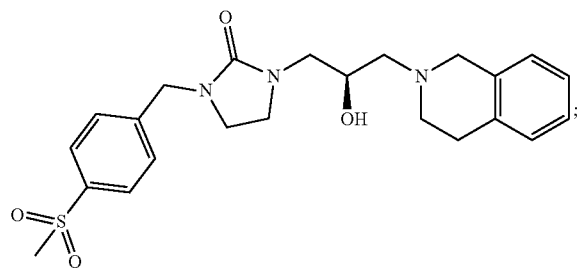 [SMILES: CS(=O)(=O)c1ccc(CN2CCN(C[C@H](O)CN3CCc4ccccc4C3)C2=O)cc1] |
| 67 | 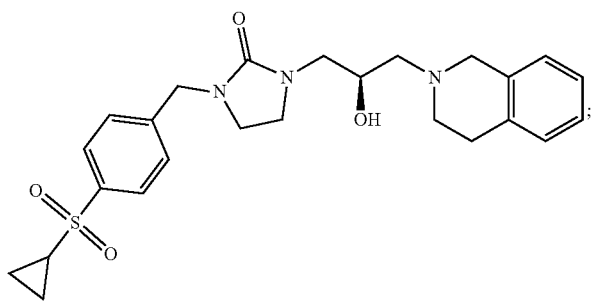 [SMILES: O=C1N(Cc2ccc(S(=O)(=O)C3CC3)cc2)CCN1C[C@H](O)CN1CCc2ccccc2C1] |
| 68 | 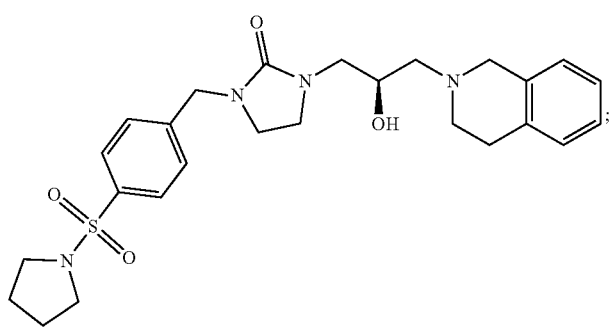 [SMILES: O=C1N(Cc2ccc(S(=O)(=O)N3CCCC3)cc2)CCN1C[C@H](O)CN1CCc2ccccc2C1] |

-continued

| Example No. | Structure |
| --- | --- |
| 69 | (structure) |
| 70 | (structure) |
| 71 | (structure) |
| 72 | (structure) |
| 73 | (structure) |

-continued
| Example No. | Structure |
|---|---|
| 74 | 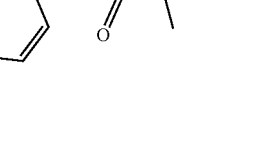 |
| 75 | 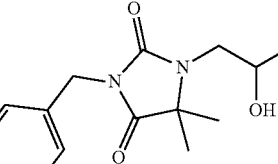 |
| 76 | 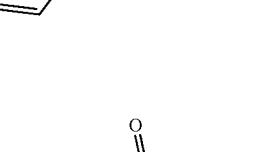 |
| 77 | 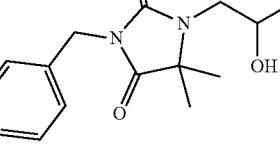 |
| 78 | 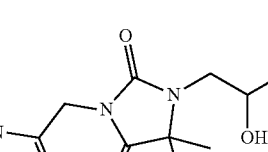 |
| 79 | 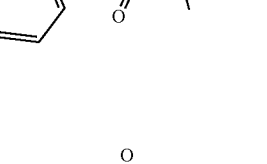 |

| Example No. | Structure |
|---|---|
| 80 | 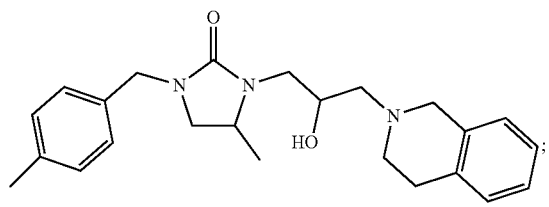 [SMILES: Cc1ccc(CN2CC(C)N(CC(O)CN3CCc4ccccc4C3)C2=O)cc1] |
| 81 | 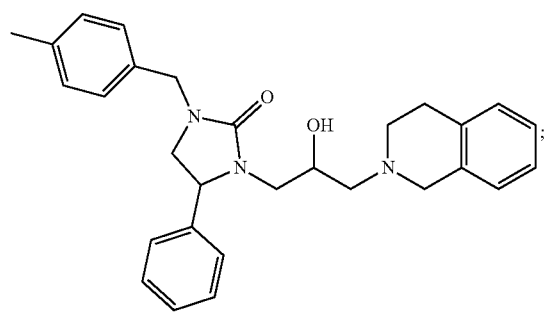 [SMILES: Cc1ccc(CN2CC(c3ccccc3)N(CC(O)CN3CCc4ccccc4C3)C2=O)cc1] |
| 82 | 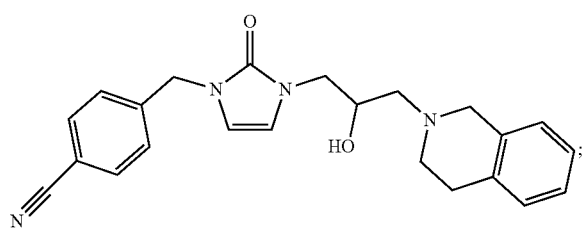 [SMILES: N#Cc1ccc(Cn2ccn(CC(O)CN3CCc4ccccc4C3)c2=O)cc1] |
| 82a | 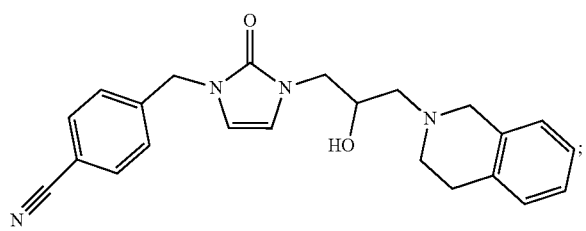 [SMILES: N#Cc1ccc(Cn2ccn(CC(O)CN3CCc4ccccc4C3)c2=O)cc1] |
| 82b | 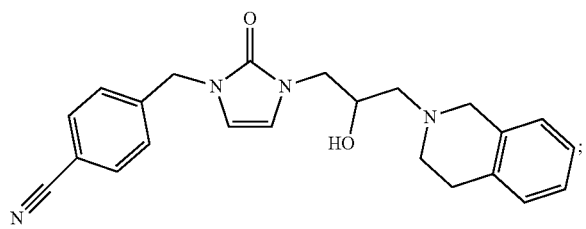 [SMILES: N#Cc1ccc(Cn2ccn(CC(O)CN3CCc4ccccc4C3)c2=O)cc1] |
| 83 | 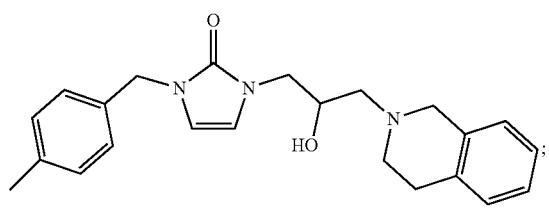 [SMILES: Cc1ccc(Cn2ccn(CC(O)CN3CCc4ccccc4C3)c2=O)cc1] |

| Example No. | Structure |
|---|---|
| 84 | 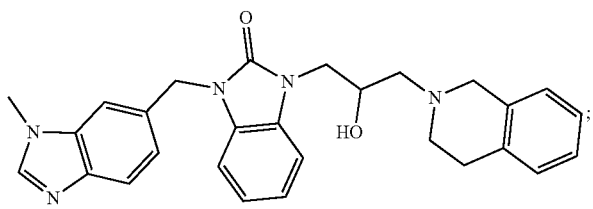 [SMILES: Cn1cnc2ccc(Cn3c(=O)n(CC(O)CN4CCc5ccccc5C4)c4ccccc43)cc21] |
| 84a | 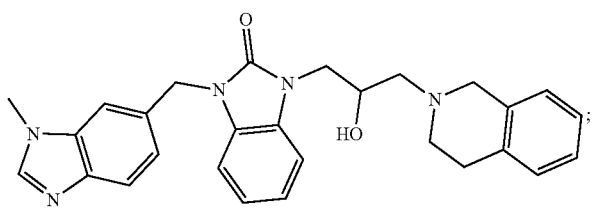 [SMILES: Cn1cnc2ccc(Cn3c(=O)n(CC(O)CN4CCc5ccccc5C4)c4ccccc43)cc21] |
| 84b | 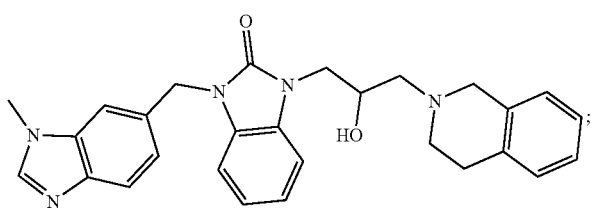 [SMILES: Cn1cnc2ccc(Cn3c(=O)n(CC(O)CN4CCc5ccccc5C4)c4ccccc43)cc21] |
| 85 | 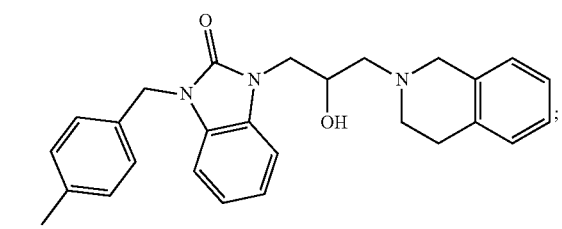 [SMILES: Cc1ccc(Cn2c(=O)n(CC(O)CN3CCc4ccccc4C3)c3ccccc32)cc1] |
| 86 | 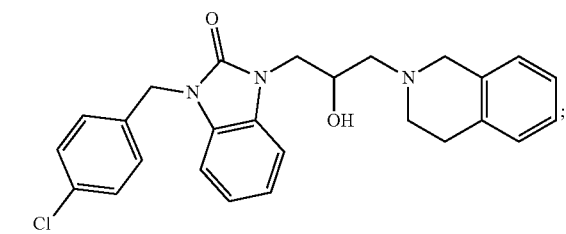 [SMILES: O=c1n(Cc2ccc(Cl)cc2)c2ccccc2n1CC(O)CN1CCc2ccccc2C1] |
| 87 | 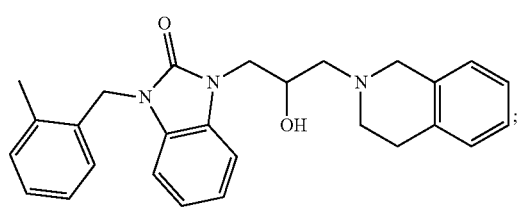 [SMILES: Cc1ccccc1Cn1c(=O)n(CC(O)CN2CCc3ccccc3C2)c2ccccc21] |
| 88 | 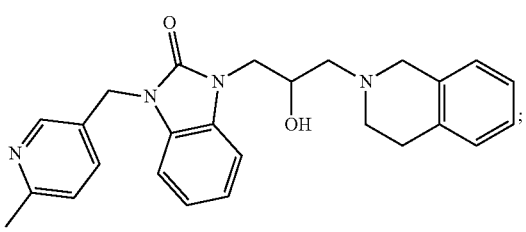 |

-continued
| Example No. | Structure |
|---|---|
| 89 | 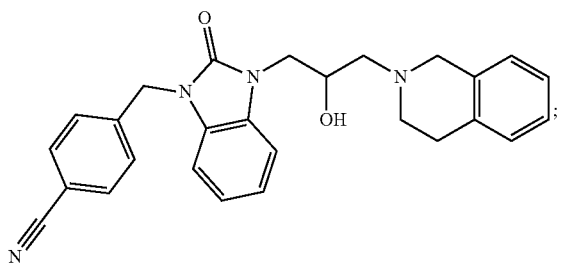 [SMILES: N#Cc1ccc(Cn2c(=O)n(CC(O)CN3CCc4ccccc4C3)c3ccccc32)cc1] |
| 90 | 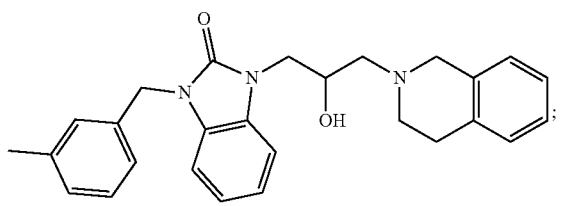 [SMILES: Cc1cccc(Cn2c(=O)n(CC(O)CN3CCc4ccccc4C3)c3ccccc32)c1] |
| 91 | 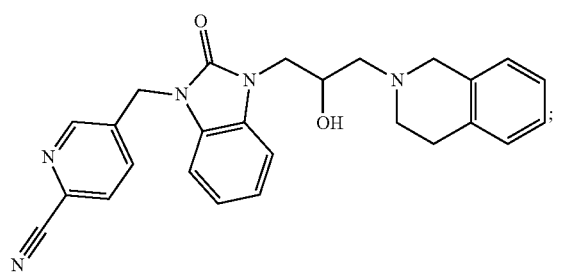 [SMILES: N#Cc1ccc(Cn2c(=O)n(CC(O)CN3CCc4ccccc4C3)c3ccccc32)cn1] |
| 92 | 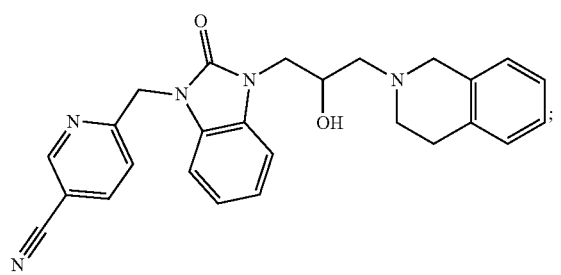 [SMILES: N#Cc1ccc(Cn2c(=O)n(CC(O)CN3CCc4ccccc4C3)c3ccccc32)nc1] |
| 93 | 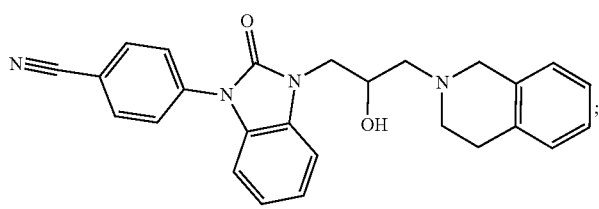 [SMILES: N#Cc1ccc(-n2c(=O)n(CC(O)CN3CCc4ccccc4C3)c3ccccc32)cc1] |
| 94 | 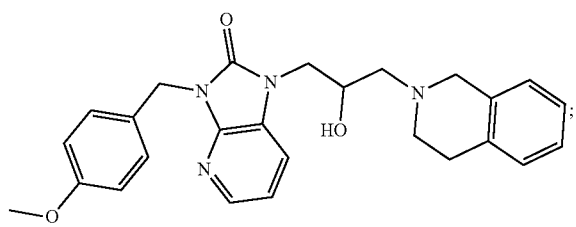 [SMILES: COc1ccc(Cn2c(=O)n(CC(O)CN3CCc4ccccc4C3)c3cccnc32)cc1] |

-continued
| Example No. | Structure |
|---|---|
| 95 | 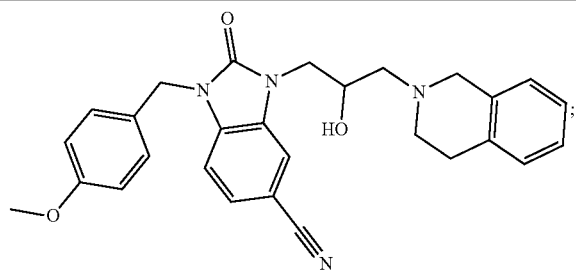 [SMILES: COc1ccc(Cn2c(=O)n(CC(O)CN3CCc4ccccc4C3)c3cc(C#N)ccc32)cc1] |
| 96 | 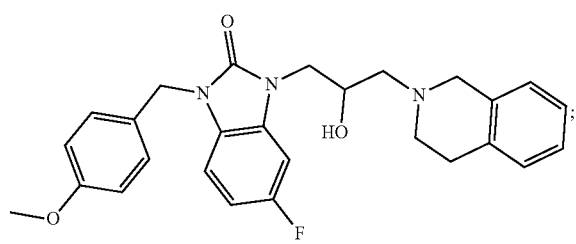 [SMILES: COc1ccc(Cn2c(=O)n(CC(O)CN3CCc4ccccc4C3)c3cc(F)ccc32)cc1] |
| 97 | 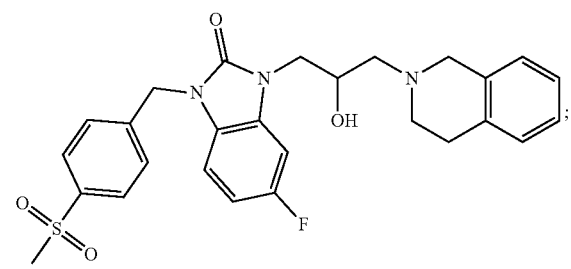 [SMILES: CS(=O)(=O)c1ccc(Cn2c(=O)n(CC(O)CN3CCc4ccccc4C3)c3cc(F)ccc32)cc1] |
| 98 | 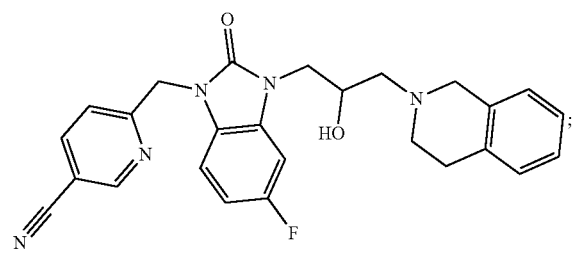 [SMILES: N#Cc1ccc(Cn2c(=O)n(CC(O)CN3CCc4ccccc4C3)c3cc(F)ccc32)nc1] |
| 99 | 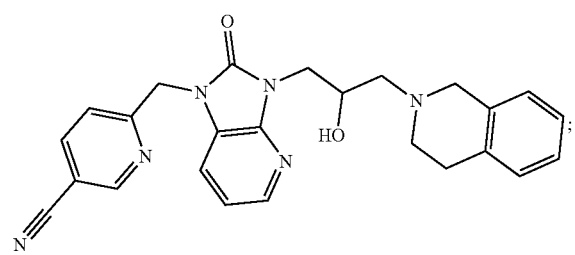 [SMILES: N#Cc1ccc(Cn2c(=O)n(CC(O)CN3CCc4ccccc4C3)c3ncccc32)nc1] |
| 100 | 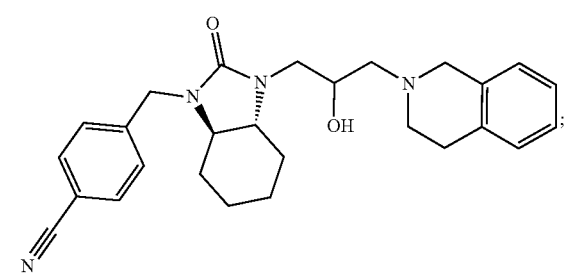 [SMILES: N#Cc1ccc(CN2C(=O)N(CC(O)CN3CCc4ccccc4C3)[C@@H]3CCCC[C@H]32)cc1] |

-continued
| Example No. | Structure |
|---|---|
| 101 | 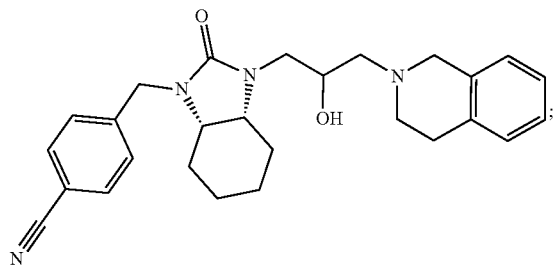 [SMILES: N#Cc1ccc(CN2C(=O)N(CC(O)CN3CCc4ccccc4C3)[C@@H]3CCCC[C@@H]32)cc1] |
| 102 | 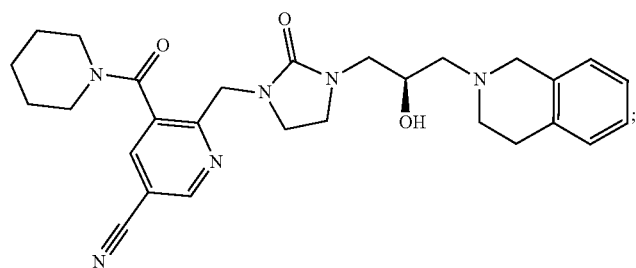 [SMILES: N#Cc1cnc(CN2CCN(C[C@H](O)CN3CCc4ccccc4C3)C2=O)c(C(=O)N2CCCCC2)c1] |
| 103 | 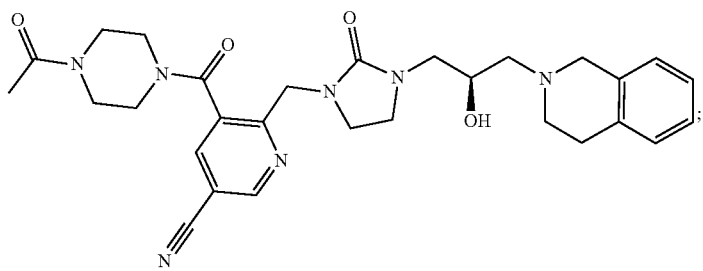 [SMILES: CC(=O)N1CCN(C(=O)c2cc(C#N)cnc2CN2CCN(C[C@H](O)CN3CCc4ccccc4C3)C2=O)CC1] |
| 104 | 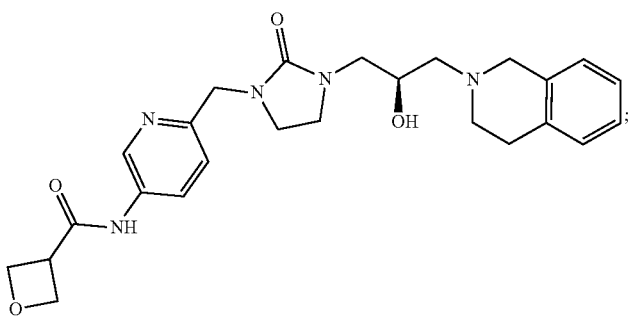 [SMILES: O=C(Nc1ccc(CN2CCN(C[C@H](O)CN3CCc4ccccc4C3)C2=O)nc1)C1COC1] |
| 105 | 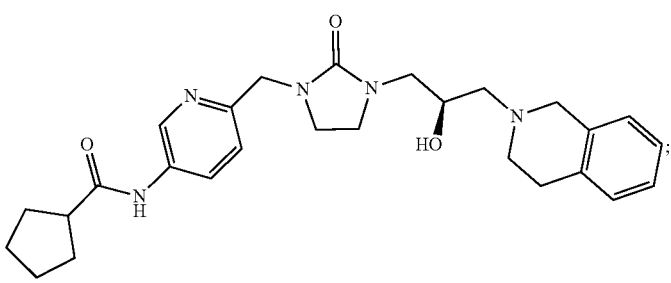 [SMILES: O=C(Nc1ccc(CN2CCN(C[C@H](O)CN3CCc4ccccc4C3)C2=O)nc1)C1CCCC1] |

| Example No. | Structure |
|---|---|
| 106 | 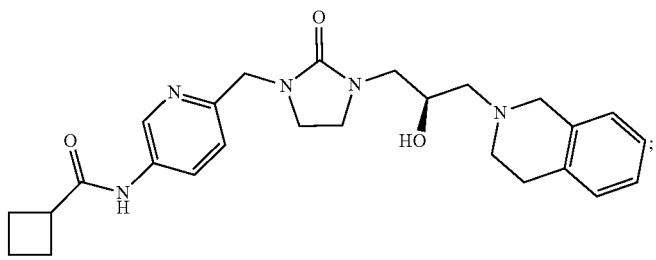 [SMILES: O=C(Nc1ccc(CN2CCN(C[C@H](O)CN3CCc4ccccc4C3)C2=O)nc1)C1CCC1] |
| 107 | 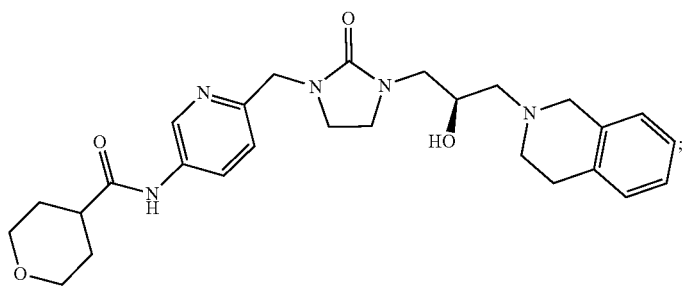 [SMILES: O=C(Nc1ccc(CN2CCN(C[C@H](O)CN3CCc4ccccc4C3)C2=O)nc1)C1CCOCC1] |
| 108 | 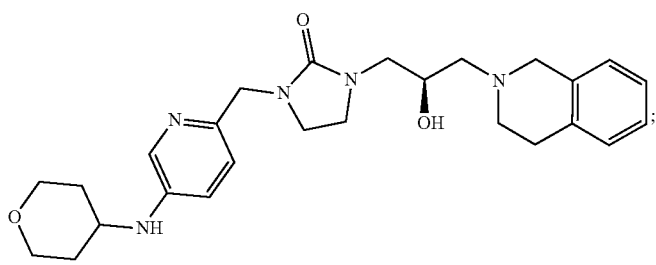 [SMILES: O=C1N(Cc2ccc(NC3CCOCC3)cn2)CCN1C[C@H](O)CN1CCc2ccccc2C1] |
| 109 | 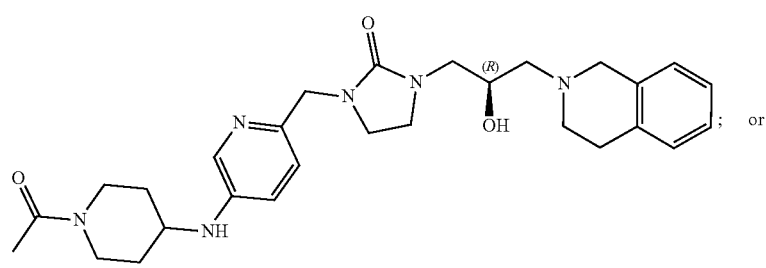 ; or |
| 110 | 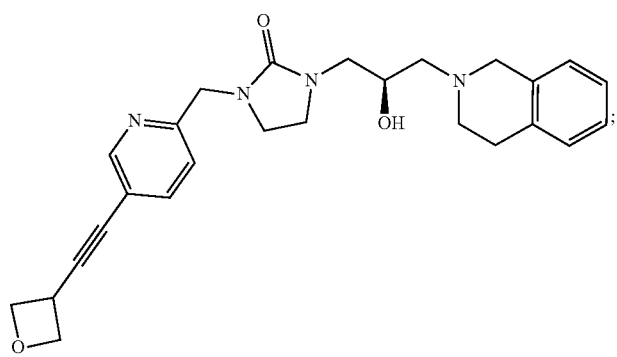 [SMILES: O=C1N(Cc2ccc(C#CC3COC3)cn2)CCN1C[C@H](O)CN1CCc2ccccc2C1] |
or a pharmaceutically acceptable salt or a stereoisomer thereof.

According to yet another embodiment, the present invention provides a compound or a pharmaceutically acceptable salt or a stereoisomer thereof, selected from:

| Example No. | IUPAC Name |
|---|---|
| 1 | 1-(3-(3,4-dihydroisoquinolin-2(1H)-yl)-2-hydroxypropyl)-3-((1-methyl-1H-benzo[d]imidazol-6-yl)methyl)imidazolidin-2-one; |
| 1a | Isomer-1 of 1-(3-(3,4-dihydroisoquinolin-2(1H)-yl)-2-hydroxypropyl)-3-((1-methyl-1H-benzo[d]imidazol-6-yl)methyl)imidazolidin-2-one; |
| 1b | Isomer-2 of 1-(3-(3,4-dihydroisoquinolin-2(1H)-yl)-2-hydroxypropyl)-3-((1-methyl-1H-benzo[d]imidazol-6-yl)methyl)imidazolidin-2-one; |
| 2 | 4-((3-(3-(3,4-dihydroisoquinolin-2(1H)-yl-2-hydroxypropyl-4,4-dimethyl-2-oxoimidazolidin-1-yl)methyl)benzonitrile; |
| 2a | Isomer-1 of 4-((3-(3-(3,4-dihydroisoquinolin-2(1H)-yl)-2-hydroxypropyl)-4,4-dimethyl-2-oxoimidazolidin-1-yl)methyl)benzonitrile; |
| 2b | Isomer-2 of 4-((3-(3-(3,4-dihydroisoquinolin-2(1H)-yl)-2-hydroxypropyl)-4,4-dimethyl-2-oxoimidazolidin-1-yl)methyl)benzonitrile; |
| 3 | 1-(3-(3,4-dihydroisoquinolin-2(1H)-yl)-2-hydroxypropyl)-3-(4-(dimethylamino)benzyl)imidazolidin-2-one; |
| 4 | 1-(3-(3,4-dihydroisoquinolin-2(1H)-yl)-2-hydroxypropyl)-3-((1-methyl-1H-pyrazol-5-yl)methyl)imidazolidin-2-one; |
| 5 | 3-(3-(3,4-dihydroisoquinolin-2(1H)-yl)-2-hydroxypropyl)-4,4-dimethyl-1-(4-methylbenzyl)imidazolidin-2-one; |
| 6 | 4-(3-(3,4-dihydroisoquinolin-2(1H)-yl)-2-hydroxypropyl)-6-((6-methylpyridin-3-yl)methyl)-4,6-diazaspiro[2.4]heptan-5-one; |
| 7 | 3-(3-(3,4-dihydroisoquinolin-2(1H)-yl)-2-hydroxypropyl)-4,4-dimethyl-1-((6-methylpyridin-3-yl)methyl)imidazolidin-2-one; |
| 8 | 1-(3-(3,4-dihydroisoquinolin-2(1H)-yl)-2-hydroxypropyl)-3-((6-methylpyridin-3-yl)methyl)-1,3-diazaspiro[4.4]nonan-2-one; |
| 9 | 5-(3-(3,4-dihydroisoquinolin-2(1H)-yl)-2-hydroxypropyl)-7-((6-methylpyridin-3-yl)methyl)-5,7-diazaspiro[3.4]octan-6-one; |
| 10 | 1-(3-(3,4-dihydroisoquinolin-2(1H)-yl)-2-hydroxypropyl)-4,4-dimethyl-3-(4-methylbenzyl)imidazolidin-2-one; |
| 11 | 1-(3-(3,4-Dihydroisoquinolin-2(1H)-yl)-2-hydroxypropyl)-3-(4-(methyl-sulfonyl)benzyl)imidazolidin-2-one; |
| 12 | 5-((3-(3-(3,4-dihydroisoquinolin-2(1H)-yl)-2-hydroxypropyl)-4,4-dimethyl-2-oxoimidazolidin-1-yl)methyl)picolinonitrile; |
| 13 | 1-(3-(3,4-dihydroisoquinolin-2(1H)-yl)-2-hydroxypropyl)-3-((6-methoxypyridin-3-yl)methyl)imidazolidin-2-one; |
| 14 | 4-((3-(3-(3,4-Dihydroisoquinolin-2(1H)-yl)-2-hydroxypropyl)-5,5-dimethyl-2-oxoimidazolidin-1-yl)methyl)benzonitrile; |
| 15 | 1-(3-(3,4-Dihydroisoquinolin-2(1H)-yl)-2-hydroxypropyl)-3-(4-methyl-benzyl)imidazolidin-2-one; |
| 15a | Isomer 1 of 1-(3-(3,4-Dihydroisoquinolin-2(1H)-yl)-2-hydroxypropyl)-3-(4-methylbenzyl)imidazolidin-2-one; |
| 15b | Isomer 2 of 1-(3-(3,4-Dihydroisoquinolin-2(1H)-yl)-2-hydroxypropyl)-3-(4-methylbenzyl)imidazolidin-2-one; |
| 16 | 1-(3-(3,4-Dihydroisoquinolin-2(1H)-yl)-2-hydroxypropyl)-3-(2-methylbenzyl)imidazolidin-2-one; |
| 16a | Isomer-1 of 1-(3-(3,4-Dihydroisoquinolin-2(1H)-yl)-2-hydroxypropyl)-3-(2-methylbenzyl)imidazolidin-2-one; |
| 16b | Isomer-2 of 1-(3-(3,4-Dihydroisoquinolin-2(1H)-yl)-2-hydroxypropyl)-3-(2-methylbenzyl)imidazolidin-2-one; |
| 17 | 1-(3-(3,4-Dihydroisoquinolin-2(1H)-yl)-2-hydroxypropyl)-3-(4-methylbenzyl)imidazolidine-2,4-dione; |
| 18 | 4-((3-(3-(3,4-dihydroisoquinolin-2(1H)-yl)-2-hydroxypropyl)-2-oxoimidazolidin-1-yl)methyl)benzonitrile; |
| 18a | Isomer-1 of 4-((3-(3-(3,4-dihydroisoquinolin-2(1H)-yl)-2-hydroxypropyl)-2-oxoimidazolidin-1-yl)methyl)benzonitrile; |
| 18b | Isomer-2 of 4-((3-(3-(3,4-dihydroisoquinolin-2(1H)-yl)-2-hydroxypropyl)-2-oxoimidazolidin-1-yl)methyl)benzonitrile; |
| 19 | 1-(3-(3,4-dihydroisoquinolin-2(1H)-yl)-2-hydroxypropyl)-3-((6-methylpyridin-3-yl)methyl)imidazolidin-2-one; |
| 20 | 1-benzyl-3-(3-(3,4-dihydroisoquinolin-2(1H)-yl)-2-hydroxypropyl)imidazolidin-2-one; |
| 21 | 5-((3-(3-(3,4-dihydroisoquinolin-2(1H)-yl)-2-hydroxypropyl)-2-oxoimidazolidin-1-yl)methyl)picolinonitrile; |
| 22 | 1-(3-(3,4-dihydroisoquinolin-2(1H)-yl)-2-hydroxypropyl)-3-((6-methylpyridin-2-yl)methyl)imidazolidin-2-one; |
| 23 | 4-((3-(3-(3,4-dihydroisoquinolin-2(1H)-yl)-2-hydroxypropyl)-2,5-dioxoimidazolidin-1-yl)methyl)benzonitrile; |
| 24 | 4-((3-(3-(3,4-dihydroisoquinolin-2(1H)-yl)-2-hydroxypropyl)-4,4-dimethyl-2,5-dioxoimidazolidin-1-yl)methyl)benzonitrile; |
| 25 | 1-((6-Chloropyridin-3-ylmethyl)-3-(3-(3,4-dihydroisoquinolin-2(1H)-yl)-2-hydroxypropyl)imidazolidin-2-one; |

-continued

| Example No. | IUPAC Name |
|---|---|
| 26 | 1-(3-(3,4-dihydroisoquinolin-2(1H)-yl)-2-hydroxypropyl)-3-((6-isopropylpyridin-3-yl)methyl)imidazolidin-2-one; |
| 27 | 1-(3-(3,4-dihydroisoquinolin-2(1H)-yl)-2-hydroxypropyl)-3-((6-ethylpyridin-3-yl)methyl)imidazolidin-2-one; |
| 28 | 1-(3-(3,4-Dihydroisoquinolin-2(1H)-yl)-2-hydroxypropyl)-3-((6-(prop-1-en-2-yl)pyridin-3-yl)methyl)imidazolidin-2-one; |
| 29 | 1-(3-(3,4-Dihydroisoquinolin-2(1H)-yl)-2-hydroxypropyl)-3-((6-isopropylpyridin-3-yl)methyl)-5,5-dimethylimidazolidine-2,4-dione; |
| 30 | 1-(3-(3,4-Dihydroisoquinolin-2(1H)-yl)-2-hydroxypropyl)-3-((5-isopropylpyridin-2-yl)methyl)-5,5-dimethylimidazolidine-2,4-dione; |
| 31 | 1-(3-(3,4-Dihydroisoquinolin-2(1H)-yl)-2-hydroxypropyl)-3-((5-isopropylpyridin-2-yl)methyl)imidazolidin-2-one; |
| 32 | 1-((6-Acetylpyridin-3-yl)methyl)-3-(3-(3,4-dihydroisoquinolin-2(1H)-yl)-2-hydroxypropyl)imidazolidin-2-one; |
| 33 | 4-(3-(3-(3,4-dihydroisoquinolin-2(1H)-yl)-2-hydroxypropyl)-2-oxoimidazolidin-1-yl)benzonitrile; |
| 34 | 1-(3-(3,4-dihydroisoquinolin-2(1H)-yl)-2-hydroxypropyl)-3-(5-(piperidine-1-carbonyl)pyridin-2-yl)imidazolidin-2-one; |
| 35 | 6-((3-(3-(3,4-Dihydroisoquinolin-2(1H)-yl)-2-hydroxypropyl)-2-oxoimidazolidin-1-yl)methyl)nicotinonitrile; |
| 35a | Isomer-1 of 6-((3-(3-(3,4-Dihydroisoquinolin-2(1H)-yl)-2-hydroxypropyl)-2-oxoimidazolidin-1-yl)methyl)nicotinonitrile; |
| 35b | Isomer-2 of 6-((3-(3-(3,4-Dihydroisoquinolin-2(1H)-yl)-2-hydroxypropyl)-2-oxoimidazolidin-1-yl)methyl)nicotinonitrile; |
| 36 | 6-((3-(3-(3,4-Dihydroisoquinolin-2(1H)-yl)-2-hydroxypropyl)-2-oxoimidazolidin-1-yl)methyl)picolinonitrile; |
| 37 | 4-((3-(3-(3,4-Dihydroisoquinolin-2(1H)-yl)-2-hydroxypropyl)-2-oxo-imidazolidin-1-ylmethyl)-2-methylbenzonitrile; |
| 38 | 6-((3-(3-(3,4-Dihydroisoquinolin-2(1H)-yl)-2-hydroxypropyl)-4,4-dimethyl-2-oxoimidazolidin-1-yl)methyl)nicotinonitrile; |
| 39 | 4-((3-(3-(3,4-Dihydroisoquinolin-2(1H)-yl)-2-hydroxypropyl)-2-oxo-imidazolidin-1-yl)methyl)-2-fluorobenzonitrile; |
| 40 | 1-(3-(3,4-Dihydroisoquinolin-2(1H)-yl)-2-hydroxypropyl)-3-((6-(trifluoromethyl)pyridin-3-yl)methyl)imidazolidin-2-one; |
| 41 | 4-((3-(3-(3,4-Dihydroisoquinolin-2(1H)-yl)-2-hydroxypropyl)-2-oxoimidazolidin-1-yl)methyl)-2-methoxybenzonitrile; |
| 42 | 4-((3-(3-(3,4-Dihydroisoquinolin-2(1H)-yl)-2-hydroxypropyl)-2-oxoimidazolidin-1-ylmethyl)-picolinonitrile; |
| 43 | 1-(3-(3,4-Dihydroisoquinolin-2(1H)-yl)-2-hydroxypropyl)-3-(isochroman-7-ylmethyl)imidazolidin-2-one; |
| 44 | 5-((3-(3-(3,4-Dihydroisoquinolin-2(1H)-yl)-2-hydroxypropyl)-2-oxoimidazolidin-1-yl)methyl)-1-methylpyridin-2(1H)-one; |
| 45 | 3-(3-(3,4-dihydroisoquinolin-2(1H)-yl)-2-hydroxypropyl)-4,4-dimethyl-1-(4-(methylsulfonyl)benzyl)imidazolidin-2-one; |
| 46 | 6-((3-(3-(3,4-Dihydroisoquinolin-2(1H)-yl)-2-hydroxypropyl)-2-oxoimidazolidin-1-yl)methyl)nicotinamide; |
| 47 | 4-((3-(3-(3,4-dihydroisoquinolin-2(1H)-yl)-2-hydroxypropyl)-2-oxoimidazolidin-1-yl)methyl)benzamide; |
| 48 | (R)-6-((3-(3-(3,4-Dihydroisoquinolin-2(1H)-yl)-2-hydroxypropyl)-2-oxoimidazolidin-1-yl)methyl)nicotinamide; |
| 49 | (R)-6-((3-(3-(3,4-Dihydroisoquinolin-2(1H)-yl)-2-hydroxypropyl)-2-oxo-imidazolidin-1-yl)methyl)-N-methylnicotinamide; |
| 50 | (R)-N-Cyclopropyl-6-((3-(3-(3,4-di-hydroisoquinolin-2(1H)-yl)-2-hydroxypropyl)-2-oxoimidazolidin-1-yl)methyl)nicotinamide; |
| 51 | (R)-1-((5-(Azetidine-1-carbonyl)pyridin-2-yl)methyl)-3-(3-(3,4-dihydro-isoquinolin-2(1H)-yl)-2-hydroxypropyl)imidazolidin-2-one; |
| 52 | (R)-1-(3-(3,4-dihydroisoquinolin-2(1H)-yl)-2-hydroxypropyl)-3-((3-(piperidine-1-carbonyl)pyridin-2-yl)methyl)imidazolidin-2-one; |
| 53 | (R)-1-(3-(3,4-dihydroisoquinolin-2(1H)-yl)-2-hydroxypropyl)-3-((5-(pyrrolidine-1-carbonyl)pyridin-2-yl)methyl)imidazolidin-2-one; |
| 54 | (R)-1-(3-(3,4-dihydroisoquinolin-2(1H)-yl)-2-hydroxypropyl)-3-((5-(piperidine-1-carbonyl)pyridin-2-yl)methyl)imidazolidin-2-one; |
| 55 | (R)-1-((5-(4-acetylpiperazine-1-carbonylpyridin-2-yl)methyl)-3-(3-(3,4-dihydroisoquinolin-2(1H)-yl)-2-hydroxypropyl)imidazolidin-2-one; |
| 56 | (R)-1-((5-(3,3-difluoropyrrolidine-1-carbonylpyridin-2-yl)methyl)-3-(3-(3,4-dihydroisoquinolin-2(1H)-yl)-2-hydroxypropyl)imidazolidin-2-one; |
| 57 | (R)-1-(3-(3,4-dihydroisoquinolin-2(1H)-yl)-2-hydroxypropyl)-3-((5-(morpholine-4-carbonyl)pyridin-2-yl)methyl)imidazolidin-2-one; |
| 58 | (R)-1-((5-(4,4-difluoropiperidine-1-carbonyl)pyridin-2-yl)methyl)-3-(3-(3,4-dihydroisoquinolin-2(1H)-yl)-2-hydroxypropyl)imidazolidin-2-one; |
| 59 | (R)-1-(3-(3,4-dihydroisoquinolin-2(1H)-yl)-2-hydroxypropyl)-3-((4-(piperidine-1-carbonyl)pyridin-2-yl)methyl)imidazolidin-2-one; |
| 60 | (R)-1-(3-(3,4-dihydroisoquinolin-2(1H)-yl)-2-hydroxypropyl)-3-((6-(piperidine-1-carbonyl)pyridin-2-yl)methyl)imidazolidin-2-one; |
| 61 | (R)-6-((3-(3-(3,4-dihydroisoquinolin-2(1H)-yl)-2-hydroxypropyl)-2-oxoimidazolidin-1-ylmethyl)-N-(oxetan-3-yl)nicotinamide; |

| Example No. | IUPAC Name |
|---|---|
| 62 | 1-((R)-3-(3,4-dihydroisoquinolin-2(1H)-yl)-2-hydroxypropyl)-3-((5-((R)-3-fluoropyrrolidine-1-carbonyl)pyridin-2-yl)methyl)imidazolidin-2-one; |
| 63 | (R)-1-((5-(2-oxa-6-azaspiro[3.3]heptane-6-carbonyl)pyridin-2-yl)methyl)-3-(3-(3,4-dihydroisoquinolin-2(1H)-yl)-2-hydroxypropyl)imidazolidin-2-one; |
| 64 | 1-((5-(3-oxa-8-azabicyclo[3.2.1]octane-8-carbonyl)pyridin-2-yl)methyl)-3-((R)-3-(3,4-dihydroisoquinolin-2(1H)-yl)-2-hydroxypropyl)imidazolidin-2-one; |
| 65 | (R)-1-((5-(3,3-difluoroazetidine-1-carbonyl)pyridin-2-yl)methyl)-3-(3-(3,4-dihydroisoquinolin-2(1H)-yl)-2-hydroxypropyl)imidazolidin-2-one; |
| 66 | (R)-1-(3-(3,4-dihydroisoquinolin-2(1H)-yl)-2-hydroxypropyl)-3-(4-(methyl-sulfonyl)benzyl)imidazolidin-2-one; |
| 67 | (R)-1-(4-(cyclopropylsulfonyl)benzyl)-3-(3-(3,4-dihydroisoquinolin-2(1H)-yl)-2-hydroxypropyl)imidazolidin-2-one; |
| 68 | (R)-1-(3-(3,4-dihydroisoquinolin-2(1H)-yl)-2-hydroxypropyl)-3-(4-(pyrrolidin-1-ylsulfonyl)benzyl)imidazolidin-2-one; |
| 69 | (R)-1-(3-(3,4-dihydroisoquinolin-2(1H)-yl)-2-hydroxypropyl)-3-(4-(piperidin-1-ylsulfonyl)benzyl)imidazolidin-2-one; |
| 70 | (R)-1-(3-(3,4-dihydroisoquinolin-2(1H)-yl)-2-hydroxypropyl)-3-(3-(pyrrolidin-1-ylsulfonyl)benzyl)imidazolidin-2-one; |
| 71 | (R)-1-(3-(3,4-dihydroisoquinolin-2(1H)-yl)-2-hydroxypropyl)-3-45-(pyrrolidin-1-ylsulfonyl)pyridin-2-yl)methyl)imidazolidin-2-one; |
| 72 | (R)-1-((2-((1-acetylpiperidin-4-yl)amino)pyridin-4-yl)methyl)-3-(3-(3,4-dihydroisoquinolin-2(1H)-yl)-2-hydroxypropyl)imidazolidin-2-one; |
| 73 | 6-((3-(3-(3,4-dihydroisoquinolin-2(1H)-yl)-2-hydroxypropyl)-2,5-dioxoimidazolidin-1-yl)methyl)nicotinonitrile; |
| 74 | 6-((3-(3-(3,4-dihydroisoquinolin-2(1H)-yl)-2-hydroxypropyl)-4,4-dimethyl-2,5-dioxoimidazolidin-1-yl)methyl)nicotinonitrile; |
| 75 | 4-((3-(3-(3,4-Dihydroisoquinolin-2(1H)-yl)-2-hydroxypropyl)-4,4-dimethyl-2,5-dioxoimidazolidin-1-yl)methyl)-2-methoxybenzonitrile; |
| 76 | 1-(3-(3,4-dihydroisoquinolin-2(1H)-yl)-2-hydroxypropyl)-3-(isochroman-7-ylmethyl)-5,5-dimethylimidazolidine-2,4-dione; |
| 77 | 1-(3-(3,4-Dihydroisoquinolin-2(1H)-yl)-2-hydroxypropyl)-5,5-dimethyl-3-((5-(trifluoromethyl)pyridin-2-yl)methyl)imidazolidine-2,4-dione; |
| 78 | 1-(3-(3,4-Dihydroisoquinolin-2(1H)-yl)-2-hydroxypropyl)-5,5-dimethyl-3-((1-methyl-6-oxo-1,6-dihydropyridin-3-yl)methyl)imidazolidine-2,4-dione; |
| 79 | 1-(3-(3,4-Dihydroisoquinolin-2(1H)-yl)-2-hydroxypropyl)-5,5-dimethyl-3-(4-(methylsulfonyl)benzyl)imidazolidine-2,4-dione; |
| 80 | 3-(3-(3,4-Dihydroisoquinolin-2(1H)-yl)-2-hydroxypropyl)-4-methyl-1-(4-methylbenzyl)imidazolidin-2-one; |
| 81 | 3-(3-(3,4-Dihydroisoquinolin-2(1H)-yl)-2-hydroxypropyl)-1-(4-methylbenzyl)-4-phenylimidazolidin-2-one; |
| 82 | 4-((3-(3-(3,4-Dihydroisoquinolin-2(1H)-yl)-2-hydroxypropyl)-2-oxo-2,3-di-hydro-1H-imidazol-1-yl)methyl)benzonitrile; |
| 82a | Isomer 1 of 4-((3-(3-(3,4-Dihydroisoquinolin-2(1H)-yl)-2-hydroxypropyl)-2-oxo-2,3-dihydro-1H-imidazol-1-yl)methyl)benzonitrile; |
| 82b | Isomer 2 of 4-((3-(3-(3,4-Dihydroisoquinolin-2(1H)-yl)-2-hydroxypropyl)-2-oxo-2,3-dihydro-1H-imidazol-1-yl)methyl)benzonitrile; |
| 83 | 1-(3-(3,4-dihydroisoquinolin-2(1H)-yl)-2-hydroxypropyl)-3-(4-methylbenzyl)-1,3-dihydro-2H-imidazol-2-one; |
| 84 | 1-(3-(3,4-dihydroisoquinolin-2(1H)-yl)-2-hydroxypropyl)-3-((1-methyl-1H-benzo[d]imidazol-6-yl)methyl)-1,3-dihydro-2H-benzo[d]imidazol-2-one; |
| 84a | Isomer 1 of 1-(3-(3,4-Dihydroisoquinolin-2(1H)-yl)-2-hydroxypropyl)-3-((1-methyl-1H-benzo[d]imidazol-6-yl)methyl)-1,3-dihydro-2H-benzo[d]imidazol-2-one; |
| 84b | Isomer 2 of 1-(3-(3,4-Dihydroisoquinolin-2(1H)-yl)-2-hydroxypropyl)-3-((1-methyl-1H-benzo[d]imidazol-6-yl)methyl)-1,3-dihydro-2H-benzo[d]imidazol-2-one; |
| 85 | 1-(3-(3,4-Dihydroisoquinolin-2(1H)-yl)-2-hydroxypropyl)-3-(4-methylbenzyl)-1,3-dihydro-2H-benzo[d]imidazol-2-one; |
| 86 | 1-(4-Chlorobenzyl)-3-(3-(3,4-dihydroisoquinolin-2(1H)-yl)-2-hydroxypropyl)-1,3-dihydro-2H-benzo[d]imidazol-2-one; |
| 87 | 1-(3-(3,4-Dihydroisoquinolin-2(1H)-yl)-2-hydroxypropyl)-3-(2-methylbenzyl)-1,3-dihydro-2H-benzo[d]imidazol-2-one; |
| 88 | 1-(3-(3,4-Dihydroisoquinolin-2(1H)-yl)-2-hydroxypropyl)-3-((6-methylpyridin-3-yl)methyl)-1,3-dihydro-2H-benzo[d]imidazol-2-one; |
| 89 | 4-((3-(3-(3,4-Dihydroisoquinolin-2(1H)-yl)-2-hydroxypropyl)-2-oxo-2,3-dihydro-1H-benzo[d]imidazol-1-yl)methyl)benzonitrile; |
| 90 | 1-(3-(3,4-Dihydroisoquinolin-2(1H)-yl)-2-hydroxypropyl)-3-(3-methylbenzyl)-1,3-dihydro-2H-benzo[d]imidazol-2-one; |
| 91 | 5-((3-(3-(3,4-Dihydroisoquinolin-2(1H)-yl)-2-hydroxypropyl)-2-oxo-2,3-dihydro-1H-benzo[d]imidazol-1-yl)methyl)picolinonitrile; |
| 92 | 5-((3-(3-(3,4-Dihydroisoquinolin-2(1H)-yl)-2-hydroxypropyl)-2-oxo-2,3-dihydro-1H-benzo[d]imidazol-1-yl)methyl)picolinonitrile; |
| 93 | 4-(3-(3-(3,4-Dihydroisoquinolin-2(1H)-yl)-2-hydroxypropyl)-2-oxo-2,3-dihydro-1H-benzo[d]imidazol-1-yl)benzonitrile; |
| 94 | 1-(3-(3,4-Dihydroisoquinolin-2(1H)-yl)-2-hydroxypropyl)-3-(4-methoxybenzyl)-1,3-dihydro-2H-imidazo[4,5-b]pyridin-2-one; |

| Example No. | IUPAC Name |
|---|---|
| 95 | 3-(3-(3,4-Dihydroisoquinolin-2(1H)-yl)-2-hydroxypropyl)-1-(4-methoxybenzyl)-2-oxo-2,3-dihydro-1H-benzo[d]imidazole-5-carbonitrile; |
| 96 | 3-(3-(3,4-Dihydroisoquinolin-2(1H)-yl)-2-hydroxypropyl)-5-fluoro-1-(4-methoxybenzyl)-1,3-dihydro-2H-benzo[d]imidazol-2-one; |
| 97 | 3-(3-(3,4-Dihydroisoquinolin-2(1H)-yl)-2-hydroxypropyl)-5-fluoro-1-(4-(methylsulfonyl)benzyl)-1,3-dihydro-2H-benzo[d]imidazol-2-one; |
| 98 | 6-((3-(3-(3,4-Dihydroisoquinolin-2(1H)-yl)-2-hydroxypropyl)-5-fluoro-2-oxo-2,3-dihydro-1H-benzo[d]imidazol-1-yl)methyl)nicotinonitrile; |
| 99 | 6-43-(3-(3,4-dihydroisoquinolin-2(1H)-yl)-2-hydroxypropyl)-2-oxo-2,3-dihydro-1H-imidazo[4,5-b]pyridin-1-yl)methyl)nicotinonitrile; |
| 100 | 4-(((3aR,7aR)-3-(3-(3,4-Dihydroisoquinolin-2(1H)-yl)-2-hydroxypropyl)-2-oxooctahydro-1H-benzo[d]imidazol-1-yl)methyl)benzonitrile; |
| 101 | 4-(((3aR,7aS)-3-(3-(3,4-dihydroisoquinolin-2(1H)-yl)-2-hydroxypropyl)-2-oxooctahydro-1H-benzo[d]imidazol-1-yl)methyl)benzonitrile; |
| 102 | (R)-6-((3-(3-(3,4-dihydroisoquinolin-2(1H)-yl)-2-hydroxypropyl)-2-oxoimidazolidin-1-yl)methyl)-5-(piperidine-1-carbonyl)nicotinonitrile; |
| 103 | R)-5-(4-acetylpiperazine-1-carbonyl)-6-((3-(3-(3,4-dihydroisoquinolin-2(1H)-yl)-2-hydroxypropyl)-2-oxoimidazolidin-1-yl)methyl)nicotinonitrile; |
| 104 | (R)-N-(6-((3-(3-(3,4-dihydroisoquinolin-2(1H)-yl)-2-hydroxypropyl)-2-oxoimidazolidin-1-yl)methyl)pyridin-3-yl)oxetane-3-carboxamide; |
| 105 | (R)-N-(6-((3-(3-(3,4-dihydroisoquinolin-2(1H)-yl)-2-hydroxypropyl)-2-oxoimidazolidin-1-yl)methyl)pyridin-3-yl)cyclopentanecarboxamide; |
| 106 | (R)-N-(6-((3-(3-(3,4-dihydroisoquinolin-2(1H)-yl)-2-hydroxypropyl)-2-oxoimidazolidin-1-yl)methyl)pyridin-3-yl)cyclobutanecarboxamide; |
| 107 | (R)-N-(6-((3-(3-(3,4-dihydroisoquinolin-2(1H)-yl)-2-hydroxypropyl)-2-oxoimidazolidin-1-yl)methyl)pyridin-3-yl)tetrahydro-2H-pyran-4-carboxamide; |
| 108 | (R)-1-(3-(3,4-dihydroisoquinolin-2(1H)-yl)-2-hydroxypropyl)-3-((5-((tetrahydro-2H-pyran-4-yl)amino)pyridin-2-yl)methyl)imidazolidin-2-one; |
| 109 | (R)-1-(3-(3,4-dihydroisoquinolin-2(1H)-yl)-2-hydroxypropyl)-3-((5-((tetrahydro-2H-pyran-4-yl)amino)pyridin-2-yl)methyl)imidazolidin-2-one; |
| 110 | (R)-1-(3-(3,4-dihydroisoquinolin-2(1H)-yl)-2-hydroxypropyl)-3-((5-(oxetan-3-ylethynyl)pyridin-2-yl)methyl)imidazolidin-2-one; |

Pharmaceutical Compositions

In certain embodiments, present invention provides a pharmaceutical composition comprising the compound of formula (I) or a pharmaceutically acceptable salt or a stereoisomer thereof or a pharmaceutically acceptable carrier or excipient.

In certain embodiments, the pharmaceutical composition of the invention further comprises at least one agent selected from an anticancer agent, a chemotherapy agent and an antiproliferative compound.

In certain embodiments, an anticancer agent, a chemotherapy agent and an antiproliferative compound is selected from 1) an aldosterone synthase inhibitor; 2) an ALK inhibitor; an apoptosis inducer; 3) an aromatase inhibitor; 4) a CART cell (e.g., a CART cell targeting CD19; 5) a BCR-ABL inhibitor; 6) a BRAF inhibitor; 7) a CDK4/6-inhibitor; 8) a CEACAM (e.g., CEACAM-1, -3 and/or -5) inhibitor; 9) a c-KIT inhibitor; 10) a c-MET inhibitor; 10) a cRAP inhibitor; 11) a CTLA4 inhibitor; 12) a cytochrome P450 inhibitor (e.g., a CYP17 inhibitor); 13) an EGF inhibitor; 14) an ERK1/2 ATP inhibitor; 15) an FGF inhibitor (e.g., a FGFR2 or FGFR4 inhibitor); 16) a Flt3 inhibitor (e.g., FLK2/STK1); 17) a P-Glycoprotein 1 inhibitor; 18) a HDAC inhibitor; 19) a HDM2 inhibitor; 20) a HER3 inhibitor; 21) a histamine release inhibitor; 22) an HSP90 inhibitor: 23) an IAP inhibitor; 24) an IDH inhibitor; 25) an IDO inhibitor 26) an IGF-1R inhibitor; 27) an iron chelating agent; 28) a Janus inhibitor; 29) a LAG-3 inhibitor; 30) an M-CSF inhibitor; 31) a MEK inhibitor; 32) an mTOR inhibitor; 33) a p53 inhibitor (e.g., an inhibitor of a p53/Mdm2 interaction); 34) a PDGFRβ inhibitor; 35) a PKC inhibitor; 36) a PI3K inhibitor; 37) a PIM inhibitor; 38) a PRLR inhibitor; 39) a Raf kinase C inhibitor; 40) a smoothened (SMO) receptor inhibitor; 41) a somatostatin agonist and/or a growth hormone release inhibitor; 42) a transduction modulator and/or angiogenesis inhibitor; 43) a VEGFR-2 inhibitor (e.g., FLK-1/KDR); 44) a tyrosine kinase inhibitor (e.g., CSF-1R tyrosine kinase); 45) a Wnt signaling inhibitor 46) a Bcl-2 inhibitor; 47) a Mcl-1 inhibitor; 48) a BTK inhibitor; 49) dual active molecules such as CUDC-907 (a dual PI3K/HDAC inhibitor); and 50) BET bromodomain inhibitor.

The compositions and methods of the present invention may be utilized to treat an individual in need thereof. In certain embodiments, the individual is a mammal such as a human or a non-human mammal. When administered to an animal, such as human, the composition or the compound is preferably administered as a pharmaceutical composition comprising, for example, a compound of the invention or a pharmaceutically acceptable carrier. Pharmaceutically acceptable carriers are well known in the art and include, for example, aqueous solutions such as water or physiologically buffered saline or other solvents or vehicles such as glycols, glycerol, oils such as olive oil or injectable organic esters. In a preferred embodiment, when such pharmaceutical compositions are for human administration, particularly for invasive routes of administration (i.e., routes, such as injection or implantation, that circumvent transport or diffusion through an epithelial barrier), the aqueous solution is pyrogen-free or substantially pyrogen-free. The excipients can be chosen, for example, to effect delayed release of an agent or to selectively target one or more cells, tissues or organs. The pharmaceutical composition can be in dosage unit form such as tablet, capsule (including sprinkle capsule and gelatin capsule), granule, lyophile for reconstitution, powder, solution, syrup, suppository, injection or the like. The composition can also be present in a transdermal delivery system, e.g., a skin patch. The composition can also be present in a solution suitable for topical administration, such as an eye drop.

A pharmaceutically acceptable carrier can contain physiologically acceptable agents that act, for example, to stabilize, increase solubility or to increase the absorption of a compound such as a compound of the invention. Such physiologically acceptable agents include, for example, carbohydrates, such as glucose, sucrose or dextrans, antioxidants, such as ascorbic acid or glutathione, chelating agents, low molecular weight proteins or other stabilizers or excipients. The choice of a pharmaceutically acceptable carrier, including a physiologically acceptable agent, depends, for example, on the route of administration of the composition. The preparation of pharmaceutical composition can be a self-emulsifying drug delivery system or a self-microemulsifying drug delivery system. The pharmaceutical composition (preparation) also can be a liposome or other polymer matrix, which can have incorporated therein, for example, a compound of the invention. Liposomes, for example, which comprise phospholipids or other lipids, are nontoxic, physiologically acceptable and metabolizable carriers that are relatively simple to make and administer.

The formulations may conveniently be presented in unit dosage form and may be prepared by any methods well known in the art of pharmacy. The amount of active ingredient which can be combined with a carrier material to produce a single dosage form will vary depending upon the host being treated, the particular mode of administration. The amount of active ingredient that can be combined with a carrier material to produce a single dosage form will generally be that amount of the compound which produces a therapeutic effect. Generally, out of one hundred percent, this amount will range from about 1 percent to about ninety-nine percent of active ingredient, preferably from about 5 percent to about 70 percent, most preferably from about 10 percent to about 30 percent.

Methods of preparing these formulations or compositions include the step of bringing into association an active compound, such as a compound of the invention, with the carrier and, optionally, one or more accessory ingredients. In general, the formulations are prepared by uniformly and intimately bringing into association a compound of the present invention with liquid carriers or finely divided solid carriers or both and then, if necessary, shaping the product.

Formulations of the invention suitable for oral administration may be in the form of capsules (including sprinkle capsules and gelatin capsules), cachets, pills, tablets, lozenges (using a flavored basis, usually sucrose and acacia or tragacanth), lyophile, powders, granules or as a solution or a suspension in an aqueous or non-aqueous liquid or as an oil-in-water or water-in-oil liquid emulsion or as an elixir or syrup or as pastilles (using an inert base, such as gelatin and glycerin or sucrose and acacia) and/or as mouth washes and the like, each containing a predetermined amount of a compound of the present invention as an active ingredient. Compositions or compounds may also be administered as a bolus, electuary or paste.

In certain embodiments, present invention provides a combination comprising the compound of formula (I) and pharmaceutically acceptable salt or a stereoisomer thereof and one or more therapeutically active co-agents.

In certain embodiments, present invention provides a combination comprising the compound of formula (I) and pharmaceutically acceptable salt or a stereoisomer thereof and one or more therapeutically active co-agents Agents for Combination Therapies In certain embodiments, a compound of Formula (I) can be conjointly administered with another therapeutic agent, e.g., 1) an aldosterone synthase inhibitor; 2) an ALK inhibitor; an apoptosis inducer; 3) an aromatase inhibitor; 4) a CART cell (e.g., a CART cell targeting CD19); 5) a BCR-ABL inhibitor; 6) a BRAF inhibitor; 7) a CDK inhibitor; 8) a CEACAM (e.g., CEACAM-1, -3 and/or -5) inhibitor; 9) a c-KIT inhibitor; 10) a c-MET inhibitor; 10) a cRAP inhibitor; 11) a CTLA4 inhibitor; 12) a cytochrome P450 inhibitor (e.g., a CYP17 inhibitor); 13) an EGF inhibitor; 14) an ERK1/2 ATP inhibitor; 15) an FGF inhibitor (e.g., a FGFR2 or FGFR4 inhibitor); 16) a Flt3 inhibitor (e.g., FLK2/STK1); 17) a P-Glycoprotein 1 inhibitor; 18) a HDAC inhibitor; 19) a HDM2 inhibitor; 20) a HER3 inhibitor; 21) a histamine release inhibitor; 22) an HSP90 inhibitor: 23) an IAP inhibitor; 24) an IDH inhibitor; 25) an IDO inhibitor 26) an IGF-1R inhibitor; 27) an iron chelating agent; 28) a Janus inhibitor; 29) a LAG-3 inhibitor; 30) an M-CSF inhibitor; 31) a MEK inhibitor; 32) an mTOR inhibitor; 33) a p53 inhibitor (e.g., an inhibitor of a p53/Mdm2 interaction); 34) a PDGFRβ inhibitor; 35) a PKC inhibitor; 36) a PI3K inhibitor; 37) a PIM inhibitor; 38) a PRLR inhibitor; 39) a Raf kinase C inhibitor; 40) a smoothened (SMO) receptor inhibitor; 41) a somatostatin agonist and/or a growth hormone release inhibitor; 42) a transduction modulator and/or angiogenesis inhibitor; 43) a VEGFR-2 inhibitor (e.g., FLK-1/KDR); 44) a tyrosine kinase inhibitor (e.g., CSF-1R tyrosine kinase); 45) a Wnt signaling inhibitor 46) a Bcl-2 inhibitor; 47) a Mcl-1 inhibitor; 48) a BTK inhibitor; 49) dual active molecules such as CUDC-907 (a dual PI3K/HDAC inhibitor); and 50) BET bromodomain inhibitor.

Additional therapeutic agents suitable for conjoint administration with the compounds and compositions disclosed herein have been described, for example, in the following publications: WO2016/100882; WO2016/054555; WO2016/040892; WO2015/097536; WO2015/088847; WO2015/069770; WO2015/026634; WO 2015/009856; EP 1377609 B1; Antonia, et al. Clin. Cancer Res. 2014 20:6258-6268; and Melero, et al. Nature Reviews Cancer 2015 15:457-472. Each publication is incorporated herein by reference in its entirety.

In certain embodiments, the present invention relates to a pharmaceutical composition comprising at least one compound according to compound of formula (I) or a pharmaceutically acceptable salt or a stereoisomer thereof or a pharmaceutically acceptable carrier or excipient.

Methods of Treatment

In certain embodiments, the present invention provides compound of formula (I) or a pharmaceutically acceptable salt or a stereoisomer thereof, as described herein, for use as a medicament.

In certain embodiments, the present invention relates to use of compound of formula (I) or a pharmaceutically acceptable salt or a stereoisomer thereof, in the manufacture of a medicament for inhibiting protein arginine methyltransferase 5 (PRMT5).

In certain embodiments, the invention provides the use of compound of formula (I) or a pharmaceutically acceptable salt or a stereoisomer thereof, as described herein, in the manufacture of medicament for the treatment of diseases or disorders mediated by PRMT5.

In certain embodiments, the invention provides a method of treating cancer or proliferative disorder, comprising administration of a therapeutically effective amount of compound of formula (I) or a pharmaceutically acceptable salt or a stereoisomer thereof.

In certain embodiments, the present invention provides methods for inhibiting growth of tumour cells and/or metastasis by administering a therapeutically effective amount of compound of formula (I) or a pharmaceutically acceptable salt or a stereoisomer thereof.

In certain embodiments, the present invention relates to method for the treatment or prevention of diseases or disorders mediated by PRMT5, comprising administering to a subject in need thereof a therapeutically effective amount of a compound of formula (I) or a pharmaceutically acceptable salt or a stereoisomer thereof.

In certain embodiments, the present invention provides the method for the treatment or prevention of a cancer, an inflammatory disorder, an autoimmune disease, metabolic disorder, a hereditary disorder, a hormone-related disease, immunodeficiency disorders, a condition associated with cell death, a destructive bone disorder, thrombin-induced platelet aggregation, liver disease and a cardiovascular disorder, comprising administering to a subject in need thereof a therapeutically effective amount of a compound of formula (I) or a pharmaceutically acceptable salt or a stereoisomer thereof.

In certain embodiments, the use of compound of formula (I) or a pharmaceutically acceptable salt or a stereoisomer thereof in the manufacture of a medicament for the treatment of cancer, inflammatory disorder, autoimmune disease, metabolic disorder, hereditary disorder, hormone-related disease, immunodeficiency disorders, condition associated with cell death, destructive bone disorder, thrombin-induced platelet aggregation, liver disease and a cardiovascular disorder.

In certain embodiments, the invention provides the use of the compounds of the present invention in the manufacture of medicament for the treatment and prevention of a proliferative disease. In certain embodiments, the proliferative disease is cancer. In certain embodiments, the proliferative disease is benign neoplasm, a disease associated with angiogenesis, an inflammatory disease, an autoinflammatory disease or an autoimmune disease. In certain embodiments, the cancer is a lymphoma. In certain embodiments, the cancer is leukemia. In certain embodiments, the cancer is Hodgkin's lymphoma. In certain embodiments, the cancer is non-Hodgkin's lymphoma. In certain embodiments, the cancer is Burkitt's lymphoma. In certain embodiments, the cancer is diffuse large B-cell lymphoma (DLBCL). In certain embodiments, the cancer is MALT lymphoma. In some embodiments, the cancer is germinal center B-cell-like diffuse large B-cell lymphoma (GCB-DLBCL) or primary mediastinal B-cell lymphoma (PMBL). In some embodiments, the cancer is activated B-cell-like diffuse large B-cell lymphoma (ABC-DLBCL).

In any of the foregoing embodiments, the cancer or proliferative disorder is selected the group consisting of a solid tumor, benign or malignant tumor, carcinoma of the brain, kidney, lung, liver, stomach, vagina, ovaries, esophageal, gastric tumors, breast, bladder, colon, prostate, pancreas, lung, cervix, testis, skin, bone or thyroid; sarcoma, glioblastomas, neuroblastomas, multiple myeloma, gastrointestinal cancer, a tumor of the neck and head, an epidermal hyperproliferation, psoriasis, prostate hyperplasia, a neoplasia, adenoma, adenocarcinoma, rectum adenocarcinoma, colon adenocarcinoma, lung adenocarcinoma keratoacanthoma, epidermoid carcinoma, hepatocellular carcinoma, large cell carcinoma, renal cell carcinoma, oligodendoglioma, ovarian clear cell carcinoma, ovarian serous crystadenocarcinoma, non-small-cell lung carcinoma, lymphomas, Hodgkins and Non-Hodgkins, a mammary carcinoma, follicular carcinoma, papillary carcinoma, seminoma, melanoma; hematopoietic carcinoma, hematological malignancies selected from leukemia, diffuse large B-cell lymphoma (DLBCL), activated B-cell-like DLBCL, chronic lymphocytic leukemia (CLL), chronic lymphocytic lymphoma, primary effusion lymphoma, Burkitt lymphoma/leukemia, acute lymphocytic leukemia, B-cell pro lymphocytic leukemia, lymphoplasmacytic lymphoma, Waldenstrom's macroglobulnemia (WM), splenic marginal zone lymphoma, intravascular large B-cell lymphoma, plasmacytoma and multiple myeloma.

In certain embodiments, the present invention relates to method of inhibiting protein arginine methyltransferase 5 (PRMT5), comprising administering to a subject in need thereof a therapeutically effective amount of a compound of formula (I) or a pharmaceutically acceptable salt or a stereoisomer thereof.

In certain embodiments, the present invention relates to compound of formula (I) or a pharmaceutically acceptable salt or a stereoisomer thereof, for use in the treatment or prevention of diseases or disorders mediated by PRMT5.

In certain embodiments, the diseases or disorders mediated by PRMT5 is cancer, a blood disorder, an inflammatory disorder, an autoimmune disease, proliferative disorder, metabolic disorder, a hereditary disorder, a hormone-related disease, immunodeficiency disorders, a condition associated with cell death, a destructive bone disorder, thrombin-induced platelet aggregation, liver disease or a cardiovascular disorder.

In certain embodiments, the diseases or disorders mediated by PRMT5 is cancer, a blood disorder, metabolic disorder, inflammation, autoimmune disease or hemoglobinopathy.

In certain embodiments, the cancer as specified herein, is selected from medulloblastoma, glioblastoma, melanoma, ovarian cancer, lung cancer, prostate cancer, breast cancer, colon cancer, gastric cancer, esophageal cancer and hepatocellular carcinoma.

In certain embodiments, the blood disorder is sickle cell anemia or beta-thalessemia.

In certain embodiments, the metabolic disorder is diabetes or obesity.

In certain embodiments, the present invention relates to use of compound of formula (I) or a pharmaceutically acceptable salt or a stereoisomer thereof, in the manufacture of a medicament for the treatment or prevention of cancer.

In certain embodiments, the present invention relates to use of compound of formula (I) or a pharmaceutically acceptable salt or a stereoisomer thereof, in the manufacture of a medicament for the treatment or prevention of diseases or disorders selected from medulloblastoma, glioblastoma, melanoma, ovarian cancer, lung cancer, prostate cancer, breast cancer, colon cancer, gastric cancer, esophageal cancer and hepatocellular carcinoma.

In certain embodiments, the present invention provides a compound of formula (I):

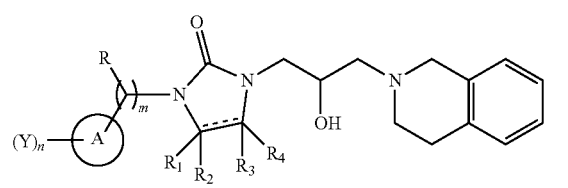

or a pharmaceutically acceptable salt or a stereoisomer thereof; for use in the treatment of cancer, wherein, ~~~~~ represents a single bond or double bond;

A is aryl, heteroaryl, cycloalkyl or heterocycloalkyl;

Y is hydrogen, —SO$_2$R$_a$, —NR$_a$R$_b$, —C(O)R$_a$, —C(O)NR$_a$R$_b$, —NHC(O)R$_a$, —COOH, cyano, halogen, haloalkyl, alkyl, alkenyl, alkynyl, alkoxy, hydroxyl or oxo; wherein the said alkyl, alkenyl and alkynyl are optionally substituted with 1 to 3 groups selected from hydroxyl, halogen, acyl and heterocycloalkyl;

R is hydrogen, alkyl or halogen;

R$_a$ is hydrogen, alkyl, halogen, alkoxy, heterocycloalkyl or cycloalkyl; wherein the heterocycloalkyl and cycloalkyl are optionally substituted with 1 to 3 groups selected from alkyl, hydroxyl, halogen and acyl;

R$_b$ is hydrogen or alkyl;

R$_1$ is hydrogen or alkyl; R$_2$ is hydrogen, alkyl or absent; or R$_1$ and R$_2$ together represents an oxo group;

R$_3$ is hydrogen or alkyl; R$_4$ is hydrogen, alkyl, aryl or absent; or R$_3$ and R$_4$ together with the atoms to which they are attached form 3- to 8-membered cycloalkyl ring;

alternatively, R$_1$ and R$_3$ together with the atoms to which they are attached form, an optionally substituted aryl, heteroaryl or cycloalkyl, wherein the optional substituent is selected from 1 to 3 occurrences of R$_5$;

R$_5$ is alkyl, halogen or cyano;

'n' is 1, 2 or 3;

'm' is 0 or 1.

Definitions

Unless defined otherwise, all technical and scientific terms used herein have the same meaning as is commonly understood by one of skill in art to which the subject matter herein belongs. As used in the specification and the appended claims, unless specified to the contrary, the following terms have the meaning indicated in order to facilitate the understanding of the present invention.

As used herein, the term 'compound(s)' comprises the compounds disclosed in the present invention.

As used herein, the phrase "compound(s) of present invention" means the compounds described in this specification or a pharmaceutically acceptable salt or a stereoisomer thereof.

The singular forms "a", "an" and "the" encompass plural references unless the context clearly indicates otherwise.

As used herein, the terms "optional" or "optionally" mean that the subsequently described event or circumstance may occur or may not occur and that the description includes instances where the event or circumstance occurs as well as instances in which it does not.

For example, "optionally substituted alkyl" refers to the alkyl may be substituted as well as the event or circumstance where the alkyl is not substituted.

The term "substituted" refers to moieties having substituents replacing hydrogen on one or more carbons of the backbone. It will be understood that "substitution" or "substituted with" includes the implicit proviso that such substitution is in accordance with permitted valence of the substituted atom and the substituent and that the substitution results in a stable compound, e.g., which does not spontaneously undergo transformation such as by rearrangement, cyclization, elimination, etc. As used herein, the term "substituted" is contemplated to include all permissible substituents of organic compounds. In a broad aspect, the permissible substituents include acyclic and cyclic, branched and unbranched, carbocyclic and heterocyclic, aromatic and non-aromatic substituents of organic compounds. The permissible substituents can be one or more and the same or different for appropriate organic compounds. For purposes of this invention, the heteroatoms such as nitrogen may have hydrogen substituents and/or any permissible substituents of organic compounds described herein which satisfy the valences of the heteroatoms. Substituents can include any substituents described herein, for example, a halogen, a hydroxyl, a carbonyl (such as a carboxyl, an alkoxycarbonyl, a formyl or an acyl), a thiocarbonyl (such as a thioester, a thioacetate or a thioformate), an alkoxyl, an oxo, a phosphoryl, a phosphate, a phosphonate, a phosphinate, an amino, an amido, an amidine, an imine, a cyano, a nitro, an azido, a sulfhydryl, an alkylthio, a sulfate, a sulfonate, a sulfamoyl, a sulfonamido, a sulfonyl, a heteroaryl, a heterocycloalkyl, an aralkyl or an aromatic or heteroaromatic moiety. It will be understood by those skilled in the art that substituents can themselves be substituted, if appropriate.

As used herein, the term "alkyl" refers to saturated aliphatic groups, including but not limited to $C_1$-$C_{10}$ straight-chain alkyl groups or $C_3$-$C_{10}$ branched-chain alkyl groups. Preferably, the "alkyl" group refers to $C_1$-$C_6$ straight-chain alkyl groups or $C_3$-$C_6$ branched-chain alkyl groups. Most preferably, the "alkyl" group refers to $C_1$-$C_4$ straight-chain alkyl groups or $C_3$-$C_8$ branched-chain alkyl groups. Examples of "alkyl" include, but are not limited to, methyl, ethyl, 1-propyl, 2-propyl, n-butyl, sec-butyl, tert-butyl, 1-pentyl, 2-pentyl, 3-pentyl, neo-pentyl, 1-hexyl, 2-hexyl, 3-hexyl, 1-heptyl, 2-heptyl, 3-heptyl, 4-heptyl, 1-octyl, 2-octyl, 3-octyl and 4-octyl. The "alkyl" group may be optionally substituted.

As used herein, the term "alkenyl" refers to a carbon chain which contains at least one carbon-carbon double bond and which may be linear or branched or combinations thereof. Examples of "alkenyl" include, but not limited to, vinyl, allyl, isopropenyl, pentenyl, hexenyl, heptenyl, 1-propenyl, 2-butenyl and 2-methyl-2-butenyl. The "alkenyl" group may be optionally substituted.

As used herein, the term "alkynyl" refers to straight or branched carbon chains with one or more triple bonds wherein the number atoms is in the range $C_2$ to $C_6$. The "alkynyl" group may be optionally substituted.

As used herein, the term "halo" or "halogen" alone or in combination with other term(s) means fluorine, chlorine, bromine or iodine.

As used herein, the term "haloalkyl" means alkyl substituted with one or more halogen atoms, wherein the halo and alkyl groups are as defined above. The term "halo" is used herein interchangeably with the term "halogen" meaning F, $C_1$, Br or I. Examples of "haloalkyl" include, but are not limited to fluoromethyl, difluoromethyl, chloromethyl, trifluoromethyl and 2,2,2-trifluoroethyl.

As used herein, the term "hydroxy" or "hydroxyl" alone or in combination with other term(s) means —OH.

As used herein, the term "oxo" refers to =O group.

As used herein, the term "alkoxy" refers to the group —O-alkyl, where alkyl groups are as defined above. Exemplary $C_1$-$C_{10}$ alkoxy group include but are not limited to methoxy, ethoxy, n-propoxy, n-butoxy or t-butoxy. An alkoxy group can be optionally substituted with one or more suitable groups.

As used herein, the term "cyano" refers to —CN group.

As used herein, "amino" refers to an —NH$_2$ group.

As used herein the term "cycloalkyl" alone or in combination with other term(s) means $C_3$-$C_{10}$ saturated cyclic hydrocarbon ring. A cycloalkyl may be a single ring, which typically contains from 3 to 7 carbon ring atoms. Examples of single-ring cycloalkyls include but are not limited to cyclopropyl, cyclobutyl, cyclopentyl, cyclohexyl and cycloheptyl. A cycloalkyl may alternatively be polycyclic or contain more than one ring. Examples of polycyclic cycloalkyls include bridged, fused and spirocyclic carbocyclyls.

As used herein, the term "heterocycloalkyl" refers to a non-aromatic, saturated or partially saturated, bridged bicyclic, spirocyclic, monocyclic or polycyclic ring system of 3 to 15 member having at least one heteroatom or heterogroup selected from O, N, S, S(O), S(O)$_2$, NH or C(O) with the remaining ring atoms being independently selected from the group consisting of carbon, oxygen, nitrogen and sulfur. The term "heterocycloalkyl" also refers to the bridged bicyclic ring system having at least one heteroatom or heterogroup selected from O, N, S, S(O), S(O)$_2$, NH or C(O). Examples of "heterocycloalkyl" include, but are not limited to azetidinyl, oxetanyl, imidazolidinyl, pyrrolidinyl, oxazolidinyl, thiazolidinyl, pyrazolidinyl, tetrahydrofuranyl, piperidinyl, piperazinyl, tetrahydropyranyl, morpholinyl, thiomorpholinyl, 1,4-dioxanyl, pyridin-2(1H)-one, dioxidothiomorpholinyl, oxapiperazinyl, oxapiperidinyl, tetrahydrofuryl, tetrahydropyranyl, tetrahydrothiophenyl, dihydropyranyl, indolinyl, indolinylmethyl, aza-bicyclooctanyl, azocinyl, chromanyl, isochromanyl xanthenyl, 2-oxa-6-azaspiro[3.3]heptanyl, 3-oxa-8-azabicyclo[3.2.1]octanyl and N-oxides thereof. Attachment of a heterocycloalkyl substituent can occur via either a carbon atom or a heteroatom. A heterocycloalkyl group can be optionally substituted with one or more suitable groups by one or more aforesaid groups. Preferably "heterocycloalkyl" refers to 5- to 6-membered ring selected from the group consisting of azetidinyl, oxetanyl, imidazolidinyl, pyrrolidinyl, oxazolidinyl, thiazolidinyl, pyrazolidinyl, tetrahydrofuranyl, piperidinyl, piperazinyl, tetrahydropyranyl, morpholinyl, thiomorpholinyl, 1,4-dioxanyl, pyridin-2(1H)-one, and N-oxides thereof. More preferably, "heterocycloalkyl" includes azetidinyl, pyrrolidinyl, morpholinyl and piperidinyl. All heterocycloalkyl are optionally substituted by one or more aforesaid groups.

As used herein, the term "heteroaryl" refers to an aromatic heterocyclic ring system containing 5 to 20 ring atoms, suitably 5 to 10 ring atoms, which may be a single ring (monocyclic) or multiple rings (bicyclic, tricyclic or polycyclic) fused together or linked covalently. Preferably, "heteroaryl" is a 5- to 6-membered ring. The rings may contain from 1 to 4 heteroatoms selected from N, O and S, wherein the N or S atom is optionally oxidized or the N atom is optionally quarternized. Any suitable ring position of the heteroaryl moiety may be covalently linked to the defined chemical structure.

Examples of heteroaryl include, but are not limited to: furanyl, thienyl, pyrrolyl, pyrazolyl, imidazolyl, oxazolyl, cinnolinyl, isoxazolyl, thiazolyl, isothiazolyl, 1H-tetrazolyl, oxadiazolyl, triazolyl, pyridyl, pyrimidinyl, pyrazinyl, pyridazinyl, benzoxazolyl, benzisoxazolyl, benzothiazolyl, benzofuranyl, benzothienyl, benzotriazinyl, benzimidazolyl, indolyl, isoindolyl, indazolyl, quinolinyl, isoquinolinyl, quinazolinyl, quinoxalinyl, purinyl, pteridinyl, α-carboline, indolizinyl, benzoisothiazolyl, benzoxazolyl, pyrrolopyridyl, pyrazolopyrimidyl, furopyridinyl, benzothiadiazolyl, benzooxadiazolyl, benzotriazolyl, benzotriadiazolyl and the like. Preferably "heteroaryl" refers to 5- to 6-membered ring selected from the group consisting of furanyl, thienyl, pyrrolyl, pyrazolyl, imidazolyl, oxazolyl, cinnolinyl, isoxazolyl, thiazolyl, isothiazolyl, 1H-tetrazolyl, oxadiazolyl, triazolyl, pyridyl, pyrimidinyl, pyrazinyl and pyridazinyl. More preferably, pyrazolyl, pyridyl, oxazolyl, furanyl or benzimidazolyl. All heteroaryls are optionally substituted by one or more groups selected from alkyl, halogen, hydroxyl, carboxylic acid, alkoxycarbonyl, formyl, acyl, thiocarbonyl, thioester, thioacetate, thioformate, alkoxyl, oxo, phosphoryl, a phosphate, phosphonate, phosphinate, amino, amido, amidine, imine, cyano, nitro, azido, sulfhydryl, alkylthio, sulfate, sulfonate, sulfamoyl, sulfonamido and sulfonyl group.

As used herein, the term "aryl" is optionally substituted monocyclic, bicyclic or polycyclic aromatic hydrocarbon ring system of about 6 to 14 carbon atoms. Examples of a $C_6$-$C_{14}$ aryl group include, but are not limited to phenyl, naphthyl, biphenyl, anthryl, fluorenyl, indanyl, biphenylenyl and acenaphthyl. Aryl group can be optionally substituted with one or more substituents selected from alkyl, halogen, hydroxyl, carboxylic acid, alkoxycarbonyl, formyl, acyl, thiocarbonyl, thioester, thioacetate, thioformate, alkoxyl, oxo, phosphoryl, a phosphate, phosphonate, phosphinate, amino, amido, amidine, imine, cyano, nitro, azido, sulfhydryl, alkylthio, sulfate, sulfonate, sulfamoyl, sulfonamido and sulfonyl group The term "acyl" refers to a group $R^X$—CO— wherein $R^X$ is an optionally substituted alkyl group defined above. Examples of 'acyl' groups are, but not limited to, $CH_3CO$—, $CH_3CH_2CO$—, $CH_3CH_2CH_2CO$— or $(CH_3)_2CHCO$—.

The term "monocyclic ring" refers to a saturated, partially saturated or aromatic one ring of atom.

The term "bicyclic ring" refers to a saturated, partially saturated or aromatic two fused ring of atom.

The term "fused ring" refers to a ring which is part of a ring system with two rings having at least one bond and two atoms in common.

The term "spiro" refers to a ring system consisting of two rings having only one carbon atom in common.

The term "heteroatom" as used herein designates a sulfur, nitrogen or oxygen atom.

The term "bridged bicyclic" refers to a two rings share three or more atoms, separating the two bridgehead atoms by a bridge containing at least one atom.

As used herein, the term "comprise" or "comprising" is generally used in the sense of include, that is to say permitting the presence of one or more features or components As used herein, the term "or" means "and/or" unless stated otherwise.

As used herein, the term "including" as well as other forms, such as "include", "includes" and "included" is not limiting.

As used herein, the term "composition" is intended to encompass a product comprising the specified ingredients in the specified amounts, as well as any product which results, directly or indirectly, from combination of the specified ingredients in the specified amounts. By "pharmaceutically acceptable" it is meant the carrier, diluent or excipient must be compatible with the other ingredients of the formulation and not deleterious to the recipient thereof.

As used herein, the term "pharmaceutical composition" refers to a composition(s) containing a therapeutically effective ntt least one compound of formula (I) or a pharmaceutically acceptable salt thereof; or a pharmaceutically acceptable carrier.

The pharmaceutical composition(s) usually contain(s) about 1% to 99%, for example, about 5% to 75% or from about 10% to about 30% by weight of the compound of formula (I) or (II) or pharmaceutically acceptable salts thereof. The amount of the compound of formula (I) or pharmaceutically acceptable salts thereof in the pharmaceutical composition(s) can range from about 1 mg to about 1000 mg or from about 2.5 mg to about 500 mg or from about 5 mg to about 250 mg or in any range falling within the broader range of 1 mg to 1000 mg or higher or lower than the afore mentioned range.

As used herein, the term "treat", "treating" and "treatment" refer to a method of alleviating or abrogating a disease and/or its attendant symptoms.

As used herein, the term "prevent", "preventing" and "prevention" refer to a method of preventing the onset of a disease and/or its attendant symptoms or barring a subject from acquiring a disease. As used herein, "prevent", "preventing" and "prevention" also include delaying the onset of a disease and/or its attendant symptoms and reducing a subject's risk of acquiring a disease.

As used herein, the term "subject" that may be interchangeable with 'patient', refers to an animal, preferably a mammal and most preferably a human.

As used herein, the term, "therapeutically effective amount" refers to an amount of a compound of formula (I) or a pharmaceutically acceptable salt or a stereoisomer thereof; or a composition comprising the compound of formula (I) or a pharmaceutically acceptable salt or a stereoisomer thereof, effective in producing the desired therapeutic response in a particular patient suffering from a diseases or disorder, in particular their use in diseases or disorder associated with cancer. Particularly, the term "therapeutically effective amount" includes the amount of the compound of formula (I) or a pharmaceutically acceptable salt or a stereoisomer thereof, when administered, that induces a positive modification in the disease or disorder to be treated or is sufficient to prevent development of or alleviate to some extent, one or more of the symptoms of the disease or disorder being treated in a subject. In respect of the therapeutic amount of the compound, the amount of the compound used for the treatment of a subject is low enough to avoid undue or severe side effects, within the scope of sound medical judgment can also be considered. The therapeutically effective amount of the compound or composition will be varied with the particular condition being treated, the severity of the condition being treated or prevented, the duration of the treatment, the nature of concurrent therapy, the age and physical condition of the end user, the specific compound or composition employed the particular pharmaceutically acceptable carrier utilized.

The term "pharmaceutically acceptable salt" refers to a product obtained by reaction of the compound of the present invention with a suitable acid or a base. Pharmaceutically acceptable salts of the compounds of this invention include those derived from suitable inorganic bases such as Li, Na, K, Ca, Mg, Fe, Cu, Al, Zn and Mn salts; Examples of pharmaceutically acceptable, nontoxic acid addition salts are salts of an amino group formed with inorganic acids such as hydrochloride, hydrobromide, hydroiodide, nitrate, sulfate, bisulfate, phosphate, isonicotinate, acetate, lactate, salicylate, citrate, tartrate, pantothenate, bitartrate, ascorbate, succinate, maleate, gentisinate, fumarate, gluconate, glucaronate, saccharate, formate, benzoate, glutamate, methanesulfonate, ethanesulfonate, benzenesulfonate, 4-methylbenzenesulfonate or p-toluenesulfonate salts and the like. Certain compounds of the invention (compound of formula (I)) can form pharmaceutically acceptable salts with various organic bases such as lysine, arginine, guanidine, diethanolamine or metformin. Suitable base salts include, but are not limited to, aluminum, calcium, lithium, magnesium, potassium, sodium or zinc salts.

"Pharmaceutically acceptable" means that, which is useful in preparing a pharmaceutical composition that is generally safe, non-toxic and neither biologically nor otherwise undesirable and includes that which is acceptable for veterinary as well as human pharmaceutical use.

The present invention also provides methods for formulating the disclosed compounds as for pharmaceutical administration.

In a preferred embodiment, when such pharmaceutical compositions are for human administration, particularly for invasive routes of administration (i.e., routes, such as injection or implantation, that circumvent transport or diffusion through an epithelial barrier), the aqueous solution is pyrogen-free or substantially pyrogen-free. The excipients can be chosen, for example, to effect delayed release of an agent or to selectively target one or more cells, tissues or organs. The pharmaceutical composition can be in dosage unit form such as tablet, capsule (including sprinkle capsule and gelatin capsule), granule, lyophile for reconstitution, powder, solution, syrup, suppository, injection or the like. The composition can also be present in a transdermal delivery system, e.g., a skin patch. The composition can also be present in a solution suitable for topical administration, such as an eye drop.

The term "stereoisomers" refers to any enantiomers, diastereoisomers or geometrical isomers of the compounds of formula (I), wherever they are chiral or when they bear one or more double bonds. When the compounds of the formula (I) and related formulae are chiral, they can exist in racemic or in optically active form. It should be understood that the invention encompasses all stereochemical isomeric forms, including diastereomeric, enantiomeric and epimeric forms, as well as d-Isomers and l-Isomers and mixtures thereof. Individual stereoisomers of compounds can be prepared synthetically from commercially available starting materials which contain chiral centers or by preparation of mixtures of enantiomeric products followed by separation such as conversion to a mixture of diastereomers followed by separation or recrystallization, chromatographic techniques, direct separation of enantiomers on chiral chromatographic columns or any other appropriate method known in the art. Starting compounds of particular stereochemistry are either commercially available or can be made and resolved by techniques known in the art. Additionally, the compounds of the present invention may exist as geometric Isomers. The present invention includes all cis, trans, syn, anti, entgegen (E) and zusammen (Z) Isomers as well as the appropriate mixtures thereof.

The compounds of the present invention may be used as single drug or as a pharmaceutical composition in which the compound is mixed with various pharmacologically acceptable materials.

Abbreviations

The following abbreviations are used in this specification: DMSO—Dimethylsulfoxide; DIPEA—N,N-Diisopropylethylamine; THF—Tetrahydrofuran; IPA—Isopropyl alcohol; NaH— Sodium hydride; $OsO_4$— Osmium tetraoxide; $NaIO_4$— Sodium Periodate; $K_2CO_3$— Potassium carbonate; CuI— Copper iodide; TFA—Trifluoro acetic acid; $NaBH_4$— Sodium borohydride; TBAI—Tetra butyl ammonium iodide; DMAP—4-Dimethyl-aminopyridine; $PBr_3$— Phosphorous tribromide; EtOAc—Ethyl Acetate; TMSOTf—Trimethylsilyl trifluoromethanesulfonate; $Pd(dppf)Cl_2$—[1,1'-Bis(diphenylphosphino)ferrocene]palladium (II) dichloride; $PPh_3$—Triphenyl phosphine; $NH_4Cl$—Ammonium chloride; $SOCl_2$—Thionyl chloride; $Pd_2(dba)_3$—Tris(dibenzylideneacetone)dipalladium(0);

dppf—1,1'-Bis(diphenylphosphino)ferrocene; HATU—1-[Bis(dimethylamino)methylene]-1H-1,2,3-triazolo[4,5-b]pyridinium 3-oxid hexafluorophosphate; DEA—Diethanolamine; DME—Dimethoxy ethane; $Zn(CN)_2$— Zinc cyanide; CDI—1,1'-Carbonyldiimidazole; conc—Concentrated; $CHCl_3$—Chloroform; $CDCl_3$//chloroform-d—Deuterated Chloroform; DMSO-$d_6$—Deuterated dimethylsulfoxide; DCM—Dichloromethane; DMF—N, N—Dimethylformamide; RT—Room temperature; g—Gram; h—Hours; $^1H$— Proton; J—Coupling Constant; LC-MS— Liquid Chromatography-Mass Spectroscopy; HPLC—High-performance liquid chromatography; chiral HPLC—chiral high-performance liquid chromatography; M—Molar; MHz—Mega Hertz (frequency); MS—Mass Spectroscopy; mmol—Milli Mole; mL—Milli Litre; min—Minutes; mol—Moles; $M^+$—Molecular ion; m/z—mass to charge ratio; N—Normality; NMR—Nuclear Magnetic Resonance; TEA—Triethyl amine; rt/RT—Room temperature; s—Singlet; d—Doublet, t—Triplet; q—Quartet; m—Multiplet; dd—doublet of doublets; td—triplet of doublets; qd—quartet of doublets; ddd—doublet of doublet of doublets; dt—doublet of triplets; ddt—doublet of doublet of triplets; p—pentate; TLC—Thin Layer Chromatography; THF—Tetrahydrofuran; μ—Micron; μL—Micro liter and δ—Delta.

Experiments

Purification Methods Used:
A=Column chromatography, Column Chiral Pak IA (10 mm×250 mm, 5 micron); Mobile Phase: IPA:MeOH (7:3) (A), 0.1% DEA/Acetonitrile (B); Flow Rate: 9 mL/min; Isocratic: 40:60 (A:B).
B=Column chromatography, Column Chiral Pak IA (10 mm×250 mm, 5 micron); Mobile Phase: n-Hexane (A); 0.1% DEA in IPA:Ethanol (80:20) (B); Flow Rate: 8 mL/min; Isocratic: 93:7 (A:B).

Intermediate 1: 6-(Chloromethyl)-1-methyl-1H-benzo[d]imidazole (A-1)

To a stirred solution of (1-methyl-1H-benzo[d]imidazol-6-yl) methanol (1.8 g, 11.098 mmol) in 60.0 mL of $CHCl_3$ was added $SOCl_2$ (5.4 mL) at 0° C. The reaction mixture was stirred for 12 h at RT. The reaction mixture was quenched with water and basified with $Na_2CO_3$ and extracted with DCM. The combined extracts were washed with water and brine solution, dried over anhydrous sodium sulphate and concentrated to give the title compound (1.8 g, 90.0%); LCMS $[M+H]^+$181.2.

Intermediate 2: 1-((6-Chloropyridin-3-yl)methyl)-3-(oxiran-2-ylmethyl)imidazolidin-2-one (B-2)

a) 1-((6-Chloropyridin-3-yl)methyl)imidazolidin-2-one (B-1)

To a stirred solution of imidazolidin-2-one (5.0 g, 58.07 mmol) in 200 mL of THF, was added potassium tert-butoxide (6.5 g, 58.07 mmol). The reaction mixture was stirred for 1 h at RT followed by addition of 2-chloro-5-(chloromethyl)pyridine (9.4 g, 58.07 mmol). The mixture was stirred for 4 h, MeOH (1.0 mL) was added followed by stirring for 12 h at RT. The reaction mixture was diluted with water and extracted with 10% methanol and chloroform mixture. The combined extracts were washed with water and brine and dried over anhydrous sodium sulphate. The organic layer was concentrated. The residue obtained was triturated with diethyl ether and dried on vacuum to give the title compound (1.5 g, 12.19%); LCMS $[M+H]^+$ 212.2.

b) 1-((6-Chloropyridin-3-yl)methyl)-3-(oxiran-2-ylmethyl)imidazolidin-2-one (B-2)

To a stirred solution of 1-((6-chloropyridin-3-yl)methyl) imidazolidin-2-one (1.5 g, 7.1 mmol) in 20.0 mL of DMF was added NaH (0.426 g, 10.6 mmol) at 0° C. The reaction mixture was stirred for 30 min at 0° C. Epibromohydrin (1.46 g, 10.6 mmol) was then added followed by stirring for 12 h at RT. The reaction mixture was quenched with water and extracted with ethyl acetate. The combined extracts were washed with water and brine, dried over anhydrous sodium sulphate and concentrated. The residue was used without further purification (1.5 g, 79.36%); LCMS $[M+H]^+$ 268.2.

Intermediate 3: 1-(2-((tert-Butyldimethylsilyl)oxy)-3-(3,4-dihydroisoquinolin-2(1H)-yl)-propyl)imidazolidin-2-one (C-6)

a) Tert-Butyl (2-((4-methoxybenzyl)amino)ethyl) carbamate (C-1)

To a stirred solution of 4-methoxybenzaldehyde (1.0 g, 7.34 mmol) in 250 mL of methanol was added tert-butyl (2-aminoethyl)carbamate (1.29 g, 8.07 mmol) followed by stirring for 2 h at RT. The reaction mixture was cooled to 0° C. followed by addition of $NaBH_4$ (1.39 g, 36.7 mmol). Stirring was continued for 12 h at RT. The reaction mixture was concentrated, the residue was diluted with water and extracted with DCM. The combined extracts were washed with water and brine and then dried over anhydrous sodium sulphate. The organic layer was concentrated to give the title compound (2.0 g, 97.56%); LCMS $[M+H]^+$281.3.

b) 1-(4-Methoxybenzyl)imidazolidin-2-one (C-2)

To a stirred solution of tert-butyl (2-((4-methoxybenzyl) amino)ethyl)carbamate (2.0 g, 7.13 mmol) in 30 mL of THF was added potassium tert-butoxide (2.4 g, 21.4 mmol). The reaction mixture was stirred for 12 h at reflux temperature followed by addition of ethyl acetate. The organic layer was washed with water and brine and dried over anhydrous sodium sulphate. The residue was purified by Combi flash column chromatography eluted with 5% MeOH/DCM to give the title compound (1.0 g, 68%). LCMS $[M+H]^+$207.3.

c) 1-(4-Methoxybenzyl)-3-(oxiran-2-ylmethyl)imidazolidin-2-one (C-3)

To a stirred solution of 1-(4-methoxybenzyl)imidazolidin-2-one (1.0 g, 4.84 mmol) in 20 mL of THF was added NaH (0.29 g, 7.27 mmol) at 0° C. The reaction mixture was stirred for 30 min at 0° C. followed by addition of epibromohydrin (0.996 g, 7.27 mmol). The reaction mixture was stirred for 12 h at RT. The reaction mixture was diluted with water and extracted with ethyl acetate. The combined extracts were washed with water and brine and dried over anhydrous sodium sulphate. The residue was purified by Combi flash column chromatography eluted with 0-5% MeOH/DCM to give light yellow liquid compound (0.6 g, 47.61%). LCMS $[M+H]^+$263.3.

d) 1-(3-(3,4-Dihydroisoquinolin-2(1H)-yl)-2-hydroxypropyl)-3-(4-methoxybenzyl)imidazolidin-2-one (C-4)

To a 50 mL sealed tube, were added 1-(4-methoxybenzyl)-3-(oxiran-2-yl-methyl)imidazolidin-2-one (0.25 g, 0.953 mmol), 1,2,3,4-tetrahydroisoquinoline (0.139 g, 1.04 mmol), DIPEA (0.37 g, 2.85 mmol) and IPA (5.0 mL). The reaction mixture was stirred for 12 h at 100° C. The reaction mixture was distilled out and the residue (0.4 g) was purified by preparative HPLC to give the title compound (0.32 g). Prep HPLC conditions: Mobile phase: (A): 0.05% TFA in water, (B): Acetonitrile; Column: Waters×bridge c18 [(150 mm×21.2 mm), 5.µm]; Flow 20 ml/min; [Time/% B 0/30, 2/40, 10/70]; $^1$H NMR (400 MHz, CDCl$_3$) δ: 7.23-7.17 (m, 2H), 7.12 (dtd, 3H), 7.03-6.99 (m, 1H), 6.88-6.84 (m, 2H), 4.31 (d, 2H), 3.99 (ddt, 1H), 3.80 (s, 3H), 3.62 (d, 1H), 3.52-3.41 (m, 3H), 3.22-3.14 (m, 3H), 2.98-2.86 (m, 4H), 2.74 (t, 1H), 2.61-2.51 (m, 2H). LCMS [M+H]$^+$396.

e) 1-(3-(3,4-Dihydroisoquinolin-2(1H)-yl)-2-hydroxypropyl)imidazolidin-2-one (C-5)

To a 250 mL single neck round bottom flask were added 1-(3-(3,4-dihydro-isoquinolin-2(1H)-yl)-2-hydroxypropyl)-3-(4-methoxybenzyl)imidazolidin-2-one (16.0 g, 40.506 mmol) and trifluoro acetic acid (160.0 mL). The reaction mixture was stirred for 12 h at 75° C. The reaction mixture was concentrated and the residue was dissolved in DCM. The combined extracts were washed with saturated sodium bicarbonate solution and water and brine, then dried over anhydrous sodium sulphate. The organic layer was concentrated to give the title compound (5.79 g, 52.02%); LCMS [M+1] 276.3.

f) 1-(2-((tert-Butyldimethylsilyl)oxy)-3-(3,4-dihydroisoquinolin-2(1H)-yl)propyl)imidazolidin-2-one (C-6)

To a stirred solution of 1-(3-(3,4-dihydroisoquinolin-2(1H)-yl)-2-hydroxy-propyl)imidazolidin-2-one (4.0 g, 14.529 mmol) in 100.0 mL of DCM was added DIPEA (5.62 g, 43.587 mmol) and tert-butyldimethylsilyl trifluoromethanesulfonate (4.6 g, 17.435 mmol) at −78° C. The reaction mixture was stirred for 2 h at −78° C. and 1 hour at 0° C. The reaction mixture was diluted with DCM. The combined extracts were washed with saturated sodium bicarbonate solution and brine solution then dried over anhydrous sodium sulphate. The residue obtained was purified by Combi flash column chromatography eluted with 0-3% MeOH/DCM to give the title compound (2.79 g, 47%); LCMS [M+H]$^+$390.4.

Intermediate 4: 1-(4-Methylbenzyl)imidazolidin-2-one (D-1)

To a stirred solution of imidazolidin-2-one (4.0 g, 46.46 mmol) in 100 mL of THF was added potassium tet-butoxide (5.2 g, 46.46 mmol). The reaction mixture was stirred for 45 min at RT followed by addition of 1-(bromomethyl)-4-methylbenzene (8.59 g, 46.46 mmol). After stirring for 2 h MeOH (2 mL) was added to the reaction mixture followed by stirring for 12 h at RT. The reaction mixture was diluted with ethyl acetate. The combined extracts were washed with water and brine, dried over anhydrous sodium sulphate and concentrated. The residue was purified by SiO$_2$ column chromatography eluted with 5% MeOH/CHCl$_3$ to give white solid (2.0 g, 22.7%); LCMS [M+H]$^+$191.

Intermediate 5: 3-(4-Methylbenzyl)imidazolidine-2,4-dione (E-1)

To a stirred solution of imidazolidine-2,4-dione (1.5 g, 14.9 mmol) in 80 mL of DMF were added NaH (0.65 g, 16.4 mmol) and 1-(bromomethyl)-4-methylbenzene (2.77 g, 14.9 mmol) at 0° C. The reaction mixture was stirred for 12 h at RT. The reaction mixture was diluted with water and extracted with ethyl acetate. The combined extracts were washed with water and brine followed by drying over anhydrous sodium sulphate. The organic layer was concentrated to give the title compound (1.5 g, 12.19%). LCMS [M+H]$^+$205.

Intermediate 6: 4-((2,5-Dioxoimidazolidin-1-yl)methyl)benzonitrile (F-1)

To a stirred solution of imidazolidine-2,4-dione (3.0 g, 29.9 mmol) in 30 mL of DMF was added portion wise NaH (0.72 g, 29.9 mmol) at 0° C. The reaction mixture was stirred for 30 min at 0° C. followed by addition of TBAI (0.1 g, 16.4 mmol) and 4-(bromomethyl)benzonitrile (5.8 g, 29.9 mmol). The reaction mixture was stirred for 12 h at RT followed by diluting with water and extracting with ethyl acetate. The combined extracts were washed with water and brine, dried over anhydrous sodium sulphate and concentrated to give the title compound (3.0 g, 46.8%). $^1$H NMR (300 MHz, DMSO-d$_6$) δ 8.2 (s, −1H), 7.82-7.80 (dd, 1H), 7.46-7.43 (dd, 2H), 4.68 (s, 2H), 4.08 (s, 2H).

Intermediate 7: 4-((4,4-Dimethyl-2,5-dioxoimidazolidin-1-yl)methyl)benzonitrile (G-1)

To a stirred solution of 5,5-dimethylimidazolidine-2,4-dione (3.0 g, 23.4 mmol) in 50 mL of DMF, were added potassium carbonate (9.7 g, 70.2 mmol) and 4-(bromomethyl)benzonitrile (5.4 g, 28.0 mmol) at 0° C. The reaction mixture was stirred for 12 h at RT. The organic layer was washed with water and brine solution and dried over anhydrous sodium sulphate. The mixture was then diluted with water and extracted with ethyl acetate. The combined extracts were washed with water and brine and dried over anhydrous sodium sulphate and concentrated to give the title compound (3.0 g, 53.5%); $^1$H NMR (400 MHz, DMSO-d$_6$) δ 8.4 (s, 1H), 7.8-7.805 (dd, 2H), 7.41-7.39 (dd, 2H), 4.6 (s, 2H), 1.29 (s, 6H).

Intermediate 8: 1-(Bromomethyl)-4-(trifluoromethyl)benzene (H-1)

To a stirred solution of (5-(trifluoromethyl)pyridin-2-yl)methanol (0.70 g, 4.0 mmol) in 30.0 mL of DCM was added PBr$_3$ (0.6 mL, 6.0 mmol) at 0° C. followed by stirring for 6 h at RT. The reaction mixture was quenched with water, basified by saturated sodium bicarbonate and extracted with DCM. The combined extracts were washed with water and brine solution, dried over anhydrous sodium sulphate and concentrated to give the title compound (0.5 g, 52.08%). $^1$H NMR (300 MHz, DMSO-d$_6$) δ 8.962 (s, 1H), 8.274-8.241 (m, 1H), 7.811-7.783 (d, 1H), 4.786 (s, 2H).

Intermediate 9: 5-(Chloromethyl)-1-methylpyridin-2(1H)-one (I-1)

To a stirred solution of 5-(hydroxymethyl)-1-methylpyridin-2(1H)-one (0.2 g, 1.43 mmol) in 10.0 mL of DCM was added SOCl$_2$ (0.256 g, 2.15 mmol) at 0° C. followed by stirring for 3 h at RT. The reaction mixture was quenched with water, basified by saturated sodium bicarbonate and extracted with DCM. The combined extracts were washed with water and brine solution, dried over anhydrous sodium sulphate and concentrated to give the title compound (0.03 g, 13.63%). $^1$H NMR (300 MHz, DMSO-d$_6$) δ 7.881-7.873 (d, 1H), 7.505-7.464 (m, 1H), 6.434-6.403 (d, 1H), 4.595 (s, 2H), 3.407 (s, 3H).

Intermediate 10: 7-(Bromomethyl)isochromane (J-6)

a) 1-Bromo-4-(2-((2-methoxyethoxy)methoxy)ethyl) benzene (J-1)

To a stirred solution of 2-(4-bromophenyl)ethan-1-ol (5.0 g, 24.86 mmol) in 120 mL of DCM was added 1-(chloromethoxy)-2-methoxyethane (4.64 g, 37.29 mmol) and DIPEA (4.81 g, 37.29 mmol) at 0° C. followed by stirring for 16 h at RT. The reaction mixture was quenched with water and extracted with DCM. The combined extracts were washed with 1 N aqueous HCl and brine solution, dried over anhydrous sodium sulphate and concentrated to give the title compound (7.1 g, 97.49%). $^1$H NMR (300 MHz, CDCl$_3$) δ 7.41 (d, 1H), 7.39 (d, 1H), 7.13-7.11 (m, 1H), 7.11-7.07 (m, 1H), 4.69 (s, 2H), 3.76 (t, 2H), 3.61-3.55 (m, 2H), 3.52-3.46 (m, 2H), 3.38 (s, 3H), 2.84 (t, 2H).

b) 7-bromoisochromane (J-2)

To a stirred solution of 1-bromo-4-(2-((2-methoxyethoxy) methoxy)ethyl)benzene (7.10 g, 24.55 mmol) in 100 mL of acetonitrile was added dropwise TMSOTf (01.63 g, 7.36 mmol) at 0° C. followed by stirring for 16 h at RT. The reaction mixture was quenched with saturated sodium bicarbonate and concentrated. The residue was diluted with water and extracted with diethyl ether. The combined extracts were washed with brine solution and dried over anhydrous sodium sulphate. The reaction mixture was distilled out and the residue was purified by SiO$_2$ column chromatography eluted with 10% EtOAc/hexane to give the title compound (1.9 g, 36%). $^1$H NMR (300 MHz, CDCl$_3$) δ 7.30-7.26 (m, 1H), 7.15-7.10 (m, 1H), 6.99 (d, 1H), 4.73 (s, 2H), 3.95 (t, 2H), 2.80 (t, 2H).

c) 7-Vinylisochromane (J-3)

To a stirred solution of 7-bromoisochromane (1.20 g, 5.63 mmol) in 18.0 mL of ethanol, were added 1 M Cs$_2$CO$_3$ (6.0 mL) and TEA (1.13 g, 11.26 mmol) followed by degassing by argon gas for 10 min. Then potassiumvinyltrifluoborate (1.13 g, 8.44 mmol) and Pd(dppf)Cl$_2$ (0.22 g, 0.281 mmol) was added. The reaction mixture was irradiated under microwave for 1 h at 100° C. The reaction mixture was quenched with water and extracted with ethyl acetate. The combined extracts were washed brine solution and dried over anhydrous sodium sulphate. The reaction mixture was distilled out and residue was purified by SiO$_2$ column chromatography eluted with 5% EtOAc/hexane to give the title compound (0.8 g, 88%). $^1$H NMR (300 MHz, CDCl$_3$) δ 7.25-7.20 (m, 1H), 7.08 (d, 1H), 7.02 (s, 1H), 6.66 (dd, 1H), 5.70 (dd, 1H), 5.21 (dd, 1H), 4.77 (s, 2H), 3.97 (t, 2H), 2.84 (t, 2H).

d) Isochromane-7-carbaldehyde (J-4)

To a stirred solution of 7-vinylisochromane (0.8 g, 4.99 mmol) in 18.0 mL of 1,4-dioxan and 6.0 mL of water was added dropwise OsO$_4$ (0.063 g, 0.249 mmol) at 0° C. followed by stirring for 30 min. Then NaIO$_4$ (3.20 g, 14.97 mmol) was added at 0° C. followed by stirring for 1 h at RT. The reaction mixture was quenched with water and extracted with ethyl acetate. The combined extracts were washed with brine solution, dried over anhydrous sodium sulphate and concentrated to give the title compound (0.9 g). $^1$H NMR (400 MHz, CDCl$_3$) δ 9.95 (s, 1H), 7.71-7.66 (m, 1H), 7.52 (d, 1H), 7.32-7.26 (m, 1H), 4.84 (s, 2H), 4.00 (t, 2H), 2.94 (t, 2H).

e) Isochroman-7-ylmethanol (J-5)

To a stirred solution of isochromane-7-carbaldehyde (0.90 g, 5.54 mmol) in 15.0 mL of THF and 3.0 mL of MeOH was added NaBH$_4$ (0.629 g, 16.64 mmol) at 0° C. followed by stirring for 1 h at RT. The reaction mixture was concentrated and the residue was diluted with water and extracted with ethyl acetate. The combined extracts were washed with brine solution, dried over anhydrous sodium sulphate and concentrated to give the title compound (0.6 g, 73%). $^1$H NMR (300 MHz, DMSO-d$_6$) δ 7.11-7.05 (m, 2H), 6.96 (s, 1H), 5.12 (t, 1H), 4.66 (s, 2H), 4.42 (d, 2H), 3.85 (t, 2H), 2.74 (t, 2H).

f) 7-(Bromomethyl)isochromane (J-6)

To a stirred solution of isochroman-7-ylmethanol (0.6 g, 3.65 mmol) in 20.0 mL of DCM were added CBr$_4$ (2.06 g, 6.21 mmol) and PPh$_3$ (1.05 g, 4.01 mmol) at 0° C. followed by stirring for 16 h at RT. The reaction mixture was quenched with water, basified by saturated sodium bicarbonate and extracted with DCM. The combined extracts were washed with water and brine solution and dried over anhydrous sodium sulphate. The reaction mixture was distilled out and the residue obtained was purified by SiO$_2$ column chromatography eluted with 20% EtOAc/hexane to give the title compound (0.48 g, 57%). $^1$H NMR (300 MHz, DMSO-d$_6$) δ 7.23 (dd, 1H), 7.12 (d, 2H), 4.66 (s, 4H), 3.86 (t, 2H), 2.77 (t, 2H).

Example 1: 1-(3-(3,4-Dihydroisoquinolin-2(1H)-yl)-2-hydroxypropyl)-3-((1-methyl-1H-benzo[d]imidazol-6-yl)methyl)imidazolidin-2-one (K-4) and its Isomer 1 (K-5) and Isomer 2 (K-6)

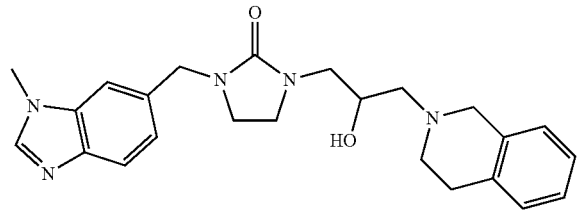

K-4 a) tert-Butyl(2-(((1-methyl-1H-benzo[d]imidazol-6-yl)methyl)amino)ethyl) carbamate (K-1)

To a stirred solution of 1-methyl-H-benzo[d]imidazole-6-carbaldehyde (3.0 g, 18.75 mmol) in 100 mL of methanol was added tert-butyl (2-aminoethyl)carbamate (4.9 g, 49 mmol) followed by stirring for 30 min at RT. The reaction mixture was cooled to 0° C. followed by addition of NaBH$_4$.

The reaction was stirred for 3 h at RT. The reaction mixture was concentrated and the residue was diluted with water and extracted with DCM. The combined extracts were washed with water and brine solution, dried over anhydrous sodium sulphate and concentrated to give the title compound (3.5 g, 71.4%); LCMS [M+H]$^+$ 305.3.

b) 1-((1-Methyl-H-benzo[d]imidazol-6-yl)methyl) imidazolidin-2-one (K-2)

To a stirred solution of tert-butyl (2-(((1-methyl-1H-benzo[d]imidazol-6-yl) methyl) amino) ethyl) carbamate (1.0 g, 3.28 mmol) in 10 mL of THF was added potassium tert-butoxide (1.107 g, 9.86 mmol) followed by stirring for 3 h at 60° C. temperature. To the reaction mixture ethyl acetate was added. The organic layer was washed with water and brine solution and then dried over anhydrous sodium sulphate. The organic layer was concentrated to give white solid (0.5 g, 66.6%). LCMS [M+H]$^+$231.2.

c) 1-((1-Methyl-H-benzo[d]imidazol-6-yl) methyl)-3-(oxiran-2-ylmethyl)imidazolidin-2-one (K-3)

To a stirred solution of 1-((1-methyl-H-benzo[d]imidazol-6-yl)methyl)imidazolidin-2-one (0.2 g, 0.86 mmol) in 5.0 mL of DMF was added NaH (0.05 g, 1.3 mmol) at 0° C. followed by stirring for 30 min at 0° C. Epichlorohydrin (0.241 g, 1.3 mmol) was then added followed by stirring for 12 h at RT. The reaction mixture was quenched with water and extracted with ethyl acetate. The combined extracts were washed with water and brine solution and then dried over anhydrous sodium sulphate. The residue was purified by preparative TLC, eluted with 5% CHCl$_3$/MeOH to give the title compound (0.11 g, 49.1%). LCMS [M+H]$^+$287.3.

d) 1-(3-(3,4-Dihydroisoquinolin-2(1H)-yl)-2-hydroxypropyl)-3-((1-methyl-H-benzo[d]imidazol-6-yl) methyl)imidazolidin-2-one (K-4)

To a 50 mL sealed tube were added 1-((1-methyl-1H-benzo[d]imidazol-6-yl) methyl)-3-(oxiran-2-ylmethyl)imidazolidin-2-one (0.11 g, 0.384 mmol), 1,2,3,4-tetrahydroisoquinoline (0.102 g, 7.68 mmol), TEA (0.16 mL, 1.153 mmol) and IPA (2.0 mL). The reaction mixture was stirred for 12 h at 100° C. The reaction mixture was distilled out and the residue was purified by neutral Al$_2$O$_3$ column chromatography eluted with 5% CHCl$_3$/MeOH to give the title compound (0.05 g, 31.2%). LCMS [M+H]$^+$ 420.4. $^1$H NMR (400 MHz, DMSO-d$_6$): δ 8.32 (s, 1H), 8.15 (s, 1H), 7.59 (d, 1H), 7.47-7.39 (m, 1H), 7.09 (dq, 3H), 7.02 (dd, 1H), 4.73 (d, 1H), 4.38 (s, 2H), 3.87 (q, 1H), 3.61 (s, 3H), 3.34 (s, 4H), 3.13 (t, 2H), 3.04 (dd, 2H), 2.80 (t, 2H), 2.73-2.63 (m, 2H), 2.48-2.36 (m, 2H).

Racemic compound K-4 (0.06 g) was separated into two enantiomers K-5 (0.015 g, isomer-1, retention time 16.275 min) and K-6 (0.01 g, isomer-2, retention time 14.246 min) using chiral column chromatography. Column: Chiral pack IC [(10 mm×250 mm), 5µ]; Mobile phase: (A): Acetonitrile (B): 0.1% DEA in EtOH:IPA (1:1); Flow: 10 ml/min; Isocratic: 95:5 (A:B)

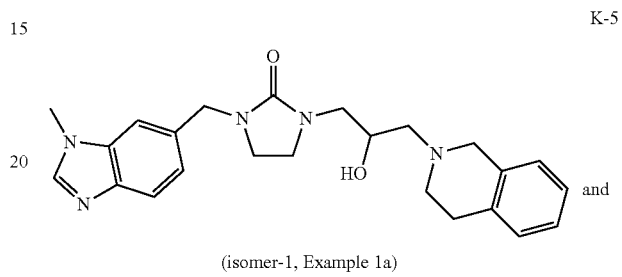

(isomer-1, Example 1a)

(isomer-2, Example 1b)

Isomer-1: LCMS [M+H]$^+$=[420.4]. $^1$H NMR (400 MHz DMSO-d$_6$) δ 8.16 (d, 1H), 7.66-7.55 (m, 1H), 7.43 (s, 2H), 7.23 (d, 1H), 7.16-6.95 (m, 3H), 4.77-4.68 (m, 1H), 4.41 (d, 2H), 3.94-3.74 (m, 4H), 3.62 (s, 2H), 3.14 (t, 2H), 3.05 (dd, 1H), 2.80 (d, 3H), 2.76-2.62 (m, 4H), 2.39-2.25 (m, 2H).

Isomer-2: LCMS [M+H]$^+$[420.4]. $^1$H NMR (400 MHz, DMSO-d$_6$) δ 8.16 (s, 1H), 7.59 (d, 1H), 7.42 (s, 1H), 7.12-6.98 (m, 5H), 4.73 (s, 1H), 4.38 (s, 2H), 3.87 (s, 1H), 3.81 (s, 3H), 3.60 (s, 2H), 3.44-3.37 (m, 2H), 3.31-3.24 (m, 1H), 3.13 (q, 2H), 3.03 (dd, 1H), 2.78 (d, 2H), 2.73-2.65 (m, 2H), 2.43 (d, 2H).

The following compounds were prepared according to the procedure described in Example 1 using appropriate starting materials. The characterization data, as well as deviations in purification method, if any, are indicated on the table below.

| Example No. | Structure | Characterization data |
|---|---|---|
| 2 | 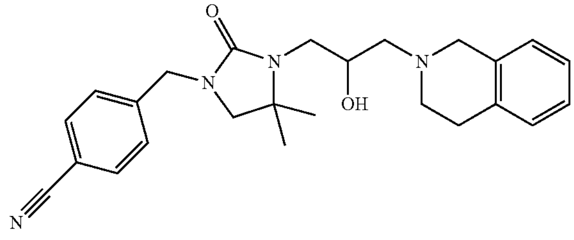 | $^1$H NMR (400 MHz, CDCl$_3$) δ: 7.63 (d, 2H), 7.37 (d, 2H), 7.17-7.05 (m, 3H), 7.04-6.99 (m, 1H), 4.49-4.36 (m, 2H), 3.98 (qd, 1H), 3.81-3.60 (m, 2H), 3.37 (dd, 1H), 3.15 (dd, 1H), 3.00 (s, 2H), 2.85 (dq, 4H), 2.59 (qd, 2H), 1.24 (d, 6H). LCMS [M + H]$^+$ 419.4. |

-continued

| Example No. | Structure | Characterization data |
|---|---|---|
| 2a | 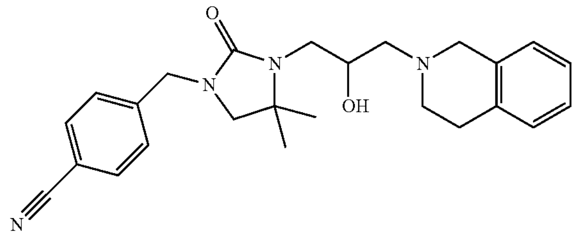 [SMILES: CC1(C)CN(Cc2ccc(C#N)cc2)C(=O)N1CC(O)CN1CCc2ccccc2C1] | $^1$H NMR (400 MHz, CDCl$_3$) δ: 7.68-7.58 (m, 2H), 7.38 (dq, 2H), 7.17-7.07 (m, 3H), 7.04-6.98 (m, 1H), 4.50-4.32 (m, 2H), 4.03-3.93 (m, 1H), 3.77 (d, 1H), 3.67 (d, 1H), 3.37 (dd, 1H), 3.15 (dd, 1H), 3.00 (d, 2H), 2.88 (dd, 2H), 2.82 (dt, 2H), 2.66-2.50 (m, 2H), 1.25 (d, 6H). LCMS [M + H]$^+$ 419.4. |
| | Isomer 1: Purification method: A (retention time 9.717 min) | |
| 2b | 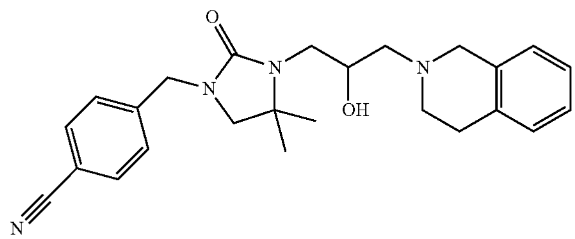 [SMILES: CC1(C)CN(Cc2ccc(C#N)cc2)C(=O)N1CC(O)CN1CCc2ccccc2C1] | $^1$H NMR (400 MHz, CDCl$_3$) δ: 7.67-7.59 (m, 2H), 7.41-7.33 (m, 2H), 7.17-7.06 (m, 3H), 7.05-6.98 (m, 1H), 4.49-4.35 (m, 2H), 4.03-3.93 (m, 1H), 3.77 (d, 1H), 3.67 (d, 1H), 3.37 (dd,1H), 3.15 (dd, 1H), 3.00 (s, 2H), 2.89 (d, 2H), 2.82 (dt, 2H), 2.66-2.49 (m, 2H), 1.25 (d, 6H). LCMS [M + H]$^+$ 419.4. |
| | Isomer 2: Purification method: A (retention time 8.526 min) | |
| 3 | 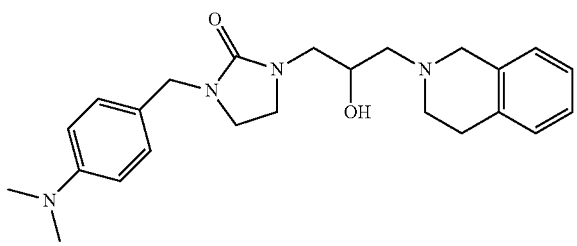 [SMILES: CN(C)c1ccc(CN2CCN(CC(O)CN3CCc4ccccc4C3)C2=O)cc1] | $^1$H NMR (400 MHz, DMSO-d$_6$) δ: 7.12-7.07 (m, 3H), 7.06-7.02 (m, 3H), 6.70-6.65 (m, 2H), 4.72 (d, 1H), 4.12 (s, 2H), 3.89 (s, 1H), 3.59 (s, 2H), 3.45-3.38 (m, 2H), 3.33-3.23 (m, 3H), 3.10-2.95 (m, 1H), 2.85 (s, 6H), 2.79 (d, 2H), 2.73-2.63 (m, 2H), 2.47-2.35 (m, 2H). LCMS [M + H]$^+$ 409.4. |
| 4 | 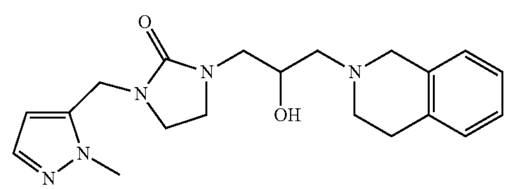 [SMILES: Cn1nccc1CN1CCN(CC(O)CN2CCc3ccccc3C2)C1=O] | $^1$H NMR (400 MHz, DMSO-d$_6$) δ: 7.32 (d, 1H), 7.12-7.06 (m, 3H), 7.04-6.99 (m, 1H), 6.15 (d, 1H), 4.74 (d, 1H), 4.32 (d, 2H), 3.86 (d, 1H), 3.75 (s, 3H), 3.60 (s, 2H), 3.45-3.36 (m, 2H), 3.31-3.21 (m, 1H), 3.14 (t, 2H), 3.02 (dd, 1H), 2.79 (t, 2H), 2.69 (dt, 2H), 2.47-2.38 (m, 2H). LCMS [M + H]$^+$ 370.4. |
| 5 | 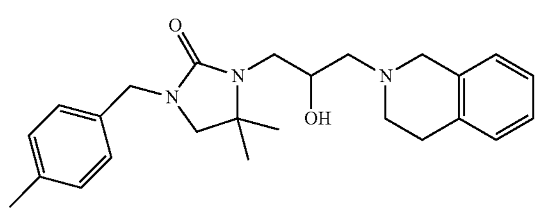 [SMILES: Cc1ccc(CN2CC(C)(C)N(CC(O)CN3CCc4ccccc4C3)C2=O)cc1] | $^1$H NMR (400 MHz, CDCl$_3$) δ: 7.14 (s, 5H), 7.13-7.09 (m, 2H), 7.05-6.98 (m, 1H), 4.41-4.27 (m, 2H), 4.01 (s, 1H), 3.86-3.69 (m, 2H), 3.35 (dd, 1H), 3.20-3.11 (m, 1H), 2.97 (s, 2H), 2.94-2.84 (m, 4H), 2.64 (t, 2H), 2.34 (s, 3H), 1.20 (d, 6H). LCMS [M + H]$^+$ 408.4. |
| 6 | 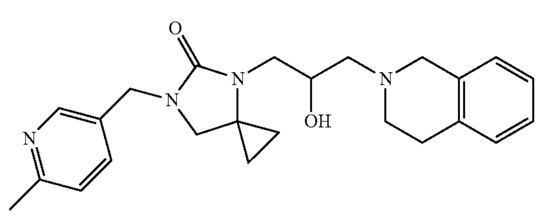 [SMILES: Cc1ccc(CN2CC3(CC3)N(CC(O)CN3CCc4ccccc4C3)C2=O)cn1] | $^1$H NMR (400 MHz, CDCl$_3$) δ: 8.39 (d, 1H), 7.55 (dd, 1H), 7.17-7.06 (m, 4H), 7.03-6.97 (m, 1H), 4.40 (q, 2H), 3.89 (ddd,1H), 3.77 (d, 1H), 3.64 (d, 1H), 3.28 (d, 1H), 3.22 (d, 1H), 3.12 (dd, 1H), 2.94-2.71 (m, 5H), 2.61 (dd, 1H), 2.55 (s, 3H), 2.52-2.45 (m, 2H), 1.29-1.10 (m, 2H), 1.07-0.95 (m, 1H). LCMS [M + H]$^+$ 407.4. |

| Example No. | Structure | Characterization data |
|---|---|---|
| 7 | 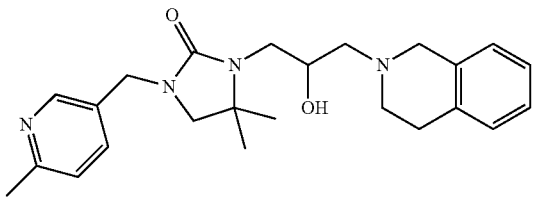 [SMILES: Cc1ccc(CN2CC(C)(C)N(CC(O)CN3CCc4ccccc4C3)C2=O)cn1] | ¹H NMR (400 MHz, CDCl₃) δ: 8.36 (d, 1H), 7.50 (dd, 1H), 7.11 (td, 4H), 7.02-6.97 (m, 1H), 4.34 (d, 2H), 3.95 (qd, 1H), 3.74 (d, 1H), 3.69-3.61 (m, 1H), 3.33 (dd, 1H), 3.12 (dd, 1H), 2.95 (d, 2H), 2.90-2.85 (m, 2H), 2.83-2.78 (m, 2H), 2.63-2.54 (m, 2H), 2.53 (s, 3H), 1.19 (d, 6H). LCMS [M + H]⁺ 409.4. |
| 8 | 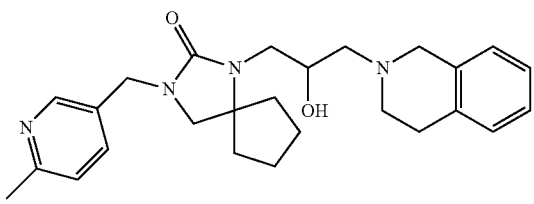 [SMILES: Cc1ccc(CN2CC3(CCCC3)N(CC(O)CN3CCc4ccccc4C3)C2=O)cn1] | ¹H NMR (300 MHz, DMSO-d₆) δ: 8.32 (d, 1H), 7.52 (dd, 1H), 7.22 (d, 1H), 7.15-6.93 (m, 4H), 4.89 (d, 1H), 4.36-4.11 (m, 2H), 3.92 (s, 1H), 3.69-3.46 (m, 2H), 3.30-3.13 (m, 3H), 3.06-2.90 (m, 2H), 2.91-2.57 (m, 3H), 2.44 (s, 3H), 2.37 (d, 1H), 2.32-2.21 (m, 1H), 1.87 (s, 2H), 1.53 (d, 6H). LCMS [M + H]⁺ 435.4. |
| 9 | 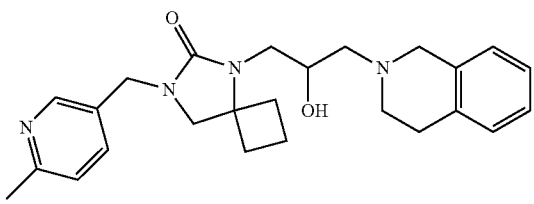 [SMILES: Cc1ccc(CN2CC3(CCC3)N(CC(O)CN3CCc4ccccc4C3)C2=O)cn1] | ¹H NMR (400 MHz, DMSO-d₆) δ: 8.37-8.28 (m, 1H), 7.52 (dd, 1H), 7.22 (d, 1H), 7.15-6.98 (m, 4H), 4.85 (s, 1H), 4.34-4.13 (m, 2H), 3.89 (s, 1H), 3.61 (s, 2H), 3.32-3.25 (m, 2H), 3.22 (d, 1H), 3.04 (dd, 1H), 2.79 (t, 2H), 2.73-2.60 (m, 3H), 2.44 (s, 5H), 2.37-2.23 (m, 1H), 1.79 (dd, 2H), 1.56 (tt, 2H). LCMS [M + H]⁺ 421.4. |
| 10 | 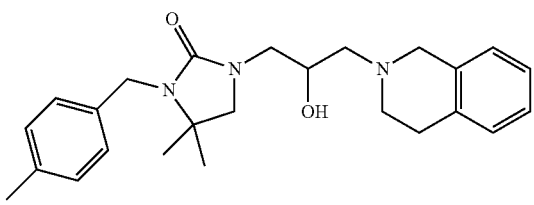 [SMILES: Cc1ccc(CN2C(=O)N(CC(O)CN3CCc4ccccc4C3)CC2(C)C)cc1] | ¹H NMR (400 MHz, CDCl₃) δ: 7.22 (d, 2H), 7.18-7.04 (m, 5H), 7.04-7.00 (m, 1H), 4.31 (s, 2H), 4.00 (dtt, 1H), 3.81 (d, 1H), 3.63 (d, 1H), 3.52-3.43 (m, 1H), 3.32-3.15 (m, 3H), 2.97-2.86 (m, 3H), 2.74 (dd, 1H), 2.63-2.51 (m, 2H), 2.32 (s, 3H), 1.15 (s, 6H). LCMS [M + H]⁺ 408.4. |
| 11 | 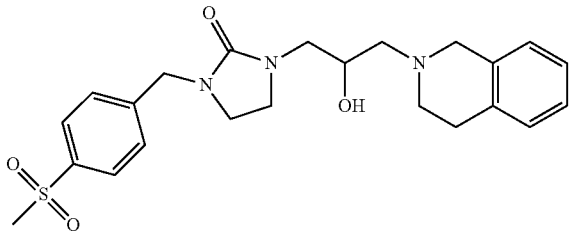 [SMILES: CS(=O)(=O)c1ccc(CN2CCN(CC(O)CN3CCc4ccccc4C3)C2=O)cc1] | ¹H NMR (400 MHz, DMSO-d₆) δ: 7.92-7.88 (m, 2H), 7.53-7.48 (m, 2H), 7.12-7.07 (m, 3H), 7.05-7.01 (m, 1H), 4.75 (d, 1H), 4.37 (s, 2H), 3.87 (ddd, 1H), 3.61 (s, 2H), 3.50-3.36 (m, 2H), 3.33-3.23 (m, 1H), 3.20 (s, 3H), 3.17 (t, 2H), 3.04 (dd, 1H), 2.80 (t, 2H), 2.71 (pd, 2H), 2.49-2.40 (m, 2H). LCMS [M + H]⁺ 444.3. |
| 12 | 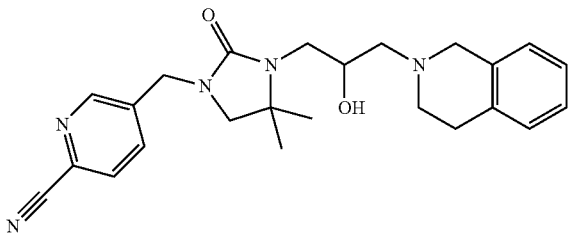 [SMILES: CC1(C)CN(Cc2ccc(C#N)nc2)C(=O)N1CC(O)CN1CCc2ccccc2C1] | ¹H NMR (400 MHz, DMSO-d₆) δ: 8.65 (d, 1H), 8.03 (d, 1H), 7.89 (dd, 1H), 7.11-7.03 (m, 4H), 4.83 (s, 1H), 4.42 (d, 2H), 3.92 (s, 1H), 3.61 (d, 2H), 3.22 (d, 1H), 3.01 (d, 2H), 2.89 (d, 1H), 2.80-2.67 (m, 4H), 2.43-2.35 (m, 2H), 1.17 (d, 6H). LCMS [M + H]⁺ 420.4. |

| Example No. | Structure | Characterization data |
|---|---|---|
| 13 | 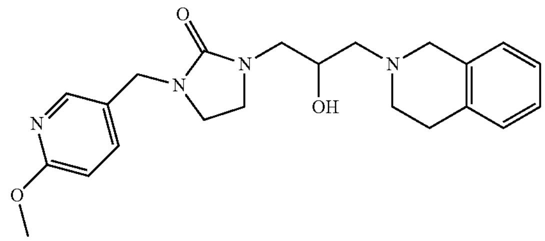 [SMILES: COc1ccc(CN2CCN(CC(O)CN3CCc4ccccc4C3)C2=O)cn1] | $^1$H NMR (300 MHz, CDCl$_3$) δ: 8.04 (d, 1H), 7.55 (dd, 1H), 7.13 (ddt, 3H), 7.04-6.98 (m, 1H), 6.73 (d, 1H), 4.30 (s, 2H), 4.04-3.94 (m, 1H), 3.93 (s, 3H), 3.82 (d, 1H), 3.77-3.70 (m, 1H), 3.67-3.49 (m, 2H), 3.49-3.40 (m, 2H), 3.24-3.11 (m, 3H), 2.99-2.85 (m, 3H), 2.80-2.67 (m, 1H), 2.62-2.47 (m, 2H). m/z 397.2. LCMS [M + H]$^+$ 397.4 |
| 14 | 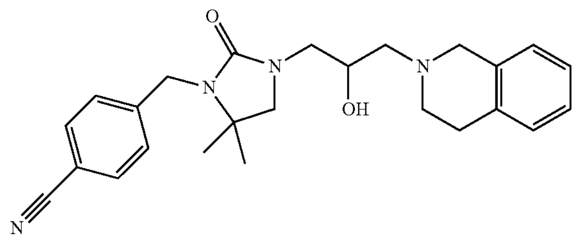 [SMILES: CC1(C)CN(CC(O)CN2CCc3ccccc3C2)C(=O)N1Cc1ccc(C#N)cc1] | $^1$H NMR (400 MHz, CDCl$_3$) δ: 7.63-7.55 (m, 2H), 7.49-7.38 (m, 2H), 7.13 (dtd, 3H), 7.05-6.95 (m, 1H), 4.36 (s, 2H), 4.06-3.92 (m, 1H), 3.82 (d, 1H), 3.62 (d, 1H), 3.49 (dd, 1H), 3.43-3.24 (m, 2H), 3.18 (dd, 1H), 3.01-2.82 (m, 3H), 2.73 (ddd, 1H), 2.64-2.44 (m, 2H), 1.17 (s, 6H). LCMS [M + H]$^+$ 419.4. |

Example 15: 1-(3-(3,4-Dihydroisoquinolin-2(1H)-yl)-2-hydroxypropyl)-3-(4-methyl-benzyl)imidazolidin-2-one (L-2) and its Isomer 1 (L-3) and Isomer 2 (L-4)

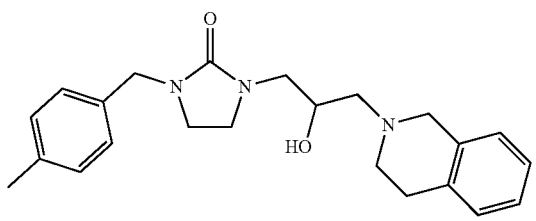

L-2 a) 1-(4-Methylbenzyl)-3-(oxiran-2-ylmethyl)imidazolidin-2-one (L-1)

To a stirred solution of 1-(4-methylbenzyl)imidazolidin-2-one (2.0 g, 10.52 mmol) in 50.0 mL of THF was added NaH (0.63 g, 15.78 mmol) at 0° C. followed by stirring the reaction mixture for 30 min at 0° C. Epibromohydrin (1.8 mL, 21.0 mmol) was added to the reaction mixture followed by stirring for 12 h at RT. The reaction mixture was quenched with water and extracted with ethyl acetate. The combined extracts were washed with water and brine solution and then dried over anhydrous sodium sulphate. The crude compound was purified by SiO$_2$ column chromatography eluted with 2% MeOH/CHCl$_3$ to give title compound (1.5 g, 60%). LCMS [M+H]$^+$ 247.3.

b) 1-(3-(3,4-Dihydroisoquinolin-2(1H)-yl)-2-hydroxypropyl)-3-(4-methylbenzyl)imidazolidin-2-one (L-2)

To a 50 mL sealed tube were added 1-(4-methylbenzyl)-3-(oxiran-2-yl-methyl)imidazolidin-2-one (0.5 g, 2.03 mmol), 1,2,3,4-tetrahydroisoquinoline (0.54 g, 7.68 mmol), DIPEA (1.08 mL, 6.09 mmol) and IPA (10 mL). The reaction mixture was stirred for 12 h at 100° C. The reaction mixture was distilled out and the residue was purified by neutral Al$_2$O$_3$ column chromatography eluted with 1% MeOH/CHCl$_3$ to give the title compound (0.6 g, 77.8%). LCMS [M+H]$^+$ 380.4. $^1$H NMR (400 MHz, DMSO-d$_6$) δ: 7.17-7.05 (m, 7H), 7.05-6.99 (m, 1H), 4.73 (d, 1H), 4.20 (s, 2H), 3.86 (qd, 1H), 3.60 (s, 2H), 3.39 (dd, 1H), 3.32-3.21 (m, 2H), 3.09 (t, 2H), 3.01 (dd, 1H), 2.80 (t, 3H), 2.75-2.63 (m, 2H), 2.45-2.36 (m, 2H), 2.27 (s, 3H).

Racemic compound (L-2, 0.45 g) was separated into two enantiomers L-3 (0.13 g, isomer-1, retention time 7.327 min) and L-4 (0.11 g, isomer-2, retention time 12.124 min) using chiral column chromatography. Column: Chiral pack IA [(20 mm×250 mm), 5μ]; Mobile phase: (A): Acetonitrile, (B): 0.1% DEA in MeOH:IPA (50:50); Flow: 15 ml/min; Isocratic: 90:10 (A:B).

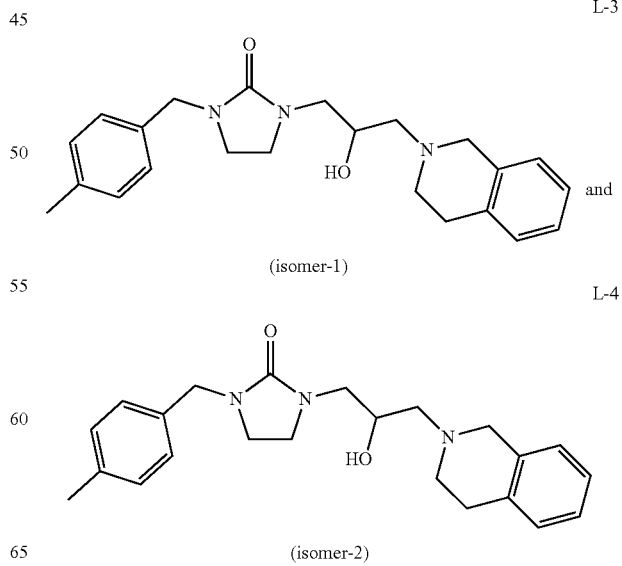

Isomer-1: LCMS [M+H]⁺380.4. ¹H NMR (400 MHz, DMSO-d₆) δ: 7.16-7.06 (m, 7H), 7.02 (dq, 1H), 4.72 (d, 1H), 4.20 (s, 2H), 3.87 (hept, 1H), 3.60 (s, 2H), 3.46-3.35 (m, 2H), 3.32-3.23 (m, 1H), 3.16-2.93 (m, 3H), 2.80 (t, 2H), 2.74-2.62 (m, 2H), 2.43 (dd, 2H), 2.27 (s, 3H). Isomer-2: LCMS [M+H]⁺ 380.4. ¹H NMR (400 MHz, DMSO-d₆) δ: 7.17-7.05 (m, 7H), 7.05-6.99 (m, 1H), 4.72 (d, 1H), 4.20 (s, 2H), 3.91-3.82 (m, 1H), 3.60 (s, 2H), 3.45-3.34 (m, 2H), 3.32-3.23 (m, 1H), 3.09 (t, 2H), 3.01 (dd, 1H), 2.80 (t, 2H), 2.75-2.65 (m, 2H), 2.48-2.39 (m, 2H), 2.27 (s, 3H).

The following compounds were prepared according to the procedure described in Example 15 using appropriate starting materials. The characterization data, as well as deviations in purification method, if any, are indicated on the table below.

| Example No. | Structure | Characterization data |
|---|---|---|
| 16 | [structure] | ¹H NMR (400 MHz, DMSO-d₆) δ: 7.16 (q, 4H), 7.12-7.05 (m, 3H), 7.03 (dd, 1H), 4.74 (d, 1H), 4.25 (d, 2H), 3.87 (d, 1H), 3.61 (s, 2H), 3.41 (ddd, 2H), 3.30-3.24 (m, 1H), 3.17-2.98 (m, 3H), 2.80 (t, 2H), 2.69 (dt, 2H), 2.46-2.39 (m, 2H), 2.25 (s, 3H). LCMS [M + H]⁺ 380.25 |
| 16a | [structure]<br>Isomer 1: Purification method: A<br>(retention time 5.550 min) | ¹H NMR [400 MHz, DMSO-d₆] δ: 7.16 (q, 4H), 7.10 (q, 3H), 7.03 (d, 1H), 4.78 (s, 1H), 4.25 (s, 2H), 3.89 (s, 1H), 3.64 (s, 2H), 3.42 (q, 1H), 3.27 (dd, 2H), 3.11 (d, 2H), 3.04 (m, 2H), 2.81 (d, 3H), 2.71 (d, 2H), 2.25 (s, 3H). LCMS [M + H]⁺ 380.2. |
| 16b | [structure]<br>Isomer 2: Purification method: A<br>(retention time 7.832 min) | ¹H NMR [400 MHz, DMSO-d₆] δ: 7.16 (q, 4H), 7.13-7.06 (m, 3H), 7.05-7.01 (d, 1H), 4.76 (s, 1H), 4.25 (s, 2H), 3.88 (s, 1H), 3.62 (s, 2H), 3.46-3.37 (q, 1H), 3.27 (dd, 2H), 3.10 (t, 2H), 3.06-2.99 (m, 2H), 2.81 (t, 3H), 2.73 (s, 2H), 2.25 (s, 3H). LCMS [M + H]⁺ 380.2. |
| 17 | [structure] | ¹H NMR (400 MHz, DMSO-d₆) δ: 7.16-7.10 (m, 7H), 7.02 (dq, 1H), 4.96 (d, 1H), 4.45 (s, 2H), 4.09 (s, 2H), 3.98 (d, 1H), 3.60 (s, 2H), 3.44 (dd, 1H), 3.27 (dd, 1H), 2.73 (dd, 4H), 2.46 (d, 2H), 2.27 (s, 3H). LCMS [M + H]⁺ 394. |
| 18 | [structure] | ¹H NMR (300 MHz, DMSO-d₆) δ: 7.86-7.75 (m, 2H), 7.49-7.33 (m, 2H), 7.14-6.95 (m, 4H), 4.75 (t, 1H), 4.34 (s, 2H), 3.86 (d, 1H), 3.60 (s, 2H), 3.49-3.36 (m, 1H), 3.26 (d, 1H), 3.16 (t, 3H), 3.03 (dd, 1H), 2.84-2.63 (m, 4H), 2.43 (d, 2H). LCMS [M + H]⁺ 391.3. |
| 18a | [structure] | ¹H NMR (300 MHz, DMSO-d₆) δ: 7.86-7.75 (m, 2H), 7.43 (d, 2H), 7.11 (d, 3H), 7.04 (d, 1H), 4.76 (s, 1H), 4.35 (s, 2H), 3.89 (s, 1H), 3.64 (d, 2H), 3.42 (q, 2H), 3.33-3.23 (m, 1H), 3.21-3.10 (m, 2H), 3.11-2.92 (m, 1H), 2.77 (d, 4H), 2.43 (d, 2H). LCMS [M + H]⁺ 391.4. |

| Example No. | Structure | Characterization data |
|---|---|---|
| | Isomer 1: Purification method: B (retention time 5.178 min) | |
| 18b | 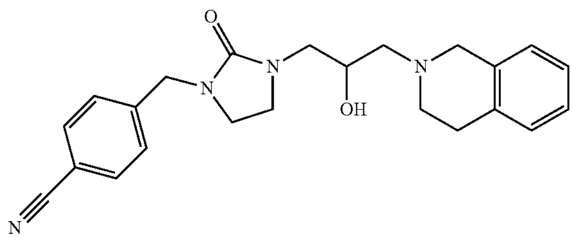 [SMILES: N#Cc1ccc(CN2CCN(CC(O)CN3CCc4ccccc4C3)C2=O)cc1] | $^1$H NMR (300 MHz, DMSO-d$_6$) δ: 7.88-7.73 (m, 2H), 7.43 (d, 2H), 7.17-6.96 (m, 4H), 4.76 (s, 1H), 4.34 (s, 2H), 3.89 (s, 1H), 3.63 (d, 2H), 3.54-3.38 (m, 2H), 3.33-2.93 (m, 4H), 2.76 (d, 4H), 2.43 (d, 2H). LCMS [M + H]$^+$ 391.3. |
| | Isomer 2: Purification method: B (retention time 7.366 min) | |
| 19 | 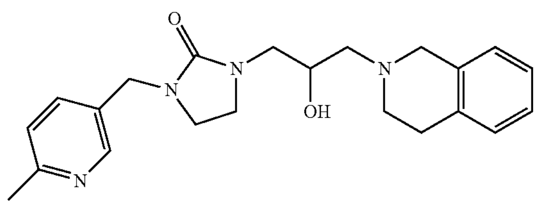 [SMILES: Cc1ccc(CN2CCN(CC(O)CN3CCc4ccccc4C3)C2=O)cn1] | $^1$H NMR (300 MHz, DMSO-d$_6$) δ: 8.37-8.28 (m, 1H), 7.52 (dd, 1H), 7.22 (d, 1H), 7.16-6.94 (m, 4H), 4.74 (d, 1H), 4.24 (s, 2H), 3.86 (d, 1H), 3.60 (s, 2H), 3.51-3.38 (m, 1H), 3.26 (dd, 1H), 3.11 (t, 3H), 3.01 (dd, 1H), 2.86-2.61 (m, 4H), 2.44 (s, 5H). LCMS [M + H]$^+$ 381.4. |
| 20 | 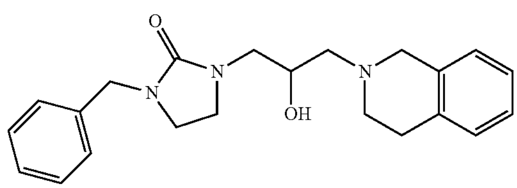 [SMILES: O=C1N(Cc2ccccc2)CCN1CC(O)CN1CCc2ccccc2C1] | $^1$H NMR (400 MHz, DMSO-d$_6$) δ: 7.38-7.30 (m, 2H), 7.29-7.25 (m, 1H), 7.25-7.20 (m, 2H), 7.13-7.05 (m, 3H), 7.03 (dq, 1H), 4.73 (d, 1H), 4.25 (s, 2H), 3.87 (h, 1H), 3.60 (s, 2H), 3.47-3.36 (m, 2H), 3.28 (dd, 1H), 3.12 (t, 2H), 3.02 (dd, 1H), 2.80 (t, 2H), 2.69 (dtd, 2H), 2.47-2.39 (m, 2H). LCMS [M + H]$^+$ 366.3. |
| 21 | 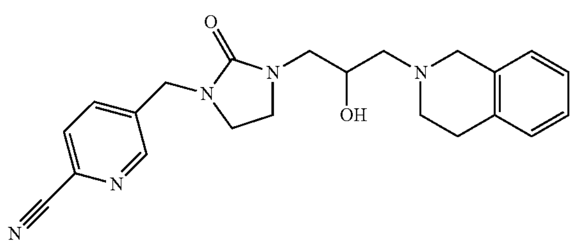 [SMILES: N#Cc1ccc(CN2CCN(CC(O)CN3CCc4ccccc4C3)C2=O)cn1] | $^1$H NMR (300 MHz, DMSO-d$_6$) δ: 8.65 (d, 1H), 8.07-7.97 (m, 1H), 7.89 (dd, 1H), 7.17-6.93 (m, 4H), 4.75 (d, 1H), 4.39 (s, 2H), 3.87 (d, 1H), 3.60 (s, 2H), 3.52-3.38 (m, 2H), 3.28-3.10 (m, 3H), 3.10-2.93 (m, 1H), 2.87-2.61 (m, 4H), 2.43 (m, 2H). LCMS [M + H]$^+$ 392.4. |
| 22 | 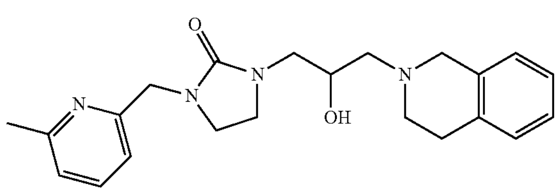 [SMILES: Cc1cccc(CN2CCN(CC(O)CN3CCc4ccccc4C3)C2=O)n1] | $^1$H NMR (300 MHz, DMSO-d$_6$) δ: 7.64 (t, 1H), 7.15-7.00 (m, 6H), 4.74 (d, 1H), 4.30 (s, 2H), 3.88 (s, 1H), 3.61 (s, 2H), 3.42 (p, 2H), 3.30-3.21 (m, 3H), 3.03 (dd, 1H), 2.79 (d, 2H), 2.74-2.67 (m, 3H), 2.44 (s, 4H). LCMS [M + H]$^+$ 381.2. |
| 23 | 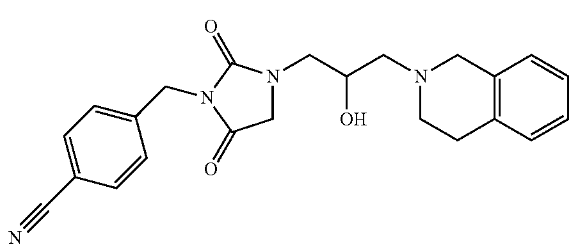 [SMILES: N#Cc1ccc(CN2C(=O)CN(CC(O)CN3CCc4ccccc4C3)C2=O)cc1] | $^1$H NMR (300 MHz, DMSO-d$_6$) δ: 7.81 (dt, 2H), 7.51-7.40 (m, 2H), 7.05 (dt, 4H), 4.96 (d, 1H), 4.61 (s, 2H), 4.14 (s, 2H), 3.98 (d, 1H), 3.60 (s, 2H), 3.44 (dd, 1H), 3.27 (dd, 1H), 2.73 (dd, 4H), 2.46 (d, 2H). LCMS [M + H]$^+$ 405. |

| Example No. | Structure | Characterization data |
|---|---|---|
| 24 | 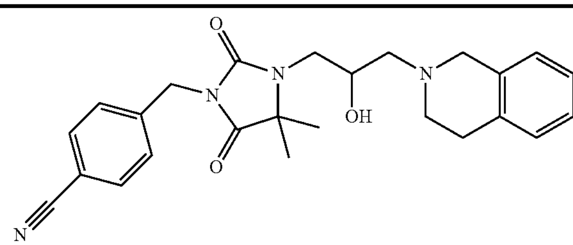 | $^1$H NMR (300 MHz, DMSO-d$_6$) δ: 7.86-7.73 (m, 2H), 7.48-7.35 (m, 2H), 7.16-6.96 (m, 4H), 4.88 (d, 1H), 4.65 (s, 2H), 4.08 (d, 1H), 3.70-3.45 (m, 3H), 3.06 (dd, 3H), 2.75 (dd, 4H), 1.35 (d, 6H). LCMS [M + H]$^+$ 433.4. |

Example 25: 1-((6-Chloropyridin-3-yl)methyl)-3-(3-(3,4-dihydroisoquinolin-2(1H)-yl)-2-hydroxypropyl)imidazolidin-2-one (M-1)

M-1

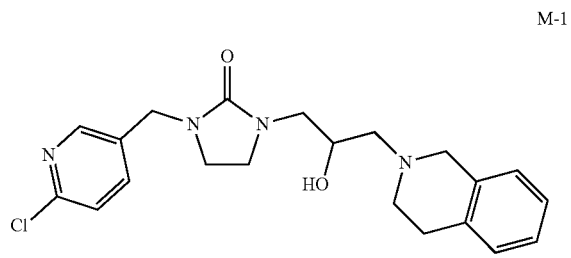 [SMILES: O=C1N(Cc2ccc(Cl)nc2)CCN1CC(O)CN1CCc2ccccc2C1]

To a 50 mL sealed tube, were added 1-((6-chloropyridin-3-yl)methyl)-3-(oxiran-2-ylmethyl)imidazolidin-2-one (1.5 g, 5.6 mmol), 1,2,3,4-tetrahydroisoquinoline (1.12 g, 8.4 mmol), DIPEA (3.0 mL, 16.8 mmol) and IPA (10 mL) and reacture mixture was stirred for 12 h at 100° C. The reaction mixture was then distilled out and the residue was purified by neutral Al$_2$O$_3$ column chromatography eluted with 1% MeOH/CHCl$_3$ to give the title compound (1.0 g, 44.44%). LCMS [M+H]$^+$401.3.

Example 26: 1-(3-(3,4-dihydroisoquinolin-2(1H)-yl)-2-hydroxypropyl)-3-((6-isopropylpyridin-3-yl)methyl)imidazolidin-2-one (N-1)

N-1

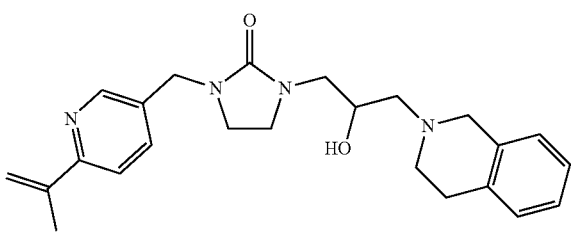

To a 50 mL sealed tube were added 1-((6-chloropyridin-3-yl)methyl)-3-(3-(3,4-dihydroisoquinolin-2(1H)-yl)-2-hydroxypropyl)imidazolidin-2-one (0.14 g, 0.35 mmol), DME (10.0 mL) and H$_2$O (2.0 mL) and the reaction mixture was degassed with Argon gas for 10 min. To this reaction mixture, were added 4,4,5,5-tetramethyl-2-(prop-1-en-2-yl)-1,3,2-dioxaborolane (0.117 g, 0.7 mmol), Na$_2$CO$_3$ (0.148 g, 1.4 mmol) and Pd(PPh$_3$)$_4$ (0.039 g, 0.035 mmol) followed by stirring the mixture for 12 h at 100° C. The reaction mixture was then filtered through Celite© bed and filtrate was diluted with ethyl acetate. The organic layer was washed with water and brine solution and then dried over anhydrous sodium sulphate. The residue (0.147 g) was purified by preparative HPLC (0.08 g, 56.33%). Preparative HPLC conditions: Mobile phase: (A): 10 mm ammonium acetate in water, (B): Acetonitrile; Column: ZORBAX [150 mm×21.2 mm), 5.μm]; Flow: 20 ml/min; [Time/% B 0/40, 2/50, 10/80]. LCMS [M+H]$^+$ 407.4. $^1$H NMR (300 MHz, DMSO-d$_6$) δ 8.44 (dd, 1H), 7.62 (dd, 2H), 7.15-6.89 (m, 4H), 5.89 (dd, 1H), 5.36-5.24 (m, 1H), 4.74 (d, 1H), 4.29 (s, 2H), 3.86 (q, 1H), 3.60 (s, 2H), 3.48-3.37 (m, 2H), 3.27 (dd, 1H), 3.14 (t, 2H), 3.02 (dd, 1H), 2.79 (t, 2H), 2.70 (dd, 2H), 2.46-2.39 (m, 2H), 2.13 (dd, 3H).

Example 27: 1-(3-(3,4-dihydroisoquinolin-2(1H)-yl)-2-hydroxypropyl)-3-((6-ethylpyridin-3-yl)methyl)imidazolidin-2-one (O-1)

O-1

The compound of Example—27 was prepared according to the procedure described in Examples 26 using M-1 as a starting material.

$^1$H NMR (300 MHz, DMSO-d$_6$) δ: 8.35 (d, 1H), 7.54 (dd, 1H), 7.23 (d, 1H), 7.13-6.96 (m, 4H), 4.73 (d 1H), 4.24 (s, 2H), 3.85 (d, 1H), 3.60 (s, 2H), 3.41 (d, 2H), 3.27 (dd, 1H), 3.17-3.08 (m, 2H), 3.01 (dd, 1H), 2.84-2.64 (m, 6H), 2.43 (d, 2H), 1.26-1.06 (m, 3H). LCMS [M+H]$^+$ 395.24

Example 28: 1-(3-(3,4-Dihydroisoquinolin-2(1H)-yl)-2-hydroxypropyl)-3-((6-(prop-1-en-2-yl)pyridin-3-yl)methyl)imidazolidin-2-one (P-1)

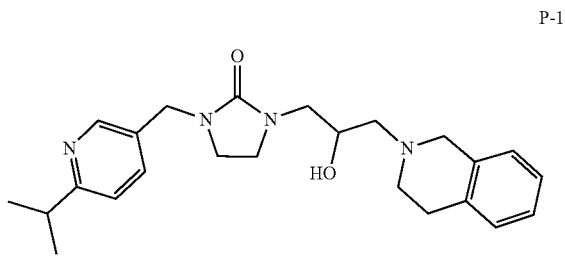 [SMILES: CC(C)c1ccc(CN2CCN(CC(O)CN3CCc4ccccc4C3)C2=O)cn1]

To a stirred solution of 1-(3-(3,4-dihydroisoquinolin-2(1H)-yl)-2-hydroxypropyl)-3-((6-(prop-1-en-2-yl)pyridin-3-yl)methyl)imidazolidin-2-one (0.12 g, 0.295 mmol) in 10 mL of methanol was added 10% palladium on carbon (0.05 g) followed by hydrogenating the reaction mixture for 12 h. The reaction mixture was filtered through Celite bed and the filtrate was concentrated. The residue (0.085 g) was purified by preparative HPLC to give the title compound (0.025 g, 20.83%). Preparative HPLC conditions: Mobile phase: (A): 0.01% TFA in water, (B): Acetonitrile, Column: Gemini n×[150 mm×21.2 mm), 5.µ]; Flow: 20 ml/min; [Time/% B 0/30, 2/40, 8/80]. LCMS [M+H]$^+$ 409.4. 1H NMR (300 MHz, DMSO-d$_6$) δ: 8.37 (d, 1H), 7.56 (dd, 1H), 7.24 (d, 1H), 7.16-6.97 (m, 4H), 4.80 (s, 1H), 4.25 (s, 2H), 3.88 (s, 1H), 3.65 (s, 2H), 3.49-3.36 (m, 2H), 3.26 (dd, 1H), 3.14 (t, 2H), 3.00 (dd, 2H), 2.77 (d, 4H), 2.46 (d, 2H), 1.21 (d, 6H).

The following compounds were prepared according to the procedure described in Examples 26 and 28 using appropriate starting materials. The characterization data is indicated on the table below.

| Example No. | Structure | Characterization data |
|---|---|---|
| 29 | 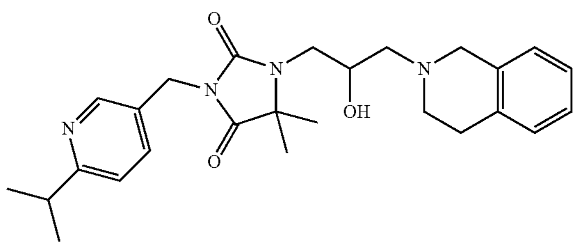 [SMILES: CC(C)c1ccc(CN2C(=O)N(CC(O)CN3CCc4ccccc4C3)C(C)(C)C2=O)cn1] | $^1$H NMR (400 MHz, DMSO-d$_6$) δ: 8.38 (d, 1H), 7.55 (dd, 1H), 7.24 (d, 1H), 7.13-6.97 (m, 4H), 4.88 (d, 1H), 4.56 (s, 2H), 4.08 (q, 2H), 3.68-3.44 (m, 2H), 3.11-2.90 (m, 2H), 2.79-2.65 (m, 4H), 2.43 (d, 2H), 1.33 (d, 6H), 1.20 (d, 6H). LCMS [M + H]$^+$ 451.6. |
| 30 | 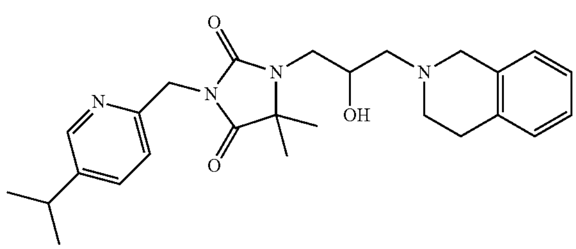 [SMILES: CC(C)c1ccc(CN2C(=O)N(CC(O)CN3CCc4ccccc4C3)C(C)(C)C2=O)nc1] | $^1$H NMR (400 MHz, DMSO-d$_6$) δ: 8.36 (d, 1H), 7.63 (dd, 1H), 7.16 (d, 1H), 7.12-6.97 (m, 4H), 4.86 (d, 1H), 4.64 (s, 2H), 4.07 (dd, 1H), 3.73-3.46 (m, 3H), 3.08 (dd, 1H), 2.95-2.86 (m, 1H), 2.82-2.61 (m, 4H), 2.43 (d, 2H), 1.38 (d, 6H), 1.19 (d, 6H). LCMS [M + H]$^+$ 451.4. |
| 31 | 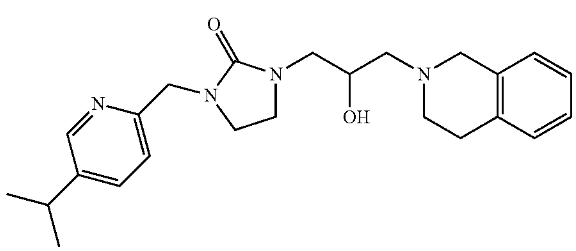 [SMILES: CC(C)c1ccc(CN2CCN(CC(O)CN3CCc4ccccc4C3)C2=O)nc1] | $^1$H NMR (300 MHz, CDCl$_3$] δ: 8.40 (d, 1H), 7.53 (m, 1H), 7.29-7.22 (m, 2H), 7.13 (m, 2H), 7.05-6.97 (m, 1H), 4.48 (t, 2H), 4.07-3.95 (m, 1H), 3.84 (d, 1H), 3.64-3.41 (m, 4H), 3.34 (dd, 2H), 3.24-3.12 (m, 1H), 2.92 (q, 4H), 2.78 (d, 2H), 2.59 (q, 2H), 2.49 (s, 6H). LCMS [M + H]$^+$ 409.5. |

Example 32: 1-((6-Acetylpyridin-3-yl)methyl)-3-(3-(3,4-dihydroisoquinolin-2(1H)-yl)-2-hydroxypropyl)imidazolidin-2-one (Q-2)

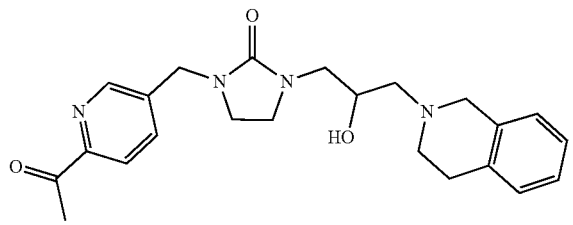

Q-2 a) 1-(3-(3,4-Dihydroisoquinolin-2(1H)-yl)-2-hydroxypropyl)-3-((6-(I-ethoxyvinyl)pyridin-3-yl)methyl)imidazolidin-2-one (Q-1)

To a 50 mL sealed tube were added 1-((6-chloropyridin-3-yl)methyl)-3-(3-(3,4-dihydroisoquinolin-2(1H)-yl)-2-hydroxypropyl)imidazolidin-2-one (0.2 g, 0.5 mmol) and toluene (5.0 mL) followed by degassing the reaction mixture with Argon gas for 10 min. To this reaction mixture were added tributyl(1-ethoxyvinyl)stannane (0.22 mL, 0.6 mmol) and bis(triphenylphosphine)palladium chloride (0.0175 g, 0.025 mmol). The reaction mixture was stirred for 16 h at 100° C. The reaction mixture was filtered through Celite bed and filtrate was concentrated. The residue was used in the next step without further purification (0.3 g). LCMS [M+H]$^+$ 437.5.

b) 1-((6-Acetylpyridin-3-yl)methyl)-3-(3-(3,4-dihydroisoquinolin-2(1H)-yl)-2-hydroxypropyl)imidazolidin-2-one (Q-2)

To a stirred solution of 1-(3-(3,4-dihydroisoquinolin-2(1H)-yl)-2-hydroxypropyl)-3-((6-(1-ethoxyvinyl)pyridin-3-yl)methyl)imidazolidin-2-one (0.3 g, 0.6 mmol) in 15 mL of THF was added 6 N HCl (6.0 mL) at 0° C. followed by stirring for 12 h at RT. The reaction mixture was concentrated and basified with saturated NaHCO$_3$ solution and extracted with 5% MeOH/DCM. The organic layer was washed with water and brine solution and then dried over anhydrous sodium sulphate. The residue was purified by Combi flash column chromatography eluted with 0-5% MeOH/CHCl$_3$ to give the title compound (0.1 g, 35.7%). LCMS [M+H]$^+$ 409.3. $^1$H NMR (400 MHz, DMSO-d$_6$) δ 8.61 (dd, 1H), 7.94 (dd, 1H), 7.84 (dd, 1H), 7.19-6.89 (m, 4H), 4.75 (d, 1H), 4.39 (s, 2H), 3.87 (h, 1H), 3.60 (s, 2H), 3.50-3.37 (m, 2H), 3.32-3.24 (m, 1H), 3.18 (t, 2H), 3.05-2.95 (m, 1H), 2.79 (t, 2H), 2.73-2.64 (m, 2H), 2.62 (s, 3H), 2.47-2.38 (m, 2H).

Example 33: 4-(3-(3-(3,4-dihydroisoquinolin-2(1H)-yl)-2-hydroxypropyl)-2-oxoimidazolidin-1-yl)benzonitrile (R-3)

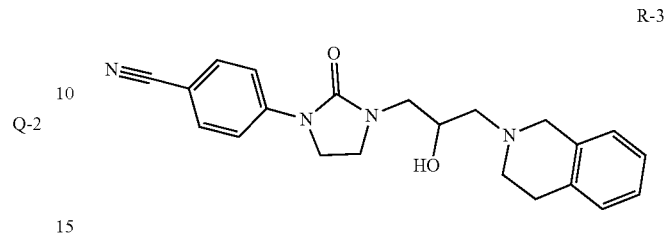

R-3 a) 4-(2-Oxoimidazolidin-1-yl)benzonitrile (R-1)

To a 50 mL sealed tube were added 4-iodobenzonitrile (3.0 g, 13.2 mmol) and n-butanol (60.0 mL) followed by degassing the reaction mixture with Argon gas for 10 min. To this reaction mixture were added imidazolidin-2-one (5.7 g, 66.0 mmol), K$_2$CO$_3$ (5.4 g, 39.6 mmol), CuI (0.3 g, 10%) and dimethyl ethylene diamine (0.35 mL, 3.9 mmol). The reaction mixture was stirred for 6 h at 100° C. The reaction mixture was concentrated and the residue purified with combi flash column chromatography eluted with 0-5% MeOH/DCM to give the title compound (1.0 g, 40.48%). LCMS [M+H]$^+$ 188.2.

b) 4-(3-(Oxiran-2-ylmethyl)-2-oxoimidazolidin-1-yl)benzonitrile (R-2)

To a stirred solution of 4-(2-oxoimidazolidin-1-yl)benzonitrile (0.75 g, 4.0 mmol) in 15.0 mL of THF was added NaH (0.24 g, 6.0 mmol) at 0° C. followed by stirring at 0° C. Epibromohydrin (0.514 mL, 6.0 mmol) was then added followed by stirring for 12 h at RT. The reaction mixture was quenched with water and extracted with ethyl acetate. The combined extracts were washed with water and brine solution, dried over anhydrous sodium sulphate and concentrated give the title compound (0.1 g, 12.0%). LCMS [M+H]$^+$244.2.

c) 4-(3-(3-(3,4-Dihydroisoquinolin-2(1H)-yl)-2-hydroxypropyl)-2-oxoimidazolidin-1-yl)benzonitrile (R-3)

To a 50 mL sealed tube were added 4-(3-(oxiran-2-ylmethyl)-2-oxoimidazolidin-1-yl)benzonitrile (0.1 g, 0.4132 mmol), 1,2,3,4-tetrahydroisoquinoline (0.08 mL, 0.6198 mmol), DIPEA (0.1 mL, 0.6198 mmol) and IPA (4.0 mL) followed by stirring for 12 h at 100° C. The reaction mixture was distilled out and the residue was purified by combi flash column chromatography eluted with 3% MeOH/DCM to give the title compound (0.035 g, 23%). LCMS [M+H]$^+$ 377.3. $^1$H NMR [400 MHz, CDCl$_3$] δ: 7.70-7.66 (m, 2H), 7.63-7.58 (m, 2H), 7.13 (dtd, 3H), 7.02-6.99 (m, 1H), 4.04 (tt, 1H), 3.89-3.80 (m, 4H), 3.80-3.71 (m, 2H), 3.65-3.47 (m, 2H), 3.26 (dd, 1H), 2.98-2.87 (m, 3H), 2.73 (dt, 1H), 2.64-2.50 (m, 2H).

Example 34: 1-(3-(3,4-dihydroisoquinolin-2(1H)-yl)-2-hydroxypropyl)-3-(5-(piperidine-1-carbonyl)pyridin-2-yl)imidazolidin-2-one (S-3)

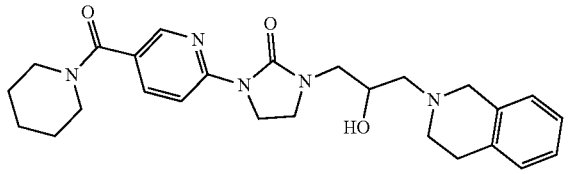

S-3

Example—34 experimental procedure is same as example—33. $^1$H NMR (400 MHz, DMSO-d$_6$) δ 8.33-8.29 (m, 1H), 8.23 (dt, 1H), 7.73 (ddd, 1H), 7.13-6.98 (m, 4H), 4.85 (d, 1H), 3.93 (t, 3H), 3.65-3.56 (m, 4H), 3.40 (d, 2H), 3.17 (dd, 2H), 2.79 (d, 3H), 2.76-2.63 (m, 3H), 1.61 (s, 2H), 1.51 (s, 4H), 1.23 (s, 2H). LCMS [M+H]$^+$464.4

Example 35: 6-((3-(3-(3,4-Dihydroisoquinolin-2(1H)-yl)-2-hydroxypropyl)-2-oxoimidazolidin-1-yl)methyl)nicotinonitrile (T-2) and its Isomer 1 (T-3) and Isomer 2 (T-4)

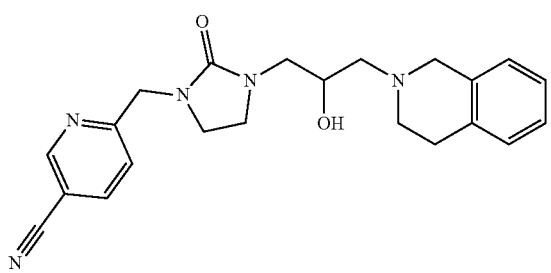

T-2 a) 6-((3-(2-((tert-Butyldimethylsilyl)oxy)-3-(3,4-dihydroisoquinolin-2(H)yl)propyl)-2-oxoimidazolidin-1-yl)methyl)nicotinonitrile (T-1)

To a stirred solution of 1-(2-((tert-butyldimethylsilyl)oxy)-3-(3,4-dihydroisoquinolin-2(1H)-yl)propyl)imidazolidin-2-one (1.0 g, 2.57 mmol) in 20 mL of THF was added NaH (0.102 g, 2.57 mmol) at 0° C. followed by stirring for 30 min at 0° C. To this reaction was mixture added 6-(bromomethyl)nicotinonitrile (0.607 g, 3.084 mmol) followed by stirring the reaction mixture for 12 h at RT. The reaction mixture was diluted with water and extracted with ethyl acetate. The combined extracts were washed with water and brine solution and then dried over anhydrous sodium sulphate. The residue was purified by Combi flash column chromatography eluted with 0-5% MeOH/DCM to give the title compound (0.95 g, 73.64%). LCMS [M+H]$^+$506.4.

b) 6-((3-(3-(3,4-Dihydroisoquinolin-2(1H)-yl)-2-hydroxypropyl)-2-oxoimidazolidin-1-yl)methyl)nicotinonitrile (T-2)

To a 250 mL single neck round bottom flask were added 6-((3-(2-((tert-butyl-dimethylsilyl)oxy)-3-(3,4-dihydroisoquinolin-2(1H)-yl)propyl)-2-oxoimidazolidin-1-yl)methyl)nicotinonitrile (0.7 g, 1.384 mmol) and 1,4-di-oxane (15.0 mL). To this reaction mixture was added 1,4-di-oxane HCl (0.7 mL) at 0° C. followed by stirring for 12 h at RT. The reaction mixture was concentrated and the residue was diluted with water and basified with solid Na$_2$CO$_3$. The mixture was extracted with 5% MeOH/DCM. The organic layer was washed with brine solution then dried over anhydrous sodium sulphate. The organic layer was concentrated. The residue (0.32 g) was purified by preparative HPLC to give the title compound (0.23 g, 42.51%). Preparative HPLC conditions: Mobile phase: (A): 0.05% TFA in water, (B): Acetonitrile; Column: X Bridge [(150 mm×21.2 mm), 5 micron]; Flow: 20 ml/min; [Time/% B 0/15, 2/25, 6/50]. LCMS [M+H]$^+$ 392.3. $^1$H NMR (300 MHz, DMSO-d$_6$) δ: 8.97 (dd, 1H), 8.28 (dd, 1H), 7.48 (dd, 1H), 7.17-6.96 (m, 4H), 4.76 (d, 1H), 4.44 (s, 2H), 3.88 (s, 1H), 3.61 (s, 2H), 3.45 (ddd, 3H), 3.26 (d, 2H), 3.03 (dd, 1H), 2.87-2.76 (m, 2H), 2.72 (d, 2H), 2.45 (d, 2H).

Racemic compound (T-2, 0.19 g) was separated into two enantiomers T-3 (0.02 g, isomer-1, retention time 8.840 min) and T-4 (0.02 g, isomer-2, retention time 7.713 min) using chiral column chromatography.

Column: Chiral pack IC [(10 mm×250 mm), 5 micron]; Mobile phase: (A): n-Hexane, (B): 0.1% DEA in EtOH: MeOH (80:20); Flow: 9 ml/min; Isocratic: 75:25(A:B).

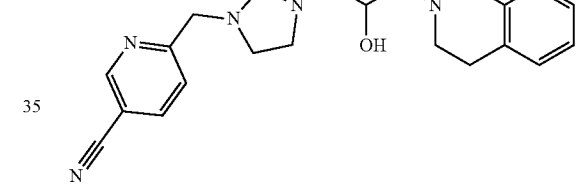

T-3

(Isomer-1)

and

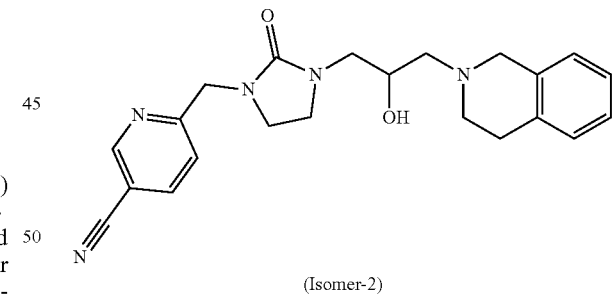

T-4

(Isomer-2)

Isomer-1: LCMS [M+H]$^+$ 392.3. $^1$H NMR (400 MHz, DMSO-d$_6$) δ: 8.97 (dd, 1H), 8.28 (dd, 1H), 7.48 (dd, 1H), 7.15-6.98 (m, 4H), 4.75 (d, 1H), 4.45 (s, 2H), 3.88 (s, 1H), 3.61 (s, 2H), 3.45 (ddd, 2H), 3.33-3.22 (m, 3H), 3.03 (dd, 1H), 2.80 (t, 2H), 2.76-2.64 (m, 2H), 2.44 (dd, 2H).

Isomer-2: LCMS [M+H]$^+$ 392.3. $^1$H NMR (400 MHz, DMSO-d$_6$) δ 8.97 (dd, 1H), 8.29 (dd, 1H), 7.48 (dd, Hz, 1H), 7.17-6.98 (m, 4H), 4.75 (d, 1H), 4.45 (s, 2H), 3.88 (s, 1H), 3.61 (s, 2H), 3.53-3.37 (m, 2H), 3.31-3.22 (m, 3H), 3.03 (dd, 1H), 2.80 (t, 2H), 2.75-2.64 (m, 2H), 2.45 (dd, 2H).

The following compounds were prepared according to the procedure described in Example 35 using appropriate starting materials. The characterization data is indicated on the table given below.

| Example No. | Structure | Characterization data |
|---|---|---|
| 36 | 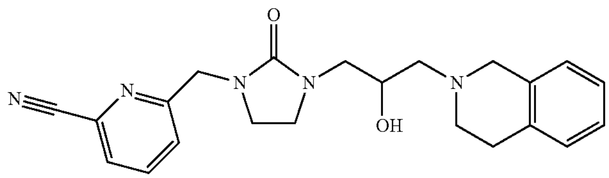 [SMILES: N#Cc1cccc(CN2CCN(CC(O)CN3CCc4ccccc4C3)C2=O)n1] | ¹H NMR (400 MHz, CDCl₃) δ: 7.81 (t, 1H), 7.61 (dd, 1H), 7.58 (dd, 1H), 7.16-7.09 (m, 3H), 7.04-7.00 (m, 1H), 4.54 (d, 2H), 4.01 (dddd, 1H), 3.83 (d, 1H), 3.66-3.52 (m, 2H), 3.46 (dd, 1H), 3.43-3.37 (m, 2H), 3.18 (dd, 3H), 2.98-2.87 (m, 3H), 2.75 (ddt, 1H), 2.62-2.51 (m, 2H). LCMS [M + H]⁺ 392.3. |
| 37 | 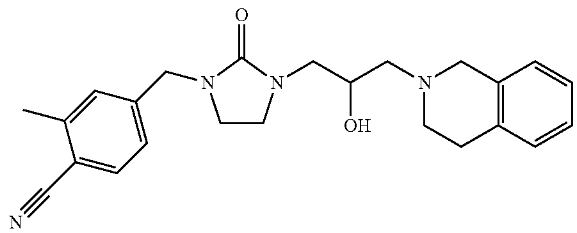 [SMILES: Cc1cc(CN2CCN(CC(O)CN3CCc4ccccc4C3)C2=O)ccc1C#N] | ¹H NMR (400 MHz, CDCl₃) δ: 7.56 (d, 1H), 7.25-7.21 (m, 1H), 7.21-7.16 (m, 1H), 7.13 (dtd, 3H), 7.04-6.98 (m, 1H), 4.38 (d, 2H), 4.00 (ddt, 1H), 3.83 (d, 1H), 3.67-3.42 (m, 5H), 3.26-3.11 (m, 3H), 2.99-2.85 (m, 3H), 2.80-2.68 (m, 1H), 2.64-2.55 (m, 2H), 2.54 (s, 3H). LCMS [M + H]⁺ 405.4. |
| 38 | 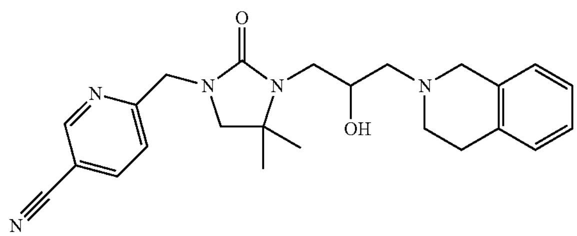 [SMILES: CC1(C)CN(Cc2ccc(C#N)cn2)C(=O)N1CC(O)CN1CCc2ccccc2C1] | ¹H NMR [300 MHz, DMSO-d₆] δ: 8.97 (s, 1H), 8.34-8.23 (m, 1H), 7.46 (d, 1H), 7.09 (d, 3H), 7.02 (d, 1H), 4.84 (s, 1H), 4.54-4.37 (m, 2H), 4.01-3.86 (m, 1H), 3.61 (d, 2H), 3.22 (dd, 1H), 3.17-3.05 (m, 2H), 2.90 (dd, 1H), 2.84-2.63 (m, 4H), 2.45-2.38 (m, 2H), 1.20 (d, 6H). LCMS [M + H]⁺ 420.4. |
| 39 | 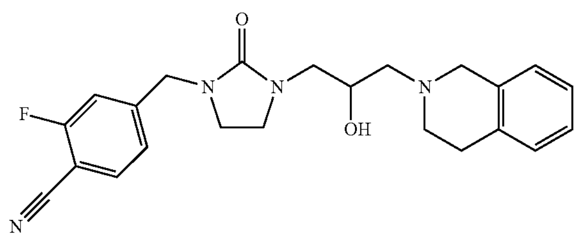 [SMILES: N#Cc1ccc(CN2CCN(CC(O)CN3CCc4ccccc4C3)C2=O)cc1F] | ¹H NMR (400 MHz, DMSO-d₆) δ: 7.91 (td, 1H), 7.39 (d, 1H), 7.29 (d, 1H), 7.10 (dq, 3H), 7.03 (d, 1H), 4.75 (dt, 1H), 4.36 (d, 2H), 3.88 (d, 1H), 3.60 (s, 2H), 3.52-3.37 (m, 2H), 3.31-3.15 (m, 3H), 3.04 (dd, 1H), 2.79 (d, 2H), 2.70 (dt, 2H), 2.44 (d, 2H). LCMS [M + H]⁺ 409.3. |
| 40 | 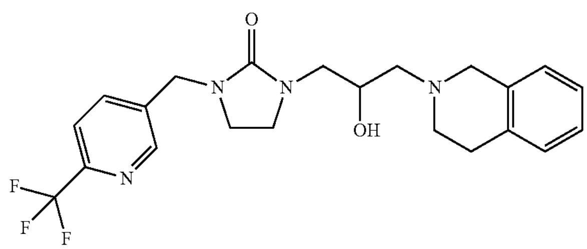 [SMILES: O=C1N(Cc2ccc(C(F)(F)F)nc2)CCN1CC(O)CN1CCc2ccccc2C1] | ¹H NMR (300 MHz, CDCl₃) δ: 8.65 (s, 1H), 7.84 (d, 1H), 7.67 (d, 1H), 7.17-7.08 (m, 3H), 7.02 (s, 1H), 4.47 (s, 2H), 3.99 (s, 1H), 3.83 (d, 1H), 3.67-3.42 (m, 4H), 3.29-3.12 (m, 3H), 2.92-2.95 (m, 3H), 2.74 (s, 1H), 2.63-2.47 (m, 3H). LCMS [M + H]⁺ 435.1. |
| 41 | 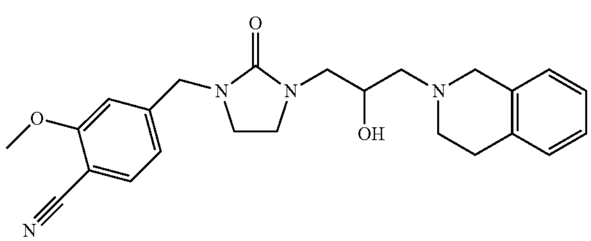 [SMILES: COc1cc(CN2CCN(CC(O)CN3CCc4ccccc4C3)C2=O)ccc1C#N] | ¹H NMR (400 MHz, DMSO-d₆) δ: 7.65 (d, 1H), 7.05 (dd, 4H), 7.02-6.96 (m, 1H), 6.91 (dd, 1H), 4.72 (d, 1H), 4.29 (s, 2H), 3.86 (s, 3H), 3.56 (s, 2H), 3.40 (s, 2H), 3.30 (s, 2H), 3.28-3.21 (m, 2H), 3.18-3.11 (m, 2H), 3.01 (dd, 1H), 2.76 (t, 2H), 2.69-2.62 (m, 2H). LCMS [M + H]⁺ 421.4. |
| 42 | 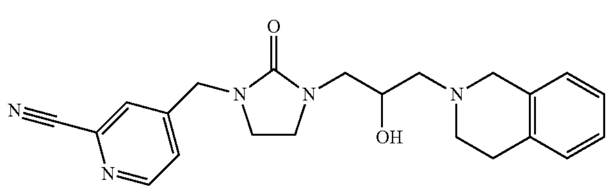 [SMILES: N#Cc1cc(CN2CCN(CC(O)CN3CCc4ccccc4C3)C2=O)ccn1] | ¹H NMR (300 MHz, DMSO-d₆) δ: 8.70 (dd, 1H), 7.91-7.87 (m, 1H), 7.60 (dd, 1H), 7.10 (d, 3H), 7.03 (d, 1H), 4.76 (d, 1H), 4.37 (s, 2H), 3.89 (s, 1H), 3.61 (s, 2H), 3.45 (dt, 2H), 3.28-3.20 (m, 3H), 3.06 (dd, 1H), 2.79 (d, 2H), 2.72 (dt, 2H), 2.45 (d, 2H). LCMS [M + H]⁺ 392.3. |

| Example No. | Structure | Characterization data |
|---|---|---|
| 43 | 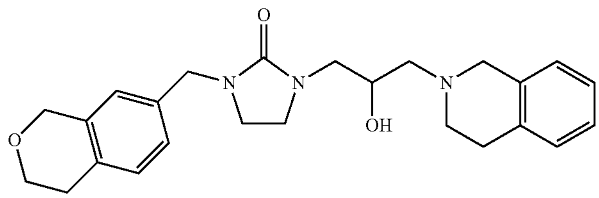 [SMILES: O=C1N(Cc2ccc3c(c2)COCC3)CCN1CC(O)CN1CCc2ccccc2C1] | ¹H NMR (400 MHz, DMSO-d₆) δ: 7.10 (s, 1H), 7.09 (q, 3H), 7.03 (d, 1H), 7.02-6.99 (m, 1H), 6.89 (d, 1H), 4.73 (d, 1H), 4.65 (s, 2H), 4.19 (s, 2H), 3.85 (t, 3H), 3.60 (s, 2H), 3.44-3.37 (m, 1H), 3.31-3.23 (m, 2H), 3.10 (t, 2H), 3.01 (dd, 1H), 2.80 (t, 2H), 2.77-2.65 (m, 4H), 2.46-2.40 (m, 2H). LCMS [M + H]⁺ 422.4. |
| 44 | 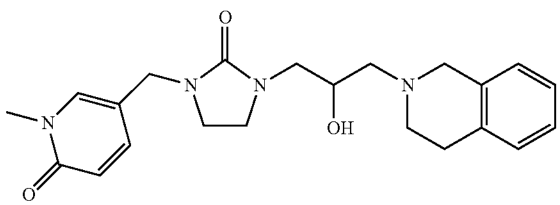 [SMILES: Cn1cc(CN2CCN(CC(O)CN3CCc4ccccc4C3)C2=O)ccc1=O] | ¹H NMR (400 MHz, DMSO-d₆) δ: 7.60 (d, 1H), 7.29 (dd, 1H), 7.15-7.06 (m, 3H), 7.02 (dd, 1H), 6.37 (d, 1H), 4.72 (s, 1H), 3.98 (s, 2H), 3.85 (d, 1H), 3.60 (s, 2H), 3.41 (s, 3H), 3.39 (dd, 1H), 3.26 (dd, 2H), 3.12 (t, 2H), 3.00 (dd, 1H), 2.79 (t, 2H), 2.69 (d, 2H), 2.44 (dt, 2H). LCMS [M + H]⁺ 397.4. |
| 45 | 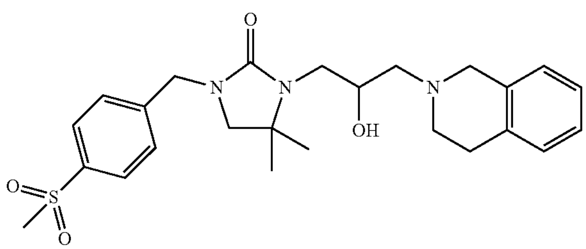 [SMILES: CC1(C)CN(Cc2ccc(S(C)(=O)=O)cc2)C(=O)N1CC(O)CN1CCc2ccccc2C1] | ¹H NMR (400 MHz, CDCl₃) δ: 7.95-7.88 (m, 2H), 7.50-7.44 (m, 2H), 7.19-7.07 (m, 3H), 7.06-6.97 (m, 1H), 4.57-4.31 (m, 2H), 3.99 (qd, 1H), 3.77 (d, 2H), 3.67 (d, 1H), 3.38 (dd, 1H), 3.16 (dd, 1H), 3.04 (s, 3H), 2.89 (t, 2H), 2.82 (dt, 4H), 2.60 (qd, 2H), 1.25 (d, 6H). LCMS [M + H]⁺ 472.2. |

Example 46: 6-((3-(3-(3,4-Dihydroisoquinolin-2 (1H)-yl)-2-hydroxypropyl)-2-oxoimidazolidin-1-yl) methyl)nicotinamide (U-2)

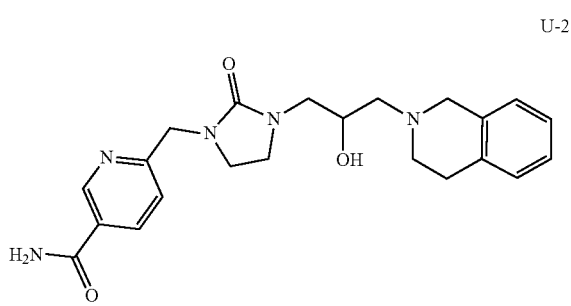 [SMILES: NC(=O)c1ccc(CN2CCN(CC(O)CN3CCc4ccccc4C3)C2=O)nc1]

a) 6-((3-(3-(3,4-Dihydroisoquinolin-2(1H)-yl)-2-hydroxypropyl)-2-oxoimidazolidin-1-yl)methyl) nicotinic acid with hydrochloride salt (U-1)

To a stirred solution of 6-((3-(3-(3,4-dihydroisoquinolin-2(1H)-yl)-2-hydroxypropyl)-2-oxoimidazolidin-1-yl) methyl)nicotinonitrile (0.2 g, 0.511 mmol) in 15 mL of 1,4-di-oxane was added 6 N HCl (15 mL) followed by stirring for 36 h at 100° C. The reaction mixture was concentrated and the residue was used in the next step without further purification (0.2 g, 95.69%). LCMS [M+H]⁺ 411.3.

b) 6-((3-(3-(3,4-Dihydroisoquinolin-2(1H)-yl)-2-hydroxypropyl)-2-oxoimidazolidin-1-yl)methyl) nicotinamide (U-2)

To a stirred solution of 6-((3-(3-(3,4-dihydroisoquinolin-2(1H)-yl)-2-hydroxypropyl)-2-oxoimidazolidin-1-yl) methyl)nicotinic acid with hydrochloride salt (0.2 g, 0.487 mmol) in 10 mL of DMF were added DIPEA (0.35 mL g, 1.951 mmol), HATU (0.278 mL g, 0.731 mmol) and NH₄Cl (0.26, 4.878 mmol) at 0° C. followed by stirring for 12 h at RT. The reaction mixture was diluted with water and extracted with ethyl acetate. The combined extracts were washed with water and brine solution and then dried over anhydrous sodium sulphate. The residue was purified by preparative TLC eluted with 5% MeOH/DCM to give light brown solid (0.025 g, 12.56%). LCMS [M+H]⁺ 410.4. ¹H NMR (400 MHz, DMSO-d₆) δ: 8.96 (dd, 1H), 8.24-8.08 (m, 2H), 7.58 (s, 1H), 7.36 (d, 1H), 7.12 (s, 4H), 4.78 (s, 1H), 4.40 (s, 2H), 3.90 (s, 1H), 3.63 (s, 2H), 3.52-3.38 (m, 2H), 3.33-3.21 (m, 5H), 3.04 (dd, 1H), 2.81 (s, 2H), 2.73 (s, 2H).

Example 47: 4-((3-(3-(3,4-dihydroisoquinolin-2 (1H)-yl)-2-hydroxypropyl)-2-oxoimidazolidin-1-yl) methyl)benzamide

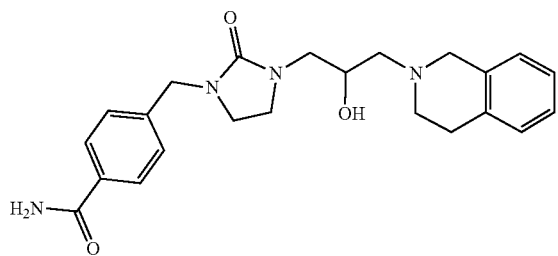 [SMILES: NC(=O)c1ccc(CN2CCN(CC(O)CN3CCc4ccccc4C3)C2=O)cc1]

Example 47 was prepared according to the procedure described in Example 46 using appropriate starting materials.

¹H NMR (400 MHz, DMSO-$d_6$) δ: 7.95 (s, 1H), 7.86-7.81 (m, 2H), 7.35 (s, 1H), 7.30 (d, 2H), 7.12-7.06 (m, 3H), 7.05-6.99 (m, 1H), 4.74 (d, 1H), 4.30 (s, 2H), 3.87 (q, 1H), 3.61 (s, 2H), 3.41 (dd, 2H), 3.28 (dd, 1H), 3.13 (t, 2H), 3.07-2.99 (m, 1H), 2.79 (d, 2H), 2.69 (dt, 2H), 2.44 (dd, 2H). LCMS [M+H]⁺409.4.

Example 48: (R)-6-((3-(3-(3,4-Dihydroisoquinolin-2 (1H)-yl)-2-hydroxypropyl)-2-oxoimidazolidin-1-yl) methyl)nicotinamide (W-8)

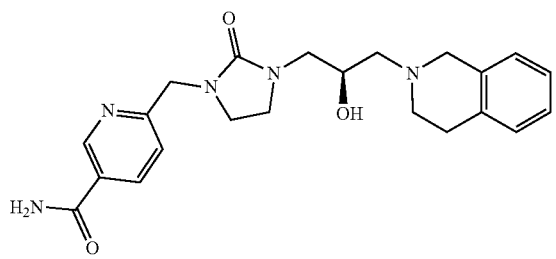

W-8 a) (R)-2-(oxiran-2-ylmethyl)-1,2,3,4-tetrahydroisoquinoline (W-1)

To a stirred solution of 1,2,3,4-tetrahydroisoquinoline (25.0 g, 187.701 mmol) in 250 mL of THF was added KF (54.52 g, 938.5 mmol) at 0° C. followed by stirring for 1 h at 0° C.

To this reaction mixture was added (S)-oxiran-2-ylmethyl 3-nitrobenzenesulfonate (53.52 g, 206.47 mmol) dropwise by dissolving in THF. The reaction mixture was stirred for 16 h at RT. The precipitated solids were filtered and the filtrate was concentrated to give brown sticky liquid (47.0 g). LCMS [M+H]⁺ 190.

b) (S)-1-((2-Aminoethyl)amino)-3-(3,4-dihydroisoquinolin-2(1H)-yl)propan-2-ol (W-2)

To a stirred solution of (R)-2-(oxiran-2-ylmethyl)-1,2,3, 4-tetrahydroisoquinoline (30.0 g, 158.512 mmol) in 600 mL of ethanol was added ethane-1,2-diamine (95.1 g, 1585.12 mmol) followed by stirring for 12 h at 45° C. The reaction mixture was concentrated to give yellow sticky liquid (40.0 g). LCMS [M+H]⁺250.

c) (R)-1-(3-(3,4-Dihydroisoquinolin-2(1H)-yl)-2-hydroxypropyl)imidazolidin-2-one (W-3)

To a stirred solution of (S)-1-((2-aminoethyl)amino)-3-(3,4-dihydroisoquinolin-2(1H)-yl)propan-2-ol (40.0 g, 160.642 mmol) in 600 mL of DCM were added DMAP (3.91 g, 32.128 mmol) and CDI (39.07 g, 240.96 mmol) portion wise at 0° C. The reaction mixture was stirred for 12 h at RT. The reaction mixture was filtered through Celite bed. The filtrate was washed with water and brine solution, dried over anhydrous sodium sulphate and concentrated. The residue was purified by Combi flash column chromatography eluted with 0-5% MeOH/DCM to give the title compound (18.0 g, 40.85%). LCMS [M+H]⁺276.3.

d) (R)-1-(2-((tert-Butyldimethylsilyl)oxy)-3-(3,4-dihydroisoquinolin-2(1H)-yl)propyl)imidazolidin-2-one (W-4)

To a stirred solution of (R)-1-(3-(3,4-dihydroisoquinolin-2(1H)-yl)-2-hydroxypropyl)imidazolidin-2-one (16.9 g, 58.181 mmol) in 800.0 mL of DCM were added DIPEA (18.8 g, 145.454 mmol) and trimethylsilyltrifluoromethanesulfonate (16.91 g, 63.99 mmol) at -78° C. The reaction mixture was stirred for 2 h at -78° C. and 1 h at 0° C. The reaction mixture was diluted with DCM. The combined extracts were washed with saturated NaHCO₃ solution and brine solution, dried over anhydrous sodium sulphate and concentrated. The residue was purified by Combi flash column chromatography eluted with 0-3% MeOH/DCM to give the title compound (9.0 g, 39.8%). LCMS [M+H]⁺ 390.4.

e) (R)-6-((3-(2-((tert-Butyldimethylsilyl)oxy)-3-(3, 4-dihydroisoquinolin-2(1H)-yl)propyl)-2-oxoimidazolidin-1-yl)methyl)nicotinonitrile (W-5)

To a stirred solution of (R)-1-(2-((tert-butyldimethylsilyl) oxy)-3-(3,4-dihydro-isoquinolin-2(1H)-yl)propyl)imidazolidin-2-one (3.0 g, 7.712 mmol) in 100 mL of THF was added NaH (0.34 g, 8.483 mmol) at 0° C. followed by stirring for 30 min at 0° C. To this reaction mixture was added 6-(bromomethyl)nicotinonitrile (1.82 g, 9.254 mmol) followed by stirring for 12 h at RT. The reaction mixture was diluted with water and extracted with ethyl acetate. The organic layer was washed with water and brine solution, dried over anhydrous sodium sulphate and concentrated. The residue was purified by Combi flash column chromatography eluted with 0-5% MeOH/DCM to give the title compound (1.7 g, 43.70%). LCMS [M+H]⁺506.4.

f) (R)-6-((3-(3-(3,4-dihydroisoquinolin-2(1H)-yl)-2-hydroxypropyl)-2-oxoimidazolidin-1-yl)methyl) nicotinonitrile (W-6)

To a 250 mL single neck round bottom flask were added (R)-6-((3-(2-((tert-butyldimethylsilyl)oxy)-3-(3,4-dihydroisoquinolin-2(1H)-yl)propyl)-2-oxoimidazolidin-1-yl) methyl)nicotinonitrile (1.7 g, 3.361 mmol) and 1,4-di-oxane (35.0 mL). To this reaction mixture was added 1,4-di-oxane HCl (3.4 mL) at 0° C. followed by stirring for 12 h at RT. The reaction mixture was concentrated. The residue was diluted with water and basified with solid Na₂CO₃ followed by extracting with 5% MeOH/DCM. The combined extracts were washed with brine solution, dried over anhydrous sodium sulphate and concentrated. The residue was purified by Combi flash column chromatography eluted with 0-5% MeOH/DCM to give the title compound (0.8 g, 61.06%). LCMS [M+H]$^+$392.3.

g) (R)-6-((3-(3-(3,4-Dihydroisoquinolin-2(1H)-yl)-2-hydroxypropyl)-2-oxoimidazolidin-1-yl)methyl) nicotinic acid with hydrogen chloride salt (W-7)

To a stirred solution of (R)-6-((3-(3-(3,4-dihydroisoquinolin-2(1H)-yl)-2-hydroxypropyl)-2-oxoimidazolidin-1-yl) methyl)nicotinonitrile (0.75 g, 1.918 mmol) in 15 mL of 1,4-di-oxane was added 6 N HCl (15 mL). The reaction mixture was stirred for 36 h at 100° C. The reaction mixture was concentrated. The residue was used in the next step without further purification (0.9 g). LCMS [M+H]$^+$411.3.

h) (R)-6-((3-(3-(3,4-Dihydroisoquinolin-2(1H)-yl)-2-hydroxypropyl)-2-oxoimidazolidin-1-yl)methyl) nicotinamide (W-8)

To a stirred solution of (R)-6-((3-(3-(3,4-dihydroisoquinolin-2(1H)-yl)-2-hydroxypropyl)-2-oxoimidazolidin-1-yl) methyl)nicotinic acid with hydrogen chloride salt (0.2 g, 0.487 mmol) in 10 mL of DMF were added DIPEA (0.315 g, 2.439 mmol), HATU (0.278 mL g, 0.731 mmol) and NH$_4$Cl (0.078, 1.463 mmol) at 0° C. The reaction mixture was stirred for 12 h at RT. The reaction mixture was diluted with water and extracted with ethyl acetate. The combined extracts were washed with water and brine solution, dried over anhydrous sodium sulphate and concentrated. The residue was purified by preparative TLC plates eluted with 5% MeOH/DCM to give light brown solid (0.02 g, 10.05%). LCMS [M+H]$^+$410.4; $^1$H NMR (400 MHz, DMSO-d$_6$) δ: 8.96 (d, 1H), 8.22-8.10 (m, 2H), 7.58 (s, 1H), 7.35 (d, 1H), 7.15-6.98 (m, 4H), 4.78 (s, 1H), 4.40 (s, 2H), 3.90 (s, 1H), 3.63 (s, 2H), 3.52-3.38 (m, 2H), 3.33-3.21 (m, 5H), 3.04 (dd, 1H), 2.81 (s, 2H), 2.73 (s, 2H).

The following compounds were prepared according to the procedure described in Example 48 using appropriate starting materials. The characterization data is indicated on the table given below.

| Example No. | Structure | Characterization data |
|---|---|---|
| 49 | 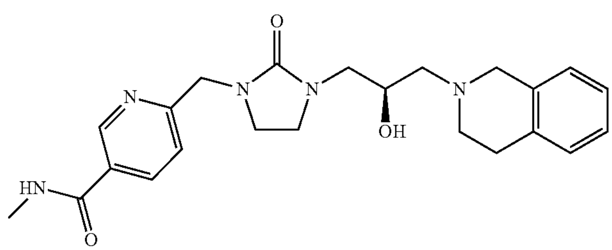 [SMILES: CNC(=O)c1ccc(CN2CCN(C[C@H](O)CN3CCc4ccccc4C3)C2=O)nc1] | $^1$H NMR (400 MHz, DMSO-d$_6$) δ: 8.92 (d, 1H), 8.61 (q, 1H), 8.15 (dd, 1H), 7.36 (d, 1H), 7.09 (d, 4H), 4.41 (s, 2H), 3.93 (s, 1H), 3.54-3.37 (m, 2H), 3.45 (h, 2H), 3.32-3.21 (m, 5H), 3.07 (s, 1H), 2.90-2.81 (m, 2H), 2.79 (d, 3H), 1.31-1.15 (m, 3H). LCMS [M + H] $^+$ 424.4. |
| 50 | 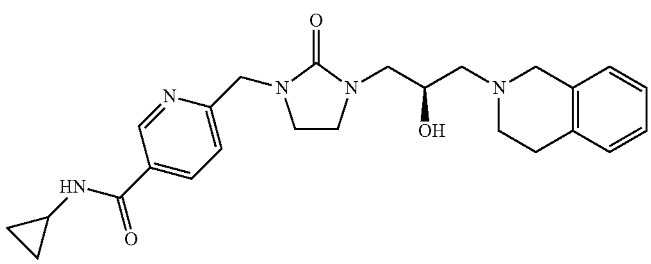 [SMILES: O=C(NC1CC1)c1ccc(CN2CCN(C[C@H](O)CN3CCc4ccccc4C3)C2=O)nc1] | $^1$H NMR (400 MHz, DMSO-d$_6$) δ: 8.89 (d, 1H), 8.61 (d, 1H), 8.13 (dd, 1H), 7.35 (d, 1H), 7.09 (d, 4H), 4.40 (s, 2H), 3.94 (s, 1H), 3.45 (h, 2H), 3.30-3.20 (m, 5H), 3.08 (s, 2H), 2.93-2.76 (m, 4H), 1.31-1.15 (m, 3H), 0.71 (td, 2H), 0.61-0.52 (m, 2H). LCMS [M + H] $^+$ 450.4. |
| 51 | 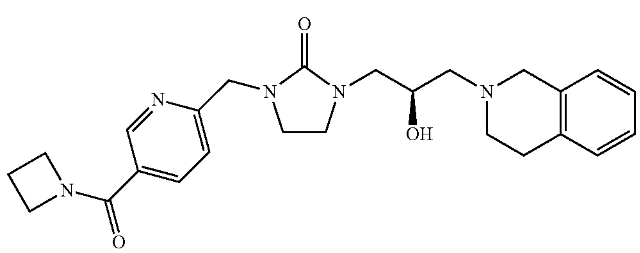 [SMILES: O=C(c1ccc(CN2CCN(C[C@H](O)CN3CCc4ccccc4C3)C2=O)nc1)N1CCC1] | $^1$H NMR (400 MHz, DMSO-d$_6$) δ: 8.77-8.68 (m, 1H), 7.99 (dt, 1H), 7.35 (d, 1H), 7.12 (d, 4H), 4.41 (s, 2H), 4.32 (t, 2H), 4.06 (t, 2H), 3.62 (dd, 1H), 3.44 (dq, 3H), 3.32-3.20 (m, 2H), 3.19-3.03 (m, 2H), 2.89 (s, 2H), 2.34-2.21 (m, 2H), 1.32-1.15 (m, 6H). LCMS [M + H] $^+$ 450.4. |
| 52 | 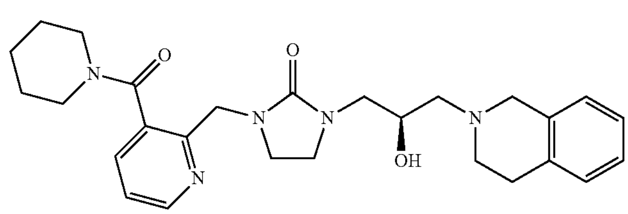 [SMILES: O=C(c1cccnc1CN1CCN(C[C@H](O)CN2CCc3ccccc3C2)C1=O)N1CCCCC1] | $^1$H NMR (400 MHz, DMSO-d6) δ 8.55 (dt, 1H), 7.68-7.63 (m, 1H), 7.36 (dd, 1H), 7.14-6.96 (m, 4H), 4.71 (d, 2H), 4.38 (s, 1H), 4.32-4.22 (m, 1H), 3.84 (d, 2H), 3.73 (s, 1H), 3.60 (s, 2H), 3.41 (d, 3H), 3.23 (t, 2H), 3.11-3.02 (m, 2H), 2.75 (dt, 4H), 2.43 (q, 2H), 1.66-1.46 (m, 4H), 1.40 (s, 2H). LCMS [M + H] $^+$ 478.4. |

| Example No. | Structure | Characterization data |
|---|---|---|
| 53 | 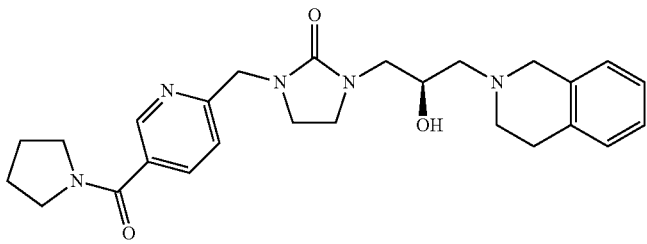 [SMILES: O=C(c1ccc(CN2CCN(C[C@H](O)CN3CCc4ccccc4C3)C2=O)nc1)N1CCCC1] | ¹H NMR (400 MHz, Chloroform-d) δ 8.71 (d, 1H), 7.84 (dd, 2.2 Hz, 1H), 7.38 (d, 1H), 7.13 (dt, 3H), 7.03-6.99 (m, 1H), 4.54 (d, 2H), 4.01 (ddt, 1H), 3.83 (d, 1H), 3.70-3.52 (m, 5H), 3.51-3.42 (m, 3H), 3.36 (t, 2H), 3.19 (dd, 1H), 2.97-2.88 (m, 3H), 2.75 (dd, 1H), 2.63-2.52 (m, 2H), 1.95 (dq, 4H). LCMS [M + H] $^+$ 464.4. |
| 54 | 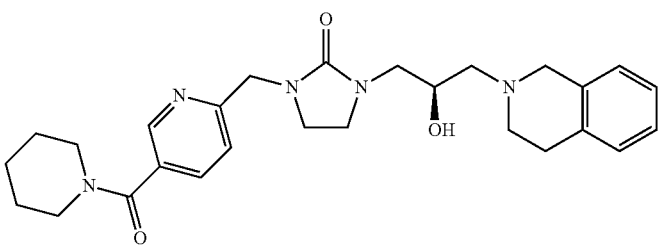 [SMILES: O=C(c1ccc(CN2CCN(C[C@H](O)CN3CCc4ccccc4C3)C2=O)nc1)N1CCCCC1] | ¹H NMR (400 MHz, Chloroform-d) δ 8.58 (dd, 1H), 7.72 (dd, 1H), 7.38 (dd, 1H), 7.13 (dt, 3H), 7.05-6.98 (m, 1H), 4.54 (d, 2H), 4.04-3.98 (m, 1H), 3.87-3.79 (m, 1H), 3.72 (s, 2H), 2.80-2.71 (m, 1H), 3.67-3.53 (m, 3H), 3.49 (s, 3H), 3.45 (dd, 1H), 3.37 (t, 3H), 3.19 (dd, 1H), 2.91 (d, 3H), 2.64-2.51 (m, 2H), 1.69 (s, 4H). LCMS [M + H] $^+$ 478.4 |
| 55 | 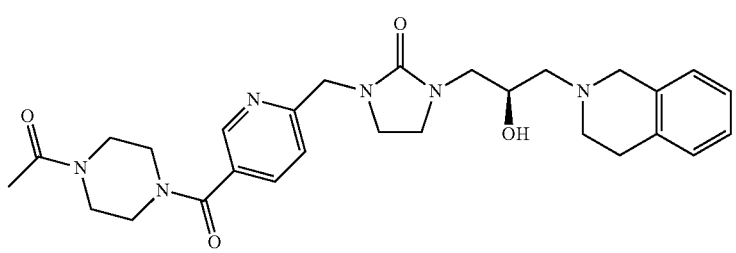 [SMILES: CC(=O)N1CCN(C(=O)c2ccc(CN3CCN(C[C@H](O)CN4CCc5ccccc5C4)C3=O)nc2)CC1] | ¹H NMR (400 MHz, Chloroform-d) δ 8.61 (d, 1H), 7.75 (dd, 1H), 7.42 (d, 1H), 7.14 (dt, 3H), 7.05-6.99 (m, 1H), 4.56 (d, 2H), 4.01 (s, 1H), 3.83 (d, 2H), 3.66-3.60 (m, 3H), 3.59-3.51 (m, 3H), 3.50-3.44 (m, 3H), 3.39 (t, 3H), 3.18 (dd, 2H), 2.98-2.87 (m, 3H), 2.75 (s, 1H), 2.63-2.51 (m, 2H), 2.20-2.10 (m, 3H). LCMS [M + H] $^+$ 521.4. |
| 56 | 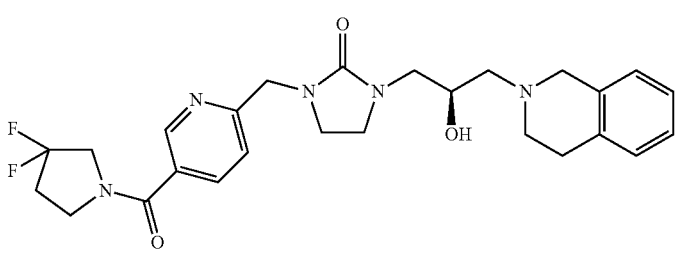 [SMILES: O=C(c1ccc(CN2CCN(C[C@H](O)CN3CCc4ccccc4C3)C2=O)nc1)N1CCC(F)(F)C1] | ¹H NMR (400 MHz, DMSO-d6) δ 8.69 (s, 1H), 7.97 (d, 1H), 7.34 (d, 1H), 7.12-7.00 (m, 4H), 5.36-5.27 (m, 1H), 4.74 (d, 1H), 4.40 (s, 2H), 3.99-3.84 (m, 4H), 3.71 (t, 2H), 3.61 (s, 2H), 3.44 (dt, 3H), 3.30-3.26 (m, 2H), 3.03 (dd, 1H), 2.79 (d, 2H), 2.71 (q, 2H), 2.46-2.38 (m, 4H). LCMS [M + H] $^+$ 500.7. |
| 57 | 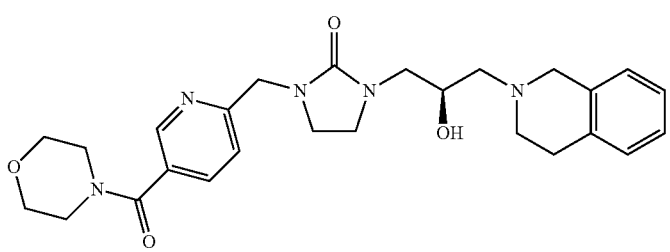 [SMILES: O=C(c1ccc(CN2CCN(C[C@H](O)CN3CCc4ccccc4C3)C2=O)nc1)N1CCOCC1] | ¹H NMR (400 MHz, DMSO-d6) δ 8.55 (d, 1H), 7.81 (dd, 1H), 7.36-7.29 (m, 1H), 7.12-6.98 (m, 4H), 5.31 (s, 1H), 4.73 (d, 1H), 4.38 (s, 2H), 3.86 (s, 1H), 3.59 (s, 5H), 3.50-3.37 (m, 3H), 3.29-3.24 (m, 3H), 3.02 (dd, 2H), 2.78 (d, 2H), 2.69 (q, 2H), 2.43 (dd, 4H). LCMS [M + H] $^+$ 480.6. |
| 58 | 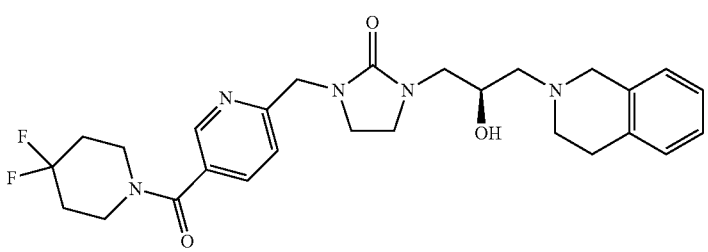 [SMILES: O=C(c1ccc(CN2CCN(C[C@H](O)CN3CCc4ccccc4C3)C2=O)nc1)N1CCC(F)(F)CC1] | ¹H NMR (400 MHz, DMSO-d6) δ 8.60 (dd, 1H), 7.87 (dd, 1H), 7.35 (dd, 1H), 7.13-7.02 (m, 4H), 4.75 (d, 1H), 4.40 (s, 2H), 3.89 (d, 1H), 3.72 (s, 2H), 3.61 (s, 5H), 3.53-3.39 (m, 3H), 3.33-3.26 (m, 3H), 3.11-2.99 (m, 2H), 2.80 (t, 2H), 2.75-2.65 (m, 3H), 2.45 (dd, 2H). LCMS [M + H] $^+$ 514.6. |

-continued

| Example No. | Structure | Characterization data |
|---|---|---|
| 59 | 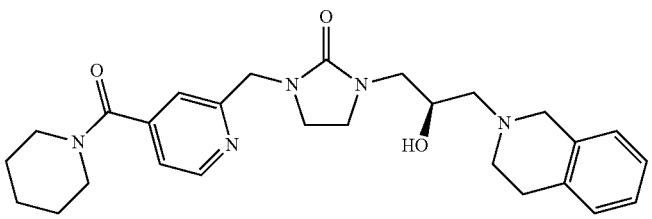 [SMILES: O=C(c1ccnc(CN2CCN(C[C@H](O)CN3CCc4ccccc4C3)C2=O)c1)N1CCCCC1] | ¹H NMR (300 MHz, Methanol-d4) δ 8.59 (dd, 1H), 7.37-7.28 (m, 2H), 7.14-6.98 (m, 4H), 4.51 (s, 2H), 4.14-4.03 (m, 1H), 3.79-3.64 (m, 4H), 3.64-3.53 (m, 2H), 3.45-3.33 (m, 4H), 3.21 (dd, 1H), 3.01-2.80 (m, 4H), 2.65-2.56 (m, 2H), 1.68 (s, 4H), 1.54 (s, 2H) 1.29 (s, 2H). LCMS [M + H] + 478.4. |
| 60 | 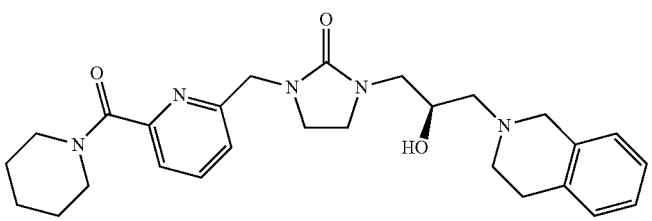 [SMILES: O=C(c1cccc(CN2CCN(C[C@H](O)CN3CCc4ccccc4C3)C2=O)n1)N1CCCCC1] | ¹H NMR (400 MHz, Methanol-d4) δ 7.88 (t, 1H), 7.42 (d, 2H), 7.14-6.99 (m, 4H), 4.48 (s, 2H), 4.07 (dt, 1H), 3.76 (s, 2H), 3.70 (t, 2H), 3.61-3.52 (m, 2H), 3.45-3.32 (m, 5H), 3.19 (dd, 1H), 2.90 (dd, 4H), 2.63 (d, 2H), 1.69 (d, 4H), 1.59-1.51 (m, 2H). LCMS [M + H] + 478.4. |
| 61 | 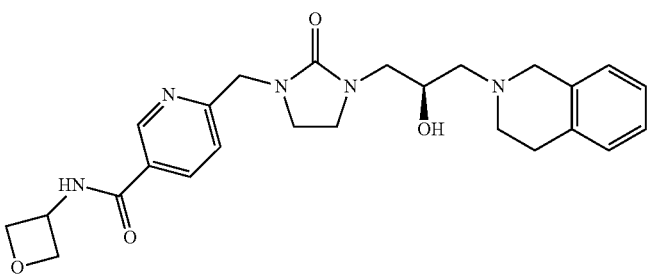 [SMILES: O=C(NC1COC1)c1ccc(CN2CCN(C[C@H](O)CN3CCc4ccccc4C3)C2=O)nc1] | ¹H NMR (400 MHz, DMSO-d6) δ 8.94 (dd, 1H), 8.20-8.13 (m, 1H), 7.41-7.34 (m, 1H), 7.12-6.99 (m, 4H), 4.87-4.81 (m, 1H), 4.74 (d, 1H), 4.49-4.40 (m, 3H), 4.30 (ddt, 2H), 3.89 (d, 1H), 3.58 (d, 3H), 3.53-3.38 (m, 3H), 3.28 (q, 3H), 3.03 (dd, 1H), 2.80 (t, 2H), 2.71 (hept, 2H), 2.45 (dd, 2H). LCMS [M + H] + 466.4. |
| 62 | 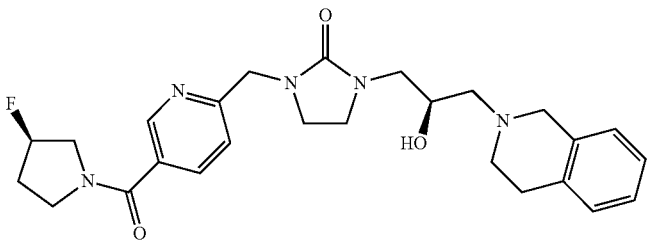 [SMILES: O=C(c1ccc(CN2CCN(C[C@H](O)CN3CCc4ccccc4C3)C2=O)nc1)N1CC[C@@H](F)C1] | ¹H NMR (400 MHz, Methanol-d4) δ 8.69 (dd, 1H), 7.98 (ddd, 1H), 7.47 (d, 1H), 7.17-7.01 (m, 4H), 4.52 (s, 2H), 4.11 (s, 2H), 3.89-3.69 (m, 4H), 3.66-3.55 (m, 3H), 3.48-3.36 (m, 3H), 3.34 (d, 1H), 3.23 (dd, 2H), 2.95 (s, 3H), 2.70 (s, 2H), 2.20 (dd, 2H). LCMS [M + H] + 482.4. |
| 63 | 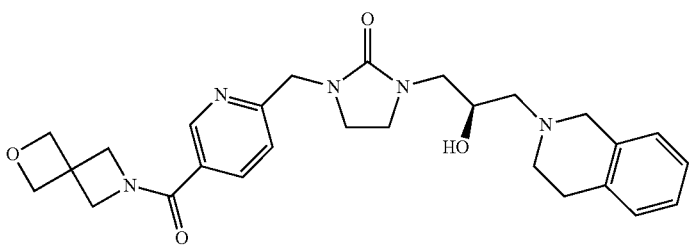 [SMILES: O=C(c1ccc(CN2CCN(C[C@H](O)CN3CCc4ccccc4C3)C2=O)nc1)N1CC2(COC2)C1] | ¹H NMR (400 MHz, DMSO-d6) δ 8.99 (d, 1H), 8.28 (d, 1H), 7.11-6.98 (m, 4H), 4.71 (d, 1H), 4.39 (d, 2H), 4.05 (dp, 1H), 3.84 (d, 1H), 3.60 (s, 2H), 3.45-3.37 (m, 2H), 3.32-3.22 (m, 4H), 3.09 (s, 3H), 2.79 (t, 2H), 2.74-2.65 (m, 2H), 2.43 (dd, 2H), 1.56 (s, 4H), 1.43 (s, 2H). LCMS [M + H] + 492.8. |
| 64 | 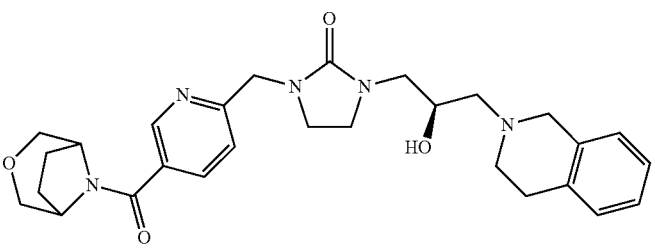 [SMILES: O=C1N(Cc2ccc(C(=O)N3C4CCC3COC4)cn2)CCN1C[C@H](O)CN1CCc2ccccc2C1] | ¹H NMR (400 MHz, DMSO-d6) δ 8.63 (dd, 1H), 7.90 (dd, 1H), 7.36-7.31 (m, 1H), 7.06 (d, 4H), 4.75 (s, 1H), 4.53 (s, 1H), 4.40 (s, 2H), 3.96-3.84 (m, 3H), 3.63 (d, 4H), 3.55-3.38 (m, 3H), 3.33-3.25 (m, 1H), 3.18-3.10 (m, 2H), 3.10-2.99 (m, 2H), 2.80 (s, 1H), 2.71 (s, 3H), ), 2.44 (s, 1H), 1.88 (s, 4H). LCMS [M + H] + 506.0 |

| Example No. | Structure | Characterization data |
|---|---|---|
| 65 | 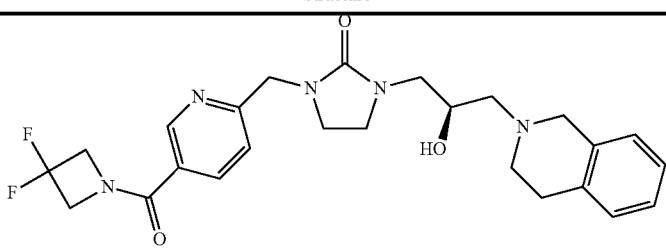 | ¹H NMR (400 MHz, Methanol-d4) δ 8.82 (s, 1H), 8.10 (dd, 1H), 7.97 (s, 1H), 7.49 (d, 1H), 7.35-7.17 (m, 3H), 4.75 (s, 2H), 4.60 (d, 2H), 4.54 (s, 3H), 4.45 (s, 1H), 4.34 (dt, 1H), 3.85 (s, 1H), 3.69-3.53 (m, 3H), 3.46 (t, 3H), 3.40-3.32 (m, 3H), 3.17 (d, 2H). LCMS [M + H] ⁺ 486. |

15

The following compounds were prepare according to the procedure described for compound W-6 in Example 48 using appropriate starting material. The characterization data is indicated on the table given below.

| Example No. | Structure | Characterization data |
|---|---|---|
| 66 | 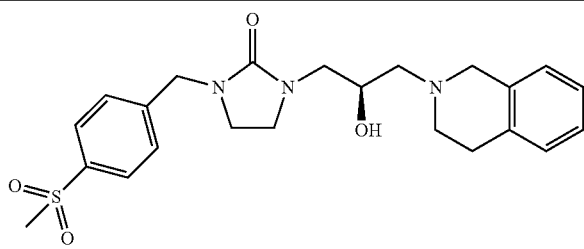 | ¹H NMR (400 MHz, DMSO-d₆) δ: 7.93-7.85 (m, 2H), 7.50 (d, 2H), 7.14-7.04 (m, 3H), 7.04-7.00 (m, 1H), 4.75 (d, 1H), 4.37 (s, 2H), 3.88 (s, 1H), 3.61 (s, 2H), 3.44 (dt, 3H), 3.20 (s, 3H), 3.16 (d, 2H), 3.04 (dd, 1H), 2.80 (t, 2H), 2.70 (dt, 2H), 2.47-2.39 (m, 2H). LCMS [M + H] ⁺ 444.1. |
| 67 | 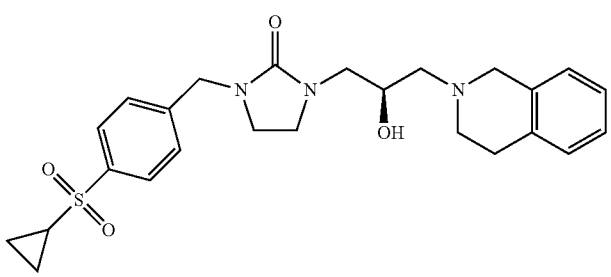 [SMILES: O=C1N(Cc2ccc(S(=O)(=O)C3CC3)cc2)CCN1C[C@H](O)CN1CCc2ccccc2C1] | ¹H NMR (400 MHz, Chloroform-d) δ 7.86 (d, 2H), 7.43 (d, 2H), 7.36-7.17 (m, 3H), 7.10 (d, 1H), 4.55-4.30 (m, 5H), 3.72-3.43 (m, 4H), 3.42-3.07 (m, 8H), 2.46 (tt, 1H), 1.34 (dt, 2H), 1.04 (tt, 2H). LCMS |
| 68 | 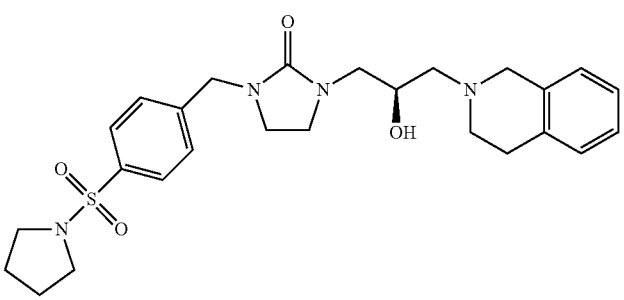 [SMILES: O=C1N(Cc2ccc(S(=O)(=O)N3CCCC3)cc2)CCN1C[C@H](O)CN1CCc2ccccc2C1] | ¹H NMR (400 MHz, Chloroform-d) δ 7.84-7.76 (m, 2H), 7.43 (d, 2H), 7.13 (dtd, 3H), 7.05-6.99 (m, 1H), 4.50-4.39 (m, 2H), 4.04-3.98 (m, 1H), 3.84 (d, 1H), 3.68-3.43 (m, 5H), 3.30-3.23 (m, 4H), 3.23-3.14 (m, 2H), 2.99-2.86 (m, 3H), 2.76 (d, 1H), 2.64-2.48 (m, 2H), 1.82-1.71 (m. 4H). LCMS [M + H] ⁺ 499.4. |
| 69 | 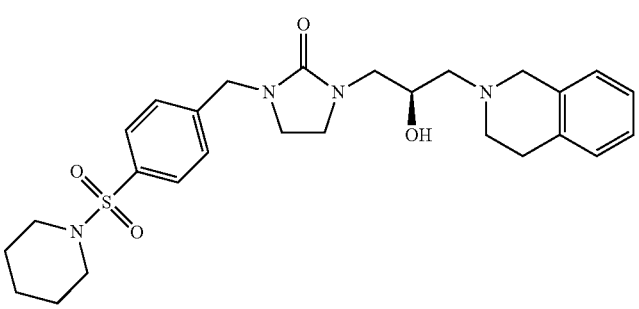 [SMILES: O=C1N(Cc2ccc(S(=O)(=O)N3CCCCC3)cc2)CCN1C[C@H](O)CN1CCc2ccccc2C1] | ¹H NMR (400 MHz, Chloroform-d) δ 7.76-7.68 (m, 2H), 7.43 (d, 2H), 7.14 (dt, 3H), 7.05-7.00 (m, 1H), 4.45 (d, 2H), 4.02 (dd, 1H), 3.85 (d, 1H), 3.69-3.44 (m, 4H), 3.29-3.14 (m, 3H), 2.98 (t, 5H), 2.92 (d, 2H), 2.76 (t, 1H), 2.65-2.53 (m, 2H), 1.65 (d, 4H), 1.47-1.38 (m, 2H). |

| Example No. | Structure | Characterization data |
|---|---|---|
| 70 | 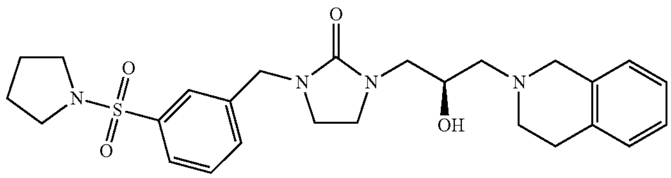 [SMILES: O=C1N(Cc2cccc(S(=O)(=O)N3CCCC3)c2)CCN1C[C@H](O)CN1CCc2ccccc2C1] | ¹H NMR (400 MHz, DMSO-d6) δ 7.70-7.49 (m, 4H), 7.06 (dt, 3H), 7.01-6.96 (m, 1H), 3.04-2.95 (m, 3H), 4.69 (d, 1H), 4.34 (d, 2H), 3.57 (s, 3H), 3.45-3.33 (m, 1H), 3.25 (dd, 1H), 3.16-3.05 (m, 7H), 2.75 (d, 3H), 2.68 (d, 3H), 2.40 (dd, 2H), 3.86-3.79 (m, 2H). LCMS [M + H] ⁺ |
| 71 | 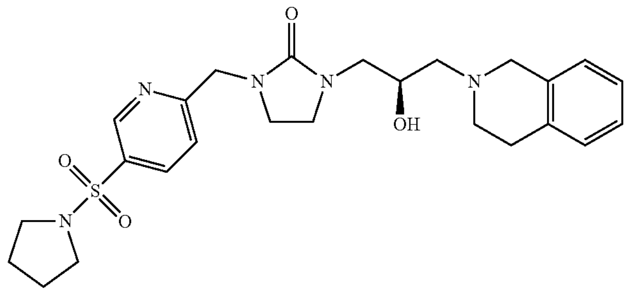 [SMILES: O=C1N(Cc2ccc(S(=O)(=O)N3CCCC3)cn2)CCN1C[C@H](O)CN1CCc2ccccc2C1] | ¹H NMR (400 MHz, Methanol-d4) δ 8.90 (dd, 1H), 8.19 (dd, 1H), 7.57 (dd, 1H), 7.15-6.99 (m, 4H), 4.56 (s, 2H), 4.09 (tt, 1H), 3.76 (s, 2H), 3.64-3.56 (m, 2H), 3.45 (ddd, 2H), 3.36 (dd, 1H), 3.27-3.19 (m, 5H), 2.97-2.82 (m, 4H), 2.68-2.57 (m, 2H), 1.79-1.74 (m, 4H). LCMS |
| 72 | 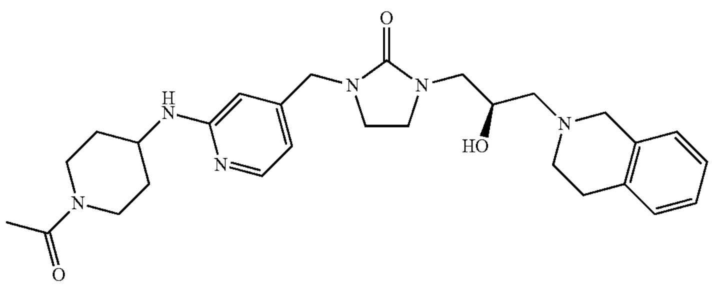 [SMILES: CC(=O)N1CCC(Nc2cc(CN3CCN(C[C@H](O)CN4CCc5ccccc5C4)C3=O)ccn2)CC1] | ¹H NMR (400 MHz, DMSO-d6) δ 7.91-7.86 (m. 1H), 7.13-7.06 (m, 3H), 7.06-6.99 (m, 1H), 6.50 (d, 1H), 6.36-6.28 (m, 2H), 4.73 (d, 1H), 4.20 (d, 1H), 4.09 (s, 2H), 3.90 (d, 3H), 3.76 (d, 1H), 3.61 (s, 2H), 3.50-3.37 (m, 2H), 3.29 (dd, 1H), 3.20-3.08 (m, 3H), 3.05-2.99 (m, 1H), 2.79 (d, 3H), 2.71 (p, 3H), 2.44 (dt, 3H), 1.99 (d, 3H), 1.88 (dd, 2H). |

Example 73: 6-((3-(3-(3,4-dihydroisoquinolin-2 (1H)-yl)-2-hydroxypropyl)-2,5-dioxoimidazolidin-1-yl)methyl)nicotinonitrile (X-4)

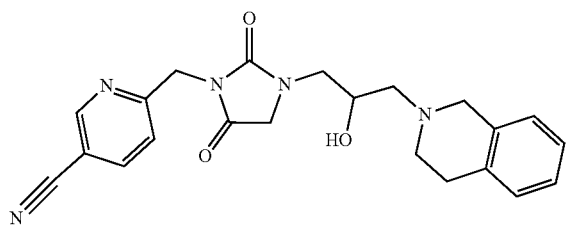

X-4 a) 3-((5-Bromopyridin-2-yl)methyl)imidazolidine-2, 4-dione (X-1)

To a stirred solution of imidazolidine-2,4-dione (1.0 g, 9.9 mmol) in 20 mL of DMF was added portion wise NaH (0.399 g, 9.9 mmol) at 0° C. followed by stirring for 30 min at 0° C. To this reaction mixture was added TBAI (0.1 g, 0.00027 mmol) and 5-bromo-2-(bromomethyl)pyridine (2.4 g, 9.9 mmol) followed by stirring the mixture for 12 h at RT. The reaction mixture was diluted with water and extracted with ethyl acetate. The combined extracts were washed with water and brine solution, dried over anhydrous sodium sulphate and concentrated to give the title compound (1.0 g, 37.73%). ¹H NMR (300 MHz, DMSO-d₆) δ 8.616-8.609 (d, 1H), 8.175 (s, 1H), 8.044-8.008 (dd, 1H), 7.340-7.312 (dd, 1H), 4.620 (s, 2H), 4.017 (s, 2H).

b) 3-((5-bromopyridin-2-yl)methyl)-1-(oxiran-2-ylmethyl)imidazolidine-2,4-dione (X-2)

To a stirred solution of 3-((5-bromopyridin-2-yl)methyl) imidazolidine-2,4-dione (1.0 g, 3.9 mmol) in 20 mL of DMF was added NaH (0.23 g, 5.8 mmol) at 0° C. followed by stirring for 30 min at 0° C. To this reaction mixture was added epibromohydrin (0.8 mL g, 5.8 mmol) followed by stirring for 12 h at RT. The reaction mixture was diluted with water and extracted with ethyl acetate. The combined extracts were washed with water and brine solution, dried over anhydrous sodium sulphate and concentrated to give the title compound (1.0 g, 78.74). LCMS [M+H]⁺ 326.2. [M+2] 329.2.

c) 3-((5-Bromopyridin-2-yl)methyl)-1-(3-(3,4-dihydroisoquinolin-2(1H)-yl)-2-hydroxypropyl)imidazolidine-2,4-dione (X-3)

To a 50 mL sealed tube were added 3-((5-bromopyridin-2-yl)methyl)-1-(oxiran-2-ylmethyl)imidazolidine-2,4-dione (1.0 g, 3.0 mmol), 1,2,3,4-tetrahydroisoquinoline (0.6 g, 4.5 mmol), DIPEA (1.6 mL, 9.1 mmol) and IPA (10 mL). The reaction mixture was stirred for 12 h at 100° C. The reaction mixture was distilled out and the residue was purified by neutral Al₂O₃ column chromatography eluted with 0-1%

MeOH/CHCl₃ to give the title compound (1.0 g, 72.99%). ¹H NMR (400 MHz, DMSO-d₆) δ: 8.613-8.607 (d, 1H), 8.032-8.05 (dd, 1H), 7.333-7.311 (d, 1H), 7.108-7.002 (m, 4H), 4.963-4.951 (d, 1H), 4.406 (s, 2H), 4.159 (s, 2H), 3.968-3.940 (m, 1H), 3.617-3.594 (d, 2H), 3.46 (dd, 1H), 3.28 (dd, 1H), 2.82-2.60 (m, 4H), 2.47 (d, 2H).

d) 6-((3-(3-(3,4-Dihydroisoquinolin-2(1H)-yl)-2-hydroxypropyl)-2,5-dioxoimidazolidin-1-yl)methyl)nicotinonitrile (X-4)

To a 50 mL sealed tube were added 3-((5-bromopyridin-2-yl)methyl)-1-(3-(3,4-dihydroisoquinolin-2(1H)-yl)-2-hydroxypropyl)imidazolidine-2,4-dione (0.3 g, 0.655 mmol) and DMA (10.0 mL) followed by degassing the reaction mixture with argon gas for 10 min. To this reaction mixture were added Pd₂(dba)₃ (0.029 g, 0.032 mmol), Zn (0.042 g, 0.655 mmol), dppf (0.006 g, 0.01 mmol) and Zn(CN)₂ (0.092 g, 0.786 mmol). The reaction mixture was stirred for 12 h at 110° C. The reaction mixture was filtered through Celite bed and the filtrate was diluted with ethyl acetate. The organic layer was washed with water and brine solution, dried over anhydrous sodium sulphate and concentrated. The residue was purified by combiflash column chromatography eluted with 0-3% MeOH/DCM to give the title compound (0.1 g, 37.73%). LCMS [M+H]⁺ 406.3. ¹H NMR (400 MHz, DMSO-d₆) δ: 8.98-8.87 (m, 1H), 8.34-8.24 (m, 1H), 7.61-7.50 (m, 1H), 7.15-6.96 (m, 4H), 4.96 (d, 1H), 4.73 (s, 2H), 4.18 (s, 2H), 3.95 (d, 1H), 3.60 (s, 2H), 3.46 (dd, 1H), 3.28 (dd, 1H), 2.82-2.60 (m, 4H), 2.47 (d, 2H).

Example 74: 6-((3-(3-(3,4-dihydroisoquinolin-2(1H)-yl)-2-hydroxypropyl)-4,4-dimethyl-2,5-dioxoimidazolidin-1-yl)methyl)nicotinonitrile (Y-5)

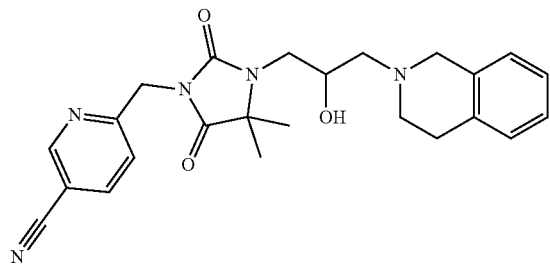

Y-5 a) 3-(4-Methoxybenzyl)-5,5-dimethylimidazolidine-2,4-dione (Y-1)

To a stirred solution of 5,5-dimethylimidazolidine-2,4-dione (5.0 g, 39.0 mmol) in 50 mL of DMF was added K₂CO₃ (16.18 g, 117.06 mmol) and 1-(chloromethyl)-4-methoxybenzene (7.3 g, 46.8 mmol) followed by stirring for 16 h at RT. The reaction mixture was diluted with water and extracted with ethyl acetate. The organic layer was washed with water and brine solution, dried over anhydrous sodium sulphate and concentrated to give the title compound (8.5 g, 88.5%). ¹H NMR (300 MHz, DMSO-d₆) δ 8.352 (s, 1H), 7.174-7.145 (dd, 2H), 6.909-6.871 (dd, 2H), 4.438 (s, 2H), 3.720 (s, 3H), 1.270 (s, 6H).

b) 3-(4-Methoxybenzyl)-5,5-dimethyl-1-(oxiran-2-ylmethyl)imidazolidine-2,4-dione (Y-2)

To a stirred solution of 3-(4-methoxybenzyl)-5,5-dimethylimidazolidine-2,4-dione (1.0 g, 4.03 mmol) in 20 mL of DMF was added NaH (0.24 g, 6.04 mmol) at 0° C. followed by stirring for 30 min at 0° C. To this reaction mixture was added epibromohydrin (0.828 g, 6.04 mmol) followed by stirring for 12 h at RT. The reaction mixture was diluted with water and extracted with ethyl acetate. The combined extracts were washed with water and brine solution, dried over anhydrous sodium sulphate and concentrated to give the title compound (1.1 g, 60.10%). ¹H NMR (300 MHz, CDCl₃) δ 7.336-7.330 (dd, 2H), 6.856-6.826 (dd, 2H), 4.601 (s, 2H), 3.965-3.904 (dd, 1H), 3.782 (s, 3H), 3.092-3.083 (m, 1H), 2.964-2.837 (m, 2H), 2.622-2.598 (m, 1H), 1.466 (s, 3H), 1.352 (s, 3H).

c) 1-(3-(3,4-Dihydroisoquinolin-2(1H)-yl)-2-hydroxypropyl)-3-(4-methoxybenzyl)-5,5-dimethylimidazolidine-2,4-dione (Y-3)

To a 100 mL sealed tube were added 3-(4-methoxybenzyl)-5,5-dimethyl-1-(oxiran-2-ylmethyl)imidazolidine-2,4-dione (1.1 g, 3.6 mmol), 1,2,3,4-tetrahydroisoquinoline (0.72 g, 5.4 mmol), DIPEA (1.93 mL, 10.8 mmol) and IPA (20 mL). The reaction mixture was stirred for 12 h at 100° C. The reaction mixture was distilled out and the residue was purified by combi-flash column chromatography eluted with 0-2% MeOH/CHCl₃ to give the title compound (1.2 g, 76.43%). LCMS [M+H]⁺ 438.5.

d) 1-(3-(3,4-Dihydroisoquinolin-2(1H)-yl)-2-hydroxypropyl)-5,5-dimethylimidazolidine-2,4-dione (Y-4)

To a stirred solution of 1-(3-(3,4-dihydroisoquinolin-2(1H)-yl)-2-hydroxypropyl)-3-(4-methoxybenzyl)-5,5-dimethylimidazolidine-2,4-dione (0.5 g, 1.143 mmol) in 2.5 mL of triflic acid was added TFA (5.0 mL). The reaction mixture was stirred for 12 h at 80° C. and then concentrated. The residue was partitioned between saturated NaHCO₃ solution and ethyl acetate. The organic layer was separated and washed with water and brine solution, dried over anhydrous sodium sulphate and concentrated. The residue was purified with combi flash column chromatography eluted with 0-5% MeOH/DCM to give the title compound (0.22 g, 60%). LCMS [M+H]⁺ 318.2.

e) 6-((3-(3-(3,4-Dihydroisoquinolin-2(1H)-yl)-2-hydroxypropyl)-4,4-dimethyl-2,5-dioxoimidazolidin-1-yl)methyl)nicotinonitrile (Y-5)

To a stirred solution of 1-(3-(3,4-dihydroisoquinolin-2(1H)-yl)-2-hydroxypropyl)-5,5-dimethylimidazolidine-2,4-dione (0.1 g, 0.31 mmol) in 5.0 mL of DMF were added potassium carbonate (0.13 g, 0.946 mmol) and 6-(bromomethyl)nicotinonitrile (0.092 g, 0.47 mmol) at 0° C. The reaction mixture was stirred for 12 h at RT. The organic layer was washed with water and brine solution and then dried over anhydrous sodium sulphate. The reaction mixture was diluted with water and extracted with ethyl acetate. The organic layer was washed with water and brine solution, dried over anhydrous sodium sulphate and concentrated. The residue was purified with preparative TLC eluted with 4% MeOH/CHCl₃ to give the title compound (0.025 g, 18.6%). LCMS [M+H]⁺ 434.1. ¹H NMR (400 MHz, DMSO-d₆) δ: 8.95-8.87 (m, 1H), 8.28 (dd, 1H), 7.55-7.49 (m, 1H), 7.14-6.95 (m, 4H), 4.86 (d, 1H), 4.77 (s, 2H), 4.07 (s, 1H), 3.71-3.44 (m, 3H), 3.08 (dd, 1H), 2.83-2.62 (m, 4H) 2.43 (d, 2H), 1.39 (d, 6H).

The following compounds were prepared according to the procedure described in Example 74 using appropriate starting materials. The characterization data is indicated on the table given below.

| Example No. | Structure | Characterization data |
|---|---|---|
| 75 | 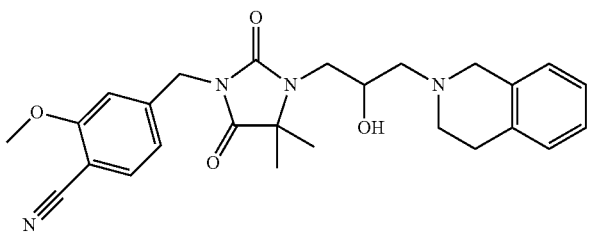 [SMILES: COc1cc(CN2C(=O)N(CC(O)CN3CCc4ccccc4C3)C(C)(C)C2=O)ccc1C#N] | $^1$H NMR (400 MHz, DMSO-d$_6$) δ: 7.68 (d, 1H), 7.09 (dd, 4H), 7.03-6.99 (m, 1H), 6.87 (dd, 1H), 4.87 (d, 1H), 4.64 (s, 2H), 4.08 (s, 1H), 3.89 (s, 3H), 3.65 (d, 2H), 3.51 (dd, 2H), 3.08 (dd, 1H), 2.78 (d, 2H), 2.75-2.63 (m, 3H), 1.37 (d, 6H). LCMS [M + H]$^+$ 463.4. |
| 76 | 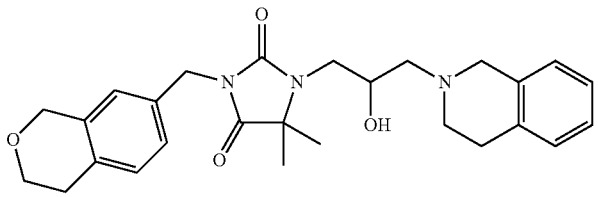 [SMILES: CC1(C)C(=O)N(Cc2ccc3c(c2)COCC3)C(=O)N1CC(O)CN1CCc2ccccc2C1] | $^1$H NMR (400 MHz, DMSO-d$_6$) δ: 7.09 (dd, 4H), 7.02 (d, 2H), 6.88 (s, 1H), 4.87 (d, 1H), 4.63 (s, 2H), 4.48 (s, 2H), 4.06 (s, 1H), 3.84 (t, 2H), 3.67-3.60 (m, 1H), 3.60-3.54 (m, 1H), 3.53-3.45 (m, 1H), 3.05 (dd, 1H), 2.81-2.64 (m, 8H), 1.32 (d, 6H). LCMS [M + H]$^+$ 464.4. |
| 77 | 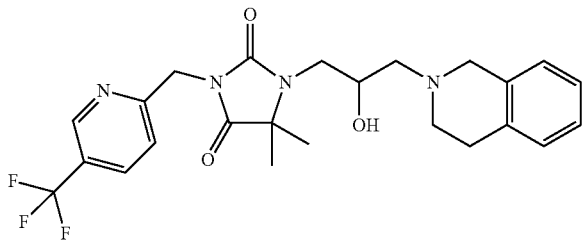 [SMILES: CC1(C)C(=O)N(Cc2ccc(C(F)(F)F)cn2)C(=O)N1CC(O)CN1CCc2ccccc2C1] | $^1$H NMR (400 MHz, DMSO-d$_6$) δ: 8.88 (d, 1H), 8.18 (dd, 1H), 7.54 (d, 1H), 7.12-7.05 (m, 3H), 7.04-6.99 (m, 1H), 4.86 (d, 1H), 4.79 (s, 2H), 4.07 (s, 1H), 3.61 (q, 2H), 3.51 (d, 1H), 3.09 (m, 3H), 2.78 (d, 2H), 2.74-2.71 (m, 1H), 2.71-2.65 (m, 1H), 1.39 (d, 6H). LCMS [M + H]$^+$ 477.2. |
| 78 | 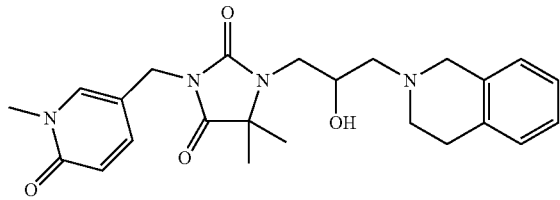 [SMILES: Cn1cc(CN2C(=O)N(CC(O)CN3CCc4ccccc4C3)C(C)(C)C2=O)ccc1=O] | $^1$H NMR (400 MHz, DMSO-d$_6$) δ: 7.66 (d, 1H), 7.33 (dd, 1H), 7.10 (q, 3H), 7.05-6.98 (m, 1H), 6.40-6.33 (m, 1H), 4.85 (d, 1H), 4.30 (s, 2H), 4.06 (s, 1H), 3.61 (q, 2H), 3.49 (dd, 2H), 3.39 (d, 3H), 3.03 (dd, 1H), 2.78 (d, 2H), 2.74-2.63 (m, 3H), 1.31 (d, 6H). LCMS [M + H]$^+$ 439.4. |
| 79 | 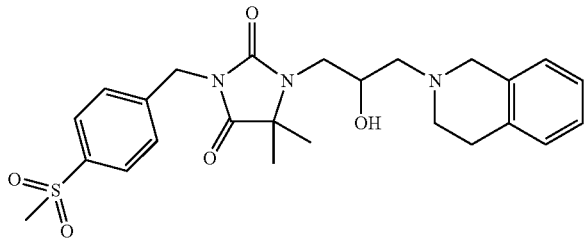 [SMILES: CC1(C)C(=O)N(Cc2ccc(S(C)(=O)=O)cc2)C(=O)N1CC(O)CN1CCc2ccccc2C1] | $^1$H NMR (400 MHz, DMSO-d$_6$) δ: 7.90 (d, 1H), 7.88 (d, 1H), 7.50 (d, 1H), 7.48 (d, 1H), 7.09 (dd, 3H), 7.02 (dd, 1H), 4.87 (d, 1H), 4.67 (s, 2H), 4.07 (d, 1H), 3.61 (d, 2H), 3.56-3.47 (m, 1H), 3.20 (s, 3H), 3.03 (dd, 1H), 2.67 (dt, 4H), 2.48-2.41 (m, 2H), 1.36 (d, 6H). LCMS [M + H]$^+$ 486.4. |

Example 80. 3-(3-(3,4-Dihydroisoquinolin-2(1H)-yl)-2-hydroxypropyl)-4-methyl-1-(4-methylbenzyl)imidazolidin-2-one (Z-4)

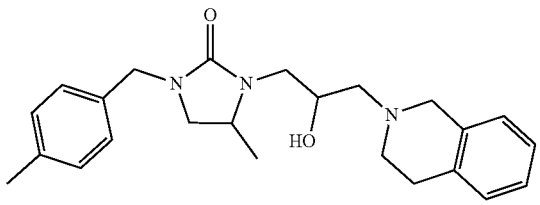

Z-4 a) 1-((4-Methylbenzyl)amino)propan-2-ol (Z-1)

To a stirred solution of 4-methylbenzaldehyde (3.2 g, 26.6 mmol) in 20 mL of ethanol was added 1-aminopropan-2-ol (1.0 g, 13.3 mmol) followed by stirring for 30 min at RT. The reaction mixture was cooled to 0° C. and NaBH$_4$ (1.05 g, 27.9 mmol) was added followed by stirring for 12 h at RT. The reaction mixture was concentrated. The residue was diluted with water and extracted with DCM. The combined extracts were washed with water and brine solution, dried over anhydrous sodium sulphate and concentrated to give the title compound (1.80 g, 75.63%). LCMS [M+H]$^+$ 180.3.

b) 4-Methyl-1-(4-methylbenzyl)imidazolidin-2-one (Z-2)

To a 50 mL sealed tube were added 1-((4-methylbenzyl)amino)propan-2-ol (1.8 g, 10.0 mmol) and urea (2.41 g, 40.0 mmol) followed by stirring for 2 h at 200° C. The reaction mixture was diluted with water and extracted with ethyl acetate. The organic layer was washed with water and brine solution, dried over anhydrous sodium sulphate and concentrated. The residue was purified by SiO$_2$ column chromatography eluted with 2% MeOH/DCM to give the title compound (0.5 g, 24.50%). LCMS [M+H]$^+$ 205.3.

c) 4-Methyl-1-(4-methylbenzyl)-3-(oxiran-2-ylmethyl)imidazolidin-2-one (Z-3)

To a stirred solution of 4-methyl-1-(4-methylbenzyl)imidazolidin-2-one (0.5 g, 2.4 mmol) in 10.0 mL of THF was added NaH (0.146 g, 3.66 mmol) at 0° C. followed by stirring for 30 min at RT. To this reaction mixture was added epibromohydrin (0.501 g, 3.66 mmol) followed by stirring for 12 h at RT. The reaction mixture was quenched with water and extracted with ethyl acetate. The organic layer was washed with water and brine solution, dried over anhydrous sodium sulphate and concentrated. The residue was purified by SiO$_2$ column chromatography eluted with 1% MeOH/DCM to give the title compound (0.4 g, 63.0%). LCMS [M+H]$^+$ 261.3.

d) 3-(3-(3, 4-Dihydroisoquinolin-2(1H)-yl)-2-hydroxypropyl)-4-methyl-1-(4-methylbenzyl)imidazolidin-2-one (Z-4)

To a 50 mL sealed tube were added 4-methyl-1-(4-methylbenzyl)-3-(oxiran-2-ylmethyl)imidazolidin-2-one (0.2 g, 0.768 mmol), 1,2,3,4-tetrahydroisoquinoline (0.122 g, 0.921 mmol), DIPEA (0.297 g, 2.3 mmol) and IPA (10.0 mL). The reaction mixture was stirred for 12 h at 100° C. The reaction mixture was distilled out and the residue was purified by SiO$_2$ column chromatography eluted with 3% MeOH/DCM to give the title compound (0.080 g, 26.49%). LCMS [M+H]$^+$ 394.4. $^1$H NMR [400 MHz, CD$_3$OD] δ: 7.13 (d, 4H), 7.12-7.06 (m, 3H), 7.02 (dd, 1H), 4.28 (d, 2H), 4.11-4.01 (m, 1H), 3.75-3.70 (m, 2H), 3.52-3.33 (m, 3H), 3.09-3.00 (m, 1H), 2.95-2.81 (m, 4H), 2.77 (dd, 1H), 2.68-2.52 (m, 2H), 2.38-2.25 (s, 3H), 1.21 (dd, 3H).

Example 81: 3-(3-(3,4-dihydroisoquinolin-2(1H)-yl)-2-hydroxypropyl)-1-(4-methylbenzyl)-4-phenylimidazolidin-2-one

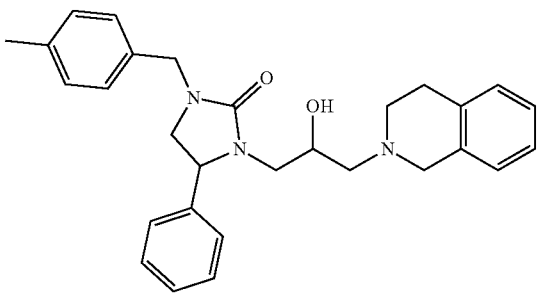 [SMILES: Cc1ccc(CN2CC(c3ccccc3)N(CC(O)CN3CCc4ccccc4C3)C2=O)cc1]

The following compound was prepared according to the procedure described in Example 80 using appropriate starting material.
$^1$H NMR (400 MHz, CD$_3$OD) δ: 7.39-7.28 (m, 3H), 7.26 (dp, 2H), 7.21-7.10 (m, 4H), 7.10-7.01 (m, 3H), 7.02-6.92 (m, 1H), 4.82 (ddd, 2H), 4.44-4.27 (m, 2H), 3.98 (tt, 1H), 3.69-3.54 (m, 3H), 3.50-3.37 (m, 1H), 3.06 (ddd, 1H), 2.89-2.77 (m, 2H), 2.77-2.67 (m, 2H), 2.55-2.49 (m, 1H), 2.50-2.35 (m, 1H), 2.30 (d, 3H). LCMS [M+H]$^+$456.4.

Example 82: 4-((3-(3-(3,4-dihydroisoquinolin-2(1H)-yl)-2-hydroxypropyl)-2-oxo-2,3-dihydro-1H-imidazol-1-yl)methyl)benzonitrile (AA-4) and its Isomer 1 (AA-5) and Isomer 2 (AA-6)

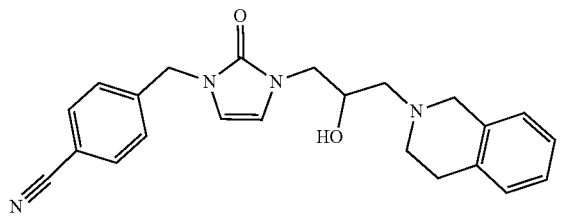

AA-4 a) 1-(4-Cyanobenzyl)-3-(2,2-diethoxyethyl)urea (AA-1)

To a stirred solution of triphosgene (1.94 g, 6.54 mmol) in 30.0 mL of DCM was added mixture of 4-(aminomethyl)benzonitrile hydrochloride (3.0 g, 17.7 mmol) and DIPEA (4.65 g) in 30.0 mL of DCM at 0° C. followed by stirring for 30 min at 0° C. To this reaction mixture were added mixture of 2,2-diethoxyethan-1-amine (2.36 g, 17.7 mmol) and DIPEA (4.50 g) in 30.0 mL of DCM at 0° C. followed by stirring for 30 min at 0° C. The reaction mixture was quenched with water and extracted with ethyl acetate. The combined extracts were washed with brine solution, dried over anhydrous sodium sulphate and concentrated to give the title compound (4.0 g, 78.43%). LCMS [M+H]+292.3.

b) 4-((2-Oxo-2,3-dihydro-1H-imidazol-1-yl)methyl) benzonitrile (AA-2)

To a stirred solution of 1-(4-cyanobenzyl)-3-(2,2-diethoxyethyl)urea (4.0 g, 13.7 mmol) in 40.0 mL of acetonitrile were added TFA (5.0 mL) and water (5.0 mL) at 0° C. followed by stirring for 6 hours at RT. The reaction mixture was concentrated under reduced pressure. The residue was diluted with water, basified by saturated sodium bicarbonate and extracted with ethyl acetate. The combined extracts were washed with brine solution, dried over anhydrous sodium sulphate and concentrated. The residue was purified by SiO$_2$ column chromatography eluted with 2% MeOH/DCM to give the title compound (2.50 g, 91.90%). LCMS [M+H]+200.2.

c) 4-((3-(Oxiran-2-ylmethyl)-2-oxo-2,3-dihydro-1H-imidazol-1-yl)methyl) benzonitrile (AA-3)

To a stirred solution of 4-((2-oxo-2,3-dihydro-H-imidazol-1-yl)methyl)benzonitrile (0.5 g, 2.51 mmol) in 10.0 mL of THF was added NaH (0.150 g, 3.76 mmol) at 0° C. followed by stirring for 30 minutes at 0° C. To this reaction mixture was added epibromohydrin (0.515 g, 3.76 mmol) at 0° C. followed by stirring for 12 hours at RT. The reaction mixture was quenched with water and extracted with ethyl acetate. The combined extracts were washed with water and brine solution and dried over anhydrous sodium sulphate. The reaction mixture was distilled out and the residue was purified by SiO$_2$ column chromatography eluted with 1% MeOH/DCM to give the title compound (0.18 g, 28.12%). LCMS [M+H]+256.2.

d) 4-((3-(3-(3,4-Dihydroisoquinolin-2(1H)-yl)-2-hydroxypropyl)-2-oxo-2,3-dihydro-1H-imidazol-1-yl)methyl)benzonitrile (AA-4)

To a 50 mL sealed tube were added 4-((3-(oxiran-2-ylmethyl)-2-oxo-2,3-dihydro-1H-imidazol-1-yl)methyl) benzonitrile (0.18 g, 0.705 mmol), 1,2,3,4-tetrahydroisoquinoline (0.140 g, 1.05 mmol), DIPEA (0.273 g, 2.11 mmol) and IPA (5.0 mL). The reaction mixture was stirred for 12 h at 100° C. The reaction mixture was distilled out and the residue was purified by SiO$_2$ column chromatography eluted with 3% MeOH/DCM to give the title compound (0.130 g, 47.61%). LCMS [M+H]+ 389.2. $^1$H NMR [400 MHz, CDCl$_3$] δ: 7.66-7.61 (m, 2H), 7.39-7.33 (m, 2H), 7.17-7.09 (m, 3H), 7.03-6.99 (m, 1H), 6.48 (d, 1H), 6.14 (d, 1H), 4.86 (s, 2H), 4.12-4.04 (m, 1H), 3.92 (dd, 1H), 3.82 (d, 1H), 3.65-3.59 (m, 2H), 2.97-2.86 (m, 3H), 2.74 (dd, 1H), 2.62 (dd, 1H), 2.49 (dd, 1H).

Racemic compound (AA-4, 0.06 g) was separated into two enantiomers AA-5 (0.03 g, isomer-1, retention time 4.355 min) and AA-6 (0.03 g, isomer-2, retention time 6.437 min) using chiral column chromatography. Column: Chiral pack IA [(20 mm×250 mm), 5 micron]; Mobile phase: (A): Acetonitrile, (B): 0.1% DEA in EtOH: MeOH (1:1); Flow: 15 ml/min; Isocratic: 70:30 (A:B).

Isomer 1: LCMS [M+H]+389.2. $^1$H NMR (400 MHz, CDCl$_3$) δ: 7.68-7.59 (m, 2H), 7.40-7.32 (m, 2H), 7.20-6.95 (m, 4H), 6.48 (d, 1H), 6.14 (d, 1H), 4.86 (s, 2H), 4.14-4.00 (m, 1H), 3.92 (dd, 1H), 3.82 (d, 1H), 3.68-3.56 (m, 2H), 2.99-2.83 (m, 3H), 2.74 (dd, 1H), 2.62 (dd, 1H), 2.49 (dd, 1H).

Isomer 2: LCMS [M+H]+ 389.2. $^1$H NMR (400 MHz, CDCl$_3$) δ: 7.18-7.04 (m, 7H), 7.01-6.95 (m, 1H), 6.36 (d, 1H), 6.08 (d, 1H), 4.74 (d, 2H), 4.06 (dddd, 1H), 3.89 (dd, 1H), 3.79 (d, 1H), 3.67-3.55 (m, 2H), 2.94-2.83 (m, 3H), 2.80-2.66 (m, 1H), 2.60 (dd, 1H), 2.49 (dd, 1H).

The following compound was prepared according to the procedure described in Example 82 using appropriate starting material. The characterization data is mentioned in the table below.

| Example No. | Structure | Characterization data |
|---|---|---|
| 83 | 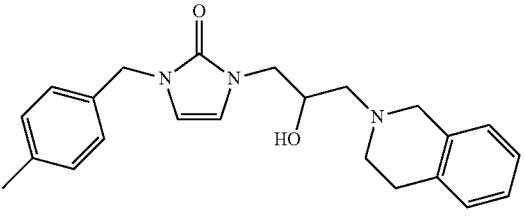<br>(BB-4) | $^1$H NMR (400 MHz, CDCl$_3$) δ: 7.24-7.04 (m, 7H), 7.02-6.98 (m, 1H), 6.37 (d, 1H), 6.09 (d, 1H), 4.76 (d, 2H), 4.08 (m, 1H), 3.91 (dd, 1H), 3.80 (d, 1H), 3.68-3.59 (m, 2H), 2.95-2.86 (m, 3H), 2.79-2.69 (m, 1H), 2.61 (dd, 1H), 2.50 (dd, 1H), 2.33 (s, 3H). LCMS [M + H] + 378.2. |

Example 84: 1-(3-(3,4-Dihydroisoquinolin-2(1H)-yl)-2-hydroxypropyl)-3-((1-methyl-1H-benzo[d]imidazol-6-yl)methyl)-1,3-dihydro-2H-benzo[d]imidazol-2-one (CC-3) and its Isomer 1 (CC-4) and Isomer 2 (CC-5)

CC-3

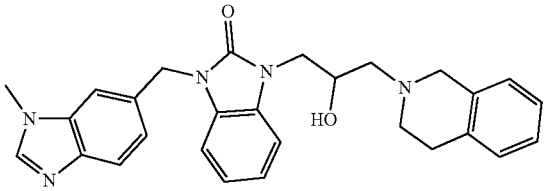

a) 1-((1-Methyl-1H-benzo[d]imidazol-6-yl)methyl)-1,3-dihydro-2H-benzo[d] imidazol-2-one (CC-1)

To a 50 mL sealed tube were added tert-butyl 2-oxo-2,3-dihydro-1H-benzo-[d]imidazole-1-carboxylate (0.20 g, 0.85 mmol), 6-(chloromethyl)-1-methyl-1H-benzo[d]imidazole (0.185 g, 1.02 mmol), $K_2CO_3$ (0.177 g, 1.28 mmol), KI (0.014 g, 0.085 mmol) and DMF (10.0 mL). The reaction mixture was stirred for 12 h at 110° C. The reaction mixture was quenched with water and extracted with ethyl acetate. The combined extracts were washed with water and brine solution, dried over anhydrous sodium sulphate and concentrated. The residue was purified by $SiO_2$ column chromatography eluted with 2% MeOH/DCM to give the title compound (0.2 g, 70.67%). LCMS [M+H]$^+$ 279.3.

b) 1-((1-Methyl-1H-benzo[d]imidazol-6-yl)methyl)-3-(oxiran-2-ylmethyl)-1,3-dihydro-2H-benzo[d]imidazol-2-one (CC-2)

To a stirred solution of 1-((1-methyl-H-benzo[d]imidazol-6-yl)methyl)-1,3-dihydro-2H-benzo[d]imidazol-2-one (0.2 g, 0.71 mmol) in 10.0 mL of DMF was added NaH (0.043 g, 1.07 mmol) at 0° C. followed by stirring at 0° C. To this reaction mixture added epibromohydrin (0.199 g, 2.15 mmol) followed by stirring for 12 h at RT. The reaction mixture was quenched with water and extracted with ethyl acetate. The combined extracts were washed with water and brine solution, dried over anhydrous sodium sulphate and concentrated to give the title compound (0.2 g, 84.38%). LCMS [M+H]$^+$ 335.3.

c) 1-(3-(3,4-Dihydroisoquinolin-2(1H)-yl)-2-hydroxypropyl)-3-((1-methyl-H-benzo[d]imidazol-6-yl)methyl)-1,3-dihydro-2H-benzo[d]imidazol-2-one (CC-3)

To a 50 mL sealed tube were added-((1-methyl-H-benzo[d]imidazol-6-yl)methyl)-3-(oxiran-2-ylmethyl)-1,3-dihydro-2H-benzo[d]imidazol-2-one (0.2 g, 0.59 mmol), 1,2,3,4-tetrahydroisoquinoline (0.159 g, 1.19 mmol), DIPEA (0.231 g, 1.79 mmol) and IPA (10.0 mL). The reaction mixture was stirred for 12 h at 100° C. The reaction mixture was distilled out and the residue was purified by $SiO_2$ column chromatography eluted with 3% MeOH/DCM to give the title compound (0.075 g, 26.88%). LCMS [M+H]$^+$ 468.5. $^1$H NMR (400 MHz, DMSO-d$_6$) δ 8.15 (s, 1H), 7.66-7.47 (m, 2H), 7.28-7.12 (m, 2H), 7.15-7.04 (m, 4H), 7.05-6.88 (m, 3H), 5.20-5.02 (m, 2H), 4.98 (d, 1H), 4.11 (t, 1H), 4.03 (dd, 1H), 3.80 (s, 3H), 3.78 (s, 1H), 3.61 (s, 2H), 2.83-2.60 (m, 4H), 2.62-2.51 (m, 2H).

Racemic compound (CC-3, 0.015 g) was separated into two enantiomers CC-4 (0.004 g, isomer-1, retention time 22.229 min) and CC-5 (0.004 g, isomer-2, retention time 28.530 min) using chiral column chromatography. Column: Chiral pack IA [(20 mm×250 mm), 5 micron]; Mobile phase: (A): Acetonitrile, (B): 0.1% DEA in EtOH; Flow: 20 ml/min; Isocratic: 75:25 (A:B).

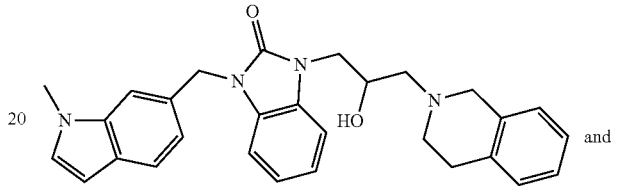

CC-4 and

CC-5

Isomer 1: LCMS[M+H]468.5. $^1$H NMR (400 MHz, CD$_3$OD) δ: 8.18 (s, 1H), 7.66 (d, 1H), 7.59-7.53 (in, 1H), 7.33-7.22 (in, 2H), 7.177-6.96 (m, 7H), 5.28-5.10 (m, 2H), 4.35 (ddd, 1H), 4.10 (dd, 1H), 3.99 (dd, 1H), 3.85 (d, 5H), 3.08-2.92 (m, 2H), 2.85 (ddd, 4H). Isomer 2: LCMS [M+H]$^+$ 468.5. $^1$H NMR (400 MHz, CD$_3$OD) δ: 8.18 (s, 1H), 7.65 (d, 1H), 7.57 (d, 1H), 7.33-7.22 (m, 2H), 7.21-6.91 (m, 7H), (5.25-5.08 (s, 2H), 4.36 (t, 1H), 4.10 (dd, 1H), 3.99 (dd, 1H), 3.85 (d, H), 3.01 (q, 2H), 2.95-2.77 (m, 4H).

The following compounds were prepared according to the procedure described in Example 84 using appropriate starting materials. The characterization data is indicated on the table given below.

| Example No. | Structure | Characterization data |
| --- | --- | --- |
| 85 | 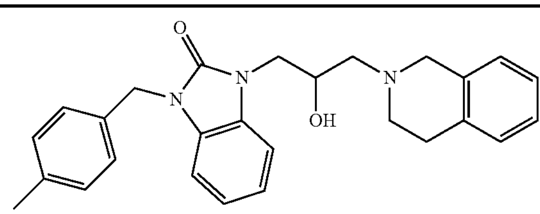 | $^1$H NMR (400 MHz, DMSO-d$_6$) δ: 7.20 (dd, 3H), 7.15-7.04 (m, 5H), 7.04-6.99 (m, 3H), 6.99-6.92 (m, 1H), 5.05-4.86 (m, 3H), 4.05 (ddd, 2H), 3.80 (dd, 1H), 3.60 (s, 2H), 2.70 (dtd, 5H), 2.60-2.53 (m, 1H), 2.24 (s, 3H). LCMS [M + H]$^+$ 428.7. |
| 86 | 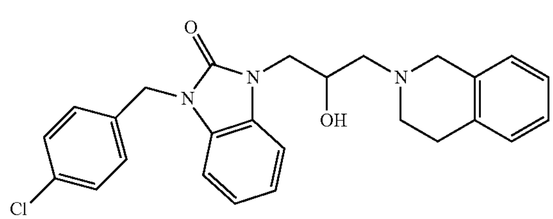 [SMILES: O=c1n(Cc2ccc(Cl)cc2)c2ccccc2n1CC(O)CN1CCc2ccccc2C1] | $^1$H NMR (400 MHz, DMSO-d$_6$) δ: 7.42-7.35 (m, 2H), 7.35-7.29 (m, 2H), 7.22 (dd, 1H), 7.12-7.05 (m, 3H), 7.05-6.92 (m, 4H), 5.09-4.89 (m, 3H), 4.05 (ddd, 2H), 3.80 (dd, 1H), 3.61 (s, 2H), 2.78-2.63 (m, 4H), 2.59-2.52 (m, 2H). LCMS [M + H]$^+$ 448.3. |

| Example No. | Structure | Characterization data |
|---|---|---|
| 87 | 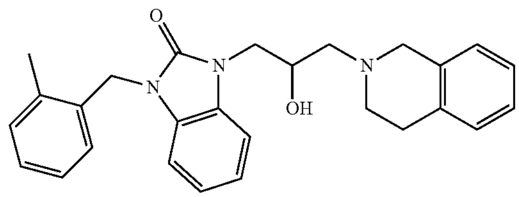 [SMILES: Cc1ccccc1Cn1c(=O)n(CC(O)CN2CCc3ccccc3C2)c2ccccc21] | ¹H NMR (400 MHz, DMSO-d₆) δ: 7.25 (dd, 1H), 7.22-7.12 (m, 2H), 7.11-7.00 (m, 6H), 6.95 (td, 1H), 6.87 (dd, 1H), 6.84-6.80 (m, 1H), 5.08-4.85 (m, 3H), 4.19-3.96 (m, 2H), 3.84 (dd, 1H), 3.60 (s, 2H), 2.85-2.60 (m, 4H), 2.61-2.52 (m, 2H), 2.34 (s, 3H). LCMS [M + H] ⁺ 428.4. |
| 88 | 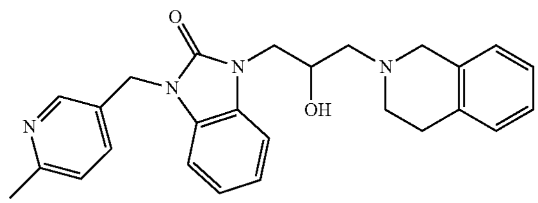 [SMILES: Cc1ccc(Cn2c(=O)n(CC(O)CN3CCc4ccccc4C3)c3ccccc32)cn1] | ¹H NMR (400 MHz, DMSO-d₆) δ: 8.47 (d, 1H), 7.57 (dd, 1H), 7.25-7.14 (m, 2H), 7.14-7.05 (m, 4H), 7.07-6.94 (m, 3H), 4.99 (dd, 3H), 4.08 (d, 1H), 4.00 (dd, 1H), 3.79 (dd, 1H), 3.69-3.56 (m, 2H), 2.81-2.71 (m, 2H), 2.68 (td, 2H), 2.60-2.52 (m, 2H), 2.40 (s, 3H). LCMS [M + H] ⁺ 429.4. |
| 89 | 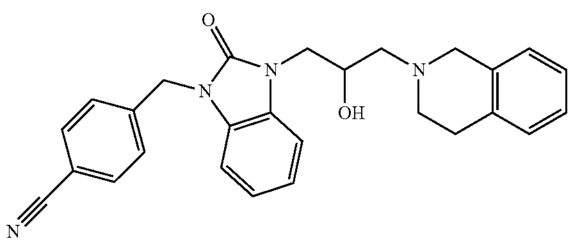 [SMILES: N#Cc1ccc(Cn2c(=O)n(CC(O)CN3CCc4ccccc4C3)c3ccccc32)cc1] | ¹H NMR (400 MHz, DMSO-d₆) δ: 7.88-7.69 (m, 2H), 7.53-7.40 (m, 2H), 7.24 (dd, 1H), 7.13-7.04 (m, 3H), 7.05-6.92 (m, 4H), 5.19-5.05 (m, 2H), 4.99 (d, 1H), 4.11 (d, 1H), 4.01 (dd, 1H), 3.81 (dd, 1H), 3.61 (d, 2H), 2.81-2.70 (m, 2H), 2.68 (s, 1H), 2.70-2.40 (m, 3H). LCMS [M + 1] 439.3. |
| 90 | 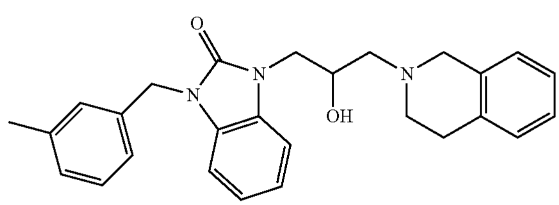 [SMILES: Cc1cccc(Cn2c(=O)n(CC(O)CN3CCc4ccccc4C3)c3ccccc32)c1] | ¹H NMR (300 MHz, DMSO-d₆) δ: 7.30-6.91 (m, 12H), 5.08-4.79 (m, 3H), 4.10 (q, 2H), 4.01 (dd, 1H), 3.81 (dd, 1H), 3.60 (s, 2H), 2.82-2.59 (m, 5H), 2.25 (s, 3H). LCMS [M + H] ⁺ 428.5. |
| 91 | 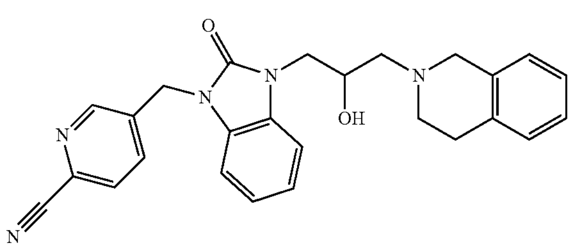 [SMILES: N#Cc1ccc(Cn2c(=O)n(CC(O)CN3CCc4ccccc4C3)c3ccccc32)cn1] | ¹H NMR (300 MHz, DMSO-d₆) δ: 8.82-8.69 (m, 1H), 8.07-7.81 (m, 2H), 7.31-7.18 (m, 1H), 7.20-6.85 (m, 7H), 5.19 (s, 2H), 5.00 (d, 1H), 4.19-3.93 (m, 2H), 3.88-3.72 (m, 2H), 3.61 (s, 3H), 2.84-2.61 (m, 4H). LCMS [M + H] ⁺ 440.3. |
| 92 | 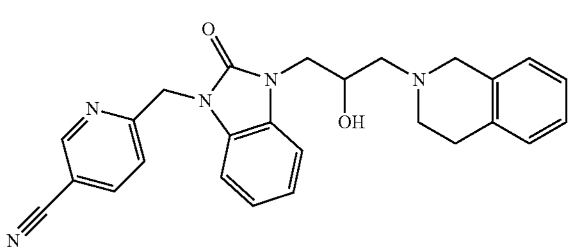 [SMILES: N#Cc1ccc(Cn2c(=O)n(CC(O)CN3CCc4ccccc4C3)c3ccccc32)nc1] | ¹H NMR (400 MHz, DMSO-d₆) δ: 8.91 (dd, 1H), 8.22 (dd, 1H), 7.39 (dd, 1H), 7.21 (dt, 1H), 7.11-6.86 (m, 7H), 5.24-5.08 (m, 2H), 4.96 (d, 1H), 4.07 (q, 1H), 3.97 (dd, 1H), 3.77 (dd, 1H), 3.57 (s, 2H), 2.77-2.66 (m, 2H), 2.66-2.53 (m, 2H), 2.53-2.48 (m, 2H). LCMS [M + H] ⁺ 440.4. |

Example 93: 4-(3-(3-(3,4-Dihydroisoquinolin-2(1H)-yl)-2-hydroxypropyl)-2-oxo-2,3-di-hydro-1H-benzo[d]imidazol-1-yl)benzonitrile (DD-4)

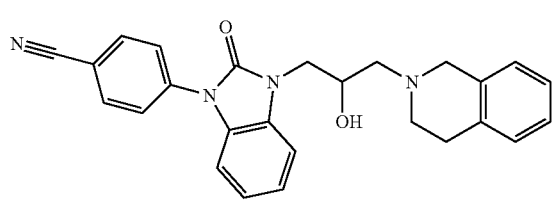

DD-4 a) Tert-Butyl 3-(oxiran-2-ylmethyl)-2-oxo-2,3-di-hydro-1H-benzo[d]imidazole-1-carboxylate (DD-1)

To a stirred solution of tert-butyl 2-oxo-2,3-dihydro-1H-benzo[d]imidazole-1-carboxylate (2.0 g, 8.54 mmol) in 30.0 mL of DMF was added NaH (0.3 g, 12.8 mmol) at 0° C. followed by stirring at 0° C. To this reaction mixture was added epibromohydrin (3.512 mL, 25.6 mmol) followed by stirring for 12 h at RT. The reaction mixture was quenched with water and extracted with ethyl acetate. The combined extracts were washed with water and brine solution, dried over anhydrous sodium sulphate and concentrated to give the title compound (2.05 g, 82.99%). LCMS [M+H]$^+$291.3.

b) Tert-Butyl 3-(3-(3,4-dihydroisoquinolin-2(1H)-yl)-2-hydroxypropyl)-2-oxo-2,3-dihydro-1H-benzo[d]imidazole-1-carboxylate (DD-2)

To a 50 mL sealed tube were added tert-butyl 3-(oxiran-2-ylmethyl)-2-oxo-2,3-dihydro-1H-benzo[d]imidazole-1-carboxylate (2.0 g, 6.88 mmol), 1,2,3,4-tetrahydroisoquinoline (1.376 g, 10.33 mmol), DIPEA (2.66 g, 20.64 mmol) and IPA (20.0 mL). The reaction mixture was stirred for 12 h at 100° C. The reaction mixture was concentrated to give the title compound (1.7 g, 58.41%). LCMS [M+H]$^+$424.5.

c) 1-(3-(3,4-Dihydroisoquinolin-2(1H)-yl)-2-hydroxypropyl)-1,3-dihydro-2H-benzo[d]imidazol-2-one (DD-3)

To a stirred solution of tert-butyl 3-(3-(3,4-dihydroisoquinolin-2(1H)-yl)-2-hydroxypropyl)-2-oxo-2,3-dihydro-1H-benzo[d]imidazole-1-carboxylate (1.02 g, 2.0 mmol) in DCM was added TFA (1.14 g, 10.0 mmol) at 0° C. followed by stirring for 12 h at RT. The reaction mixture was concentrated. The residue was diluted with water, basified with solid Na$_2$CO$_3$ and extracted with ethyl acetate. The combined extracts were washed with brine solution, dried over anhydrous sodium sulphate and concentrated to give the title compound (0.713 g, 91.6%). LCMS [M+H]$^+$324.4.

d) 4-(3-(3-(3,4-Dihydroisoquinolin-2(1H)-yl)-2-hydroxypropyl)-2-oxo-2,3-dihydro-1H-benzo[d]imidazol-1-yl)benzonitrile (DD-4)

To a 50 mL sealed tube were added 1-(3-(3,4-dihydroisoquinolin-2(1H)-yl)-2-hydroxypropyl)-1,3-dihydro-2H-benzo[d]imidazol-2-one (0.2 g, 0.6 mmol), 4-iodobenzonitrile (0.139 g, 0.6 mmol) and toluene (10.0 mL). The reaction mixture was degassed with Argon gas for 10 min. To this reaction mixture added K$_2$CO$_3$ (0.168 g, 1.2 mmol), CuI (0.007 g, 0.04 mmol) and trans cyclohexyl diamine (0.13 g, 0.12 mmol). The reaction mixture was stirred for 12 h at 100° C. The reaction mixture was concentrated. The residue was purified with combi flash column chromatography eluted with 0-5% MeOH/CHCl$_3$ to give title compound (0.1 g, 62.5%). LCMS [M+H]$^+$ 425.3. $^1$H NMR (300 MHz, DMSO-d$_6$) δ: 8.05-7.95 (m, 2H), 7.75-7.65 (m, 2H), 7.34 (dd, 1H), 7.21-6.94 (m, 7H), 5.05 (d, 1H), 4.15 (dt, 1H), 4.05 (dd, 1H), 3.86 (dd, 1H), 3.58 (s, 2H), 2.80-2.54 (m, 6H).

Example 94: 1-(3-(3,4-Dihydroisoquinolin-2(1H)-yl)-2-hydroxypropyl)-3-(4-methoxy-benzyl)-1,3-dihydro-2H-imidazo[4,5-b]pyridin-2-one (EE-6)

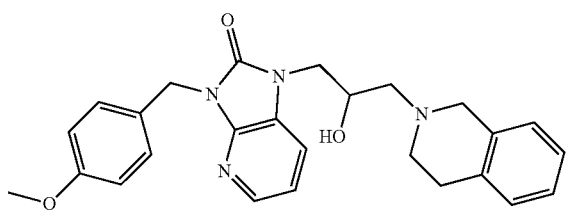

EE-6 a) N-(4-Methoxybenzyl)-3-nitropyridin-2-amine (EE-1)

To a 500 mL sealed tube were added 2-chloro-3-nitropyridine (10.0 g, 63.0 mmol) and (4-methoxyphenyl) methanamine (9.51 g, 69.3 mmol), DIPEA (24.42 g, 189.0 mmol) and isopropanol (150.0 mL) followed by stirring for 12 h at 100° C. The reaction mixture was distilled out and the residue was triturated with diethyl ether and dried under reduced pressure to give yellow solid (15.0 g, 92.02%). $^1$H NMR [300 MHz, DMSO-d$_6$] δ: 8.89-8.85 (t, 1H), 8.46-8.40 (m, 2H), 7.30-7.27 (d, 2H), 6.87-6.84 (d, 2H), 6.78-6.73 (m, 1H), 4.71-4.69 (d, 2H), 3.70 (s, 3H).

b) N$^2$-(4-Methoxybenzyl) pyridine-2, 3-diamine (EE-2)

To a stirred solution of N-(4-methoxybenzyl)-3-nitropyridin-2-amine (10.0 g, 38.5 mmol) in 100 mL of THF were added Zn (25.07 g, 385.0 mmol) and NH$_4$Cl (20.82 g, 385.7 mmol) in H$_2$O (75.0 mL) at 0° C. followed by stirring at 60° C. for 3 h. The reaction mixture was filtered on Celite bed, the filterate was diluted with water and extracted with ethyl acetate. The combined extracts were washed with brine solution, dried over anhydrous sodium sulphate and concentrated. The residue was purified by SiO$_2$ column chromatography eluted with 3% MeOH/DCM to give the title compound (7.0 g, 79.54%). LCMS [M+H]$^+$ 230.3.

c) Ethyl (2-((4-methoxybenzyl) amino) pyridin-3-yl) carbamate (EE-3)

To a stirred solution of N2-(4-methoxybenzyl) pyridine-2,3-diamine (7.0 g, 30.5 mmol) in 100 mL of chloroform was added ethyl chloroformate (9.93 g, 91.5 mmol) at 0° C. followed by stirring for 12 h at 60° C. The reaction mixture was diluted with water and extracted with DCM. The combined extracts were washed saturated sodium bi carbonate and brine solution, dried over anhydrous sodium sulphate and concentrated to give the title compound (8.0 g, 87.05%). LCMS [M+H]+ 302.3.

d) 3-(4-Methoxybenzyl)-1,3-dihydro-2H-imidazo[4,5-b]pyridin-2-one (EE-4)

To a stirred solution of ethyl (2-((4-methoxybenzyl) amino) pyridin-3-yl) carbamate (8.0 g, 26.5 mmol) in 100 mL of ethanol was added 24.0 mL of sodium ethoxide (21% in ethanol) followed by refluxing the mixture for 12 h. The reaction mixture was concentrated under reduced pressure, the crude product was diluted with water and extracted with ethyl acetate. The combined extracts were washed with brine solution, dried over anhydrous sodium sulphate and concentrated. The residue was triturated with diethyl ether and dried on vacuum to give light brown solid (4.80 g, 71.0%). LCMS [M+H]+256.3.

e) 3-(4-Methoxybenzyl)-1-(oxiran-2-ylmethyl)-1,3-dihydro-2H-imidazo[4,5-b]pyridin-2-one (EE-5)

To a stirred solution of 3-(4-methoxybenzyl)-1,3-dihydro-2H-imidazo [4,5-b]pyridin-2-one (4.0 g, 15.6 mmol) in 60.0 mL of DMF was added NaH (0.94 g, 23.5 mmol) at 0° C. followed by stirring for 30 min at 0° C. To this reaction mixture was added epibromohydrin (3.22 g, 23.5 mmol) followed by stirring for 12 h at RT. The reaction mixture was quenched with water and extracted with ethyl acetate. The combined extracts were washed with water and brine solution, dried over anhydrous sodium sulphate and concentrated. The residue was purified by SiO2 column chromatography eluted with 1% MeOH/DCM to give the title compound (4.70, 96.90%). LCMS [M+H]+312.3.

f) 1-(3-(3,4-Dihydroisoquinolin-2(1H)-yl)-2-hydroxypropyl)-3-(4-methoxybenzyl)-1,3-dihydro-2H-imidazo[4,5-b]pyridin-2-one (EE-6)

To a 100 mL sealed tube were added 3-(4-methoxybenzyl)-1-(oxiran-2-ylmethyl)-1,3-dihydro-2H-imidazo[4,5-b]pyridin-2-one (4.70 g, 15.0 mmol), 1,2,3,4-tetrahydroisoquinoline (2.99 g, 22.5 mmol), DIPEA (5.81 g, 45.0 mmol) and IPA (50.0 mL). The reaction mixture was stirred for 12 h at 100° C. The reaction mixture was distilled out and the residue was purified by SiO2 column chromatography eluted with 2% MeOH/DCM to give the title compound (5.0 g, 75.07%). LCMS [M+H]+ 445.4. 1H NMR [400 MHz, CDCl3]: δ 8.07-8.03 (m, 1H), 7.50-7.45 (m, 2H), 7.43 (dd, 1H), 7.17-7.07 (m, 3H), 7.01-6.95 (m, 2H), 6.86-6.80 (m, 2H), 5.12 (s, 2H), 4.20-4.09 (m, 1H), 4.07 (d, 1H), 3.87 (dd, 1H), 3.82-3.78 (m, 1H), 3.78-3.74 (m, 3H), 3.58 (d, 1H), 2.96-2.84 (m, 3H), 2.76-2.66 (m, 1H), 2.64 (d, 1H), 2.53 (dd, 1H).

Example 95: 3-(3-(3,4-Dihydroisoquinolin-2(1H)-yl)-2-hydroxypropyl)-1-(4-methoxy-benzyl)-2-oxo-2,3-dihydro-1H-benzo[d]imidazole-5-carbonitrile (FF-5)

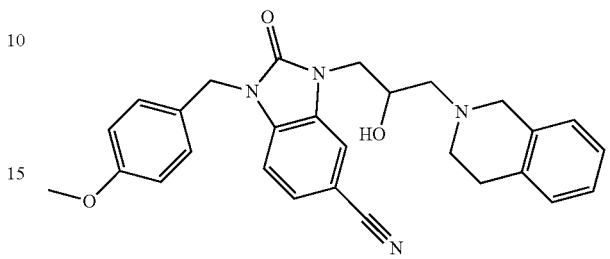

FF-5 a) 4-((4-Methoxybenzyl) amino)-3-nitrobenzonitrile (FF-1)

To a stirred solution of 4-fluoro-3-nitrobenzonitrile (5.0 g, 30.1 mmol) in 50.0 mL of DMF was added (4-methoxyphenyl)methanamine (4.95 g, 36.1 mmol) and NaHCO3 (9.57 g, 90.3 mmol) followed by stirring for 12 h at RT. The reaction mixture was diluted with water and the precipitated solid was filtered and dried on vacuum to give yellow solid (9.0 g). 1H NMR [300 MHz, DMSO-d6]: δ 9.11-9.07 (t, 1H), 8.51 (d, 1H), 7.77-7.73 (dd, 1H), 7.31-7.28 (d, 2H), 7.04-7.01 (d, 1H), 6.92-6.87 (m, 2H), 4.67-4.59 (d, 2H), 3.17 (s, 3H).

b) 3-Amino-4-((4-methoxybenzyl)amino)benzonitrile (FF-2)

To a stirred solution of 4-((4-methoxybenzyl) amino)-3-nitrobenzonitrile (9.0 g, 31.7 mmol) in 120 mL of THF were added Zn (20.65 g, 317.0 mmol) and NH4Cl (17.11 g, 317.0 mmol) in H2O (60.0 mL) at 0° C. followed by stirring at 65° C. for 3 h. The reaction mixture filtered on Celite bed, the filtrate was diluted with water and extracted with ethyl acetate. The combined extracts were washed with brine solution, dried over anhydrous sodium sulphate and concentrated. The residue was purified by SiO2 column chromatography eluted with 3% MeOH/DCM to give the title compound (7.0 g, 87.5%). 1H NMR [400 MHz, DMSO-d6]: δ 7.26-7.24 (m, 2H), 6.90-6.77 (m, 4H), 6.38-6.36 (d, 1H), 6.00 (m, 1H), 5.02 (s, 2H), 4.30-4.29 (d, 2H), 3.72 (s, 3H).

c) 1-(4-Methoxybenzyl)-2-oxo-2,3-dihydro-1H-benzo[d]imidazole-5-carbonitrile (FF-3)

To a stirred solution of 3-amino-4-((4-methoxybenzyl)amino)benzonitrile (1.0 g, 3.94 mmol) in 20 mL of THF was added CDI (0.703 g, 4.3 mmol) at 0° C. followed by stirring for 12 h at RT. The reaction mixture was diluted with water and extracted with ethyl acetate. The combined extracts were washed with brine solution, dried over anhydrous sodium sulphate and concentrated to give the title compound (0.55 g, 50.0%). LCMS [M+H]+278.0.

d) 1-(4-Methoxybenzyl)-3-(oxiran-2-ylmethyl)-2-oxo-2,3-dihydro-1H-benzo[d]imidazole-5-carbonitrile (FF-4)

To a stirred solution of 1-(4-methoxybenzyl)-2-oxo-2,3-dihydro-1H-benzo[d]-imidazole-5-carbonitrile (0.5 g, 1.79 mmol) in 10.0 mL of DMF was added NaH (0.107 g, 2.68 mmol) at 0° C. followed by stirring for 30 min at 0° C. To this reaction mixture was added epibromohydrin (0.367 g, 2.68 mmol) at 0° C. followed by stirring for 12 h at RT. The reaction mixture was quenched with water and extracted with ethyl acetate. The combined extracts were washed with water and brine solution, dried over anhydrous sodium sulphate and concentrated. The residue was purified by SiO$_2$ column chromatography eluted with 1% MeOH/DCM to give the title compound (0.65 g). LCMS [M+H]$^+$ 336.2.

e) 3-(3-(3,4-Dihydroisoquinolin-2(1H)-yl)-2-hydroxypropyl)-1-(4-methoxybenzyl)-2-oxo-2,3-dihydro-1H-benzo[d]imidazole-5-carbonitrile (FF-5)

To a 100 mL sealed tube were added 1-(4-methoxybenzyl)-3-(oxiran-2-ylmethyl)-2-oxo-2,3-dihydro-1H-benzo[d]imidazole-5-carbonitrile (0.65 g, 1.94 mmol), 1,2,3,4-tetrahydroisoquinoline (0.389 g, 2.62 mmol), DIPEA (0.752 g, 5.82 mmol) and IPA (10.0 mL). The reaction mixture was stirred for 12 h at 100° C. The reaction mixture was distilled out and the residue was purified by SiO$_2$ column chromatography eluted with 2% MeOH/DCM to give the title compound (0.70 g, 77.09%). LCMS [M+H]$^+$ 469.1. $^1$H NMR [300 MHz, DMSO-d$_6$]: δ 7.70 (d, 1H), 7.48-7.43 (m, 1H), 7.26 (dd, 3H), 7.13-6.99 (m, 4H), 6.87 (d, 2H), 4.99 (dd, 3H), 4.13-3.99 (m, 2H), 3.85 (dd, 1H), 3.70 (d, 3H), 3.61 (s, 2H), 2.79-2.68 (m, 6H).

Example 96: 3-(3-(3,4-Dihydroisoquinolin-2(1H)-yl)-2-hydroxypropyl)-5-fluoro-1-(4-methoxybenzyl)-1,3-dihydro-2H-benzo[d]imidazol-2-one (GG-5)

GG-5

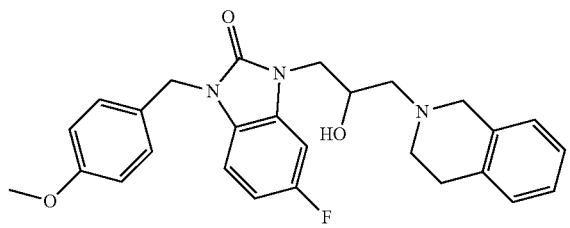

a) 4-Fluoro-N1-(4-methoxybenzyl)-2-nitroaniline (GG-1)

To a stirred solution of 1,4-difluoro-2-nitrobenzene (5.0 g, 31.4 mmol) in 100.0 mL of DMF was added (4-methoxyphenyl)methanamine (4.74 g, 34.5 mmol) and NaHCO$_3$ (5.27 g, 62.8 mmol) followed by stirring for 12 h at RT. The reaction mixture was diluted with water and the precipitated solid was filtered and dried under reduced pressure to give yellow solid (5.10 g, 59.30%). $^1$H NMR [300 MHz, DMSO-d$_6$]: δ 8.58-8.54 (t, 1H), 8.51 (d, 1H), 7.88-7.84 (dd, 1H), 7.49-7.42 (m, 1H), 7.31-7.28 (d, 2H), 7.02-6.88 (m, 2H), 4.54-4.53 (d, 2H), 3.72 (s, 3H).

b) 4-Fluoro-N1-(4-methoxybenzyl) benzene-1,2-diamine (GG-2)

To a stirred solution of 4-fluoro-N-(4-methoxybenzyl)-2-nitroaniline (5.0 g, 18.0 mmol) in 75 mL of THF were added Zn (11.76 g, 180.0 mmol) and NH$_4$Cl (9.72 g, 180.0 mmol) in H$_2$O (50.0 mL) at 0° C. followed by stirring at 65° C. for 3 h. The reaction mixture filtered on Celite bed, the filterate was diluted with water and extracted with ethyl acetate. The combined extracts were washed with brine solution, dried over anhydrous sodium sulphate and concentrated. The residue was purified by SiO$_2$ column chromatography eluted with 3% MeOH/DCM to give the title compound (4.0 g, 90.90%). $^1$H NMR [300 MHz, DMSO-d$_6$]: δ 7.28-7.25 (d, 2H), 6.88-6.85 (d, 2H), 6.37-6.32 (dd, 1H), 6.28-6.23 (m, 1H), 6.17-6.13 (m, 1H), 4.91 (s, 2H), 4.82-4.80 (t, 1H), 4.16-4.14 (d, 2H), 3.71 (s, 3H).

c) 5-Fluoro-1-(4-methoxybenzyl)-1,3-dihydro-2H-benzo[d]imidazol-2-one (GG-3)

To a stirred solution of 4-fluoro-N1-(4-methoxybenzyl) benzene-1,2-diamine (4.0 g, 16.2 mmol) in 40 mL of THF was added CDI (53.16 g, 19.4 mmol) at 0° C. followed by stirring for 12 h at RT. The reaction mixture was diluted with water and extracted with ethyl acetate. The combined extracts were washed with brine solution, dried over anhydrous sodium sulphate and concentrated to give the title compound (3.10 g, 70.3%). LCMS [M+H]$^+$ 273.1.

d) 5-Fluoro-1-(4-methoxybenzyl)-3-(oxiran-2-ylmethyl)-1,3-dihydro-2H-benzo [d]imidazol-2-one (GG-4)

To a stirred solution of 5-fluoro-1-(4-methoxybenzyl)-1,3-dihydro-2H-benzo[d]-imidazol-2-one (2.0 g, 7.3 mmol) in 30.0 mL of DMF was added NaH (0.436 g, 10.9 mmol) at 0° C. followed by stirring for 30 min at 0° C. To this reaction mixture was added epibromohydrin (1.49 g, 10.9 mmol). The reaction mixture was stirred for 12 h at RT. The reaction mixture was quenched with water and extracted with ethyl acetate. The combined extracts were washed with water and brine solution, dried over anhydrous sodium sulphate and concentrated. The residue was purified by SiO$_2$ column chromatography eluted with 1% MeOH/DCM to give the title compound (1.40 g, 58.57%). LCMS [M+H]$^+$ 329.1.

e) 3-(3-(3,4-Dihydroisoquinolin-2(1H)-yl)-2-hydroxypropyl)-5-fluoro-1-(4-methoxybenzyl)-1,3-dihydro-2H-benzo[d]imidazol-2-one (GG-5)

To a 100 mL sealed tube were added 5-fluoro-1-(4-methoxybenzyl)-3-(oxiran-2-ylmethyl)-1,3-dihydro-2H-benzo [d]imidazol-2-one (1.4 g, 4.26 mmol), 1,2,3,4-tetrahydroisoquinoline (0.85 g, 6.39 mmol), DIPEA (1.65 g, 12.7 mmol) and IPA (20.0 mL) followed by stirring for 12 h at 100° C. The reaction mixture was distilled out and the residue was purified by SiO$_2$ column chromatography eluted with 2% MeOH/DCM to give the title compound (1.40 g, 71.42%). LCMS [M+H]$^+$462.2. $^1$H NMR [300 MHz, DMSO-d$_6$]: δ 7.24 (d, 2H), 7.13-7.00 (m, 6H), 6.88-6.77 (m, 3H), 5.00-4.90 (m, 3H), 4.11-3.96 (m, 2H), 3.78 (dd, 1H), 3.69 (d, 3H), 3.61 (s, 2H), 2.80-2.67 (m, 6H).

The following compound was prepared according to the procedure described in Example 96 using appropriate starting material. The characterization data is indicated on the table given below.

| Example No. | Structure | Characterization data |
|---|---|---|
| 97 | 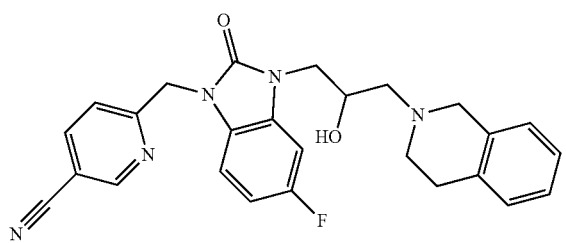 | $^1$H NMR (400 MHz, DMSO-d$_6$) δ: 7.88-7.86 (t, 2H) 7.56-7.51 (d, 2H) 7.19 (dd, 1H), 7.12-7.01 (m, 5H) 6.82 (ddd, 1H), 5.13 (d, 2H), 5.00 (d, 1H), 4.14-3.96 (m, 2H), 3.80 (dd, 1H), 3.62 (d, 2H), 3.17 (s, 3H) 2.80-2.65 (m, 5H), 2.58 (dd, 1H) LCMS [M + H]$^+$ 510.3. |

Example 98: 6-((3-(3-(3,4-Dihydroisoquinolin-2 (1H)-yl)-2-hydroxypropyl)-5-fluoro-2-oxo-2,3-dihydro-1H-benzo[d]imidazol-1-yl)methyl)nicotinonitrile (HH-2)

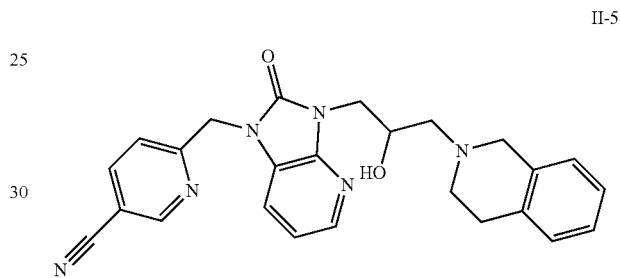

HH-2 a) 1-(3-(3,4-Dihydroisoquinolin-2(1H)-yl)-2-hydroxypropyl)-6-fluoro-1,3-dihydro-2H-benzo[d]imidazol-2-one (HH-1)

To a 100 mL sealed tube were added 3-(3-(3,4-dihydroisoquinolin-2(1H)-yl)-2-hydroxypropyl)-5-fluoro-1-(4-methoxybenzyl)-1,3-dihydro-2H-benzo[d]imidazol-2-one (1.20 g, 2.6 mmol) and TFA (12.0 mL). The reaction mixture was stirred for 48 h at 90° C. The reaction mixture was distilled out and the residue was diluted with water and extracted with DCM. The combined extracts were washed with saturated sodium bicarbonate and brine solution, dried over anhydrous sodium sulphate and concentrated. The residue was purified by SiO$_2$ column chromatography eluted with 3% MeOH/DCM to give the title compound (0.45 g, 50.73%). LCMS [M+H]$^+$342.3.

b) 6-((3-(3-(3,4-Dihydroisoquinolin-2(1H)-yl)-2-hydroxypropyl)-5-fluoro-2-oxo-2,3-dihydro-1H-benzo[d]imidazol-1-yl)methyl)nicotinonitrile (HH-2)

To a stirred solution of 1-(3-(3,4-dihydroisoquinolin-2 (1H)-yl)-2-hydroxypropyl)-6-fluoro-1,3-dihydro-2H-benzo [d]imidazol-2-one (0.250 g, 0.73 mmol) in 30.0 mL of THF was added NaH (0.029 g, 7.32 mmol) at 0° C. The reaction mixture was stirred for 30 min at 0° C. To this reaction mixture was added 6-(bromomethyl)nicotinonitrile (0.144 g, 7.32 mmol) at 0° C. followed by stirring for 12 h at RT. The reaction mixture was quenched with water and extracted with ethyl acetate. The combined extracts were washed brine solution, dried over anhydrous sodium sulphate and concentrated. The residue was purified by SiO$_2$ column chromatography eluted with 2% MeOH/DCM to give the title compound (0.22 g, 65.86%). LCMS [M+H]$^+$ 458.3. $^1$H NMR [400 MHz, DMSO-d$_6$]: δ 8.94 (dd, 2.14 Hz, 1H), 8.26 (dd, 1H), 7.44 (dd, 1H), 7.19 (dd, 1H), 7.11-7.07 (m, 3H), 7.02-6.97 (m, 2H), 6.83-6.78 (m, 1H), 5.20 (d, 2H), 5.00 (d, 1H), 4.10-3.99 (m, 1H), 3.82-3.77 (m, 1H), 3.60 (d, 2H), 2.75-2.67 (m, 5H), 2.57 (d, 2H).

Example 99: 6-((3-(3-(3,4-dihydroisoquinolin-2 (1H)-yl)-2-hydroxypropyl)-2-oxo-2,3-dihydro-1H-imidazo[4,5-b]pyridin-1-yl)methyl)nicotinonitrile (II-5)

II-5 a) 1,3-Dihydro-2H-imidazo[4,5-b]pyridin-2-one (II-1)

To a 250 mL sealed tube were added pyridine-2,3-diamine (5.0 g, 45.8 mmol), CDI (0.703 g, 4.3 mmol) and THF (75.0 mL) followed by stirring for 5 h at 70° C. The reaction mixture was diluted with water and the precipitated solid was filtered and dried on vacuum to give the title compound (5.0 g, 81.96%). LCMS [M+H]$^+$ 136.2.

b) Tert-Butyl 2-oxo-2,3-dihydro-H-imidazo[4,5-b] pyridine-1-carboxylate (II-2)

To a stirred solution of 1,3-dihydro-2H-imidazo[4,5-b] pyridin-2-one (2.0 g, 14.8 mmol) in 20.0 mL of DMF was added NaH (0.592 g, 14.8 mmol) at 0° C. followed by stirring for 1 hour at 0° C. To this reaction mixture was added Boc anhydride (3.23 g, 14.8 mmol) at 0° C. followed by stirring for 12 h at RT. The reaction mixture was quenched with water and extracted with ethyl acetate. The organic layer was washed with water and brine solution and dried over anhydrous sodium sulphate. The organic layer was concentrated to give the title compound (1.20 g, 34.58%). $^1$H NMR [300 MHz, DMSO-d$_6$]: δ 11.90 (bs, 1H), 8.03-8.02 (d, 1H), 7.83-7.81 (d, 1H), 7.10-7.06 (m, 1H), 1.58 (s, 9H).

c) Tert-Butyl 3-(oxiran-2-ylmethyl)-2-oxo-2,3-dihydro-1H-imidazo[4,5-b]pyridine-1-carboxylate (II-3)

To a stirred solution of tert-butyl 2-oxo-2,3-dihydro-H-imidazo[4,5-b]pyridine-1-carboxylate (1.0 g, 4.25 mmol) in 15.0 mL of DMF was added NaH (0.254 g, 6.37 mmol) at 0° C. followed by stirring for 30 min at 0° C. To this reaction mixture was added epibromohydrin (0.873 g, 6.37 mmol) at 0° C. followed by stirring for 12 h at RT. The reaction mixture was quenched with water and extracted with ethyl acetate. The combined extracts were washed with water and brine solution, dried over anhydrous sodium sulphate and concentrated. The residue was purified by SiO$_2$ column chromatography eluted with 1% MeOH/DCM to give the title compound (0.40 g, 32.52%). LCMS [M+H]$^+$292.3.

d) 3-(3-(3,4-Dihydroisoquinolin-2(1H)-yl)-2-hydroxypropyl)-1,3-dihydro-2H-imidazo[4,5-b]pyridin-2-one (II-4)

To a 50 mL sealed tube, were added tert-butyl 3-(oxiran-2-ylmethyl)-2-oxo-2,3-dihydro-1H-imidazo[4,5-b]pyridine-1-carboxylate (0.40 g, 1.37 mmol), 1,2,3,4-tetrahydroisoquinoline (0.274 g, 2.05 mmol), DIPEA (0.531 g, 4.11 mmol) and IPA (10.0 mL). The reaction mixture was stirred for 12 hours at 100° C. The reaction mixture was distilled out and residue obtained was purified by SiO$_2$ column chromatography eluted with 2% MeOH/DCM to give title compound (0.55 g); LCMS [M+H]$^+$325.3.

e) 6-((3-(3-(3,4-Dihydroisoquinolin-2(1H)-yl)-2-hydroxypropyl)-2-oxo-2,3-dihydro-1H-imidazo[4,5-b]pyridin-1-yl)methyl)nicotinonitrile (H-5)

To a stirred solution of 3-(3-(3,4-dihydroisoquinolin-2 (1H)-yl)-2-hydroxypropyl)-1,3-dihydro-2H-imidazo[4,5-b] pyridin-2-one (0.35 g, 1.07 mmol) in 10.0 mL of DMF was added NaH (0.042 g, 1.07 mmol) at 0° C. followed by stirring for 30 min at 0° C. To this reaction mixture was added 6-(bromomethyl)nicotinonitrile (0.212 g, 1.07 mmol) at 0° C. followed by stirring for 12 h at RT. The reaction mixture was quenched with water and extracted with ethyl acetate. The organic layer was washed brine solution and dried over anhydrous sodium sulphate. The reaction mixture was distilled out and the residue was purified by SiO$_2$ column chromatography eluted with 2% MeOH/DCM to give the title compound (0.20 g, 42.46%). LCMS [M+H]$^+$ 441.3. $^1$H NMR [300 MHz, DMSO-d$_6$]: δ 8.92 (d, 1H), 8.25-8.23 (dd, 1H), 8.00-7.98 (dd, 1H), 7.49-7.47 (dd, 1H), 7.33-7.31 (dd, 1H), 7.10-6.99 (m, 5H), 5.18-5.16 (d, 2H), 5.02-5.00 (d, 1H), 4.30 (m, 1H), 3.96-3.95 (m, 2H), 3.58 (d, 1H), 3.52 (d, 1H), 2.68-2.67 (m, 4H), 2.57-2.52 (m, 2H).

Example 100: 4-(((3aR,7aR)-3-(3-(3,4-Dihydroisoquinolin-2(1H)-yl)-2-hydroxypropyl)-2-oxooctahydro-1H-benzo[d]imidazol-1-yl)methyl)benzonitrile (JJ-5)

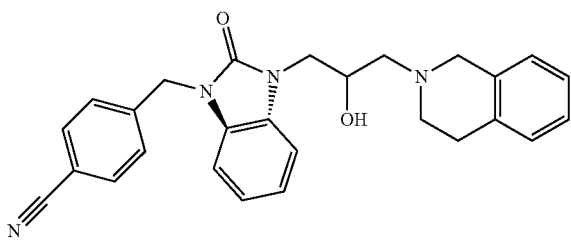

a) Tert-Butyl ((1R,2R)-2-aminocyclohexyl)carbamate (JJ-1)

To a stirred solution of (1S,2S)-cyclohexane-1,2-diamine (3.00 g, 26.272 mmol) in 1,4-dioxane (45 mL) was added Boc-anhydride (3.00 mL, 13.136 mmol) in 1,4-dioxane (45 mL) at 0° C. followed by stirring at ambient temperature (25-27° C.) for 16 h. To the concentrated reaction mixture was added water and the mixture was filtered. The filtrate was extracted with DCM. The combined extracts were washed with water and brine solution, dried over anhydrous sodium sulphate and concentrated to give the title compound as pale yellow oil (3.00 g, 53.6%). LCMS [M+H]$^+$ 215.3.

b) Tert-Butyl ((1R,2R)-2-((4-cyanobenzyl)amino) cyclohexyl)carbamate (JJ-2)

To a stirred solution of tert-butyl ((1R,2R)-2-aminocyclohexyl)carbamate (1.50 g, 6.99 mmol) in methanol was added 4-cyanobenzaldehyde (0.92 g, 6.99 mmol) followed by stirring at ambient temperature (25-27° C.) for 5 h. To the reaction mixture was added portion wise NaBH$_4$ (1.32 g, 34.99 mmol) at 0-5° C. followed by stirring for 12 h at ambient temperature. The reaction mixture was concentrated. The residue was dissolved in water (100 mL) and extracted with DCM. The combined extracts were washed with brine solution, dried over anhydrous sodium sulphate and concentrated. The residue was purified by combi flash column chromatography eluted with 0-60% ethyl acetate/ hexane to give the title compound as pale yellow oil (1.50 g, 32.6%). LCMS [M+H]$^+$330.1.

c) 4-(((3aS,7aS)-2-Oxooctahydro-1H-benzo[d]imidazol-1-yl)methyl) benzonitrile (JJ-3)

To a stirred solution of tert-butyl ((1R,2R)-2-((4-cyanobenzyl)amino) cyclohexyl) carbamate (4.559 mmol) in THF (30 mL) was added potassium tert-butoxide (1.53 g, 13.677 mmol) at 0° C. followed by refluxing for 3 h. The reaction mixture was diluted with water (50 mL) and extracted with ethyl acetate. The combined extracts were washed with brine solution and dried over anhydrous sodium sulphate. The organic layer was concentrated and the residue was purified by combi flash column chromatography eluted with 0-60% ethyl acetate/hexane to give the title compound as pale yellow oil (0.3 g, 27.3%). LCMS [M+H]$^+$ 256.3.

d) 4-(((3aS,7aS)-3-(Oxiran-2-ylmethyl)-2-oxooctahydro-1H-benzo[d]imidazol-1-yl)methyl)benzonitrile (JJ-4)

To a stirred solution of 4-(((3aS,7aS)-2-oxooctahydro-1H-benzo[d]imidazol-1-yl)methyl) benzonitrile (0.30 g, 1.176 mmol) in THF (20 mL) was added NaH (0.07 g, 1.764 mmol) at 0° C. followed by stirring for 1 h. To the reaction mixture was added dropwise epibromohydrine (0.15 mL, 1.764 mmol) followed by stirring the mixture for 12 h at ambient temperature. The reaction mixture was quenched with ice cold water and extracted with ethyl acetate. The combined extracts were washed with brine solution, dried over anhydrous sodium sulphate and concentrated to give the title compound as pale yellow oil (0.2 g, 55.6%). LCMS [M+H]$^+$ 312.3.

e) 4-(((3aS,7aS)-3-(3-((1H-Benzo[d]imidazol-2-yl) amino)-2-hydroxypropyl)-2-oxooctahydro-1H-benzo [d]imidazol-1-yl)methyl)benzonitrile (JJ-5)

To a stirred solution of 4-(((3aS,7aS)-3-(oxiran-2-ylmethyl)-2-oxooctahydro-1H-benzo[d]imidazol-1-yl)methyl) benzonitrile (0.2 g, 0.643 mmol) in IPA (10 mL) was added DIPEA (0.33 mL, 1.929 mmol) and 1,2,3,4-tetrahydroisoquinoline (0.10 mL, 0.771 mmol) at 0° C. followed by stirring at 100° C. for 12 h in a sealed tube. The reaction mixture was concentrated and purified by combi flash column chromatography eluted with 0-4% DCM/MeOH to give the title compound as pale yellow oil (0.07 g, 25.0%). LCMS [M+H]⁺ 445.4. ¹H NMR [400 MHz, DMSO-d₆] δ 7.79-7.77 (d, 2H), 7.47-7.45 (d, 2H), 7.10-7.09 (m, 3H), 7.033 (d, 1H), 4.70-4.69 (d, 1H), 4.42-4.38 (m, 1H), 4.27-4.23 (d, 1H), 3.89 (s, 1H) 3.59 (s, 2H), 3.3 (s, 1H), 3.05-2.90 (m, 2H), 2.79-2.78 (m, 2H), 2.67 (m, 3H), 2.43-2.39 (m, 2H), 2.08 (s, 1H), 1.78-1.30 (m, 3H) 1.22 (m, 4H).

The following compound was prepared according to the procedure described in Example 100 using appropriate starting material. The characterization data is indicated on the table given below.

| Example No. | Structure | Characterization data |
|---|---|---|
| 101 | 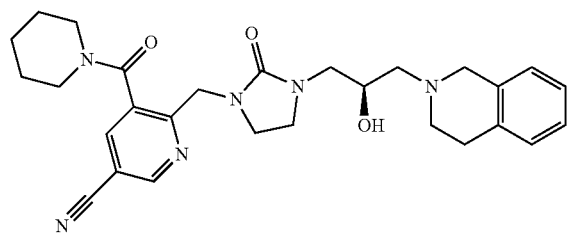 | ¹H NMR [300 MHz, DMSO-d₆] δ: 7.80 (dt, 2H), 7.47 (dd, 2H), 7.09 (d, 3H), 7.02 (d, 1H), 4.75 (dd, 1H), 4.45 (dd, 1H), 4.23 (d, 1H), 3.85 (s, 1H), 3.69-3.47 (m, 4H), 3.32-3.23 (m, 1H), 2.86-2.62 (m, 5H), 2.44-2.42 (m, 2H) 1.84 (s, 1H), 1.64-1.49 (m, 4H), 1.20 (d, 3H). LCMS [M + H] ⁺ 445.4. |

Example 102: (R)-6-((3-(3-(3,4-dihydroisoqumolhn-2(1H)-yl)-2-hydroxypropyl)-2-oxoimidazolidin-1-yl)methyl)-5-(piperidine-1-carbonyl)nicotinonitrile (LL-4)

LL-4 a) (R)-5-bromo-2-((3-(2-((tert-butyldimethylsilyl)oxy)-3-(3,4-dihydroisoquinolin-2(1H)-yl)propyl)-2-oxoimidazolidin-1-yl)methyl)nicotinic acid (LL-1)

Experimental procedure is same as compound W-5 in Example 48 to get 0.16 g of title compound. LCMS [M+] 603.3, [M+2] 605.3 b) (R)-1-((5-bromo-3-(piperidine-1-carbonyl)pyridin-2-yl)methyl)-3-(2-((tert-butyldimethylsilyl)oxy)-3-(3,4-dihydroisoquinolin-2(1H)-yl)propyl)imidazolidin-2-one (LL-2)

Experimental procedure is same as compound W-8 in Example 48 to get (0.1 g, 57.47%) of title compound. LCMS [M+] 670.3, [M+2] 672.3 c) (R)-6-((3-(2-((tert-butyldimethylsilyl)oxy)-3-(3,4-dihydroisoquinolin-2(1H)-yl)propyl)-2-oxoimidazolidin-1-yl)methyl)-5-(piperidine-1-carbonyl)nicotinonitrile (LL-3)

Experimental procedure is same as compound X-4 in Example 73 to get (0.07 g, 76.92%) of title compound. LCMS [M+H]⁺617.5 d) (R)-6-((3-(3-(3,4-dihydroisoquinolin-2(1H)-yl)-2-hydroxypropyl)-2-oxoimidazolidin-1-yl)methyl)-5-(piperidine-1-carbonyl)nicotinonitrile (LL-4)

Experimental procedure is same as compound T-2 in Example 35. The residue obtained was purified by Prep. TLC plates eluted with 6% MeOH in CHCl₃ to get (0.015 g, 27.27%) of title compound. LCMS [M+H]⁺ 503.6. ¹H NMR (400 MHz, DMSO-d₆) δ 8.99 (d, 1H), 8.28 (d, 1H), 7.11-6.98 (m, 4H), 4.71 (d, 1H), 4.39 (d, 2H), 4.05 (dp, 1H), 3.84 (d, 1H), 3.60 (s, 2H), 3.45-3.37 (m, 2H), 3.32-3.22 (m, 4H), 3.09 (s, 3H), 2.79 (t, 2H), 2.74-2.65 (m, 2H), 2.43 (dd, 2H), 1.56 (s, 4H), 1.43 (s, 2H).

The following compound was prepared according to the procedure described in Example 102 using appropriate starting materials. The characterization data is indicated on the table given below.

| Example No. | Structure | Characterization data |
|---|---|---|
| 103 | 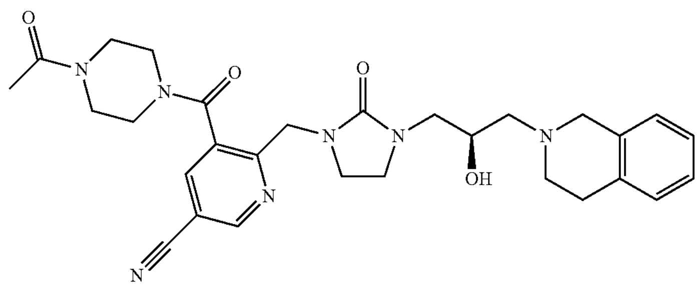 [SMILES: CC(=O)N1CCN(C(=O)c2cc(C#N)cnc2CN2CCN(C[C@H](O)CN3CCc4ccccc4C3)C2=O)CC1] | $^1$H NMR (400 MHz, Methanol-d4) δ 8.91 (t, 1H), 8.19 (dd, 1H), 7.17-6.98 (m, 4H), 4.54 (d, 2H), 4.05 (td, 1H), 3.74 (s, 3H), 3.69-3.64 (m, 1H), 3.54 (dt, 4H), 3.39 (d, 2H), 3.34 (d, 2H), 3.26 (d, 2H), 3.18 (s, 2H), 2.89 (dd, 4H), 2.64-2.54 (m, 2H), 2.10 (d, 3H). LCMS [M + H] $^+$ 546.4. |

Example 104: (R)—N-(6-((3-(3-(3,4-dihydroisoquinolin-2(1H)-yl)-2-hydroxypropyl)-2-oxoimidazolidin-1-yl)methyl)pyridin-3-yl)oxetane-3-carboxamide (NN-6)

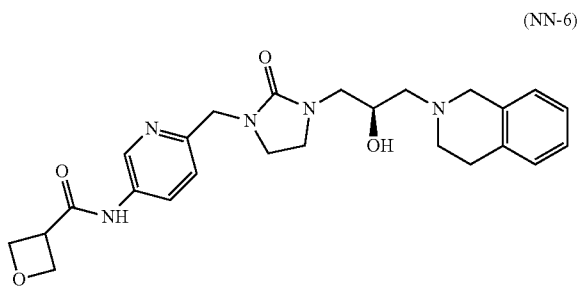 [SMILES: O=C(Nc1ccc(CN2CCN(C[C@H](O)CN3CCc4ccccc4C3)C2=O)nc1)C1COC1]

(NN-6)

a) (R)-1-((5-bromopyridin-2-yl)methyl)-3-(2-((tert-butyldimethylsilyl)oxy)-3-(3,4-dihydroisoquinolin-2(1H)-yl)propyl)imidazolidin-2-one (NN-1)

To a stirred solution of (R)-1-(2-((tert-butyldimethylsilyl)oxy)-3-(3,4-dihydroisoquinolin-2(1H)-yl)propyl)imidazolidin-2-one (30.0 g, 76.998 mmol) in 400.0 mL of THF was added NaH (60%) (4.61 g, 115.497 mmol) at 0° C. and the reaction mixture was allowed to stirred for 30 min at RT, again the reaction mixture was cooled to 0° C. and added 2-bromo-5-(bromomethyl)pyridine (Intermediate-2) (22.98 g, 92.397 mmol) in THF (250.0 ml) drop wise and stirred for 12 hours at RT. After completion of reaction (monitored by TLC, eluent: 5% Methanol in DCM), the reaction mixture was diluted with water and extracted with Ethyl acetate. The combined organics were washed with water, brine solution, dried over anhydrous sodium sulphate and concentrated under reduced pressure. The residue obtained was purified by column chromatography (SiO$_2$, 2-3% MeOH in DCM) to give title compound (40.0 g, 93.0%). $^1$H NMR (300 MHz, DMSO-d$_6$) δ 8.29 (dd, 1H), 7.62 (q, 2H), 7.13-7.06 (m, 3H), 7.05-6.97 (m, 1H), 4.26 (s, 2H), 4.03 (t, 1H), 3.59 (d, 2H), 3.47-3.37 (m, 1H), 3.32-3.12 (m, 5H), 2.86-2.65 (m, 4H), 2.48-2.40 (m, 2H), 0.83 (d, 9H), 0.06--0.03 (m, 6H).

b) (R)-1-(2-((tert-butyldimethylsilyl)oxy)-3-(3,4-dihydroisoquinolin-2(1H)-yl)propyl)-3-((5-((diphenylmethylene)amino)pyridin-2-yl)methyl)imidazolidin-2-one (NN-2)

To a sealed tube, were added (R)-1-((5-bromopyridin-2-yl)methyl)-3-(2-((tert-butyldimethylsilyl)oxy)-3-(3,4-dihydroisoquinolin-2(1H)-yl)propyl)imidazolidin-2-one (2.0 g, 3.5 mmol), 1,4-Di-Oxane (20 mL), diphenylmethanimine (0.76 g, 4.2 mmol), Cesium carbonate (2.28 g, 7.0 mmol), Pd$_2$(dba)$_3$ (0.16 g, 0.175 mmol) and Xanthphos (0.202 g, 0.35 mmol) and the reaction mixture was degassed with Argon gas for 10 minutes and stirred for 12 hours at 100° C. After completion of reaction (monitored by TLC, eluent: 5% Methanol in DCM), the reaction mixture was filtered through Celite bed and filtrate was concentrated under reduced pressure. The residue was purified with column chromatography (SiO$_2$, 1% MeOH in DCM) to give the title compound (2.2 g, 95.65%). LCMS [M+H]$^+$660.2 c) (R)-1-((5-aminopyridin-2-yl)methyl)-3-(3-(3,4-dihydroisoquinolin-2(1H)-yl)-2-hydroxypropyl)imidazolidin-2-one (NN-4)

To a stirred solution of (R)-1-(2-((tert-butyldimethylsilyl)oxy)-3-(3,4-dihydroisoquinolin-2(1H)-yl)propyl)-3-((5-((diphenylmethylene)amino)pyridin-2-yl)methyl)imidazolidin-2-one (1.4 g, 2.27 mmol) in 20 mL of THF was added 10 mL of 2N HCl solution at 0° C. and stirred for 12 h at RT. After completion of reaction (monitored by TLC, eluent: 5% Methanol in DCM), the mixture was washed with ether and aqueous layer was basified with sodium carbonate and extracted with 10% MeOH in DCM. The combined organics were washed with water, brine solution, dried over anhydrous sodium sulphate and concentrated. The residue was purified by combiflash column chromatography (SiO$_2$, 10% MeOH in DCM) to give the title compound (0.33 g, 24.81%). LCMS [M+H]$^+$496.3 and 0.48 g of (R)-1-((5-aminopyridin-2-yl)methyl)-3-(3-(3,4-dihydroisoquinolin-2(1H)-yl)-2-hydroxypropyl)imidazolidin-2-one. LCMS [M+H]$^+$382.0.

d) (R)—N-(6-((3-(2-((tert-butyldimethylsilyl)oxy)-3-(3,4-dihydroisoquinolin-2(1H)-yl)propyl)-2-oxoimidazolidin-1-yl)methyl)pyridin-3-yl)oxetane-3-carboxamide (NN-5)

Experimental procedure is same as compound W-8 in example—48 to get 0.127 g of title compound. LCMS [M+H]$^+$580.3 e) (R)—N-(6-((3-(3-(3,4-dihydroisoquinolin-2(1H)-yl)-2-hydroxypropyl)-2-oxoimidazolidin-1-yl)methyl)pyridin-3-yl)oxetane-3-carboxamide (NN-6)

To a stirred solution of (R)—N-(6-((3-(2-((tert-butyldimethylsilyl)oxy)-3-(3,4-dihydroisoquinolin-2(1H)-yl)propyl)-2-oxoimidazolidin-1-yl)methyl)pyridin-3-yl)oxetane- 3-carboxamide (0.127 g, 0.219 mmol) in 5.0 mL of THF was added TBAF (1M solution in THF) (0.659 mL, 0.657 mmol) at 0° C. and the reaction mixture was stirred for 12 h at room temperature. After completion of reaction (monitored by TLC, eluent: 5% Methanol in CHCl$_3$), the reaction mixture was concentrated under reduced pressure and residue was diluted with water and extracted with ethyl acetate. The combined extracts were washed with brine solution and dried over anhydrous sodium sulphate. The crude was purified by column chromatography (SiO$_2$, 3% MeOH in CHCl$_3$) to get (0.054 g, 53.46%) of title compound. LCMS [M+H]$^+$ 466.1. $^1$H NMR (400 MHz, DMSO-d$_6$) δ 10.15 (s, 1H), 8.68 (d, 1H), 8.02 (dd, 1H), 7.23 (d, 1H), 7.15-6.95 (m, 4H), 4.79-4.63 (m, 4H), 4.30 (s, 2H), 3.97 (q, 1H), 3.87 (s, 1H), 3.60 (s, 2H), 3.45 (td, 3H), 3.29-3.20 (m, 3H), 3.02 (dd, 1H), 2.79 (d, 2H), 2.70 (q, 2H), 2.45-2.40 (m, 2H).

The following compounds were prepared according to the procedure described for compound Example 104 using appropriate starting material. The characterization data is indicated on the table given below.

| Example No. | Structure | Characterization data |
|---|---|---|
| 105 | 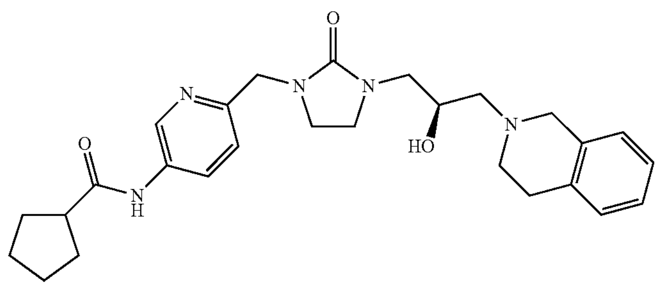 [SMILES: O=C(Nc1ccc(CN2CCN(C[C@H](O)CN3CCc4ccccc4C3)C2=O)nc1)C1CCCC1] | $^1$H NMR (400 MHz, DMSO-d6) δ 10.08 (s, 1H), 8.68 (d, 1H), 8.01 (dd, 1H), 7.20 (d, 1H), 7.14-6.99 (m, 4H), 4.75 (s, 1H), 4.29 (s, 2H), 3.88 (s, 1H), 3.60 (d, 2H), 3.48-3.40 (m, 1H), 3.29-3.14 (m, 4H), 3.02 (dd, 1H), 2.86-2.65 (m, 3H), 2.45 (s, 1H), 2.06-1.96 (m, 1H), 1.94-1.81 (m, 2H), 1.78-1.63 (m, 3H), 1.55 (d, 3H), 1.31 (p, 2H). LCMS [M + H] $^+$ 478. |
| 106 | 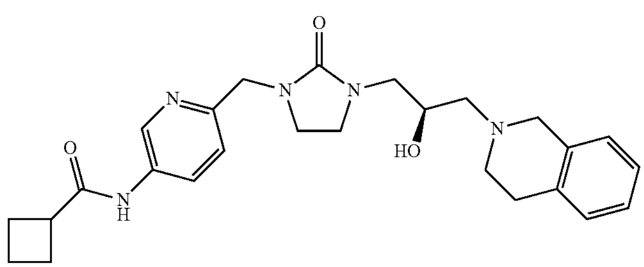 [SMILES: O=C(Nc1ccc(CN2CCN(C[C@H](O)CN3CCc4ccccc4C3)C2=O)nc1)C1CCC1] | $^1$H NMR (400 MHz, DMSO-d6) δ 9.94 (s, 1H), 8.68 (d, 1H), 8.01 (dd, 1H), 7.20 (d, 1H), 7.06 (dt, 4H), 4.74 (s, 1H), 4.29 (s, 2H), 3.87 (s, 1H), 3.65-3.56 (m, 1H), 3.43 (ddd, 1H), 3.32-3.15 (m, 4H), 3.02 (dd, 1H), 2.79 (d, 1H), 2.72 (d, 2H), 2.44 (s, 1H), 2.34-2.29 (m, 2H), 2.27-2.05 (m, 3H), 1.95 (dt, 2H), 1.88-1.69 (m, 1H), 1.56 (s, 1H), 1.31 (q, 1H). LCMS [M + H] $^+$ 464. |
| 107 | 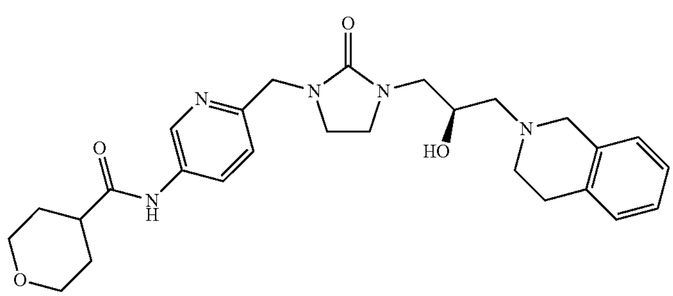 [SMILES: O=C(Nc1ccc(CN2CCN(C[C@H](O)CN3CCc4ccccc4C3)C2=O)nc1)C1CCOCC1] | $^1$H NMR (400 MHz, DMSO-d6) δ 10.13 (s, 1H), 8.69 (dd, 1H), 8.07-7.92 (m, 1H), 7.22 (d, 1H), 7.16-6.94 (m, 4H), 4.76 (s, 1H), 4.30 (s, 2H), 3.91 (ddd, 2H), 3.61 (tdd, 2H), 3.48-3.38 (m, 2H), 3.33-3.14 (m, 4H), 3.03 (dd, 1H), 2.80 (d, 2H), 2.76-2.57 (m, 3H), 2.46 (s, 2H), 1.79-1.64 (m, 3H), 1.57 (t, 1H), 1.36-1.22 (m, 2H). LCMS [M + H] $^+$ 494.3. |

The following compounds were prepared according to the procedure described for compounds NN-2 and NN-6 in Example 104 using appropriate starting material. The characterization data is indicated on the table given below.

| Example No. | Structure | Characterization data |
| --- | --- | --- |
| 108 | 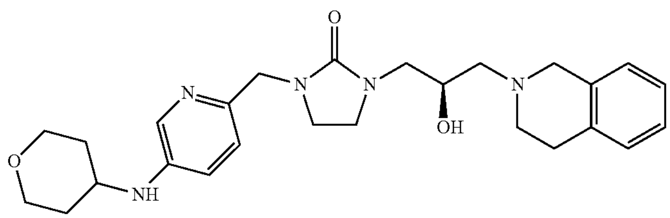 [SMILES: O=C1N(Cc2ccc(NC3CCOCC3)cn2)CCN1C[C@H](O)CN1CCc2ccccc2C1] | $^1$H NMR (400 MHz, Methanol-d4) δ 7.87 (d, 1H), 7.17-6.98 (m, 6H), 4.30 (s, 2H), 4.07 (tt, 1H), 3.95 (dt, 2H), 3.76 (s, 2H), 3.61-3.45 (m, 5H), 3.35 (d, 1H), 3.26 (d, 1H), 3.18 (dd, 2H), 2.97-2.84 (m, 4H), 2.70-2.57 (m, 2H), 2.03-1.91 (m, 2H), 1.47 (dtd, 2H). LCMS [M + H] $^+$ 466.4. |
| 109 | 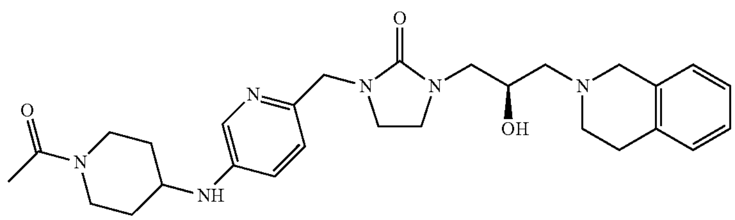 [SMILES: CC(=O)N1CCC(Nc2ccc(CN3CCN(C[C@H](O)CN4CCc5ccccc5C4)C3=O)nc2)CC1] | $^1$H NMR (400 MHz, DMSO-d6) δ 7.91 (dd, 1H), 7.12-7.00 (m, 4H), 7.00-6.90 (m, 2H), 5.74 (d, 1H), 5.32 (t, 1H), 4.72 (d, 1H), 4.16 (s, 3H), 3.86 (s, 1H), 3.76 (d, 1H), 3.60 (s, 2H), 3.52-3.37 (m, 2H), 3.26 (dd, 2H), 3.22-3.09 (m, 3H), 2.99 (dd, 2H), 2.79 (q, 3H), 2.71 (dd, 2H), 2.46-2.38 (m, 2H), 2.00 (s, 3H), 1.94-1.82 (m, 2H). LCMS [M + H] $^+$ 507.5. |

Example 110. (R)-1-(3-(3,4-dihydroisoquinolin-2(1H)-yl)-2-hydroxypropyl)-3-((5-(oxetan-3-ylethynyl)pyridin-2-yl)methyl)imidazolidin-2-one (OO-2)

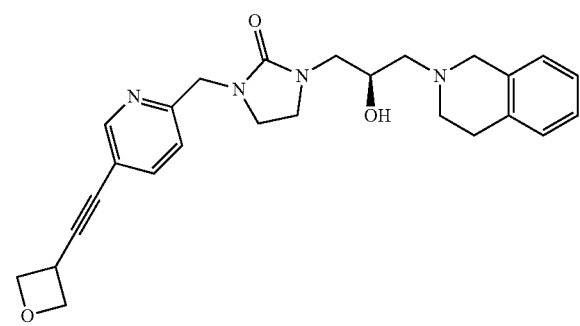

OO-2 a) (R)-1-(2-((tert-butyldimethylsilyl)oxy)-3-(3,4-dihydroisoquinolin-2(1H)-yl)propyl)-3-((5-(oxetan-3-ylethynyl)pyridin-2-yl)methyl)imidazolidin-2-one (OO-1)

To a stirred solution of (R)-1-((5-bromopyridin-2-yl)methyl)-3-(2-((tert-butyldimethylsilyl)oxy)-3-(3,4-dihydroisoquinolin-2(1H)-yl)propyl)imidazolidin-2-one (0.2 g, 0.357 mmol) in 4.0 mL of DMF was degassed with Argan gas for 10 minutes, to this reaction mixture added 3-ethynyloxetane (0.035 g, 0.428 mmol), TEA (0.108 g, 1.071 mmol) Tetrakis (0.04 g, 0.035 mmol) and CuI (0.013 g, 0.071 mmol) and stirred for 1 h at 90° C. temperature. After completion of reaction (monitored by TLC, eluent: 5% Methanol in CHCl$_3$), the reaction mixture was concentrated under reduced pressure and residue was diluted with water and extracted with ethyl acetate. The combined extracts were washed with brine solution and dried over anhydrous sodium sulphate. The crude was purified by combi-flash column chromatography (SiO$_2$, 5% MeOH in DCM) to get (0.09 g, 40%) of title compound. LCMS [M+H]$^+$561.5.

b) (R)-1-(3-(3,4-dihydroisoquinolin-2(1H)-yl)-2-hydroxypropyl)-3-((5-(oxetan-3-ylethynyl)pyridin-2-yl)methyl)imidazolidin-2-one (OO-2)

Experimental procedure is same as compound NN-6 in example—104. The crude was purified by combi-flash column chromatography (SiO$_2$, 2.5% MeOH in DCM) to get (0.03 g, 75%) of title compound. LCMS [M+H]$^+$ 447.4. $^1$H NMR (600 MHz, DMSO-d$_6$) δ 8.58 (d, 1H), 7.85 (dd, 1H), 7.28 (d, 1H), 7.16-7.00 (m, 4H), 4.81 (dd, 2H), 4.77 (s, 1H), 4.63 (dd, 2H), 4.37 (s, 2H), 4.19 (q, 1H), 3.89 (s, 1H), 3.61 (s, 2H), 3.51-3.45 (m, 2H), 3.33-3.23 (m, 3H), 3.03 (dd, 1H), 2.81 (t, 2H), 2.72 (s, 2H), 2.45 (d, 2H).

PRMT5 Inhibition Based on TR-FRET Assay:

Protein arginine methyltransferase 5 (PRMT5) is a type II arginine methyltransferase that catalyze mono- and symmetric demethylation on arginine residues of histone or non-histone proteins in presence of S-adenosylmethionine (AdoMet or SAM) a cofactor responsible for donating the methyl group. PRMT5 is reported to be overexpressed in several human cancers. To identify compounds that inhibit the PRMT5 and decrease its activity, a TR-FRET based assay has been established. Time-resolved fluorescence resonance energy transfer (TR-FRET) HTS assays are homogeneous proximity assays where the interaction of two dye-labeled binding partners is detected by the energy transfer between a donor and an acceptor dye and the subsequent light emission by the acceptor dye. PRMT5 catalyzes Histone H4 peptide [1-16] which is biotin tagged to the Lysine amino acid at carboxyl end, in presence of S-adenosyl-1-methionine (SAM) to methylate the peptide. The antibody specific to mono methylated H4 peptide (H4R3) with Ig conjugate binds to the methylated peptide, indirectly binding to the Europium lanthanide. SureLight Allophycocyanin-Streptavidin binds to the biotin tag of the peptide, therefore accepting the energy transferred from the Europium lanthanide. This energy transfer between Europium to SureLight Allophycocyanin is a direct measure of the activity/inhibition of the PRMT5 enzyme.
Reagents and Equipment:

| Reagents/Equipment | Supplier | Catalogue No. |
|---|---|---|
| Bicine | Sigma | B8660 |
| Sodium Chloride | Sigma | S9888 |
| Bovine serum albumin | Sigma | 5470 |
| Tween-20 | Sigma | P1379 |
| DMSO | Rankem | D0178 |
| DL-Dithiothreitol | Sigma | D0632 |
| SGRGKGGKGLGKGGA-K(Biotin) | AnaSpec | SGA-11292-01-QUNNS |
| PRMT5/MEP50 Complex | Reaction Biology | HMT-22-148 |
| S-(5'-Adenosyl)-L-methionine chloride dihydrochloride | Sigma | A7007 |
| Goat polyclonal to Rabbit IgG (Europium) | Abcam | ab187910 |
| Rabbit polyclonal to Histone H4 (mono methyl R3) | Abcam | ab17339 |
| SureLight Allophycocyanin-Streptavidin | Perkin Elmer | CR-130-100 |
| Potassium Fluoride | Sigma | 449148 |
| 384 well Polystyrene F-Bottom Micro plates, White, Med Binding | Greiner | 781075 |
| Victor-3 (Wallac) | Perkin Elmer | — |
| GraphPad Prism 7 | GraphPad Software, Inc. | — |
| Micropipettes | Eppendorf | — |

Assay buffer: 20 mM BICINE (pH 7.6), 25 mM NaCl, 2 mM DTT, 0.01% Tween-20 and 0.01% BSA.
Reagent Preparation:

| Reagent | Stock concentration | Working concentration | Final assay concentration |
|---|---|---|---|
| DMSO | 100% | 7.50% | 1% |
| Histone-H4 Peptide | 5 μM | 250 nM | 50 nM |
| SAM | 300 μM | 3 μM | 1 μM |
| PRMT5:MEP50 complex | 8.7 μM | 96 nM | 32 nM |
| Detection Mix | | | |
| Anti H4R3 Ab. | 6.6 μM | 60 nM | 3 nM |
| Anti IgG Europium | 6.6 μM | 60 nM | 3 nM |
| Streptavidin SAPC | 6.35 μM | 60 nM | 3 nM |
| Potassium Fluoride | 2M | 2M | 200 mM |

The compound dilutions were prepared as 7.5% DMSO stock solutions in assay buffer. To 2 μL (7.5×) of test compound, 5 μL of PRMT5 enzyme prepared in assay buffer (Final concentration of 32 nM in 15 μL reaction volume) was added and allowed for 30 minutes pre-incubation time in a white polystyrene 384-well plate at room temperature. A total of 8 μl substrate mix solution containing Biotinylated H4 peptide SGRGKGGKGLGKGGA-K (Biotin, 3 μl) and S-Adenosylmethionine (5 μl) was added to each well to start the reaction at a final concentration of 50 nM and 1 μM respectively. The reactions were incubated for 90 minutes at room temperature and then quenched with 5 μL of detection mixture per well (making final volume of each well is 20 μL solution). The plates were then read on Victor-3 with Excitation at 340 nm and Emissions collected at 615 and 665 nm in TR-FRET protocol.
The following calculations were made:

Signal at $F665/F615*10000$ of positive control/signal at $F665/F615*10000$ of substrate control. 1. Fold Activity:

$100-\{$signal at $F665/F615*1000$ of $NCE$/signal at $F665/F615*10000$ of positive control$\}*100$ Percentage inhibition:

The percentage inhibition vs. concentration of the test compound was plotted using Graphpad Prism to calculate the $IC_{50}$. For $IC_{50}$ concentrations, 1:3 dilution of compound in 100% DMSO based on potency expected from screening followed by buffer dilution from each concentration. The results are shown in Table-I.

TABLE I $IC_{50}$ of compounds of present invention on PRMT5 inhibition

| Example No. | PRMT5 $IC_{50}$ (μM) |
|---|---|
| 1 | 0.43 |
| 1a | 1.70 |
| 1b | 2.30 |
| 2 | 0.03 |
| 2a | 0.04 |
| 2b | 0.18 |
| 3 | 0.35 |
| 4 | 0.45 |
| 5 | 0.11 |
| 6 | 0.12 |
| 7 | 0.52 |
| 8 | 0.21 |
| 9 | 0.23 |
| 10 | 0.23 |
| 11 | 0.22 |
| 12 | 0.24 |
| 13 | 0.32 |
| 14 | 0.16 |
| 15 | 0.31 |
| 15a | >5 |
| 15b | 0.05 |
| 16 | 0.25 |
| 16a | 0.19 |
| 16b | >5 |
| 17 | 0.03 |
| 18 | 0.07 |
| 18a | 0.04 |
| 18b | 1.48 |
| 19 | 0.31 |
| 20 | 0.65 |
| 21 | 0.25 |
| 22 | 0.39 |
| 23 | 0.19 |
| 24 | 0.33 |
| 25 | 1.95 |
| 26 | 0.10 |
| 27 | 0.22 |

TABLE I-continued

IC$_{50}$ of compounds of present invention on PRMT5 inhibition

| Example No. | PRMT5 IC$_{50}$ (µM) |
|---|---|
| 28 | 0.13 |
| 29 | 0.12 |
| 30 | 0.13 |
| 31 | 0.05 |
| 32 | 2.10 |
| 33 | 0.21 |
| 34 | 3.42 |
| 35 | 0.09 |
| 35a | 0.06 |
| 35b | 1.75 |
| 36 | 0.59 |
| 37 | 0.08 |
| 38 | 0.16 |
| 39 | 0.22 |
| 40 | 0.11 |
| 41 | 0.07 |
| 42 | 0.37 |
| 43 | 0.27 |
| 44 | 0.61 |
| 45 | 0.11 |
| 47 | 0.59 |
| 48 | 0.12 |
| 49 | 0.18 |
| 50 | 0.09 |
| 51 | 0.05 |
| 52 | 1.55 |
| 53 | 0.07 |
| 54 | 0.03 |
| 55 | 0.06 |
| 56 | 0.03 |
| 57 | 0.05 |
| 58 | 0.03 |
| 59 | 0.58 |
| 60 | 0.08 |
| 61 | 0.06 |
| 62 | 0.10 |
| 63 | 0.12 |
| 64 | 0.07 |
| 65 | 0.07 |
| 66 | 0.03 |
| 67 | 0.01 |
| 68 | 0.03 |
| 69 | 0.01 |
| 70 | 0.13 |
| 71 | 0.05 |
| 72 | 0.04 |
| 73 | 0.27 |
| 74 | 0.58 |
| 75 | 0.34 |
| 76 | 0.23 |
| 77 | 0.84 |
| 78 | 0.98 |
| 79 | 0.15 |
| 80 | 0.18 |
| 81 | 0.61 |
| 82 | 0.15 |
| 82a | 0.77 |
| 82b | 0.12 |
| 83 | 0.50 |
| 84 | 0.07 |
| 84a | 0.01 |
| 85 | 0.08 |
| 86 | 0.05 |
| 87 | 0.04 |
| 88 | 0.04 |
| 89 | 0.05 |
| 90 | 0.26 |
| 91 | 0.07 |
| 92 | 0.18 |
| 93 | 0.11 |
| 94 | 0.43 |
| 95 | 0.08 |
| 96 | 0.13 |
| 97 | 0.04 |
| 98 | 0.08 |
| 99 | 0.21 |
| 100 | 0.12 |
| 101 | 0.08 |
| 102 | 5.44 |
| 103 | 5.46 |
| 104 | 0.03 |
| 105 | 0.04 |
| 106 | 0.07 |
| 107 | 0.10 |
| 108 | 0.10 |
| 109 | 0.04 |
| 110 | 0.02 |

Z138 Cell Proliferation Assay:

Z138 cells were seeded in a 96-well round-bottom plate and treated with varying concentration of compound. The final DMSO concentration was maintained at 0.05%. The selected compounds of present invention were screened in a 9-point dose response format starting with 10 µM and $\frac{1}{3}^{rd}$ serial dilution. On the 4$^{th}$ day, cells were spun down and media was replaced while maintaining the initial compound concentration in each well. At the end of the 7$^{th}$ day, cells were spun down and media was aspirated. 50 µL of XTT containing media was added to the wells. The plates were read using the M3 spectrophotometer at 465 nm. GI$_{50}$ values were calculated by fitting the dose response data to sigmoidal curve fitting equation using GraphPad Prism software V7. The results are shown in Table-I.

The compounds of the present invention were screened in the above mentioned assays for determining activity of the compounds in the inhibition PRMT5 enzyme. The results are summarized in the Table 1 below wherein "A" refers to GI$_{50}$ value lower than 0.5 µM, "B" refers to GI$_{50}$ value between 0.51 µM and 1.0 µM and "C" refers to GI$_{50}$ value higher than 1.0 µM. The results are shown in Table-II.

TABLE II

GI$_{50}$ of compounds of present invention on PRMT5 inhibition

| Example No. | Z-138 GI$_{50}$ (µM) |
|---|---|
| 2 | A |
| 5 | A |
| 6 | A |
| 10 | A |
| 12 | A |
| 16 | C |
| 18 | A |
| 18a | A |
| 18b | C |
| 19 | C |
| 21 | C |
| 22 | C |
| 24 | A |
| 26 | B |
| 28 | A |
| 32 | B |
| 33 | C |
| 35 | A |
| 35a | A |
| 35b | C |
| 36 | C |
| 37 | A |

TABLE II-continued

GI$_{50}$ of compounds of present invention on PRMT5 inhibition

| Example No. | Z-138 GI$_{50}$ (μM) |
|---|---|
| 38 | A |
| 39 | B |
| 40 | A |
| 41 | B |
| 45 | A |
| 48 | C |
| 51 | A |
| 53 | A |
| 54 | A |
| 55 | A |
| 56 | A |
| 57 | B |
| 58 | A |
| 60 | C |
| 61 | B |
| 62 | B |
| 63 | C |
| 64 | C |
| 65 | B |
| 66 | A |
| 67 | A |
| 68 | A |
| 69 | A |
| 70 | A |
| 71 | A |
| 72 | B |
| 74 | A |
| 79 | A |
| 80 | B |
| 82 | B |
| 82b | A |
| 86 | A |
| 88 | A |
| 89 | A |
| 91 | A |
| 92 | A |
| 93 | A |
| 94 | C |
| 95 | A |
| 96 | A |
| 98 | A |
| 100 | A |
| 104 | C |
| 105 | B |
| 108 | A |
| 109 | A |
| 110 | A |

We claim:
1. A compound of formula (I),

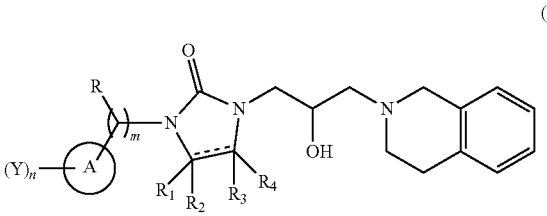

(I)

or a pharmaceutically acceptable salt or a stereoisomer thereof; wherein,
- - - - - represents a single bond or double bond;
A is aryl, heteroaryl, cycloalkyl or heterocycloalkyl;
Y is hydrogen, —SO$_2$R$_a$, —NR$_a$R$_b$, —C(O)R$_a$, —C(O)NR$_a$R$_b$, —NHC(O)R$_a$, —COOH, cyano, halogen, haloalkyl, alkyl, alkenyl, alkynyl, alkoxy, hydroxyl or oxo; wherein the said alkyl, alkenyl and alkynyl are optionally substituted with 1 to 3 groups selected from hydroxyl, halogen, acyl and heterocycloalkyl;
R is hydrogen, alkyl or halogen;
R$_a$ is hydrogen, alkyl, halogen, alkoxy, heterocycloalkyl or cycloalkyl; wherein the heterocycloalkyl and cycloalkyl are optionally substituted with 1 to 3 groups selected from alkyl, hydroxyl, halogen and acyl;
R$_b$ is hydrogen or alkyl;
R$_1$ is hydrogen or alkyl; R$_2$ is hydrogen, alkyl or absent; or R$_1$ and R$_2$ together represents an oxo group;
R$_3$ is hydrogen or alkyl; R$_4$ is hydrogen, alkyl, aryl or absent; or R$_3$ and R$_4$ together with the atoms to which they are attached form 3- to 8-membered cycloalkyl ring;
alternatively, R$_1$ and R$_3$ together with the atoms to which they are attached form, an optionally substituted aryl, heteroaryl or cycloalkyl, wherein the optional substituent is selected from 1 to 3 occurrences of R$_5$;
R$_5$ is alkyl, halogen or cyano;
'n' is 1, 2 or 3;
'm' is 0 or 1.

2. The compound of claim 1, wherein A is (C$_6$-C$_{10}$)aryl, 5- to 12-membered heterocycloalkyl or 5- to 12-membered heteroaryl.

3. The compound of claim 1, wherein A is phenyl, naphthyl, furanyl, thienyl, pyrrolyl, pyrazolyl, imidazolyl, oxazolyl, cinnolinyl, isoxazolyl, thiazolyl, isothiazolyl, 1H-tetrazolyl, oxadiazolyl, triazolyl, pyridyl, pyrimidinyl, pyrazinyl, pyridazinyl, benzoxazolyl, benzisoxazolyl, benzothiazolyl, benzofuranyl, benzothienyl, benzotriazinyl, benzimidazolyl, indolyl, isoindolyl, indazolyl, quinolinyl, isoquinolinyl, quinazolinyl, quinoxalinyl, purinyl, pteridinyl, indolizinyl, benzoisothiazolyl, benzoxazolyl, pyrrolopyridyl, pyrazolopyrimidyl, furopyridinyl, benzothiadiazolyl, benzooxadiazolyl, benzotriazolyl, benzotriadiazolyl, azetidinyl, oxetanyl, imidazolidinyl, pyrrolidinyl, oxazolidinyl, thiazolidinyl, pyrazolidinyl, tetrahydrofuranyl, piperidinyl, piperazinyl, tetrahydropyranyl, morpholinyl, thiomorpholinyl, 1,4-dioxanyl, dioxidothiomorpholinyl, oxapiperazinyl, oxapiperidinyl, tetrahydrofuryl, tetrahydropyranyl, tetrahydrothiophenyl, dihydropyranyl, indolinyl, indolinylmethyl, aza-bicyclooctanyl, azocinyl, chromanyl, isochromanyl xanthenyl, 2-oxa-6-azaspiro[3.3]heptanyl or 3-oxa-8-azabicyclo[3.2.1]octanyl.

4. The compound of claim 1, wherein Y is hydrogen, —SO$_2$R$_a$, —NR$_a$R$_b$, —C(O)R$_a$, —C(O)NR$_a$R$_b$, alkyl, alkoxy or cyano.

5. The compound of claim 1, having compound of formula (IA):

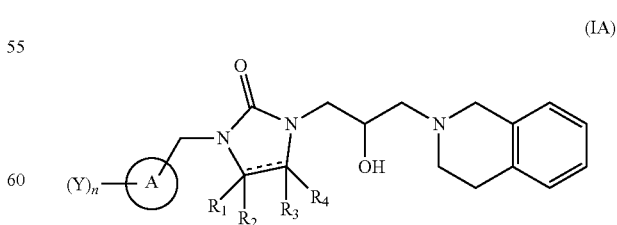

(IA)

or a pharmaceutically acceptable salt or a stereoisomer thereof;
wherein, - - - - -, A, Y, R$_1$, R$_2$, R$_3$, R$_4$ and 'n' are as defined in claim 1.

6. The compound of claim 5, wherein A is aryl or heteroaryl.

7. The compound of claim 5, wherein A is phenyl, naphthyl, furanyl, thienyl, pyrrolyl, pyrazolyl, imidazolyl, oxazolyl, cinnolinyl, isoxazolyl, thiazolyl, isothiazolyl, 1H-tetrazolyl, oxadiazolyl, triazolyl, pyridyl, pyrimidinyl, pyrazinyl, pyridazinyl, benzoxazolyl, benzisoxazolyl, benzimidazolyl, benzofuranyl, benzothienyl, benzotriazinyl, benzimidazolyl, indolyl, isoindolyl, indazolyl, quinolinyl, isoquinolinyl, quinazolinyl, quinoxalinyl, pteridinyl, indolizinyl, benzoisothiazolyl, benzoxazolyl, pyrrolopyridyl, pyrazolopyrimidyl, furopyridinyl, benzothiadiazolyl, benzooxadiazolyl, benzotriazolyl or benzotriadiazolyl.

8. The compound of claim 1, wherein A is cycloalkyl or heterocycloalkyl.

9. The compound of claim 8, wherein A is cyclopropyl, cyclobutyl, cyclopentyl, cyclohexy, cycloheptyl, azetidinyl, oxetanyl, imidazolidinyl, pyrrolidinyl, oxazolidinyl, thiazolidinyl, pyrazolidinyl, tetrahydrofuranyl, piperidinyl, piperazinyl, tetrahydropyranyl, morpholinyl, thiomorpholinyl, 1,4-dioxanyl, dioxidothiomorpholinyl, oxapiperazinyl, oxapiperidinyl, tetrahydrofuryl, tetrahydropyranyl, tetrahydrothiophenyl, dihydropyranyl, indolinyl, indolinylmethyl, aza-bicyclooctanyl, azocinyl, chromanyl, isochromanyl, xanthenyl, 2-oxa-6-azaspiro[3.3]heptanyl or 3-oxa-8-azabicyclo[3.2.1]octanyl.

10. The compound of claim 1, having compound of formula (IB)

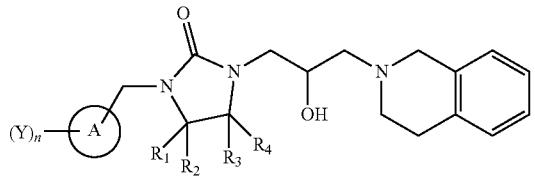

(IB)

or a pharmaceutically acceptable salt or a stereoisomer thereof; wherein, A, Y, $R_1$, $R_2$, $R_3$, $R_4$ and 'n' are as defined in claim 1.

11. The compound of claim 10, wherein $R_1$, $R_2$, $R_3$ and $R_4$ are hydrogen.

12. The compound of claim 10, wherein Y is hydrogen, —C(O)$R_a$, —C(O)N$R_a R_b$, —COOH, alkyl, alkoxy or cyano.

13. The compound of a claim 1, wherein
A is phenyl, pyridyl, benzimidazolyl or isochromanyl; wherein the said phenyl, pyridyl benzimidazolyl or isochromanyl is optionally substituted with 1 to 3 groups selected from halogen, hydroxyl, carboxylic acid, alkoxycarbonyl, formyl, acyl, thiocarbonyl, alkoxyl, oxo, amino, amido, cyano, nitro, azido, alkylthio, sulfate, sulfonate, sulfamoyl, sulfonamido and sulfonyl group;
Y is hydrogen, —SO$_2$-alkyl, —SO$_2$-cycloalkyl, —SO$_2$-heterocycloalkyl, —NH(heterocycloalkyl), —N(alkyl)$_2$, —C(O)-alkyl, —C(O)-heterocycloalkyl, —C(O)NH$_2$, —C(O)NH(alkyl), —C(O)NH(cycloalkyl), —C(O)NH(heterocycloalkyl),—NHC(O)(heterocycloalkyl), —NHC(O)(cycloalkyl), cyano, halogen, haloalkyl, alkyl, alkenyl, alkynyl, alkoxy, hydroxyl or oxo; wherein the said heterocycloalkyl and cycloalkyl, are optionally substituted with 1 to 3 groups selected from alkyl, hydroxyl, halogen and acyl;
$R_1$ is hydrogen or alkyl; $R_2$ is hydrogen, alkyl or absent;
$R_3$ is hydrogen or alkyl; $R_4$ is hydrogen, alkyl, aryl or absent;
'm' is 0 or 1; and
'n' is 1 or 2.

14. The compound of claim 1, having compound of formula (IC):

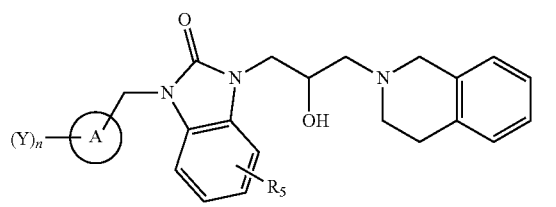

(IC)

or a pharmaceutically acceptable salt or a stereoisomer thereof; wherein, A, Y, $R_5$ and 'n' are as defined in claim 1.

15. The compound of claim 1, wherein the compound is:

| Example No. | IUPAC Name |
|---|---|
| 1 | 1-(3-(3,4-dihydroisoquinolin-2(1H)-yl)-2-hydroxypropyl)-3-((1-methyl-1H-benzo[d]imidazol-6-yl)methyl)imidazolidin-2-one; |
| 1a | Isomer-1 of 1-(3-(3,4-dihydroioquinolin-2(1H)-yl)-2-hydroxypropyl)-3-((1-methyl-1H-benzo[d]imidazol-6-yl)methyl)imidazolidin-2-one; |
| 1b | Isomer-2 of 1-(3-(3,4-dihydroisoquinolin-2(1H)-yl)-2-hydroxypropyl)-3-((1-methyl-1H-benzo[d]imidazol-6-yl)methyl)imidazolidin-2-one; |
| 2 | 4-((3-(3-(3,4-dihydroisoquinolin-2(1H)-yl)-2-hydroxypropyl)-4,4-dimethyl-2-oxoimidazolidin-1-yl)methyl)benzonitrile; |
| 2a | Isomer-1 of 4-((3-(3-(3,4-dihydroisoquinolin-2(1H)-yl)-2-hydroxypropyl)-4,4-dimethyl-2-oxoimidazolidin-1-yl)methyl)benzonitrile; |
| 2b | Isomer-2 of 4-((3-(3-(3,4-dihydroisoquinolin-2(1H)-yl)-2-hydroxypropyl)-4,4-dimethyl-2-oxoimidazolidin-1-yl)methyl)benzonitrile; |
| 3 | 1-(3-(3,4-dihydroisoquinolin-2(1H)-yl)-2-hydroxypropyl)-3-(4-(dimethylamino)benzyl)imidazolidin-2-one; |
| 4 | 1-(3-(3,4-dihydroisoquinolin-2(1H)-yl)-2-hydroxypropyl)-3-((1-methyl-1H-pyrazol-5-yl)methyl)imidazolidin-2-one; |
| 5 | 3-(3-(3,4-dihydroisoquinolin-2(1H)-yl)-2-hydroxypropyl)-4,4-dimethyl-1-(4-methylbenzyl)imidazolidin-2-one; |
| 6 | 4-(3-(3,4-dihydroisoquinolin-2(1H)-yl)-2-hydroxypropyl)-6-((6-methylpyridin-3-yl)methyl)-4,6-diazaspiro[2.4]heptan-5-one; |

-continued

| Example No. | IUPAC Name |
|---|---|
| 7 | 3-(3-(3,4-dihydroisoquinolin-2(1H)-yl)-2-hydroxypropyl)-4,4-dimethyl-1-((6-methylpyridin-3-yl)methyl)imidazolidin-2-one; |
| 8 | 1-(3-(3,4-dihydroisoquinolin-2(1H)-yl)-2-hydroxypropyl)-3-((6-methylpyridin-3-yl)methyl)-1,3-diazaspiro[4.4]nonan-2-one; |
| 9 | 5-(3-(3,4-dihydroisoquinolin-2(1H)-yl)-2-hydroxypropyl)-7-((6-methylpyridin-3-yl)methyl)-5,7-diazaspiro[3.4]octan-6-one; |
| 10 | 1-(3-(3,4-dihydroisoquinolin-2(1H)-yl)-2-hydroxypropyl)-4,4-dimethyl-3-(4-methylbenzyl)imidazolidin-2-one; |
| 11 | 1-(3-(3,4-Dihydroisoquinolin-2(1H)-yl)-2-hydroxypropyl)-3-(4-(methyl-sulfonyl)benzyl)imidazolidin-2-one; |
| 12 | 5-((3-(3-(3,4-dihydroisoquinolin-2(1H)-yl)-2-hydroxypropyl)-4,4-dimethyl-2-oxoimidazolidin-1-yl)methyl)picolinonitrile; |
| 13 | 1-(3-(3,4-dihydroisoquinolin-2(1H)-yl)-2-hydroxypropyl)-3-((6-methoxypyridin-3-yl)methyl)imidazolidin-2-one; |
| 14 | 4-((3-(3-(3,4-Dihydroisoquinolin-2(1H)-yl)-2-hydroxypropyl)-5,5-dimethyl-2-oxoimidazolidin-1-yl)methyl)benzonitrile; |
| 15 | 1-(3-(3,4-Dihydroisoquinolin-2(1H)-yl)-2-hydroxypropyl)-3-(4-methyl-benzyl)imidazolidin-2-one; |
| 15a | Isomer 1 of 1-(3-(3,4-Dihydroisoquinolin-2(1H)-yl)-2-hydroxypropyl)-3-(4-methylbenzyl)imidazolidin-2-one; |
| 15b | Isomer 2 of 1-(3-(3,4-Dihydroisoquinolin-2(1H)-yl)-2-hydroxypropyl)-3-(4-methylbenzyl)imidazolidin-2-one; |
| 16 | 1-(3-(3,4-Dihydroisoquinolin-2(1H)-yl)-2-hydroxypropyl)-3-(2-methylbenzyl)imidazolidin-2-one; |
| 16a | Isomer-1 of 1-(3-(3,4-Dihydroisoquinolin-2(1H)-yl)-2-hydroxypropyl)-3-(2-methylbenzyl)imidazolidin-2-one; |
| 16b | Isomer-2 of 1-(3-(3,4-Dihydroisoquinolin-2(1H)-yl)-2-hydroxypropyl)-3-(2-methylbenzyl)imidazolidin-2-one; |
| 17 | 1-(3-(3,4-Dihydroisoquinolin-2(1H)-yl)-2-hydroxypropyl)-3-(4-methylbenzyl)imidazolidine-2,4-dione; |
| 18 | 4-((3-(3-(3,4-dihydroisoquinolin-2(1H)-yl)-2-hydroxypropyl)-2-oxoimidazolidin-1-yl)methyl)benzonitrile; |
| 18a | Isomer-1 of 4-(3-(3,4-dihydroisoquinolin-2(1H)-yl)-2-hydroxypropyl)-2-oxoimidazolidin-1-yl)methyl)benzonitrile; |
| 18b | Isomer-2 of 4-((3-(3-(3,4-dihydroisoquinolin-2(1H)-yl)-2-hydroxypropyl)-2-oxoimidazolidin-1-yl)methyl)benzonitrile; |
| 19 | 1-(3-(3,4-dihydroisoquinolin-2(1H)-yl)-2-hydroxypropyl)-3-((6-methylpyridin-3-yl)methyl)imidazolidin-2-one; |
| 20 | 1-benzyl-3-(3-(3,4-dihydroisoquinolin-2(1H)-yl)-2-hydroxypropyl)imidazolidin-2-one; |
| 21 | 5-((3-(3-(3,4-dihydroisoquinolin-2(1H)-yl)-2-hydroxypropyl)-2-oxoimidazolidin-1-yl)methyl)picolinonitrile; |
| 22 | 1-(3-(3,4-dihydroisoquinolin-2(1H)-yl)-2-hydroxypropyl)-3-((6-methylpyridin-2-yl)methyl)imidazolidin-2-one; |
| 23 | 4-(3-(3-(3,4-dihydroisoquinolin-2(1H)-yl)-2-hydroxypropyl)-2,5-dioxoimidazolidin-1-yl)methyl)benzonitrile; |
| 24 | 4-((3-(3-(3,4-dihydroisoquinolin-2(1H)-yl)-2-hydroxypropyl)-4,4-dimethyl-2,5-dioxoimidazolidin-1-yl)methyl)benzonitrile; |
| 25 | 1-((6-Chloropyridin-3-yl)methyl)-3-(3-(3,4-dihydroisoquinolin-2(1H)-yl)-2-hydroxypropyl)imidazolidin-2-one; |
| 26 | 1-(3-(3,4-dihydroisoquinolin-2(1H)-yl)-2-hydroxypropyl)-3-((6-isopropylpyridin-3-yl)methyl)imidazolidin-2-one; |
| 27 | 1-(3-(3,4-dihydroisoquinolin-2(1H)-yl)-2-hydroxypropyl)-3-((6-ethylpyridin-3-yl)methyl)imidazolidin-2-one; |
| 28 | 1-(3-(3,4-Dihydroisoquinolin-2(1H)-yl)-2-hydroxypropyl)-3-((6-(prop-1-en-2-yl)pyridin-3-yl)methyl)imidazolidin-2-one; |
| 29 | 1-(3-(3,4-Dihydroisoquinolin-2(1H)-yl)-2-hydroxypropyl)-3-((6-isopropylpyridin-3-yl)methyl)-5,5-dimethylimidazolidine-2,4-dione; |
| 30 | 1-(3-(3,4-Dihydroisoquinolin-2(1H)-yl)-2-hydroxypropyl)-3-((5-isopropylpyridin-2-yl)methyl)-5,5-dimethylimidazolidine-2,4-dione; |
| 31 | 1-(3-(3,4-Dihydroisoquinolin-2(1H)-yl)-2-hydroxypropyl)-3-((5-isopropylpyridin-2-yl)methyl)imidazolidin-2-one; |
| 32 | 1-((6-Acetylpyridin-3-yl)methyl)-3-(3-(3,4-dihydroisoquinolin-2(1H)-yl)-2-hydroxypropyl)imidazolidin-2-one; |
| 33 | 4-(3-(3-(3,4-dihydroisoquinolin-2(1H)-yl)-2-hydroxypropyl)-2-oxoimidazolidin-1-yl)benzonitrile; |
| 34 | 1-(3-(3,4-dihydroisoquinolin-2(1H)-yl)-2-hydroxypropyl)-3-(5-(piperidine-1-carbonyl)pyridin-2-yl)imidazolidin-2-one; |
| 35 | 6-((3-(3-(3,4-Dihydroisoquinolin-2(1H)-yl)-2-hydroxypropyl)-2-oxoimidazolidin-1-yl)methyl)nicotinonitrile; |
| 35a | Isomer-1 of 6-((3-(3-(3,4-Dihydroisoquinolin-2(1H)-yl)-2-hydroxypropyl)-2-oxoimidazolidin-1-yl)methyl)nicotinonitrile; |
| 35b | Isomer-2 of 6-((3-(3-(3,4-Dihydroisoquinolin-2(1H)-yl)-2-hydroxypropyl)-2-oxoimidazolidin-1-yl)methyl)nicotinonitrile; |
| 36 | 6-((3-(3-(3,4-Dihydroisoquinolin-2(1H)-yl)-2-hydroxypropyl)-2-oxoimidazolidin-1-yl)methyl)picolinonitrile; |

-continued

| Example No. | IUPAC Name |
| --- | --- |
| 37 | 4-((3-(3-(3,4-Dihydroisoquinolin-2(1H)-yl)-2-hydroxypropyl)-2-oxo-imidazolidin-1-yl)methyl)-2-methylbenzonitrile; |
| 38 | 6-((3-(3-(3,4-Dihydroisoquinolin-2(1H)-yl)-2-hydroxypropyl)-4,4-dimethyl-2-oxoimidazolidin-1-yl)methyl)nicotinonitrile; |
| 39 | 4-((3-(3-(3,4-Dihydroisoquinolin-2(1H)-yl)-2-hydroxypropyl)-2-oxo-imidazolidin-1-yl)methyl)-2-fluorobenzonitrile; |
| 40 | 1-(3-(3,4-Dihydroisoquinolin-2(1H)-yl)-2-hydroxypropyl)-3-((6-(trifluoromethyl)pyridin-3-yl)methyl)imidazolidin-2-one; |
| 41 | 4-((3-(3-(3,4-Dihydroisoquinolin-2(1H)-yl)-2-hydroxypropyl)-2-oxoimidazolidin-1-yl)methyl)-2-methoxybenzonitrile; |
| 42 | 4-((3-(3-(3,4-Dihydroisoquinolin-2(1H)-yl)-2-hydroxypropyl)-2-oxoimidazolidin-1-yl)methyl)-picolinonitrile; |
| 43 | 1-(3-(3,4-Dihydroisoquinolin-2(1H)-yl)-2-hydroxypropyl)-3-(isochroman-7-ylmethyl)imidazolidin-2-one; |
| 44 | 5-((3-(3-(3,4-Dihydroisoquinolin-2(1H)-yl)-2-hydroxypropyl)-2-oxoimidazolidin-1-yl)methyl)-1-methylpyridin-2(1H)-one; |
| 45 | 3-(3-(3,4-dihydroisoquinolin-2(1H)-yl)-2-hydroxypropyl)-4,4-dimethyl-1-(4-(methylsulfonyl)benzyl)imidazolidin-2-one; |
| 46 | 6-((3-(3-(3,4-Dihydroisoquinolin-2(1H)-yl)-2-hydroxypropyl)-2-oxoimidazo-lidin-1-yl)methyl)nicotinamide; |
| 47 | 4-((3-(3-(3,4-dihydroisoquinolin-2(1H)-yl)-2-hydroxypropyl)-2-oxoimidazolidin-1-yl)methyl)benzamide; |
| 48 | (R)-6-((3-(3-(3,4-Dihydroisoquinolin-2(1H)-yl)-2-hydroxypropyl)-2-oxoimidazolidin-1-yl)methyl)nicotinamide; |
| 49 | (R)-6-((3-(3-(3,4-Dihydroisoquinolin-2(1H)-yl)-2-hydroxypropyl)-2-oxo-imidazolidin-1-yl)methyl)-N-methylnicotinamide; |
| 50 | (R)-N-Cyclopropyl-6-((3-(3-(3,4-di-hydroisoquinolin-2(1H)-yl)-2-hydroxypropyl)-2-oxoimidazolidin-1-yl)methyl)nicotinamide; |
| 51 | (R)-1-((5-(Azetidine-1-carbonyl)pyridin-2-yl)methyl)-3-(3-(3,4-dihydro-isoquinolin-2(1H)-yl)-2-hydroxypropyl)imidazolidin-2-one; |
| 52 | (R)-1-(3-(3,4-dihydroisoquinolin-2(1H)-yl)-2-hydroxypropyl)-3-((3-(piperidine-1-carbonyl)pyridin-2-yl)methyl)imidazolidin-2-one; |
| 53 | (R)-1-(3-(3,4-dihydroisoquinolin-2(1H)-yl)-2-hydroxypropyl)-3-((5-(pyrrolidine-1-carbonyl)pyridin-2-yl)methyl)imidazolidin-2-one; |
| 54 | (R)-1-(3-(3,4-dihydroisoquinolin-2(1H)-yl)-2-hydroxypropyl)-3-((5-(piperidine-1-carbonyl)pyridin-2-yl)methyl)imidazolidin-2-one; |
| 55 | (R)-1((5-(4-acetylpiperazine-1-carbonyl)pyridin-2-yl)methyl)-3-(3-(3,4-dihydroisoquinolin-2(1H)-yl)-2-hydroxypropyl)imidazolidin-2-one; |
| 56 | (R)-1-((5-(3,3-difluoropyrrolidine-1-carbonyl)pyridin-2-yl)methyl)-3-(3-(3,4-dihydroisoquinolin-2(1H)-yl)-2-hydroxypropyl)imidazolidin-2-one; |
| 57 | (R)-1-(3-(3,4-dihydroisoquinolin-2(1H)-yl)-2-hydroxypropyl)-3-((5-(morpholine-4-carbonyl)pyridin-2-yl)methyl)imidazolidin-2-one; |
| 58 | (R)-1-((5-(4,4-difluoropiperidine-1-carbonyl)pyridin-2-yl)methyl)-3-(3-(3,4-dihydroisoquinolin-2(1H)-yl)-2-hydroxypropyl)imidazolidin-2-one; |
| 59 | (R)-1-(3-(3,4-dihydroisoquinolin-2(1H)-yl)-2-hydroxypropyl)-3-((4-(piperidine-1-carbonyl)pyridin-2-yl)methyl)imidazolidin-2-one; |
| 60 | (R)-1-(3-(3,4-dihydroisoquinolin-2(1H)-yl)-2-hydroxypropyl)-3-((6-(piperidine-1-carbonyl)pyridin-2-yl)methyl)imidazolidin-2-one; |
| 61 | (R)-6-((3-(3-(3,4-dihydroisoquinolin-2(1H)-yl)-2-hydroxypropyl)-2-oxoimidazolidin-1-yl)methyl)-N-(oxetan-3-yl)nicotinamide; |
| 62 | 1-((R)-3-(3,4-dihydroisoquinolin-2(1H)-yl)-2-hydroxypropyl)-3-((5-((R)-3-fluoropyrrolidine-1-carbonyl)pyridin-2-yl)methyl)imidazolidin-2-one; |
| 63 | (R)-1-((5-(2-oxa-6-azaspiro[3.3]heptane-6-carbonyl)pyridin-2-yl)methyl)-3-(3-(3,4-dihydroisoquinolin-2(1H)-yl)-2-hydroxypropyl)imidazolidin-2-one; |
| 64 | 1-((5-(3-oxa-8-azabicyclo[3.2.1]octane-8-carbonyl)pyridin-2-yl)methyl)-3-((R)-3-(3,4-dihydroisoquinolin-2(1H)-yl)-2-hydroxypropyl)imidazolidin-2-one; |
| 65 | (R)-1-((5-(3,3-difluoroazetidine-1-carbonyl)pyridin-2-yl)methyl)-3-(3-(3,4-dihydroisoquinolin-2(1H)-yl)-2-hydroxypropyl)imidazolidin-2-one; |
| 66 | (R)-1-(3-(3,4-dihydroisoquinolin-2(1H)-yl)-2-hydroxypropyl)-3-(4-(methyl-sulfonyl)benzyl)imidazolidin-2-one; |
| 67 | (R)-1-(4-(cyclopropylsulfonyl)benzyl)-3-(3-(3,4-dihydroisoquinolin-2(1H)-yl)-2-hydroxypropyl)imidazolidin-2-one; |
| 68 | (R)-1-(3-(3,4-dihydroisoquinolin-2(1H)-yl)-2-hydroxypropyl)-3-(4-(pyrrolidin-1-ylsulfonyl)benzyl)imidazolidin-2-one; |
| 69 | (R)-1-(3-(3,4-dihydroisoquinolin-2(1H)-yl)-2-hydroxypropyl)-3-(4-(piperidin-1-ylsulfonyl)benzyl)imidazolidin-2-one; |
| 70 | (R)-1-(3-(3,4-dihydroisoquinolin-2(1H)-yl)-2-hydroxypropyl)-3-(3-(pyrrolidin-1-ylsulfonyl)benzyl)imidazolidin-2-one; |
| 71 | (R)-1-(3-(3,4-dihydroisoquinolin-2(1H)-yl)-2-hydroxypropyl)-3-((5-(pyrrolidin-1-ylsulfonyl)pyridin-2-yl)methyl)imidazolidin-2-one; |
| 72 | (R)-1-((2-((1-acetylpiperidin-4-yl)amino)pyridin-4-yl)methyl)-3-(3-(3,4-dihydroisoquinolin-2(1H)-yl)-2-hydroxypropyl)imidazolidin-2-one; |
| 73 | 6-((3-(3-(3,4-dihydroisoquinolin-2(1H)-yl)-2-hydroxypropyl)-2,5-dioxoimidazolidin-1-yl)methyl)nicotinonitrile; |
| 74 | 6-((3-(3-(3,4-dihydroisoquinolin-2(1H)-yl)-2-hydroxypropyl)-4,4-dimethyl-2,5-dioxoimidazolidin-1-yl)methyl)nicotinonitrile; |

| Example No. | IUPAC Name |
|---|---|
| 75 | 4-((3-(3-(3,4-Dihydroisoquinolin-2(1H)-yl)-2-hydroxypropyl)-4,4-dimethyl-2,5-dioxoimidazolidin-1-yl)methyl)-2-methoxybenzonitrile; |
| 76 | 1-(3-(3,4-dihydroisoquinolin-2(1H)-yl)-2-hydroxypropyl)-3-(isochroman-7-ylmethyl)-5,5-dimethylimidazolidine-2,4-dione; |
| 77 | 1-(3-(3,4-Dihydroisoquinolin-2(1H)-yl)-2-hydroxypropyl)-5,5-dimethyl-3-((5-(trifluoromethyl)pyridin-2-yl)methyl)imidazolidine-2,4-dione; |
| 78 | 1-(3-(3,4-Dihydroisoquinolin-2(1H)-yl)-2-hydroxypropyl)-5,5-dimethyl-3-((1-methyl-6-oxo-1,6-dihydropyridin-3-yl)methyl)imidazolidine-2,4-dione; |
| 79 | 1-(3-(3,4-Dihydroisoquinolin-2(1H)-yl)-2-hydroxypropyl)-5,5-dimethyl-3-(4-(methylsulfonyl)benzyl)imidazolidine-2,4-dione; |
| 80 | 3-(3-(3,4-Dihydroisoquinolin-2(1H)-yl)-2-hydroxypropyl)-4-methyl-1-(4-methylbenzyl)imidazolidin-2-one; |
| 81 | 3-(3-(3,4-Dihydroisoquinolin-2(1H)-yl)-2-hydroxypropyl)-1-(4-methylbenzyl)-4-phenylimidazolidin-2-one; |
| 82 | 4-((3-(3-(3,4-Dihydroisoquinolin-2(1H)-yl)-2-hydroxypropyl)-2-oxo-2,3-dihydro-1H-imidazol-1-yl)methyl)benzonitrile; |
| 82a | Isomer 1 of 4-((3-(3-(3,4-Dihydroisoquinolin-2(1H)-yl)-2-hydroxypropyl)-2-oxo-2,3-dihydro-1H-imidazol-1-yl)methyl)benzonitrile; |
| 82b | Isomer 2 of 4-((3-(3-(3,4-Dihydroisoquinolin-2(1H)-yl)-2-hydroxypropyl)-2-oxo-2,3-dihydro-1H-imidazol-1-yl)methyl)benzonitrile; |
| 83 | 1-(3-(3,4-dihydroisoquinolin-2(1H)-yl)-2-hydroxypropyl)-3-(4-methylbenzyl)-1,3-dihydro-2H-imidazol-2-one; |
| 84 | 1-(3-(3,4-Dihydroisoquinolin-2(1H)-yl)-2-hydroxypropyl)-3-((1-methyl-1H-benzo[d]imidazol-6-yl)methyl)-1,3-dihydro-2H-benzo[d]imidazol-2-one; |
| 84a | Isomer 1 of 1-(3-(3,4-Dihydroisoquinolin-2(1H)-yl)-2-hydroxypropyl)-3-((1-methyl-1H-benzo[d]imidazol-6-yl)methyl)-1,3-dihydro-2H-benzo[d]imidazol-2-one; |
| 84b | Isomer 2 of 1-(3-(3,4-Dihydroisoquinolin-2(1H)-yl)-2-hydroxypropyl)-3-((1-methyl-1H-benzo[d]imidazol-6-yl)methyl)-1,3-dihydro-2H-benzo[d]imidazol-2-one; |
| 85 | 1-(3-(3,4-Dihydroisoquinolin-2(1H)-yl)-2-hydroxypropyl)-3-(4-methylbenzyl)-1,3-dihydro-2H-benzo[d]imidazol-2-one; |
| 86 | 1-(4-Chlorobenzyl)-3-(3-(3,4-dihydroisoquinolin-2(1H)-yl)-2-hydroxypropyl)-1,3-dihydro-2H-benzo[d]imidazol-2-one; |
| 87 | 1-(3-(3,4-Dihydroisoquinolin-2(1H)-yl)-2-hydroxypropyl)-3-(2-methylbenzyl)-1,3-dihydro-2H-benzo[d]imidazol-2-one; |
| 88 | 1-(3-(3,4-Dihydroisoquinolin-2(1H)-yl)-2-hydroxypropyl)-3-((6-methylpyridin-3-yl)methyl)-1,3-dihydro-2H-benzo[d]imidazol-2-one; |
| 89 | 4-((3-(3-(3,4-Dihydroisoquinolin-2(1H)-yl)-2-hydroxypropyl)-2-oxo-2,3-dihydro-1H-benzo[d]imidazol-1-yl)methyl)benzonitrile; |
| 90 | 1-(3-(3,4-Dihydroisoquinolin-2(1H)-yl)-2-hydroxypropyl)-3-(3-methylbenzyl)-1,3-dihydro-2H-benzo[d]imidazol-2-one; |
| 91 | 5-((3-(3-(3,4-Dihydroisoquinolin-2(1H)-yl)-2-hydroxypropyl)-2-oxo-2,3-dihydro-1H-benzo[d]imidazol-1-yl)methyl)picolinonitrile; |
| 92 | 5-((3-(3-(3,4-Dihydroisoquinolin-2(1H)-yl)-2-hydroxypropyl)-2-oxo-2,3-dihydro-1H-benzo[d]imidazol-1-yl)methyl)picolinonitrile; |
| 93 | 4-(3-(3-(3,4-Dihydroisoquinolin-2(1H)-yl)-2-hydroxypropyl)-2-oxo-2,3-dihydro-1H-benzo[d]imidazol-1-yl)benzonitrile; |
| 94 | 1-(3-(3,4-Dihydroisoquinolin-2(1H)-yl)-2-hydroxypropyl)-3-(4-methoxybenzyl)-1,3-dihydro-2H-imidazo[4,5-b]pyridin-2-one; |
| 95 | 3-(3-(3,4-Dihydroisoquinolin-2(1H)-yl)-2-hydroxypropyl)-1-(4-methoxybenzyl)-2-oxo-2,3-dihydro-1H-benzo[d]imidazole-5-carbonitrile; |
| 96 | 3-(3-(3,4-Dihydroisoquinolin-2(1H)-yl)-2-hydroxypropyl)-5-fluoro-1-(4-methoxybenzyl)-1,3-dihydro-2H-benzo[d]imidazol-2-one; |
| 97 | 3-(3-(3,4-Dihydroisoquinolin-2(1H)-yl)-2-hydroxypropyl)-5-fluoro-1-(4-(methylsulfonyl)benzyl)-1,3-dihydro-2H-benzo[d]imidazol-2-one; |
| 98 | 6-((3-(3-(3,4-Dihydroisoquinolin-2(1H)-yl)-2-hydroxypropyl)-5-fluoro-2-oxo-2,3-dihydro-1H-benzo[d]imidazol-1-yl)methyl)nicotinonitrile; |
| 99 | 6-((3-(3-(3,4-dihydroisoquinolin-2(1H)-yl)-2-hydroxypropyl)-2-oxo-2,3-dihydro-1H-imidazo[4,5-b]pyridin-1-yl)methyl)nicotinonitrile; |
| 100 | 4-(((3aR,7aR)-3-(3-(3,4-Dihydroisoquinolin-2(1H)-yl)-2-hydroxypropyl)-2-oxooctahydro-1H-benzo[d]imidazol-1-yl)methyl)benzonitrile; |
| 101 | 4-(((3aR,7aS)-3-(3-(3,4-dihydroisoquinolin-2(1H)-yl)-2-hydroxypropyl)-2-oxooctahydro-1H-benzo[d]imidazol-1-yl)methyl)benzonitrile; |
| 102 | (R)-6-((3-(3-(3,4-dihydroisoquinolin-2(1H)-yl)-2-hydroxypropyl)-2-oxoimidazolidin-1-yl)methyl)-5-(piperidine-1-carbonyl)nicotinonitrile; |
| 103 | R)-5-(4-acetylpiperazine-1-carbonyl)-6-((3-(3-(3,4-dihydroisoquinolin-2(1H)-yl)-2-hydroxypropyl)-2-oxoimidazolidin-1-yl)methyl)nicotinonitrile; |
| 104 | (R)-N-(6-((3-(3-(3,4-dihydroisoquinolin-2(1H)-yl)-2-hydroxypropyl)-2-oxoimidazolidin-1-yl)methyl)pyridin-3-yl)oxetane-3-carboxamide; |
| 105 | (R)-N-(6-((3-(3-(3,4-dihydroisoquinolin-2(1H)-yl)-2-hydroxypropyl)-2-oxoimidazolidin-1-yl)methyl)pyridin-3-yl)cyclopentanecarboxamide; |
| 106 | (R)-N-(6-((3-(3-(3,4-dihydroisoquinolin-2(1H)-yl)-2-hydroxypropyl)-2-oxoimidazolidin-1-yl)methyl)pyridin-3-yl)cyclobutanecarboxamide; |
| 107 | (R)-N-(6-((3-(3-(3,4-dihydroisoquinolin-2(1H)-yl)-2-hydroxypropyl)-2-oxoimidazolidin-1-yl)methyl)pyridin-3-yl)tetrahydro-2H-pyran-4-carboxamide; |

-continued

| Example No. | IUPAC Name |
|---|---|
| 108 | (R)-1-(3-(3,4-dihydroisoquinolin-2(1H)-yl)-2-hydroxypropyl)-3-((5-((tetrahydro-2H-pyran-4-yl)amino)pyridin-2-yl)methyl)imidazolidin-2-one; |
| 109 | (R)-1-(3-(3,4-dihydroisoquinolin-2(1H)-yl)-2-hydroxypropyl)-3-((5-((tetrahydro-2H-pyran-4-yl)amino)pyridin-2-yl)methyl)imidazolidin-2-one; |
| 110 | (R)-1-(3-(3,4-dihydroisoquinolin-2(1H)-yl)-2-hydroxypropyl)-3-((5-(oxetan-3-ylethynyl)pyridin-2-yl)methyl)imidazolidin-2-one; | or a pharmaceutically acceptable salt or a stereoisomer thereof.

16. A pharmaceutical composition comprising at least one compound according to claim 1 or a pharmaceutically acceptable salt or a stereoisomer thereof or a pharmaceutically acceptable carrier or excipient.

* * * * *

UNITED STATES PATENT AND TRADEMARK OFFICE
CERTIFICATE OF CORRECTION

| | |
|---|---|
| PATENT NO. | : 11,365,205 B2 |
| APPLICATION NO. | : 16/982996 |
| DATED | : June 21, 2022 |
| INVENTOR(S) | : Dinesh Chikkanna et al. |

It is certified that error appears in the above-identified patent and that said Letters Patent is hereby corrected as shown below:

In the Specification

Column 8, Line 27, 'in' is 0 or 1 should read 'm' is 0 or 1.

Signed and Sealed this
Twenty-eighth Day of February, 2023

Katherine Kelly Vidal
*Director of the United States Patent and Trademark Office*